(12) United States Patent
Keller et al.

(10) Patent No.: US 10,000,810 B2
(45) Date of Patent: *Jun. 19, 2018

(54) MIRNA FINGERPRINT IN THE DIAGNOSIS OF MULTIPLE SCLEROSIS

(71) Applicant: Comprehensive Biomarker Center GmbH, Heidelberg (DE)

(72) Inventors: Andreas Keller, Puettlingen (DE); Eckart Meese, Huetschenhausen (DE); Anne Borries, Heidelberg (DE); Peer Friedrich Staehler, Mannheim (DE); Markus Beier, Weinheim (DE)

(73) Assignee: Hummingbird Diagnostics GmbH, Heidelberg (DE)

(*) Notice: Subject to any disclaimer, the term of this patent is extended or adjusted under 35 U.S.C. 154(b) by 36 days.

This patent is subject to a terminal disclaimer.

(21) Appl. No.: 14/873,385

(22) Filed: Oct. 2, 2015

(65) Prior Publication Data

US 2016/0053325 A1 Feb. 25, 2016

Related U.S. Application Data

(62) Division of application No. 13/376,243, filed as application No. PCT/EP2010/057943 on Jun. 7, 2010, now Pat. No. 9,187,785.

(60) Provisional application No. 61/287,521, filed on Dec. 17, 2009, provisional application No. 61/213,971, filed on Aug. 3, 2009, provisional application No. 61/184,452, filed on Jun. 5, 2009.

(30) Foreign Application Priority Data

Dec. 17, 2009 (EP) ..................................... 09015668

(51) Int. Cl.
  *C12Q 1/68* (2018.01)
  *G06F 19/20* (2011.01)
  *G06F 19/24* (2011.01)

(52) U.S. Cl.
  CPC ......... *C12Q 1/6883* (2013.01); *C12Q 1/6809* (2013.01); *C12Q 1/6886* (2013.01); *G06F 19/20* (2013.01); *G06F 19/24* (2013.01); *C12Q 2600/106* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 9,187,785 B2 * 11/2015 Keller .................. C12Q 1/6809

OTHER PUBLICATIONS

Polman et al. "Diagnostic Criteria for Multiple Sclerosis: 2010 Revisions to the MCDonali Criteria", American Neurological Association. 2011, 69, pp. 292-302 (Year: 2011).*

* cited by examiner

*Primary Examiner* — James S Ketter
(74) *Attorney, Agent, or Firm* — MacMillan, Sobanski & Todd, LLC

(57) ABSTRACT

The present invention provides novel methods for diagnosing diseases based on the determination of specific miRNAs that have altered expression levels in disease states compared to healthy controls.

20 Claims, 73 Drawing Sheets

Fig 5

Figure 1:
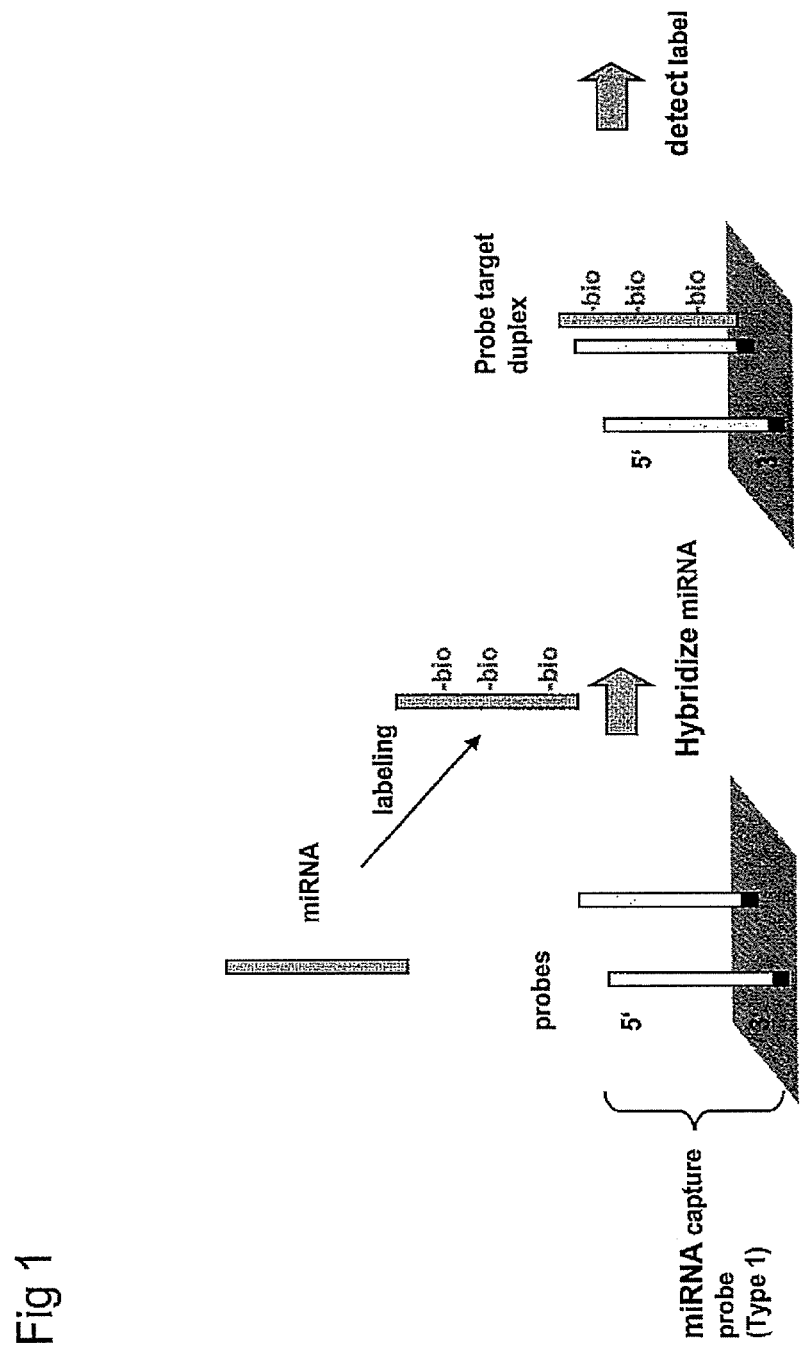

Example: human mature miRNA let-7a
ID: hsa-let-7a
Accession-Nr.: MIMAT0000062
Sequence: 5'-UGAGGUAGUAGGUUGUAUAGUU-3' (SEQ ID NO: 17)

miRNA capture probes :

■ Type 1 (miRNA Hybridization Assay)

surface-3'-ACTCCATCATCCAACATATCAA-5' (SEQ ID NO: 867)
surface-5'-AACTATACAACCTACTACCTCA-3' (SEQ ID NO: 868)

■ Type 2 (miRNA Tandem Hybridization Assay)

surface-3'-ACTCCATCATCCAACATATCAA-SP-ACTCCATCATCCAACATATCAA-5' (SEQ ID NO: 867)
surface-5'-AACTATACAACCTACTACCTCA-SP-AACTATACAACCTACTACCTCA-3' (SEQ ID NO: 868)

■ Type 3 (miRNA RAKE-Assay)

surface-5'-EL-AACTATACAACCTACTACCTCA-3' (SEQ ID NO: 868)

■ Type 4 (miRNA MPEA-Assay)

surface-3'-ACTCCATCATCCAACATATCAA-EL-5' (SEQ ID NO: 867)

Figure 6

Type 2 (miRNA Tandem Hybridization Assay)

surface-3'-ACTCCATCATCCAACATATCAA-SP-ACTCCATCATCCAACATATCAA-5'   (SEQ ID NO: 867)
surface-5'-AACTATACAACCTACCTCA-SP-AACTATACAACCTACCTCA-3'   (SEQ ID NO: 868)

With SP:

■ nucleotide sequence with n = 0 –12 nucleotides chosen on the basis of showing low complementarity to potential target sequences, therefore resulting in no to low degree of crosshybridisation to target mixture preferentially : n = 0, no spacer between the 2 miRNA probe sequence stretches

Fig 7

Type 3 (miRNA RAKE-Assay)

surface-5'-EL-AACTATACAACCTACTACCTCA-3'  (SEQ ID NO: 868)

Type 4 (miRNA MPEA-Assay)

surface-3'-ACTCCATCATCCAACATATCAA-EL-5'  (SEQ ID NO: 867)

With EL :

- nucleotide sequence with n = 0 – 30 nucleotides chosen on the basis of showing low complementarity to potential target sequences, therefore resulting in no to low degree of crosshybridisation to target mixture preferentially :      homomeric sequence stretch, $-N_n-$ with n = 1-30, N = A or C, or T, or G especially preferentially: homomeric sequence stretch, $-N_n-$ with n = 1-12, N = A or C, or T, or G surface-3'-EL-ACTCCATCATCATCCAACATATCAA-5' with EL = $N_0$......$N_{12}$ and N=T (elongation with bio-ATP)
(SEQ ID NO: 867)

FIG. 10A

| SEQ ID NO | miRNA | Sequence | median bg1 | median g2 | log median | raw pval | adj Pval | AUC |
|---|---|---|---|---|---|---|---|---|
| SEQ ID NO: 99 | hsa-miR-145 | gucaguuuuccaggaauccccu | 602,719 | 3,457 | 1,240 | 6,08E-12 | 5,25E-09 | 0,962 |
| SEQ ID NO: 313 | hsa-miR-186 | caagaauucccuuuuggcu | 265,295 | 77,719 | 1,228 | 7,91E-10 | 3,42E-07 | 0,961 |
| SEQ ID NO: 456 | hsa-miR-664 | uauucauuuauccccagccuaca | 707,168 | 285,703 | 0,906 | 4,17E-08 | 1,20E-05 | 0,916 |
| SEQ ID NO: 509 | hsa-miR-584 | uuaggUuugccuggacugag | 332,922 | 106,969 | 1,135 | 1,15E-07 | 1,98E-05 | 0,897 |
| SEQ ID NO: 11 | hsa-miR-20b | caaagugcuauagugcagguaa | 2689,207 | 5810,586 | -0,770 | 9,83E-08 | 1,98E-05 | 0,056 |
| SEQ ID NO: 51 | hsa-miR-223 | ugucaguuugucaauacccca | 5118,574 | 2579,250 | 0,685 | 1,49E-07 | 2,14E-05 | 0,964 |
| SEQ ID NO: 826 | hsa-miR-422a | acugacuuagggucagaaggc | 373,953 | 189,219 | 0,681 | 2,32E-07 | 2,87E-05 | 0,870 |
| SEQ ID NO: 667 | hsa-miR-142-3p | uguaguguuuccuacuuuuagga | 215,375 | 40,516 | 1,671 | 2,79E-07 | 3,01E-05 | 0,934 |
| SEQ ID NO: 15 | hsa-let-7c | ugagguaguagguuguauguuu | 1948,098 | 950,223 | 0,718 | 8,00E-07 | 7,68E-05 | 0,889 |
| SEQ ID NO: 196 | hsa-miR-151-3p | cuagacugaagcucugugg | 1021,363 | 571,344 | 0,581 | 1,81E-06 | 0 | 0,883 |
| SEQ ID NO: 690 | hsa-miR-491-5p | agugggaacccuuccaugagg | 241,000 | 153,563 | 0,451 | 2,05E-06 | 0 | 0,876 |
| SEQ ID NO: 505 | hsa-miR-942 | ucuucucuguuuugggccaugug | 112,969 | 38,094 | 1,087 | 5,09E-06 | 0 | 0,882 |
| SEQ ID NO: 60 | hsa-miR-361-3p | uccccaggugugauucugauuuu | 325,766 | 181,375 | 0,586 | 5,77E-06 | 0 | 0,852 |
| SEQ ID NO: 789 | hsa-miR-22* | aguucucagguggcaagcuuua | 178,938 | 103,844 | 0,544 | 6,24E-06 | 0 | 0,868 |
| SEQ ID NO: 165 | hsa-miR-140-5p | caguguuuuaccuauggguag | 105,063 | 48,250 | 0,778 | 7,99E-06 | 0 | 0,874 |
| SEQ ID NO: 635 | hsa-miR-216a | uaaucucagcuggcaacuguga | 202,219 | 315,828 | -0,446 | 8,24E-06 | 0 | 0,060 |
| SEQ ID NO: 495 | hsa-miR-1275 | gugggggagagcuguc | 210,203 | 116,969 | 0,586 | 7,04E-06 | 0 | 0,907 |
| SEQ ID NO: 465 | hsa-miR-367 | aauugcacuuuagcaaugguga | 92,500 | 160,375 | -0,550 | 8,32E-06 | 0 | 0,138 |
| SEQ ID NO: 800 | hsa-miR-146a | ugagaacugaauuccauggguu | 470,359 | 271,342 | 0,550 | 9,61E-06 | 0 | 0,862 |
| SEQ ID NO: 774 | hsa-miR-598 | uacgucaucuuguugucaucca | 140,531 | 91,000 | 0,435 | 1,29E-05 | 0 | 0,841 |
| SEQ ID NO: 523 | hsa-miR-613 | aggaaugUuccauucuuugcc | 60,781 | 19,000 | 1,163 | 1,67E-05 | 0 | 0,862 |
| SEQ ID NO: 23 | hsa-miR-18a* | acugcccuaagugcuccuucgg | 490,891 | 233,672 | 0,742 | 2,02E-05 | 0 | 0,876 |
| SEQ ID NO: 48 | hsa-miR-302b | uaagugcuuccauguuuuaguag | 54,469 | 21,406 | 0,934 | 2,23E-05 | 0 | 0,855 |
| SEQ ID NO: 748 | hsa-miR-501-5p | aaucuuugucccuggugaga | 139,938 | 79,563 | 0,565 | 2,60E-05 | 0 | 0,866 |
| SEQ ID NO: 50 | hsa-miR-30e | uguaaacauccuugacuggaag | 687,488 | 383,609 | 0,583 | 3,66E-05 | 0 | 0,836 |
| SEQ ID NO: 320 | hsa-miR-891a | ugcacgaaccugagccacuga | 134,250 | 177,000 | -0,276 | 4,27E-05 | 0 | 0,153 |
| SEQ ID NO: 823 | hsa-miR-92b* | agggacggacgcggugcagug | 400,766 | 179,266 | 0,805 | 4,65E-05 | 0 | 0,926 |
| SEQ ID NO: 232 | hsa-miR-362-5p | aaucuugguaaccuuaggugagu | 353,859 | 211,313 | 0,516 | 5,35E-05 | 0 | 0,830 |
| SEQ ID NO: 778 | hsa-miR-1301 | uugcagcugccuggagugacgcc | 240,098 | 340,063 | -0,348 | 5,65E-05 | 0 | 0,149 |
| SEQ ID NO: 602 | hsa-miR-212 | uaacagucuccagucacggcc | 62,594 | 93,656 | -0,403 | 6,35E-05 | 0 | 0,166 |
| SEQ ID NO: 135 | hsa-miR-221* | accuggcauacaaugaaguuu | 127,688 | 203,438 | -0,466 | 7,85E-05 | 0 | 0,162 |

FIG. 10A (Continued)

| SEQ ID NO | miRNA | sequence | mediang1 | mediang2 | fcmedian | logfcmedian | raw.P.val | adj.P.val | AUC |
|---|---|---|---|---|---|---|---|---|---|
| SEQ ID NO: 482 | hsa-miR-559 | uaaaguaaauaugcaccaaaa | 81,875 | 128,203 | 0,639 | -0,448 | 7,87E-05 | 0 | 0,151 |
| SEQ ID NO: 594 | hsa-miR-185* | agggcuggcuuucucugguc | 70,391 | 28,922 | 2,434 | 0,889 | 8,45E-05 | 0 | 0,866 |
| SEQ ID NO: 84 | hsa-miR-1272 | gaugaugauggcagcaaauucugaaa | 163,438 | 234,672 | 0,696 | -0,362 | 8,43E-05 | 0 | 0,131 |
| SEQ ID NO: 443 | hsa-miR-30a | uguaaacauccucgacuggaag | 747,559 | 472,016 | 1,584 | 0,460 | 9,38E-05 | 0 | 0,778 |
| SEQ ID NO: 687 | hsa-miR-1909 | cgcaggggcggugugcucaccg | 238,063 | 181,375 | 1,313 | 0,272 | 9,16E-05 | 0 | 0,843 |
| SEQ ID NO: 404 | hsa-miR-513b | uucacaaggaggugucauuuau | 60,063 | 95,219 | 0,631 | -0,461 | 0 | 0 | 0,155 |
| SEQ ID NO: 365 | hsa-miR-556-5p | gaugagcucauuguauaugag | 163,469 | 242,703 | 0,674 | -0,395 | 0 | 0 | 0,165 |
| SEQ ID NO: 552 | hsa-miR-365 | uaaugcccuaaaaauccuuau | 231,453 | 132,344 | 1,749 | 0,559 | 0 | 0 | 0,841 |
| SEQ ID NO: 379 | hsa-miR-525-5p | cuccagagggaugcacuuucu | 139,281 | 172,344 | 0,808 | -0,213 | 0 | 0 | 0,178 |
| SEQ ID NO: 814 | hsa-miR-675 | ugguggagagagggccacagug | 372,719 | 257,121 | 1,450 | 0,371 | 0 | 0 | 0,785 |
| SEQ ID NO: 455 | hsa-miR-1251 | acucuagcugcaaaggcgcu | 189,469 | 250,242 | 0,757 | -0,278 | 0 | 0 | 0,192 |
| SEQ ID NO: 632 | hsa-miR-574-3p | cacgcucaugcacacacccaca | 1063,672 | 2186,746 | 0,486 | -0,721 | 0 | 0 | 0,163 |
| SEQ ID NO: 250 | hsa-miR-499-3p | aacaucacagcaagucugugcu | 135,750 | 187,219 | 0,725 | -0,321 | 0 | 0 | 0,138 |
| SEQ ID NO: 819 | hsa-miR-1180 | uuuccggcucgcguggugugu | 186,969 | 99,344 | 1,882 | 0,632 | 0 | 0 | 0,820 |
| SEQ ID NO: 75 | hsa-miR-199a-5p | cccaguguucagacuaccuuuc | 655,146 | 394,469 | 1,661 | 0,507 | 0 | 0 | 0,809 |
| SEQ ID NO: 299 | hsa-miR-491-3p | cuuagucaagauucccucuac | 126,578 | 172,438 | 0,734 | -0,309 | 0 | 0 | 0,175 |
| SEQ ID NO: 409 | hsa-miR-29c | uagcaccauugaaaucgguua | 953,881 | 628,578 | 1,518 | 0,417 | 0 | 0 | 0,782 |
| SEQ ID NO: 641 | hsa-miR-330-3p | gcaaagcacacgccugcagaga | 344,703 | 594,125 | 0,580 | -0,544 | 0 | 0 | 0,120 |
| SEQ ID NO: 854 | hsa-miR-625 | agggggaaaguucuauagucc | 293,266 | 129,938 | 2,257 | 0,814 | 0 | 0 | 0,804 |
| SEQ ID NO: 734 | hsa-miR-17* | acugcaguagaggcacuuguag | 877,000 | 1154,039 | 0,760 | -0,275 | 0 | 0 | 0,169 |
| SEQ ID NO: 74 | hsa-let-7d* | cuauacgaccugcugccuuucu | 148,656 | 93,813 | 1,585 | 0,460 | 0 | 0 | 0,801 |
| SEQ ID NO: 398 | hsa-miR-96* | aaucaugugcagugccaauaug | 239,391 | 340,422 | 0,703 | -0,352 | 0 | 0 | 0,188 |
| SEQ ID NO: 806 | hsa-miR-125a-5p | ucccugacccuuuaaccuguga | 523,871 | 251,680 | 2,081 | 0,733 | 0 | 0 | 0,808 |
| SEQ ID NO: 817 | hsa-miR-130b* | acucuuucccugugcacuac | 84,156 | 35,969 | 2,340 | 0,850 | 0 | 0 | 0,850 |
| SEQ ID NO: 644 | hsa-miR-214 | acagcaggcacagacaggcagu | 337,141 | 526,555 | 0,640 | -0,446 | 0 | 0,01 | 0,213 |
| SEQ ID NO: 31 | hsa-miR-19b | ugugcaaauccaugcaaaacuga | 12385,297 | 10067,539 | 1,230 | 0,207 | 0 | 0,01 | 0,817 |
| SEQ ID NO: 688 | hsa-miR-629 | uggguuuacguugggagaacu | 333,625 | 60,813 | 5,486 | 1,702 | 0 | 0,01 | 0,824 |
| SEQ ID NO: 280 | hsa-miR-875-5p | uauaccucagauuuuauucagguu | 45,844 | 85,094 | 0,539 | -0,619 | 0 | 0,01 | 0,198 |
| SEQ ID NO: 107 | hsa-miR-107 | agcagcauuguacagggcuauca | 1014,779 | 2342,613 | 0,433 | -0,837 | 0 | 0,01 | 0,148 |
| SEQ ID NO: 185 | hsa-miR-208b | auaagacgaacaaaagguuugu | 106,625 | 155,875 | 0,684 | -0,380 | 0 | 0,01 | 0,205 |
| SEQ ID NO: 528 | hsa-miR-20a* | acugcauuaugagcacuuaaag | 203,156 | 264,654 | 0,768 | -0,264 | 0 | 0,01 | 0,134 |

FIG. 10A (Continued)

| SEQ ID NO | miRNA | Sequence | median ctrl | median p | qmedian | logqmedian | raw Pval | adj Pval | AUC |
|---|---|---|---|---|---|---|---|---|---|
| SEQ ID NO: 344 | hsa-miR-181b | aacauucaugcugucgguggu | 131,875 | 77,641 | 1,699 | 0,530 | 0 | 0,01 | 0,807 |
| SEQ ID NO: 491 | hsa-miR-7 | uggaagacuagugauuuuguugu | 221,484 | 80,875 | 2,739 | 1,007 | 0 | 0,01 | 0,851 |
| SEQ ID NO: 671 | hsa-miR-1908 | cggcggggacggcgauugguc | 2635,699 | 1175,980 | 2,241 | 0,807 | 0 | 0,01 | 0,815 |
| SEQ ID NO: 584 | hsa-miR-92a-2* | gggugggauuuuguugcauuac | 52,438 | 28,000 | 1,873 | 0,627 | 0 | 0,01 | 0,786 |
| SEQ ID NO: 753 | hsa-miR-106b | uaaagugcugacagugcagau | 13747,000 | 18271,367 | 0,752 | -0,285 | 0 | 0,01 | 0,207 |
| SEQ ID NO: 433 | hsa-miR-765 | uggaggagaggaagugaug | 144,219 | 90,422 | 1,595 | 0,467 | 0 | 0,01 | 0,784 |
| SEQ ID NO: 547 | hsa-miR-148a | ucagugcacuacagaacuugu | 845,109 | 1094,980 | 0,772 | -0,259 | 0 | 0,01 | 0,188 |
| SEQ ID NO: 463 | hsa-miR-367* | acuguugcuaauaugcaacucu | 99,219 | 160,594 | 0,618 | -0,482 | 0 | 0,01 | 0,194 |
| SEQ ID NO: 513 | hsa-miR-580 | uugagaaugaugaauacauuagg | 79,594 | 101,000 | 0,788 | -0,238 | 0 | 0,01 | 0,201 |
| SEQ ID NO: 274 | hsa-miR-452* | cucaucugcaagaagaaguaagug | 402,109 | 803,891 | 0,500 | -0,693 | 0 | 0,01 | 0,104 |
| SEQ ID NO: 560 | hsa-miR-103 | agcagcauugguacagggcuauga | 4825,438 | 9424,113 | 0,512 | -0,669 | 0 | 0,01 | 0,201 |
| SEQ ID NO: 151 | hsa-miR-607 | guucaaauaccagaucuauaac | 128,625 | 179,688 | 0,716 | -0,334 | 0 | 0,01 | 0,211 |
| SEQ ID NO: 34 | hsa-miR-188-3p | cucccacaucagggunugca | 206,469 | 259,949 | 0,794 | -0,230 | 0 | 0,01 | 0,217 |
| SEQ ID NO: 501 | hsa-miR-621 | ggcuagcaacagcgcuuaccu | 371,266 | 644,535 | 0,576 | -0,552 | 0 | 0,01 | 0,178 |
| SEQ ID NO: 277 | hsa-miR-92b | uauugcacugucccggcgcucc | 492,328 | 353,859 | 1,391 | 0,330 | 0 | 0,01 | 0,789 |
| SEQ ID NO: 498 | hsa-miR-136* | caucaucugucuccaaaugaguc | 100,875 | 145,625 | 0,693 | -0,367 | 0 | 0,01 | 0,190 |
| SEQ ID NO: 228 | hsa-miR-606 | aaacuacugacaaaaucaaagau | 121,578 | 182,750 | 0,665 | -0,408 | 0 | 0,01 | 0,197 |
| SEQ ID NO: 134 | hsa-miR-378* | cucugacuccaggucccugugu | 133,844 | 81,859 | 1,635 | 0,492 | 0 | 0,01 | 0,772 |
| SEQ ID NO: 13 | hsa-miR-195 | uagcagcacagaaauauuggc | 665,008 | 917,941 | 0,724 | -0,322 | 0 | 0,01 | 0,211 |
| SEQ ID NO: 494 | hsa-miR-380* | ugguugaccauagaacaugggc | 139,844 | 180,094 | 0,777 | -0,253 | 0 | 0,01 | 0,227 |
| SEQ ID NO: 558 | hsa-miR-183* | gugaauuaccgaagggccauaa | 237,781 | 164,250 | 1,448 | 0,370 | 0 | 0,01 | 0,787 |
| SEQ ID NO: 358 | hsa-miR-24 | uggcucagucaggaacag | 1714,877 | 2633,414 | 0,651 | -0,429 | 0 | 0,01 | 0,106 |
| SEQ ID NO: 137 | hsa-miR-593* | aggcaccagcaggcauugcucagc | 338,547 | 495,953 | 0,683 | -0,382 | 0 | 0,01 | 0,208 |
| SEQ ID NO: 347 | hsa-miR-9* | auaaagcuagauaaccgaaagu | 140,594 | 182,406 | 0,771 | -0,260 | 0 | 0,01 | 0,219 |
| SEQ ID NO: 259 | hsa-miR-646 | aagcagcugccugcucugagc | 316,328 | 489,273 | 0,647 | -0,436 | 0 | 0,01 | 0,176 |
| SEQ ID NO: 703 | hsa-miR-1227 | cguggccaccuuuuccccag | 157,438 | 105,266 | 1,496 | 0,403 | 0 | 0,01 | 0,752 |
| SEQ ID NO: 798 | hsa-miR-302c* | uuuaacauggggguaccugcug | 50,688 | 69,000 | 0,735 | -0,308 | 0 | 0,01 | 0,259 |
| SEQ ID NO: 457 | hsa-miR-488* | cccagauaauggcacucucaa | 126,141 | 151,813 | 0,831 | -0,185 | 0 | 0,01 | 0,248 |
| SEQ ID NO: 805 | hsa-miR-622 | acagucugcugagguuggagc | 120,484 | 159,359 | 0,756 | -0,280 | 0 | 0,01 | 0,229 |
| SEQ ID NO: 260 | hsa-miR-655 | auaauacauggunaaccucuuu | 71,547 | 116,313 | 0,615 | -0,486 | 0 | 0,01 | 0,231 |
| SEQ ID NO: 49 | hsa-miR-106a | aaaagugcuuacagugcagguag | 9424,113 | 12784,891 | 0,737 | -0,305 | 0 | 0,01 | 0,179 |

FIG. 10A (Continued)

| SEQ ID NO | miRNA | Sequence | median g1 | median g2 | median g2/median g1 | log2-median g2/median g1 | raw p val | adj p val | AUC |
|---|---|---|---|---|---|---|---|---|---|
| SEQ ID NO: 607 | hsa-miR-628-3p | ucuaguaagaguggcagucga | 313,141 | 198,219 | 1,580 | 0,457 | 0 | 0,01 | 0,777 |
| SEQ ID NO: 526 | hsa-miR-500 | uaauccuugcuaccuggugaga | 619,078 | 427,422 | 1,448 | 0,370 | 0 | 0,01 | 0,760 |
| SEQ ID NO: 9 | hsa-miR-574-5p | ugagugugugugugugaguguguu | 787,578 | 1535,777 | 0,513 | -0,668 | 0 | 0,01 | 0,145 |
| SEQ ID NO: 176 | hsa-miR-568 | auguauaaauguauacacac | 140,906 | 201,219 | 0,700 | -0,356 | 0 | 0,01 | 0,264 |
| SEQ ID NO: 511 | hsa-miR-1254 | agccuggaagcuggaggcugcagu | 197,250 | 227,516 | 0,867 | -0,143 | 0 | 0,01 | 0,231 |
| SEQ ID NO: 363 | hsa-miR-509-3-5p | uacugcagacgugguggcaaucaug | 310,703 | 512,930 | 0,606 | -0,501 | 0 | 0,01 | 0,211 |
| SEQ ID NO: 659 | hsa-miR-519e* | uucuccaaaaggaggcacuuuc | 76,375 | 122,406 | 0,624 | -0,472 | 0 | 0,01 | 0,244 |
| SEQ ID NO: 243 | hsa-miR-493* | uuguacaugguaggcuuucauu | 63,047 | 96,094 | 0,656 | -0,421 | 0 | 0,01 | 0,217 |
| SEQ ID NO: 790 | hsa-miR-1234 | ucggccugaccacccaccccac | 367,734 | 558,242 | 0,659 | -0,417 | 0 | 0,02 | 0,248 |
| SEQ ID NO: 156 | hsa-miR-29b | uagcaccauuugaaaucaguguu | 632,156 | 416,641 | 1,517 | 0,417 | 0 | 0,02 | 0,815 |
| SEQ ID NO: 269 | hsa-miR-1280 | ucccaccgcugccaccc | 5556,648 | 3055,430 | 1,819 | 0,598 | 0 | 0,02 | 0,763 |
| SEQ ID NO: 87 | hsa-miR-497 | cagcagcacacugugguuugu | 225,906 | 277,840 | 0,813 | -0,207 | 0 | 0,02 | 0,196 |
| SEQ ID NO: 172 | hsa-miR-216b | aaaucucugcaggcaaauguga | 198,953 | 303,781 | 0,655 | -0,423 | 0 | 0,02 | 0,217 |
| SEQ ID NO: 53 | hsa-let-7b | ugagguaguagguugugugguu | 3354,297 | 1788,242 | 1,876 | 0,629 | 0 | 0,02 | 0,787 |
| SEQ ID NO: 129 | hsa-miR-182 | uuuggcaaugguaaaacucacacu | 2951,227 | 4465,605 | 0,661 | -0,414 | 0 | 0,02 | 0,237 |
| SEQ ID NO: 768 | hsa-miR-221 | agcuacauugucugcuggguuuc | 272,467 | 170,750 | 1,596 | 0,467 | 0 | 0,02 | 0,777 |
| SEQ ID NO: 630 | hsa-miR-1271 | cuuggcaccuagcaagcacuca | 321,375 | 392,281 | 0,819 | -0,199 | 0 | 0,02 | 0,286 |
| SEQ ID NO: 90 | hsa-miR-1 | uggaauguaaagaaguauguau | 45,531 | 75,875 | 0,600 | -0,511 | 0 | 0,02 | 0,247 |
| SEQ ID NO: 726 | hsa-miR-601 | uggucuaggauuguuggaggag | 75,625 | 28,781 | 2,628 | 0,966 | 0 | 0,02 | 0,770 |
| SEQ ID NO: 856 | hsa-miR-181a-2* | accacugaccguugacuguacc | 196,656 | 131,906 | 1,491 | 0,399 | 0 | 0,02 | 0,776 |
| SEQ ID NO: 385 | hsa-miR-1300 | uugagaaggagcugcug | 65,344 | 99,547 | 0,656 | -0,421 | 0 | 0,02 | 0,273 |
| SEQ ID NO: 522 | hsa-miR-27a* | agggcuuagcugcuugugagca | 81,188 | 104,938 | 0,774 | -0,257 | 0 | 0,02 | 0,256 |
| SEQ ID NO: 177 | hsa-miR-648 | aagugugcagggcacuggu | 75,516 | 115,859 | 0,652 | -0,428 | 0 | 0,02 | 0,233 |
| SEQ ID NO: 28 | hsa-miR-29a | uagcaccaucugaaaucgguua | 1010,279 | 828,117 | 1,220 | 0,199 | 0 | 0,02 | 0,723 |
| SEQ ID NO: 85 | hsa-miR-1299 | uucuggaauucugugugaggga | 64,531 | 44,328 | 1,456 | 0,376 | 0 | 0,02 | 0,763 |
| SEQ ID NO: 119 | hsa-miR-1302 | uugggacaucauuauugcuaaa | 69,438 | 92,766 | 0,749 | -0,290 | 0 | 0,02 | 0,263 |
| SEQ ID NO: 155 | hsa-miR-939 | uggggagcugaggcucgggggug | 177,156 | 93,703 | 1,891 | 0,637 | 0 | 0,02 | 0,833 |
| SEQ ID NO: 22 | hsa-miR-1283 | ucuacaaaggaaagcguuucu | 161,094 | 193,188 | 0,834 | -0,182 | 0 | 0,02 | 0,217 |
| SEQ ID NO: 124 | hsa-miR-1247 | acccgucccguuccuccccgga | 143,000 | 107,500 | 1,330 | 0,285 | 0 | 0,02 | 0,773 |
| SEQ ID NO: 286 | hsa-miR-489 | gugacaucacauauacgcagc | 234,453 | 368,422 | 0,636 | -0,452 | 0 | 0,02 | 0,282 |
| SEQ ID NO: 169 | hsa-miR-1912 | uaccagagcaugcagugugaa | 229,156 | 285,344 | 0,803 | -0,219 | 0 | 0,02 | 0,180 |

FIG. 10A (Continued)

| SEQ ID NO | miRNA | Sequence | median_g1 | median_g2 | median | logmedian | rawpval | adj.pval | AUC |
|---|---|---|---|---|---|---|---|---|---|
| SEQ ID NO: 389 | hsa-miR-32* | caauuuagugugugugauauu | 49,938 | 81,938 | 0,609 | -0,495 | 0 | 0,02 | 0,219 |
| SEQ ID NO: 45 | hsa-miR-20a | uaaagugcuuauagugcagguag | 5322,336 | 7318,813 | 0,727 | -0,319 | 0 | 0,02 | 0,274 |
| SEQ ID NO: 446 | hsa-miR-1225-5p | guggguacggccagugugggg | 172,766 | 117,938 | 1,465 | 0,382 | 0 | 0,02 | 0,762 |
| SEQ ID NO: 239 | hsa-miR-342-5p | aggggugcuaucuugauuga | 249,848 | 170,625 | 1,464 | 0,381 | 0 | 0,02 | 0,740 |
| SEQ ID NO: 33 | hsa-miR-126* | cauuauuacuuuuggcuacg | 78,438 | 40,438 | 1,940 | 0,663 | 0 | 0,02 | 0,723 |
| SEQ ID NO: 485 | hsa-miR-30e* | cuuucagucgauguuuacagc | 152,438 | 107,422 | 1,419 | 0,350 | 0 | 0,02 | 0,731 |
| SEQ ID NO: 698 | hsa-miR-744 | ugcgggcuagggcuaacgca | 866,453 | 1256,912 | 0,689 | -0,372 | 0 | 0,02 | 0,240 |
| SEQ ID NO: 719 | hsa-miR-328 | cuggcccucucugcccuuccgu | 203,172 | 86,063 | 2,361 | 0,859 | 0 | 0,02 | 0,752 |
| SEQ ID NO: 813 | hsa-miR-362-3p | aacacacuuaucaggauuca | 446,391 | 279,703 | 1,596 | 0,467 | 0 | 0,02 | 0,773 |
| SEQ ID NO: 620 | hsa-let-7i* | cugcgaagcuacugccuugcu | 303,922 | 408,766 | 0,744 | -0,296 | 0 | 0,02 | 0,219 |
| SEQ ID NO: 383 | hsa-miR-548a-5p | aaaguaauugcgauuuuacc | 49,938 | 68,469 | 0,729 | -0,316 | 0 | 0,02 | 0,286 |
| SEQ ID NO: 390 | hsa-miR-33a | gugcauuguaguugcauugca | 168,473 | 215,250 | 0,783 | -0,245 | 0 | 0,02 | 0,276 |
| SEQ ID NO: 304 | hsa-miR-132* | accggcuuucgauuguacu | 34,641 | 18,875 | 1,835 | 0,607 | 0 | 0,02 | 0,739 |
| SEQ ID NO: 483 | hsa-miR-217 | uacugcaucaggaacugauugga | 217,813 | 299,188 | 0,728 | -0,317 | 0 | 0,02 | 0,244 |
| SEQ ID NO: 512 | hsa-miR-1207-5p | ugcagggaggcuggaggg | 1108,230 | 462,172 | 2,398 | 0,875 | 0 | 0,02 | 0,816 |
| SEQ ID NO: 449 | hsa-miR-570 | cgaaaacagcaauuaccuuugc | 125,156 | 159,594 | 0,784 | -0,243 | 0 | 0,02 | 0,242 |
| SEQ ID NO: 217 | hsa-miR-31* | ugcuaugccaacauaaugccau | 231,188 | 305,781 | 0,756 | -0,280 | 0 | 0,02 | 0,220 |
| SEQ ID NO: 71 | hsa-miR-503 | uagcagcgggaacaguucugag | 396,297 | 524,176 | 0,756 | -0,280 | 0 | 0,02 | 0,290 |
| SEQ ID NO: 611 | hsa-miR-1295 | uuaggccgcagaucucggguga | 141,672 | 177,688 | 0,797 | -0,227 | 0 | 0,02 | 0,284 |
| SEQ ID NO: 130 | hsa-miR-658 | ggcggagguaaguaggccguuggu | 123,781 | 71,375 | 1,734 | 0,551 | 0 | 0,02 | 0,787 |
| SEQ ID NO: 559 | hsa-miR-148b | ucagugcaucacagacacuugu | 765,852 | 953,881 | 0,803 | -0,220 | 0 | 0,02 | 0,290 |
| SEQ ID NO: 624 | hsa-miR-1226 | ucaccagccgcauuuuagcaaguuc | 157,594 | 120,781 | 1,305 | 0,266 | 0 | 0,03 | 0,759 |
| SEQ ID NO: 651 | hsa-miR-544 | auucugcauuuuagcaaguuc | 76,313 | 100,797 | 0,757 | -0,278 | 0 | 0,03 | 0,288 |
| SEQ ID NO: 619 | hsa-miR-885-3p | aggcagcgggugauguggaua | 398,484 | 226,844 | 1,757 | 0,563 | 0 | 0,03 | 0,781 |
| SEQ ID NO: 697 | hsa-miR-25* | aggcggagacuuggcaaug | 140,594 | 101,172 | 1,390 | 0,329 | 0 | 0,03 | 0,739 |
| SEQ ID NO: 272 | hsa-miR-934 | ugucuacucggagacacugg | 136,563 | 175,625 | 0,778 | -0,252 | 0 | 0,03 | 0,258 |
| SEQ ID NO: 799 | hsa-miR-99a | aaccguagauccgaucuugug | 271,453 | 160,375 | 1,693 | 0,526 | 0 | 0,03 | 0,750 |
| SEQ ID NO: 780 | hsa-miR-564 | aggcacggugucagcaggc | 217,969 | 275,764 | 0,790 | -0,235 | 0 | 0,03 | 0,228 |
| SEQ ID NO: 149 | hsa-miR-647 | guggcugcaccucuccuuc | 94,328 | 126,563 | 0,745 | -0,294 | 0 | 0,03 | 0,264 |
| SEQ ID NO: 42 | hsa-miR-29c* | ugaccgauuucucucugguguuc | 67,047 | 30,250 | 2,216 | 0,796 | 0,01 | 0,03 | 0,736 |
| SEQ ID NO: 410 | hsa-miR-1268 | cggggcugugugguggggg | 612,344 | 259,070 | 2,364 | 0,860 | 0,01 | 0,03 | 0,802 |

FIG. 10A (Continued)

| SEQ ID NO | miRNA | Sequence | median1 | median2 | qmedian | logmedian | rawP.val | adj.P.val | AUC |
|---|---|---|---|---|---|---|---|---|---|
| SEQ ID NO: 418 | hsa-miR-410 | aauauaaacacagauggccugu | 144,219 | 208,125 | 0,693 | -0,367 | 0,01 | 0,03 | 0,321 |
| SEQ ID NO: 303 | hsa-miR-1286 | ugcaggaccaagaugagcccu | 179,094 | 220,125 | 0,814 | -0,206 | 0,01 | 0,03 | 0,260 |
| SEQ ID NO: 44 | hsa-miR-34c-3p | aaucacuaaccacacggccagg | 139,688 | 203,875 | 0,685 | -0,378 | 0,01 | 0,03 | 0,231 |
| SEQ ID NO: 372 | hsa-miR-924 | agagucuugugaugucuugc | 49,156 | 64,219 | 0,765 | -0,267 | 0,01 | 0,03 | 0,275 |
| SEQ ID NO: 377 | hsa-miR-1206 | uguucaugaugauguuuaagc | 77,203 | 112,313 | 0,687 | -0,375 | 0,01 | 0,03 | 0,283 |
| SEQ ID NO: 835 | hsa-miR-450b-5p | uuuugcaauauguuuccugaaua | 102,906 | 129,094 | 0,797 | -0,227 | 0,01 | 0,03 | 0,293 |
| SEQ ID NO: 97 | hsa-miR-331-3p | gccccugggccuaucccuagaa | 1699,277 | 1162,813 | 1,461 | 0,379 | 0,01 | 0,03 | 0,742 |
| SEQ ID NO: 18 | hsa-let-7g | ugagguaguaguuuguacaguu | 1372,621 | 629,172 | 2,182 | 0,780 | 0,01 | 0,03 | 0,713 |
| SEQ ID NO: 723 | hsa-miR-1469 | cuaggcgggggcgcgggcucc | 340,547 | 253,742 | 1,342 | 0,294 | 0,01 | 0,03 | 0,730 |
| SEQ ID NO: 159 | hsa-miR-1224-5p | gugcaggacucggggcgagugg | 90,781 | 63,625 | 1,427 | 0,355 | 0,01 | 0,03 | 0,750 |
| SEQ ID NO: 541 | hsa-miR-487a | aaucauacaggacauccaguu | 121,688 | 149,875 | 0,812 | -0,208 | 0,01 | 0,03 | 0,285 |
| SEQ ID NO: 337 | hsa-miR-27b* | agagcuuagucugauuggugaac | 95,797 | 122,969 | 0,779 | -0,250 | 0,01 | 0,03 | 0,278 |
| SEQ ID NO: 141 | hsa-miR-1266 | ccucagggcuguagaacagggcu | 167,875 | 203,188 | 0,826 | -0,191 | 0,01 | 0,03 | 0,244 |
| SEQ ID NO: 467 | hsa-miR-767-5p | ugcaccauguugucugcgaug | 280,109 | 355,078 | 0,789 | -0,237 | 0,01 | 0,03 | 0,300 |
| SEQ ID NO: 202 | hsa-miR-508-5p | uacuccagagggcgucacucaug | 178,969 | 223,578 | 0,800 | -0,223 | 0,01 | 0,03 | 0,207 |
| SEQ ID NO: 779 | hsa-miR-515-5p | uucuccaaaagaaagcacuuucug | 287,500 | 336,016 | 0,856 | -0,156 | 0,01 | 0,04 | 0,339 |
| SEQ ID NO: 737 | hsa-miR-766 | acuccagcccacacagccucagc | 344,594 | 425,313 | 0,810 | -0,210 | 0,01 | 0,04 | 0,352 |
| SEQ ID NO: 140 | hsa-miR-143* | ggugcagugcugcaucucuggu | 175,281 | 219,938 | 0,797 | -0,227 | 0,01 | 0,04 | 0,246 |
| SEQ ID NO: 417 | hsa-miR-34a | uggcagugucuuagcugguugu | 87,906 | 67,344 | 1,305 | 0,266 | 0,01 | 0,04 | 0,714 |
| SEQ ID NO: 233 | hsa-miR-671-5p | aggaagcccugggaggcugag | 89,844 | 122,172 | 0,735 | -0,307 | 0,01 | 0,04 | 0,272 |
| SEQ ID NO: 133 | hsa-miR-30d | uguaaacauccccgacuggaag | 7669,605 | 6061,430 | 1,265 | 0,235 | 0,01 | 0,04 | 0,742 |
| SEQ ID NO: 378 | hsa-miR-1259 | auauaugaugacuuuagcuuu | 66,750 | 108,078 | 0,618 | -0,482 | 0,01 | 0,04 | 0,300 |
| SEQ ID NO: 100 | hsa-miR-17 | caaagugcuuacagugcagguag | 7669,605 | 9717,992 | 0,789 | -0,237 | 0,01 | 0,04 | 0,238 |
| SEQ ID NO: 438 | hsa-miR-202* | uuccuaugcauauauccucuug | 149,938 | 184,391 | 0,813 | -0,207 | 0,01 | 0,04 | 0,281 |
| SEQ ID NO: 333 | hsa-miR-376b | aucauagaggaaaauccaugu | 111,844 | 147,391 | 0,759 | -0,276 | 0,01 | 0,04 | 0,281 |
| SEQ ID NO: 63 | hsa-miR-1200 | cuccugagccauucugagccuc | 109,484 | 137,188 | 0,798 | -0,226 | 0,01 | 0,04 | 0,273 |
| SEQ ID NO: 677 | hsa-miR-193a-5p | uggguuugugcgggcgagauga | 212,063 | 133,875 | 1,584 | 0,460 | 0,01 | 0,04 | 0,717 |
| SEQ ID NO: 425 | hsa-miR-502-5p | auccuugcuaucggggugcua | 74,844 | 61,797 | 1,211 | 0,192 | 0,01 | 0,04 | 0,692 |
| SEQ ID NO: 649 | hsa-miR-1202 | gugccagucugcagugggggag | 302,703 | 341,125 | 0,887 | -0,119 | 0,01 | 0,05 | 0,302 |
| SEQ ID NO: 279 | hsa-miR-548a-3p | caaaacuggcaauuacuuuugc | 140,906 | 172,438 | 0,817 | -0,202 | 0,01 | 0,05 | 0,295 |
| SEQ ID NO: 35 | hsa-miR-624* | uaguaccaguagccuuguuuca | 128,406 | 78,219 | 1,642 | 0,496 | 0,01 | 0,05 | 0,727 |

FIG. 10A (Continued)

| SEQ ID NO | miRNA | Sequence | median g1 | median g2 | median ratio | log median | raw p-val | adj p-val | AUC |
|---|---|---|---|---|---|---|---|---|---|
| SEQ ID NO: 733 | hsa-miR-1229 | cucuccaccugcccuccacag | 257,025 | 296,609 | 0,867 | -0,143 | 0,01 | 0,05 | 0,314 |
| SEQ ID NO: 708 | hsa-miR-345 | gcugacucccuagucccaggcuc | 236,219 | 170,219 | 1,388 | 0,328 | 0,01 | 0,05 | 0,756 |
| SEQ ID NO: 844 | hsa-miR-1258 | aguuaggauuaggucuggaa | 30,281 | 8,844 | 3,424 | 1,231 | 0,01 | 0,05 | 0,764 |
| SEQ ID NO: 772 | hsa-miR-1233 | ugagcccuguccuccgag | 157,844 | 188,094 | 0,839 | -0,175 | 0,01 | 0,05 | 0,284 |
| SEQ ID NO: 419 | hsa-miR-33a* | caauguuuccacagugcaucac | 119,406 | 157,250 | 0,759 | -0,275 | 0,01 | 0,05 | 0,260 |
| SEQ ID NO: 760 | hsa-miR-139-5p | ucuacagugcacgugucuccag | 264,902 | 292,906 | 0,904 | -0,100 | 0,01 | 0,05 | 0,372 |
| SEQ ID NO: 637 | hsa-miR-23a* | ggggucccugggauggauuu | 42,266 | 30,781 | 1,373 | 0,317 | 0,01 | 0,05 | 0,696 |
| SEQ ID NO: 747 | hsa-miR-138-1* | gcuacuucacaacaccaggcc | 134,531 | 176,594 | 0,762 | -0,272 | 0,01 | 0,05 | 0,290 |
| SEQ ID NO: 586 | hsa-miR-589 | ugagaaccacgucugucucgag | 169,391 | 138,328 | 1,225 | 0,203 | 0,01 | 0,05 | 0,727 |
| SEQ ID NO: 192 | hsa-miR-24-2* | ugccuacugagcugaaacacag | 257,307 | 353,156 | 0,729 | -0,317 | 0,01 | 0,05 | 0,378 |
| SEQ ID NO: 201 | hsa-miR-144 | uacaguauagaugauuaacu | 2998,320 | 4285,270 | 0,700 | -0,357 | 0,01 | 0,05 | 0,274 |
| SEQ ID NO: 293 | hsa-miR-192* | cugcaauuucauaaggucacag | 179,625 | 194,063 | 0,926 | -0,077 | 0,01 | 0,05 | 0,329 |
| SEQ ID NO: 756 | hsa-miR-187* | ggcuacaacaggaccggc | 213,625 | 276,512 | 0,773 | -0,258 | 0,01 | 0,05 | 0,288 |
| SEQ ID NO: 633 | hsa-miR-1282 | ucguuugccuuuucugcuu | 36,625 | 6,625 | 5,528 | 1,710 | 0,01 | 0,05 | 0,721 |
| SEQ ID NO: 218 | hsa-miR-33b* | caguguccuggcaguagcagcc | 205,578 | 259,232 | 0,793 | -0,232 | 0,01 | 0,06 | 0,254 |
| SEQ ID NO: 123 | hsa-miR-603 | cacacacaauuacauuugc | 207,906 | 288,641 | 0,720 | -0,328 | 0,01 | 0,06 | 0,284 |
| SEQ ID NO: 593 | hsa-miR-548p | uagcaaaaacugcaguuacuu | 214,156 | 263,445 | 0,813 | -0,207 | 0,01 | 0,06 | 0,298 |
| SEQ ID NO: 662 | hsa-miR-516b | aucuggagguuaagaagcacuu | 64,172 | 88,531 | 0,725 | -0,322 | 0,01 | 0,06 | 0,303 |
| SEQ ID NO: 575 | hsa-miR-892a | cacugucccuuucugcguag | 74,703 | 51,438 | 1,452 | 0,373 | 0,01 | 0,06 | 0,705 |
| SEQ ID NO: 628 | hsa-miR-196a* | cggcaacaagaaaucugccugag | 208,156 | 258,695 | 0,805 | -0,217 | 0,01 | 0,06 | 0,318 |
| SEQ ID NO: 716 | hsa-miR-654-5p | ugguggccgcagaacacugc | 264,451 | 326,281 | 0,811 | -0,210 | 0,02 | 0,06 | 0,260 |
| SEQ ID NO: 682 | hsa-miR-208a | auaagacgagcaaaaagcugu | 138,313 | 134,906 | 1,025 | 0,025 | 0,02 | 0,06 | 0,362 |
| SEQ ID NO: 527 | hsa-miR-1201 | agccugauuaaaacacaugcucuga | 137,219 | 157,250 | 0,873 | -0,136 | 0,02 | 0,06 | 0,343 |
| SEQ ID NO: 539 | hsa-miR-448 | uugcauaugguaggaugcccau | 154,031 | 185,734 | 0,829 | -0,187 | 0,02 | 0,07 | 0,313 |
| SEQ ID NO: 3 | hsa-let-7i | ugagguaguaguuugugcuguu | 2307,945 | 1437,787 | 1,605 | 0,473 | 0,02 | 0,07 | 0,666 |
| SEQ ID NO: 616 | hsa-miR-374b | auauaauacaaccugcuaagug | 510,709 | 744,035 | 0,686 | -0,376 | 0,02 | 0,07 | 0,296 |
| SEQ ID NO: 841 | hsa-miR-517* | cccuagaugggaagcacugucu | 282,109 | 353,313 | 0,798 | -0,225 | 0,02 | 0,07 | 0,283 |
| SEQ ID NO: 360 | hsa-miR-103-as | ucauagcccuguacaaugcugcu | 208,313 | 279,592 | 0,745 | -0,294 | 0,02 | 0,07 | 0,300 |
| SEQ ID NO: 200 | hsa-miR-509-5p | uacucagacaguggcaauca | 322,969 | 463,547 | 0,697 | -0,361 | 0,02 | 0,07 | 0,265 |
| SEQ ID NO: 622 | hsa-miR-130b | cagugcaauaauguaaagggcau | 984,727 | 1288,578 | 0,764 | -0,269 | 0,02 | 0,07 | 0,280 |
| SEQ ID NO: 851 | hsa-miR-105* | acggauguuugagcaugugucua | 27,625 | 52,906 | 0,522 | -0,650 | 0,02 | 0,07 | 0,291 |

FIG. 10A (Continued)

| SEQ ID NO | miRNA | sequence | median | median.neg | logmedian | raw.pval | adj.pval | AUC |
|---|---|---|---|---|---|---|---|---|
| SEQ ID NO: 81 | hsa-miR-922 | gcagcagagaauaggacuacguc | 181,281 | 241,600 | -0,287 | 0,02 | 0,07 | 0,304 |
| SEQ ID NO: 178 | hsa-miR-662 | ucccacguuggugggcccagcag | 166,299 | 130,438 | 0,243 | 0,02 | 0,07 | 0,714 |
| SEQ ID NO: 143 | hsa-miR-631 | agaccuggcccagaccucaqc | 217,672 | 244,598 | -0,117 | 0,02 | 0,07 | 0,308 |
| SEQ ID NO: 503 | hsa-miR-541 | ugguggggcacagaauucuggacu | 159,188 | 190,906 | -0,182 | 0,02 | 0,07 | 0,294 |
| SEQ ID NO: 675 | hsa-miR-486-3p | cgggcagcucaguacaggau | 253,199 | 365,578 | -0,367 | 0,02 | 0,07 | 0,350 |
| SEQ ID NO: 497 | hsa-miR-1243 | aacuggaucaauuauaggagug | 121,969 | 145,766 | -0,178 | 0,02 | 0,07 | 0,304 |
| SEQ ID NO: 738 | hsa-miR-600 | acuuacagacagagccuugcuc | 119,422 | 142,906 | -0,180 | 0,02 | 0,07 | 0,371 |
| SEQ ID NO: 847 | hsa-miR-588 | uuggcccacauugguuagaac | 181,484 | 213,078 | -0,160 | 0,02 | 0,07 | 0,308 |
| SEQ ID NO: 572 | hsa-miR-589* | ucagaacaaaugccguccccaga | 180,125 | 159,172 | 0,124 | 0,02 | 0,07 | 0,687 |
| SEQ ID NO: 537 | hsa-miR-431 | ugucuugcaggccgucaugca | 232,438 | 310,016 | -0,288 | 0,02 | 0,07 | 0,283 |
| SEQ ID NO: 548 | hsa-miR-1294 | ugugagguuggcauugguugucu | 45,797 | 28,563 | 0,472 | 0,02 | 0,07 | 0,688 |
| SEQ ID NO: 68 | hsa-miR-1245 | aagugaucuaaaggccuacau | 85,875 | 107,313 | -0,223 | 0,02 | 0,07 | 0,312 |
| SEQ ID NO: 543 | hsa-miR-300 | uauacaagggcagacucucucu | 75,406 | 112,766 | -0,402 | 0,02 | 0,07 | 0,271 |
| SEQ ID NO: 701 | hsa-miR-1303 | uuuagagacgggucuugcuc | 129,313 | 86,063 | 0,407 | 0,02 | 0,07 | 0,696 |
| SEQ ID NO: 493 | hsa-miR-1255a | aggaggcaaagaauagauu | 75,453 | 111,406 | -0,390 | 0,02 | 0,08 | 0,307 |
| SEQ ID NO: 574 | hsa-miR-592 | uuggucaauaugcgaugagu | 90,969 | 120,969 | -0,285 | 0,02 | 0,08 | 0,244 |
| SEQ ID NO: 56 | hsa-miR-451 | aaacgguuaccauuacugaguu | 3657,398 | 1573,316 | 0,844 | 0,02 | 0,08 | 0,788 |
| SEQ ID NO: 43 | hsa-miR-550* | ugucuuacucccucaggcacau | 672,352 | 446,313 | 0,410 | 0,02 | 0,08 | 0,762 |
| SEQ ID NO: 704 | hsa-miR-595 | gaagugcgguggugucu | 96,922 | 158,063 | -0,489 | 0,02 | 0,08 | 0,304 |
| SEQ ID NO: 601 | hsa-miR-148a* | aaaguucugagacacucgacu | 122,375 | 107,281 | 0,132 | 0,02 | 0,08 | 0,702 |
| SEQ ID NO: 597 | hsa-miR-877 | guagaggagauggcgcaggg | 164,422 | 133,297 | 0,210 | 0,02 | 0,08 | 0,707 |
| SEQ ID NO: 327 | hsa-miR-363 | aauugcacgguauccaucugua | 2894,117 | 3780,426 | -0,267 | 0,02 | 0,08 | 0,286 |
| SEQ ID NO: 1291 | hsa-miR-1291 | uggccccugacugaagaccagcagu | 199,047 | 249,492 | -0,226 | 0,02 | 0,08 | 0,295 |
| SEQ ID NO: 290 | hsa-let-7f-2* | cuauacagucuacugucuuuc | 40,938 | 50,250 | -0,205 | 0,02 | 0,08 | 0,338 |
| SEQ ID NO: 80 | hsa-miR-1261 | auggauaaggcuuugggcuu | 40,766 | 29,563 | 0,321 | 0,02 | 0,08 | 0,688 |
| SEQ ID NO: 865 | hsa-miR-638 | agggaucgcgggcggguggcggccu | 606,984 | 394,188 | 0,432 | 0,02 | 0,08 | 0,688 |
| SEQ ID NO: 76 | hsa-miR-720 | ucucgcuggggccuca | 7180,215 | 4541,121 | 0,458 | 0,02 | 0,09 | 0,664 |
| SEQ ID NO: 866 | hsa-miR-562 | aaaguagcuguaccauuugc | 79,234 | 88,391 | -0,109 | 0,02 | 0,09 | 0,343 |
| SEQ ID NO: 718 | hsa-miR-1825 | uccagugcccucucuc | 117,484 | 79,547 | 0,390 | 0,03 | 0,09 | 0,680 |
| SEQ ID NO: 102 | hsa-let-7f-1* | cuauacaaucuauugccuucc | 41,203 | 58,703 | -0,354 | 0,03 | 0,09 | 0,318 |
| SEQ ID NO: 311 | hsa-miR-500* | augcaccugcaaggauucug | 336,797 | 382,953 | -0,128 | 0,03 | 0,09 | 0,314 |

FIG. 10A (Continued)

| SEQ ID NO | miRNA | Sequence | median1 | median2 | qmedian | logqmedian | cv_PVal | adj_PVal | AUC |
|---|---|---|---|---|---|---|---|---|---|
| SEQ ID NO: 707 | hsa-miR-455-3p | gcaguccauuggcauauacac | 216,219 | 248,695 | 0,869 | -0,140 | 0,03 | 0,09 | 0,309 |
| SEQ ID NO: 285 | hsa-miR-29b-2* | cuggtuucacauggugccuuag | 153,719 | 106,750 | 1,440 | 0,365 | 0,03 | 0,09 | 0,738 |
| SEQ ID NO: 420 | hsa-miR-502-3p | aaugcaccugggcaaggauuca | 756,129 | 835,328 | 0,905 | -0,100 | 0,03 | 0,09 | 0,379 |
| SEQ ID NO: 740 | hsa-miR-340* | uccgcucucaguuacuuuauagc | 65,688 | 46,813 | 1,403 | 0,339 | 0,03 | 0,09 | 0,663 |
| SEQ ID NO: 356 | hsa-miR-122* | aacgccauuaucacacuaaaua | 111,938 | 142,000 | 0,788 | -0,238 | 0,03 | 0,09 | 0,304 |
| SEQ ID NO: 287 | hsa-miR-566 | ggggcgugauccccaac | 145,797 | 160,656 | 0,908 | -0,097 | 0,03 | 0,1 | 0,330 |
| SEQ ID NO: 743 | hsa-miR-1179 | aagcauucuuucauuggugg | 49,750 | 78,594 | 0,633 | -0,457 | 0,03 | 0,1 | 0,302 |
| SEQ ID NO: 562 | hsa-miR-1203 | cccgagccaggaugcagcuc | 272,811 | 323,891 | 0,842 | -0,172 | 0,03 | 0,1 | 0,322 |
| SEQ ID NO: 705 | hsa-miR-1255b | cggaugagcaaagaaauggu | 130,063 | 142,313 | 0,914 | -0,090 | 0,03 | 0,1 | 0,351 |
| SEQ ID NO: 788 | hsa-miR-1228* | gugggcggggcaggugugug | 2186,746 | 1612,961 | 1,356 | 0,304 | 0,03 | 0,1 | 0,670 |
| SEQ ID NO: 324 | hsa-miR-154* | aaucauacgguuguuggaccuauu | 92,672 | 105,031 | 0,882 | -0,125 | 0,03 | 0,1 | 0,320 |
| SEQ ID NO: 305 | hsa-miR-33b | gugcaugcugugucuugaugc | 232,094 | 270,588 | 0,858 | -0,153 | 0,03 | 0,1 | 0,365 |
| SEQ ID NO: 291 | hsa-miR-1322 | gaugaugcugaugcug | 119,313 | 181,422 | 0,658 | -0,419 | 0,03 | 0,1 | 0,289 |
| SEQ ID NO: 184 | hsa-miR-623 | aucccuugcaggggcuguggggu | 115,547 | 93,000 | 1,242 | 0,217 | 0,03 | 0,1 | 0,715 |
| SEQ ID NO: 323 | hsa-miR-137 | uuauugcuuaagaauacgcguag | 149,234 | 178,281 | 0,837 | -0,178 | 0,03 | 0,1 | 0,337 |
| SEQ ID NO: 54 | hsa-miR-542-3p | ugugacagauugauaacugaaa | 144,969 | 166,813 | 0,869 | -0,140 | 0,03 | 0,11 | 0,317 |
| SEQ ID NO: 746 | hsa-miR-155* | cuccuacauauuagcauuaaca | 119,000 | 156,063 | 0,763 | -0,271 | 0,03 | 0,11 | 0,362 |
| SEQ ID NO: 195 | hsa-miR-32 | uauugcacauuacuaaguugca | 250,160 | 248,332 | 1,007 | 0,007 | 0,03 | 0,11 | 0,442 |
| SEQ ID NO: 475 | hsa-miR-34c-5p | aggcaguguaguuagcugauugc | 108,531 | 130,313 | 0,833 | -0,183 | 0,03 | 0,11 | 0,299 |
| SEQ ID NO: 828 | hsa-miR-938 | ugcccuuaaaggugaaccagu | 208,953 | 165,375 | 1,264 | 0,234 | 0,03 | 0,11 | 0,683 |
| SEQ ID NO: 307 | hsa-miR-620 | auggagauagauauacugaaau | 37,391 | 51,281 | 0,729 | -0,316 | 0,03 | 0,11 | 0,330 |
| SEQ ID NO: 314 | hsa-miR-558 | ugagcugcuguuaccaaau | 152,438 | 182,391 | 0,836 | -0,179 | 0,04 | 0,12 | 0,357 |
| SEQ ID NO: 108 | hsa-miR-34a* | caaucagcaaguauacugcccu | 162,594 | 181,688 | 0,895 | -0,111 | 0,04 | 0,12 | 0,353 |
| SEQ ID NO: 834 | hsa-miR-130a | cagugcaauguuaaaagggcau | 2267,848 | 1859,602 | 1,220 | 0,198 | 0,04 | 0,12 | 0,696 |
| SEQ ID NO: 241 | hsa-miR-1297 | uucaaguauucaggug | 77,328 | 103,219 | 0,749 | -0,289 | 0,04 | 0,12 | 0,303 |
| SEQ ID NO: 842 | hsa-miR-193b* | cggguuugagggcgagauga | 106,625 | 66,813 | 1,596 | 0,467 | 0,04 | 0,13 | 0,692 |
| SEQ ID NO: 297 | hsa-miR-582-3p | uaacuggttugaacaacugacc | 167,156 | 188,109 | 0,889 | -0,118 | 0,04 | 0,13 | 0,329 |
| SEQ ID NO: 544 | hsa-miR-1826 | auugaucaucgacacuugaacgcaau | 259,668 | 264,654 | 0,981 | -0,019 | 0,04 | 0,13 | 0,405 |
| SEQ ID NO: 839 | hsa-miR-877* | uccucuucuccccuccccag | 167,031 | 105,297 | 1,586 | 0,461 | 0,04 | 0,13 | 0,628 |
| SEQ ID NO: 19 | hsa-miR-140-3p | uaccacagggguagaaccacgg | 24650,828 | 20868,719 | 1,181 | 0,167 | 0,04 | 0,13 | 0,708 |
| SEQ ID NO: 477 | hsa-miR-628-5p | augcugacauauuuacuagagg | 109,781 | 121,875 | 0,901 | -0,105 | 0,04 | 0,14 | 0,348 |

FIG. 10A (Continued)

| SEQ ID NO | miRNA | sequence | median-ca | median-ct | gmedian | logmedian | cdwgt | adjPval | AUC |
|---|---|---|---|---|---|---|---|---|---|
| SEQ ID NO: 480 | hsa-let-7a* | cuauacaaucuacugucuuuc | 28,500 | 39,469 | 0,722 | -0,326 | 0,04 | 0,14 | 0,367 |
| SEQ ID NO: 725 | hsa-miR-886-5p | cgggucggaguuagcucaagcgg | 150,969 | 124,031 | 1,217 | 0,197 | 0,04 | 0,14 | 0,669 |
| SEQ ID NO: 229 | hsa-miR-369-3p | aauuaauacauggUUgaucuuu | 48,719 | 58,484 | 0,833 | -0,183 | 0,04 | 0,14 | 0,345 |
| SEQ ID NO: 350 | hsa-miR-635 | acuugggcacugaaacaauguCC | 187,375 | 226,094 | 0,829 | -0,188 | 0,05 | 0,14 | 0,326 |
| SEQ ID NO: 713 | hsa-miR-663 | agccgggcgccgggaccgc | 582,203 | 575,703 | 1,011 | 0,011 | 0,05 | 0,14 | 0,605 |
| SEQ ID NO: 618 | hsa-miR-483-5p | aagacgggaggaaagaagggag | 281,328 | 220,516 | 1,276 | 0,244 | 0,05 | 0,14 | 0,683 |
| SEQ ID NO: 717 | hsa-miR-326 | ccCugggccuucCucCag | 188,781 | 147,469 | 1,280 | 0,247 | 0,05 | 0,14 | 0,685 |
| SEQ ID NO: 563 | hsa-miR-135a* | uauagggauuggagccguggcg | 68,156 | 47,031 | 1,449 | 0,371 | 0,05 | 0,14 | 0,649 |
| SEQ ID NO: 638 | hsa-miR-499-5p | uuaagacuugcagugauguuu | 56,406 | 70,531 | 0,800 | -0,223 | 0,05 | 0,14 | 0,343 |
| SEQ ID NO: 481 | hsa-miR-101* | caguuaucacagugcugaugcu | 234,750 | 185,172 | 1,268 | 0,237 | 0,05 | 0,15 | 0,707 |
| SEQ ID NO: 429 | hsa-miR-615-5p | gggguccCcggugcucggauc | 125,625 | 110,219 | 1,140 | 0,131 | 0,05 | 0,15 | 0,653 |
| SEQ ID NO: 576 | hsa-miR-944 | aaauuauguacaucggaugag | 79,594 | 93,125 | 0,855 | -0,157 | 0,05 | 0,15 | 0,366 |
| SEQ ID NO: 214 | hsa-miR-520e | aaagugcuccuuuuugaggg | 51,563 | 38,094 | 1,354 | 0,303 | 0,05 | 0,15 | 0,711 |
| SEQ ID NO: 136 | hsa-miR-34b | caaucacuaacuccacuccau | 82,375 | 97,672 | 0,843 | -0,170 | 0,05 | 0,15 | 0,336 |
| SEQ ID NO: 466 | hsa-miR-124 | uaaggcacgcggugaagcc | 188,906 | 230,016 | 0,821 | -0,197 | 0,05 | 0,15 | 0,339 |
| SEQ ID NO: 359 | hsa-miR-484 | ucaggcucagucccCuccgau | 8893,313 | 7318,813 | 1,215 | 0,195 | 0,05 | 0,16 | 0,708 |
| SEQ ID NO: 636 | hsa-miR-144* | ggauaucaucauauacuguaag | 889,078 | 1078,615 | 0,824 | -0,193 | 0,05 | 0,16 | 0,324 |
| SEQ ID NO: 335 | hsa-miR-523 | gaacgcgcuucccuuuagagggu | 148,531 | 175,328 | 0,847 | -0,166 | 0,06 | 0,16 | 0,334 |
| SEQ ID NO: 729 | hsa-miR-1226* | guagggcaugcaggcCuggauggg | 265,391 | 309,375 | 0,858 | -0,153 | 0,06 | 0,16 | 0,372 |
| SEQ ID NO: 827 | hsa-miR-1250 | acggcuggaugggguggCCUUU | 88,078 | 73,188 | 1,203 | 0,185 | 0,06 | 0,16 | 0,673 |
| SEQ ID NO: 212 | hsa-miR-1262 | auggugaauuuguagaaggau | 30,281 | 21,406 | 1,415 | 0,347 | 0,06 | 0,16 | 0,649 |
| SEQ ID NO: 183 | hsa-miR-512-3p | aagugcugucaugcugaggu | 37,828 | 63,375 | 0,597 | -0,516 | 0,06 | 0,16 | 0,347 |
| SEQ ID NO: 20 | hsa-miR-339-5p | uccCugucuccagagcucacg | 734,359 | 915,141 | 0,802 | -0,220 | 0,06 | 0,16 | 0,360 |
| SEQ ID NO: 445 | hsa-miR-525-3p | gaaggcgcuuccCuuuagagcg | 132,688 | 152,875 | 0,868 | -0,142 | 0,06 | 0,16 | 0,355 |
| SEQ ID NO: 540 | hsa-miR-633 | cuaauaguauccaccacaauaaa | 191,594 | 182,031 | 1,053 | 0,051 | 0,06 | 0,16 | 0,465 |
| SEQ ID NO: 773 | hsa-miR-1290 | uggauuuuugggaucaggga | 25,828 | 36,531 | 0,707 | -0,347 | 0,06 | 0,17 | 0,329 |
| SEQ ID NO: 103 | hsa-miR-1305 | uuuucaacucuaauggagaga | 158,500 | 181,375 | 0,874 | -0,135 | 0,06 | 0,17 | 0,317 |
| SEQ ID NO: 447 | hsa-miR-223* | cguuauuugacaagcugagUU | 59,938 | 70,266 | 0,853 | -0,159 | 0,06 | 0,17 | 0,340 |
| SEQ ID NO: 639 | hsa-miR-183 | uauggcacuggUagaauucacu | 594,391 | 502,766 | 1,182 | 0,167 | 0,06 | 0,17 | 0,652 |
| SEQ ID NO: 820 | hsa-miR-575 | gagccagugguggacaggagc | 192,359 | 212,844 | 0,904 | -0,101 | 0,06 | 0,17 | 0,355 |
| SEQ ID NO: 650 | hsa-miR-202 | agagguuaugggcaugggaa | 35,719 | 44,125 | 0,809 | -0,211 | 0,06 | 0,17 | 0,382 |

FIG. 10A (Continued)

| SEQ ID NO | miRNA | Sequence | median gl | median g2 | median ratio | logmedian | raw p-val | adj p-val | value |
|---|---|---|---|---|---|---|---|---|---|
| SEQ ID NO: 585 | hsa-miR-100* | caagcuuguaucuauagguaug | 114,797 | 142,172 | 0,807 | -0,214 | 0,06 | 0,17 | 0,347 |
| SEQ ID NO: 216 | hsa-miR-106a* | cugcaauguaagcacuucuuac | 226,109 | 242,766 | 0,931 | -0,071 | 0,06 | 0,17 | 0,335 |
| SEQ ID NO: 524 | hsa-miR-220c | acacagggcugugugaagacu | 188,656 | 208,219 | 0,906 | -0,099 | 0,06 | 0,17 | 0,406 |
| SEQ ID NO: 577 | hsa-miR-576-3p | aagaugggaaaaauuggaauc | 38,984 | 46,156 | 0,845 | -0,169 | 0,06 | 0,17 | 0,341 |
| SEQ ID NO: 818 | hsa-miR-1228 | ucacaccugccucgcccc | 261,240 | 302,828 | 0,863 | -0,148 | 0,06 | 0,17 | 0,373 |
| SEQ ID NO: 754 | hsa-miR-129-3p | aagcccuuaccccaaaaagcau | 135,063 | 136,828 | 0,987 | -0,013 | 0,06 | 0,17 | 0,378 |
| SEQ ID NO: 561 | hsa-miR-548o | ccaaaacugcaguuacuuugc | 174,656 | 213,281 | 0,819 | -0,200 | 0,06 | 0,17 | 0,341 |
| SEQ ID NO: 530 | hsa-miR-425* | aucgggaaugucgugccgccc | 143,688 | 101,281 | 1,419 | 0,350 | 0,06 | 0,17 | 0,650 |
| SEQ ID NO: 221 | hsa-miR-1278 | uaguacugugcauaucaucuau | 108,094 | 125,000 | 0,865 | -0,145 | 0,06 | 0,17 | 0,366 |
| SEQ ID NO: 242 | hsa-miR-933 | ugugcgcaggagagaccucuccc | 293,516 | 360,047 | 0,815 | -0,204 | 0,06 | 0,17 | 0,363 |
| SEQ ID NO: 164 | hsa-miR-377 | aucacacaaggcaacuuugu | 214,031 | 278,391 | 0,769 | -0,263 | 0,06 | 0,17 | 0,331 |
| SEQ ID NO: 603 | hsa-miR-505 | cgucaacacuugucucucucccu | 87,344 | 66,063 | 1,322 | 0,279 | 0,06 | 0,17 | 0,657 |
| SEQ ID NO: 400 | hsa-miR-432* | cuggauggcuccuccaugcu | 109,625 | 102,250 | 1,072 | 0,070 | 0,06 | 0,17 | 0,632 |
| SEQ ID NO: 646 | hsa-miR-302d* | acuuuaacauggagcacuugc | 104,438 | 123,781 | 0,844 | -0,170 | 0,06 | 0,17 | 0,325 |
| SEQ ID NO: 14 | hsa-let-7e | ugagguaggaguuguauaguu | 537,031 | 227,672 | 2,359 | 0,858 | 0,06 | 0,17 | 0,682 |
| SEQ ID NO: 256 | hsa-miR-583 | caaagaggaaggucccauuac | 93,000 | 109,953 | 0,846 | -0,167 | 0,07 | 0,18 | 0,337 |
| SEQ ID NO: 302 | hsa-miR-127-5p | cugaagcucagagggcucugau | 216,125 | 241,391 | 0,895 | -0,111 | 0,07 | 0,18 | 0,356 |
| SEQ ID NO: 761 | hsa-miR-1307 | acucggcgugggcgucggucgug | 188,469 | 141,750 | 1,330 | 0,285 | 0,07 | 0,18 | 0,669 |
| SEQ ID NO: 110 | hsa-miR-1256 | aggcauugacucucucacuagcu | 66,281 | 112,969 | 0,587 | -0,533 | 0,07 | 0,18 | 0,351 |
| SEQ ID NO: 454 | hsa-miR-659 | cuugguucagggaggucccca | 207,313 | 153,844 | 1,348 | 0,298 | 0,07 | 0,18 | 0,681 |
| SEQ ID NO: 24 | hsa-miR-26b | uucaaguaauucaggauaggu | 756,129 | 602,609 | 1,255 | 0,227 | 0,07 | 0,18 | 0,647 |
| SEQ ID NO: 517 | hsa-miR-585 | ugggcguaucuguaugcua | 45,219 | 50,250 | 0,900 | -0,105 | 0,07 | 0,18 | 0,363 |
| SEQ ID NO: 473 | hsa-miR-21 | uagcuuaucagacugauguuga | 1570,813 | 1114,814 | 1,409 | 0,343 | 0,07 | 0,18 | 0,634 |
| SEQ ID NO: 289 | hsa-miR-28-3p | cacuagauuugugagcuccugga | 250,008 | 204,813 | 1,221 | 0,199 | 0,07 | 0,18 | 0,663 |
| SEQ ID NO: 479 | hsa-miR-370 | gccugcugggguggaaccuggu | 90,094 | 105,094 | 0,857 | -0,154 | 0,07 | 0,18 | 0,339 |
| SEQ ID NO: 7 | hsa-miR-98 | ugaggguaguaagaguaugugu | 162,125 | 73,375 | 2,210 | 0,793 | 0,07 | 0,19 | 0,696 |
| SEQ ID NO: 205 | hsa-miR-937 | auccgcucucugacucucgcc | 89,656 | 109,281 | 0,820 | -0,198 | 0,07 | 0,19 | 0,313 |
| SEQ ID NO: 181 | hsa-miR-891b | ugcaacuuaccugaguacauuga | 151,594 | 180,188 | 0,841 | -0,173 | 0,08 | 0,19 | 0,386 |
| SEQ ID NO: 334 | hsa-miR-490-5p | ccauggaucuccaggugggu | 191,813 | 225,719 | 0,850 | -0,163 | 0,08 | 0,19 | 0,335 |
| SEQ ID NO: 858 | hsa-miR-27a | uucacaguggcuaaguuccgc | 595,141 | 405,328 | 1,471 | 0,386 | 0,08 | 0,19 | 0,691 |
| SEQ ID NO: 696 | hsa-miR-1273 | gggcgacaaagcaagacucucucuu | 146,406 | 162,125 | 0,903 | -0,102 | 0,08 | 0,2 | 0,357 |

FIG. 10A (Continued)

| SEQ ID NO | miRNA | Sequence | median g1 | median g2 | qmedian | logmedian | raw p-val | adj p-val | AUC |
|---|---|---|---|---|---|---|---|---|---|
| SEQ ID NO: 850 | hsa-miR-1470 | gcccucccgcccgcugcacccccg | 234,250 | 266,260 | 0,880 | -0,128 | 0,08 | 0,2 | 0,329 |
| SEQ ID NO: 70 | hsa-miR-1288 | uggacugcccugauccuggaga | 162,156 | 181,375 | 0,894 | -0,112 | 0,08 | 0,2 | 0,331 |
| SEQ ID NO: 596 | hsa-miR-605 | uaaauccccauggugccuucuccu | 64,688 | 84,313 | 0,767 | -0,265 | 0,08 | 0,2 | 0,366 |
| SEQ ID NO: 116 | hsa-miR-599 | guugucaguuuaucaaac | 65,078 | 77,375 | 0,841 | -0,173 | 0,08- | 0,2 | 0,346 |
| SEQ ID NO: 407 | hsa-miR-519e | aagugcccucuuuuagugugu | 24,719 | 19,375 | 1,276 | 0,244 | 0,08 | 0,2 | 0,572 |
| SEQ ID NO: 261 | hsa-miR-885-5p | uccauuacacuacccgucucu | 81,641 | 65,734 | 1,242 | 0,217 | 0,08 | 0,2 | 0,653 |
| SEQ ID NO: 321 | hsa-miR-1253 | agagaagaaucagccugca | 131,453 | 147,391 | 0,892 | -0,114 | 0,08 | 0,2 | 0,349 |
| SEQ ID NO: 107 | hsa-miR-619 | gaccuggcauguuuugcccagu | 158,781 | 145,688 | 1,090 | 0,086 | 0,08 | 0,2 | 0,661 |
| SEQ ID NO: 371 | hsa-miR-708* | caacuagacgugugagcucucag | 125,031 | 135,828 | 0,921 | -0,083 | 0,08 | 0,2 | 0,390 |
| SEQ ID NO: 79 | hsa-miR-297 | auguaugugucaugugcaug | 101,531 | 118,844 | 0,854 | -0,157 | 0,08 | 0,2 | 0,387 |
| SEQ ID NO: 36 | hsa-miR-505* | gggagccaggaaguauugaugu | 257,480 | 220,938 | 1,165 | 0,153 | 0,08 | 0,2 | 0,630 |
| SEQ ID NO: 525 | hsa-miR-524-3p | gaagcgcuucccuuuggagu | 51,500 | 67,563 | 0,762 | -0,271 | 0,08 | 0,2 | 0,368 |
| SEQ ID NO: 436 | hsa-miR-501-3p | aaugcaccggcaaggaauucu | 384,297 | 445,109 | 0,863 | -0,147 | 0,08 | 0,2 | 0,348 |
| SEQ ID NO: 859 | hsa-miR-518a-3p | gaaagcgcuucccuuugcugga | 118,906 | 135,063 | 0,880 | -0,127 | 0,08 | 0,2 | 0,351 |
| SEQ ID NO: 796 | hsa-miR-1231 | gugucugggcgccuccagaugcc | 120,750 | 177,469 | 0,680 | -0,385 | 0,09 | 0,21 | 0,333 |
| SEQ ID NO: 125 | hsa-miR-1539 | uccucgcgucuccagaugcc | 132,641 | 159,844 | 0,830 | -0,187 | 0,09 | 0,21 | 0,338 |
| SEQ ID NO: 361 | hsa-miR-380 | uauggaauauggucccacaucu | 61,484 | 80,531 | 0,763 | -0,270 | 0,09 | 0,21 | 0,326 |
| SEQ ID NO: 213 | hsa-miR-153 | uugcauagucacaaaagugauc | 177,750 | 198,859 | 0,894 | -0,112 | 0,09 | 0,21 | 0,365 |
| SEQ ID NO: 831 | hsa-miR-1249 | acgcccuuccccccccucuuca | 78,516 | 105,344 | 0,745 | -0,294 | 0,09 | 0,21 | 0,353 |
| SEQ ID NO: 180 | hsa-miR-1287 | ugcuggaucaguguguucgaguc | 139,094 | 120,828 | 1,151 | 0,141 | 0,09 | 0,21 | 0,696 |
| SEQ ID NO: 219 | hsa-miR-654-3p | uauguucugcugaccaucaccuu | 67,703 | 81,953 | 0,826 | -0,191 | 0,09 | 0,21 | 0,367 |
| SEQ ID NO: 857 | hsa-miR-199b-5p | cccaguguuuagacuauccuguuc | 56,500 | 49,938 | 1,131 | 0,123 | 0,09 | 0,21 | 0,620 |
| SEQ ID NO: 370 | hsa-miR-520c-3p | aaagugcuuccccuuuuagagggu | 33,797 | 26,359 | 1,282 | 0,249 | 0,09 | 0,21 | 0,665 |
| SEQ ID NO: 55 | hsa-miR-516b* | ugcuuccuuuucagagggu | 93,781 | 69,281 | 1,354 | 0,303 | 0,09 | 0,21 | 0,643 |
| SEQ ID NO: 208 | hsa-miR-1184 | ccugcagcgacuugauggcuucc | 266,092 | 240,914 | 1,105 | 0,099 | 0,09 | 0,21 | 0,502 |
| SEQ ID NO: 757 | hsa-miR-125b | uccccugagaccccuaacuuguga | 984,727 | 780,203 | 1,262 | 0,233 | 0,09 | 0,21 | 0,630 |
| SEQ ID NO: 468 | hsa-miR-200c | uaaauacugcgguaaugauga | 182,156 | 142,531 | 1,278 | 0,245 | 0,09 | 0,22 | 0,646 |
| SEQ ID NO: 722 | hsa-miR-1909* | ugagugccgguguccugcccg | 86,188 | 110,125 | 0,783 | -0,245 | 0,09 | 0,22 | 0,380 |
| SEQ ID NO: 845 | hsa-miR-154 | uagguuauccguuguguucauug | 26,188 | 11,281 | 2,321 | 0,842 | 0,09 | 0,22 | 0,638 |
| SEQ ID NO: 504 | hsa-miR-543 | aaacauucgcggugcacuucuu | 94,125 | 105,031 | 0,896 | -0,110 | 0,1 | 0,22 | 0,349 |
| SEQ ID NO: 550 | hsa-miR-142-5p | cauaaaguagaaagcacuacu | 1372,621 | 972,602 | 1,411 | 0,345 | 0,1 | 0,22 | 0,626 |

FIG. 10A (Continued)

| SEQ ID NO | miRNA | Sequence | median g1 | median g2 | fcmedian | logmedian | raw Pval | adj.Pval | AUC |
|---|---|---|---|---|---|---|---|---|---|
| SEQ ID NO: 699 | hsa-miR-550 | agugccugagggaguaagagccc | 198,266 | 232,531 | 0,853 | -0,159 | 0,1 | 0,22 | 0,358 |
| SEQ ID NO: 413 | hsa-miR-15a* | caggccauauugugcugcuca | 228,266 | 200,031 | 1,141 | 0,132 | 0,1 | 0,22 | 0,670 |
| SEQ ID NO: 762 | hsa-miR-769-3p | cugggaucuccgggucuugguu | 47,500 | 38,438 | 1,236 | 0,212 | 0,1 | 0,23 | 0,633 |
| SEQ ID NO: 564 | hsa-miR-383 | agaucagaaggugauugugccu | 88,109 | 121,188 | 0,727 | -0,319 | 0,1 | 0,23 | 0,364 |
| SEQ ID NO: 685 | hsa-miR-181c | aacauucaaccugucggugagu | 249,816 | 181,375 | 1,377 | 0,320 | 0,1 | 0,23 | 0,700 |
| SEQ ID NO: 592 | hsa-miR-375 | uuuguucguucggcucgcguga | 50,688 | 41,375 | 1,225 | 0,203 | 0,1 | 0,23 | 0,653 |
| SEQ ID NO: 61 | hsa-miR-19a* | aguuuugcauaguuugcacuaca | 93,172 | 127,063 | 0,733 | -0,310 | 0,1 | 0,23 | 0,348 |
| SEQ ID NO: 623 | hsa-miR-1274a | gucccgucaggcgca | 271,266 | 234,672 | 1,156 | 0,145 | 0,1 | 0,24 | 0,661 |
| SEQ ID NO: 166 | hsa-miR-301a | cagugcaauaguauugucaaagc | 467,047 | 594,125 | 0,786 | -0,241 | 0,1 | 0,24 | 0,357 |
| SEQ ID NO: 227 | hsa-miR-590-3p | uaauuuuauguauaaagcuagu | 40,594 | 56,375 | 0,720 | -0,328 | 0,1 | 0,24 | 0,345 |
| SEQ ID NO: 431 | hsa-miR-657 | ggcaguucucaccucucuagg | 93,984 | 106,359 | 0,884 | -0,124 | 0,1 | 0,24 | 0,341 |
| SEQ ID NO: 441 | hsa-miR-548i | aaaguaaauugcggauuuugcc | 59,625 | 45,156 | 1,320 | 0,278 | 0,1 | 0,24 | 0,643 |
| SEQ ID NO: 118 | hsa-miR-23b | aucacauugccagggauuacc | 4027,828 | 3935,324 | 1,024 | 0,023 | 0,1 | 0,24 | 0,598 |
| SEQ ID NO: 476 | hsa-miR-429 | uaauacugucugguaaaaccgu | 117,875 | 134,438 | 0,877 | -0,131 | 0,1 | 0,25 | 0,337 |
| SEQ ID NO: 89 | hsa-miR-16 | uagcagcacguaaauauuggcg | 18271,367 | 13747,000 | 1,329 | 0,285 | 0,11 | 0,25 | 0,628 |
| SEQ ID NO: 267 | hsa-miR-519a | aaagugcaucuuuuagagugu | 72,469 | 87,828 | 0,825 | -0,192 | 0,11 | 0,25 | 0,327 |
| SEQ ID NO: 197 | hsa-miR-454 | uagugcaauauugcuuauagggu | 414,703 | 321,016 | 1,292 | 0,256 | 0,11 | 0,25 | 0,648 |
| SEQ ID NO: 298 | hsa-miR-629* | guucuccaacgacguaagccagc | 212,250 | 146,766 | 1,446 | 0,369 | 0,11 | 0,26 | 0,744 |
| SEQ ID NO: 331 | hsa-miR-222* | cucaguagccaguguagauccu | 118,672 | 128,750 | 0,922 | -0,082 | 0,12 | 0,26 | 0,351 |
| SEQ ID NO: 791 | hsa-miR-149* | agggagggacggggcugugc | 1078,615 | 664,469 | 1,623 | 0,484 | 0,12 | 0,26 | 0,697 |
| SEQ ID NO: 340 | hsa-miR-376a* | guagauuccuccucuauagagua | 53,719 | 37,875 | 1,418 | 0,349 | 0,12 | 0,26 | 0,670 |
| SEQ ID NO: 224 | hsa-miR-1468 | cucgauugccuguuucgcug | 37,203 | 29,125 | 1,277 | 0,245 | 0,12 | 0,26 | 0,643 |
| SEQ ID NO: 357 | hsa-miR-450b-3p | uugggaucauuugcauccauua | 77,344 | 95,188 | 0,813 | -0,208 | 0,12 | 0,26 | 0,360 |
| SEQ ID NO: 114 | hsa-miR-1284 | ucuauacagaccccuggcuuuc | 60,484 | 72,203 | 0,838 | -0,177 | 0,12 | 0,26 | 0,366 |
| SEQ ID NO: 692 | hsa-miR-516a-5p | uucucggagaagaagcacuuuc | 269,203 | 327,063 | 0,823 | -0,195 | 0,12 | 0,27 | 0,314 |
| SEQ ID NO: 702 | hsa-miR-650 | aggaggcagcgcugaugcug | 195,156 | 212,688 | 0,918 | -0,086 | 0,12 | 0,27 | 0,374 |
| SEQ ID NO: 640 | hsa-miR-490-3p | caaccugagcgcgacucaugcug | 140,125 | 150,313 | 0,932 | -0,070 | 0,12 | 0,27 | 0,366 |
| SEQ ID NO: 801 | hsa-miR-656 | aauauauacaguccaaccucu | 68,359 | 98,750 | 0,692 | -0,368 | 0,12 | 0,27 | 0,385 |
| SEQ ID NO: 21 | hsa-miR-361-5p | uuaucagaaucuccagggguac | 727,172 | 606,656 | 1,199 | 0,181 | 0,12 | 0,27 | 0,685 |
| SEQ ID NO: 836 | hsa-miR-432 | ucuuggaguaggucauuggugg | 28,141 | 19,938 | 1,411 | 0,345 | 0,13 | 0,27 | 0,619 |
| SEQ ID NO: 679 | hsa-miR-24-1* | ugccuacugagcugauaucagu | 184,344 | 214,344 | 0,860 | -0,151 | 0,13 | 0,27 | 0,403 |

FIG. 10A (Continued)

| SEQ ID NO | miRNA | Sequence | median g1 | median g2 | median | log median | raw P val | adj P val | AUC |
|---|---|---|---|---|---|---|---|---|---|
| SEQ ID NO: 264 | hsa-miR-337-3p | cuccuauaugaugccuuucuuc | 72,156 | 87,219 | 0,827 | -0,190 | 0,13 | 0,27 | 0,355 |
| SEQ ID NO: 453 | hsa-miR-590-5p | gagcuuauucauaaaagugcag | 318,109 | 290,625 | 1,095 | 0,090 | 0,13 | 0,27 | 0,620 |
| SEQ ID NO: 316 | hsa-miR-1263 | auguacccuggcauacugagu | 123,672 | 154,578 | 0,800 | -0,223 | 0,13 | 0,27 | 0,372 |
| SEQ ID NO: 551 | hsa-miR-889 | uaauaucggacaaccauugu | 83,563 | 85,391 | 0,979 | -0,022 | 0,13 | 0,27 | 0,417 |
| SEQ ID NO: 392 | hsa-miR-616 | agucauuggaggguugagcag | 57,531 | 68,219 | 0,843 | -0,170 | 0,13 | 0,28 | 0,381 |
| SEQ ID NO: 236 | hsa-miR-1292 | ugggaacggguuccggcagacgcug | 150,250 | 132,875 | 1,131 | 0,123 | 0,13 | 0,28 | 0,630 |
| SEQ ID NO: 794 | hsa-miR-1181 | ccgucgccgccacccgagccg | 260,195 | 288,328 | 0,902 | -0,103 | 0,13 | 0,28 | 0,301 |
| SEQ ID NO: 643 | hsa-miR-483-3p | ucacucucucucuccgucu | 97,219 | 53,109 | 1,831 | 0,605 | 0,13 | 0,28 | 0,636 |
| SEQ ID NO: 452 | hsa-miR-582-5p | uuacaguuguucaaccagaaau | 67,047 | 77,094 | 0,870 | -0,140 | 0,13 | 0,28 | 0,394 |
| SEQ ID NO: 158 | hsa-miR-18a | uaaggugcaucuagugcagauag | 2342,613 | 2951,227 | 0,794 | -0,231 | 0,13 | 0,28 | 0,402 |
| SEQ ID NO: 220 | hsa-miR-99b* | caagcucgugucugugggucccg | 111,250 | 99,547 | 1,118 | 0,111 | 0,14 | 0,29 | 0,610 |
| SEQ ID NO: 710 | hsa-miR-1321 | cagggaggugaaugugau | 37,281 | 30,391 | 1,227 | 0,204 | 0,14 | 0,29 | 0,599 |
| SEQ ID NO: 727 | hsa-miR-1298 | uucauucgcuguccagaugua | 88,141 | 115,859 | 0,761 | -0,273 | 0,14 | 0,29 | 0,353 |
| SEQ ID NO: 343 | hsa-miR-532-3p | cccuccacacccaaggcuugca | 3596,766 | 3412,176 | 1,054 | 0,053 | 0,14 | 0,29 | 0,433 |
| SEQ ID NO: 625 | hsa-miR-518e* | cucagagggaagcgcuuucug | 281,047 | 314,609 | 0,893 | -0,113 | 0,14 | 0,29 | 0,401 |
| SEQ ID NO: 579 | hsa-miR-625* | gacuauagaacuuuccccccuca | 393,625 | 308,203 | 1,277 | 0,245 | 0,14 | 0,29 | 0,670 |
| SEQ ID NO: 427 | hsa-miR-100 | aaccguagaucgaacugug | 208,375 | 159,797 | 1,304 | 0,265 | 0,14 | 0,3 | 0,538 |
| SEQ ID NO: 767 | hsa-miR-191* | gcugcguuggauuucgucccc | 87,719 | 110,094 | 0,797 | -0,227 | 0,14 | 0,3 | 0,390 |
| SEQ ID NO: 145 | hsa-miR-30c | uguaaacauccuacacucucagc | 2267,848 | 1917,672 | 1,183 | 0,168 | 0,14 | 0,3 | 0,638 |
| SEQ ID NO: 745 | hsa-miR-30b* | cugggaggugguuuuacuuc | 58,453 | 42,000 | 1,392 | 0,331 | 0,15 | 0,3 | 0,616 |
| SEQ ID NO: 388 | hsa-miR-196b | uagguaguuucuguugugg | 28,078 | 21,844 | 1,285 | 0,251 | 0,14 | 0,3 | 0,610 |
| SEQ ID NO: 786 | hsa-miR-518a-5p | cugcaaaggaagccccuuuc | 301,641 | 294,422 | 1,025 | 0,024 | 0,15 | 0,3 | 0,478 |
| SEQ ID NO: 300 | hsa-miR-519b-3p | aaagugcauccuuuuagagguu | 65,688 | 80,156 | 0,819 | -0,199 | 0,15 | 0,3 | 0,354 |
| SEQ ID NO: 706 | hsa-miR-1252 | agaaggaaauugaauucauuua | 61,141 | 84,563 | 0,723 | -0,324 | 0,15 | 0,3 | 0,380 |
| SEQ ID NO: 770 | hsa-miR-1285 | ucugggcacaaaagugagaccu | 298,891 | 307,953 | 0,971 | -0,030 | 0,15 | 0,3 | 0,416 |
| SEQ ID NO: 182 | hsa-miR-342-3p | ucucacacagaaaucgcacccgu | 3596,766 | 4186,395 | 0,859 | -0,152 | 0,15 | 0,31 | 0,378 |
| SEQ ID NO: 568 | hsa-miR-298 | agcagaagcaggaggguucuccca | 242,285 | 249,037 | 0,973 | -0,027 | 0,15 | 0,31 | 0,487 |
| SEQ ID NO: 77 | hsa-miR-1246 | aauggauuuuuggagcagg | 27,625 | 19,125 | 1,444 | 0,368 | 0,15 | 0,31 | 0,567 |
| SEQ ID NO: 62 | hsa-miR-433 | aucacauugggcuccugugu | 147,547 | 159,531 | 0,925 | -0,078 | 0,15 | 0,31 | 0,438 |
| SEQ ID NO: 838 | hsa-miR-527 | cugcaaaggaagcccuuuc. | 252,535 | 276,516 | 0,913 | -0,091 | 0,16 | 0,32 | 0,374 |
| SEQ ID NO: 492 | hsa-miR-296-5p | agggccccccucaauccgu | 343,078 | 265,949 | 1,290 | 0,255 | 0,16 | 0,32 | 0,643 |

FIG. 10A (Continued)

| SEQ ID NO | miRNA | sequence | median g1 | median g2 | qmedian | logemedian | raw pval | adj Pval | AUC |
|---|---|---|---|---|---|---|---|---|---|
| SEQ ID NO: 549 | hsa-miR-548l | aaaaguauuugcgguuuuguc | 14,344 | 27,656 | 0,519 | -0,657 | 0,16 | 0,32 | 0,376 |
| SEQ ID NO: 395 | hsa-miR-26a-2* | ccuauucuugauuacuuguuc | 10,484 | 33,344 | 0,314 | -1,157 | 0,16 | 0,32 | 0,360 |
| SEQ ID NO: 67 | hsa-miR-192 | cugaccuaugaauugacagcc | 4443,836 | 5205,789 | 0,854 | -0,158 | 0,16 | 0,32 | 0,353 |
| SEQ ID NO: 64 | hsa-miR-522 | aaaauguuccuuuagagugu | 54,938 | 44,250 | 1,242 | 0,216 | 0,16 | 0,32 | 0,603 |
| SEQ ID NO: 629 | hsa-miR-1270 | cuggagauauggaagagcugugu | 60,375 | 73,344 | 0,823 | -0,195 | 0,16 | 0,32 | 0,367 |
| SEQ ID NO: 92 | hsa-miR-138-2* | gcuauuucacgacacaggguu | 83,359 | 107,469 | 0,776 | -0,254 | 0,16 | 0,32 | 0,384 |
| SEQ ID NO: 188 | hsa-miR-146b-3p | ugcccuggacucaguucugg | 101,422 | 87,438 | 1,160 | 0,148 | 0,16 | 0,32 | 0,607 |
| SEQ ID NO: 591 | hsa-miR-190b | ugauaugutuugauauuggguu | 18,938 | 6,000 | 3,156 | 1,149 | 0,17 | 0,32 | 0,621 |
| SEQ ID NO: 654 | hsa-miR-940 | aaggcaggcgccccgccccc | 239,344 | 271,906 | 0,880 | -0,128 | 0,17 | 0,32 | 0,377 |
| SEQ ID NO: 542 | hsa-miR-149 | ucuggcucgugucucucacucc | 82,875 | 63,938 | 1,296 | 0,259 | 0,17 | 0,32 | 0,600 |
| SEQ ID NO: 96 | hsa-miR-548h | aaaauaaucgcgguuuuugc | 35,500 | 39,281 | 0,904 | -0,101 | 0,17 | 0,32 | 0,415 |
| SEQ ID NO: 234 | hsa-miR-874 | cugcccuggcccgagugaccga | 294,891 | 267,203 | 1,104 | 0,099 | 0,17 | 0,32 | 0,684 |
| SEQ ID NO: 450 | hsa-miR-320a | aaaagcugggtuugagagcga | 20868,719 | 1827,367 | 1,142 | 0,133 | 0,17 | 0,32 | 0,619 |
| SEQ ID NO: 781 | hsa-miR-634 | aaccagcaccccaacuugac | 184,500 | 217,375 | 0,849 | -0,164 | 0,17 | 0,33 | 0,390 |
| SEQ ID NO: 257 | hsa-miR-587 | uuuccauaggugaugagcac | 93,688 | 102,344 | 0,915 | -0,088 | 0,17 | 0,33 | 0,431 |
| SEQ ID NO: 208 | hsa-miR-379* | uauuaacaugguccacuaacu | 88,891 | 106,891 | 0,832 | -0,184 | 0,17 | 0,33 | 0,385 |
| SEQ ID NO: 546 | hsa-miR-486-5p | uccugacgagcugccccgag | 38923,641 | 38923,641 | 1,000 | 0,000 | 0,18 | 0,34 | 0,431 |
| SEQ ID NO: 432 | hsa-miR-651 | uuuaggauaagcugcugacuuuug | 32,719 | 19,375 | 1,689 | 0,524 | 0,18 | 0,34 | 0,620 |
| SEQ ID NO: 571 | hsa-miR-518c | caaagcgcuucucucuuuagagugu | 170,094 | 155,375 | 1,095 | 0,091 | 0,18 | 0,34 | 0,607 |
| SEQ ID NO: 342 | hsa-miR-1182 | gaggglucuuggggggaugugac | 59,516 | 43,625 | 1,364 | 0,311 | 0,18 | 0,34 | 0,612 |
| SEQ ID NO: 153 | hsa-miR-1324 | ccagacagaauucuaugcacuuc | 184,875 | 200,656 | 0,921 | -0,082 | 0,18 | 0,34 | 0,419 |
| SEQ ID NO: 694 | hsa-miR-1915 | ccccaggcgacgcggcgg | 923,578 | 910,625 | 1,014 | 0,014 | 0,18 | 0,34 | 0,588 |
| SEQ ID NO: 131 | hsa-miR-215 | augaccuaugaauugacagac | 508,645 | 442,156 | 1,150 | 0,140 | 0,18 | 0,34 | 0,602 |
| SEQ ID NO: 30 | hsa-miR-210 | cugugcgugugacagcggcuga | 1035,832 | 1247,510 | 0,830 | -0,186 | 0,18 | 0,34 | 0,384 |
| SEQ ID NO: 565 | hsa-miR-1913 | ucugccccuccgcugcugca | 340,891 | 364,984 | 0,934 | -0,068 | 0,18 | 0,35 | 0,458 |
| SEQ ID NO: 843 | hsa-miR-524-5p | cuacaaaggaagcacuuucuc | 102,531 | 106,219 | 0,965 | -0,035 | 0,18 | 0,35 | 0,427 |
| SEQ ID NO: 283 | hsa-miR-644 | aguuggcuuucuuagc | 51,563 | 43,438 | 1,187 | 0,171 | 0,18 | 0,35 | 0,619 |
| SEQ ID NO: 235 | hsa-miR-1911* | caccagcauugugucucc | 142,891 | 160,313 | 0,891 | -0,115 | 0,19 | 0,35 | 0,428 |
| SEQ ID NO: 421 | hsa-miR-379 | ugguagacuauggaacguagg | 52,531 | 53,156 | 0,988 | -0,012 | 0,19 | 0,35 | 0,424 |
| SEQ ID NO: 408 | hsa-miR-204 | uucccuuugucauccauugccu | 28,500 | 24,609 | 1,158 | 0,147 | 0,19 | 0,35 | 0,589 |
| SEQ ID NO: 608 | hsa-miR-1914 | cccugugcccggcccacuucug | 60,875 | 57,875 | 1,052 | 0,051 | 0,19 | 0,36 | 0,584 |

FIG. 10A (Continued)

| SEQ ID NO | miRNA | Sequence | median g1 | median g2 | g2/g1 median | log median | raw Pval | adj Pval | AUC |
|---|---|---|---|---|---|---|---|---|---|
| SEQ ID NO: 724 | hsa-miR-338-3p | uccagcaucagugauuuugug | 256,100 | 216,203 | 1,185 | 0,169 | 0,19 | 0,36 | 0,665 |
| SEQ ID NO: 653 | hsa-miR-760 | cggcucuggucuguggga | 79,750 | 59,188 | 1,347 | 0,298 | 0,19 | 0,36 | 0,626 |
| SEQ ID NO: 369 | hsa-miR-516a-3p | ugcuucccuuucagaggu | 43,125 | 52,469 | 0,822 | -0,196 | 0,2 | 0,36 | 0,350 |
| SEQ ID NO: 751 | hsa-miR-639 | aucgcuggcguugcgagcgcugu | 109,563 | 118,172 | 0,927 | -0,076 | 0,2 | 0,36 | 0,397 |
| SEQ ID NO: 78 | hsa-miR-338-5p | aacaauauccuggugcugagug | 81,313 | 87,828 | 0,926 | -0,077 | 0,2 | 0,36 | 0,426 |
| SEQ ID NO: 469 | hsa-miR-572 | guccgcuggcgguggcca | 171,094 | 139,281 | 1,228 | 0,206 | 0,2 | 0,36 | 0,616 |
| SEQ ID NO: 399 | hsa-miR-18b | uaaggugcaucuaguguguuag | 563,453 | 647,594 | 0,870 | -0,139 | 0,2 | 0,36 | 0,372 |
| SEQ ID NO: 744 | hsa-miR-1178 | uugcucacuguucucccuag | 59,516 | 70,938 | 0,839 | -0,176 | 0,2 | 0,36 | 0,443 |
| SEQ ID NO: 520 | hsa-miR-573 | cugaagugaugugugueacugaucag | 88,078 | 102,750 | 0,857 | -0,154 | 0,2 | 0,37 | 0,367 |
| SEQ ID NO: 588 | hsa-miR-224 | caagucacuaguuggcauucguu | 77,875 | 55,875 | 1,394 | 0,332 | 0,2 | 0,37 | 0,627 |
| SEQ ID NO: 111 | hsa-miR-20b* | acuaguauggcacuuccag | 142,406 | 149,141 | 0,955 | -0,046 | 0,21 | 0,37 | 0,386 |
| SEQ ID NO: 462 | hsa-miR-218-1* | augguuccgucaagcaccaugg | 163,234 | 171,109 | 0,954 | -0,047 | 0,21 | 0,37 | 0,420 |
| SEQ ID NO: 848 | hsa-miR-155 | uuaaugcuaaucgugauaagggu | 162,938 | 143,781 | 1,133 | 0,125 | 0,21 | 0,37 | 0,661 |
| SEQ ID NO: 69 | hsa-miR-151-5p | ucgaggagcucacagcuagu | 5683,617 | 6825,539 | 0,833 | -0,183 | 0,21 | 0,38 | 0,393 |
| SEQ ID NO: 206 | hsa-miR-346 | ugucugcccgcaugccugccucu | 116,250 | 130,656 | 0,890 | -0,117 | 0,21 | 0,38 | 0,383 |
| SEQ ID NO: 381 | hsa-miR-1293 | uggguguccuggagauuugug | 63,484 | 58,188 | 1,091 | 0,087 | 0,21 | 0,39 | 0,612 |
| SEQ ID NO: 580 | hsa-miR-1260 | auccacucucugccaca | 2027,289 | 2522,371 | 0,804 | -0,218 | 0,22 | 0,39 | 0,377 |
| SEQ ID NO: 374 | hsa-miR-512-5p | cacucagccuugaggcacuuc | 125,750 | 120,438 | 1,044 | 0,043 | 0,22 | 0,39 | 0,589 |
| SEQ ID NO: 288 | hsa-miR-1538 | cggccggcugcucugcugucu | 133,328 | 131,188 | 1,016 | 0,016 | 0,22 | 0,39 | 0,579 |
| SEQ ID NO: 2 | hsa-miR-423-5p | ugagggcagagagcgagacuuu | 5000,809 | 3412,176 | 1,466 | 0,382 | 0,22 | 0,39 | 0,620 |
| SEQ ID NO: 846 | hsa-miR-637 | acuggggcuuuucgggcucugcgu | 63,938 | 53,719 | 1,190 | 0,174 | 0,22 | 0,39 | 0,601 |
| SEQ ID NO: 731 | hsa-miR-1471 | gccgcguguggagccagugu | 179,625 | 202,219 | 0,888 | -0,118 | 0,22 | 0,39 | 0,381 |
| SEQ ID NO: 598 | hsa-miR-125a-3p | acaggugaggguucuuggagcc | 60,938 | 73,109 | 0,834 | -0,182 | 0,22 | 0,39 | 0,383 |
| SEQ ID NO: 709 | hsa-miR-96 | uuuggcacuagcacauuuugcu | 388,156 | 322,922 | 1,202 | 0,184 | 0,22 | 0,39 | 0,684 |
| SEQ ID NO: 648 | hsa-miR-454* | acccuauacauauugucucgc | 81,875 | 51,031 | 1,604 | 0,473 | 0,22 | 0,39 | 0,643 |
| SEQ ID NO: 59 | hsa-miR-602 | gacacgggcgacagcugcggcc | 175,281 | 223,578 | 0,784 | -0,243 | 0,23 | 0,4 | 0,376 |
| SEQ ID NO: 10 | hsa-miR-324-3p | acuugccccagugucugcugg | 873,297 | 911,125 | 0,958 | -0,042 | 0,23 | 0,4 | 0,450 |
| SEQ ID NO: 148 | hsa-miR-645 | ucuaggcguguacucuga | 100,875 | 120,156 | 0,840 | -0,175 | 0,23 | 0,4 | 0,411 |
| SEQ ID NO: 25 | hsa-miR-604 | aggcugcggaauucaggac | 126,750 | 135,813 | 0,933 | -0,069 | 0,23 | 0,4 | 0,434 |
| SEQ ID NO: 171 | hsa-miR-214* | ugccugucuacacuugcugugc | 104,438 | 119,922 | 0,871 | -0,138 | 0,23 | 0,4 | 0,418 |
| SEQ ID NO: 570 | hsa-miR-412 | acuucaccuguccacuagccgu | 99,703 | 105,031 | 0,949 | -0,052 | 0,23 | 0,41 | 0,413 |

FIG. 10A (Continued)

| SEQ ID NO | miRNA | Sequence | median g1 | median g2 | qmedian | logqmedian | raw.Pval | adj.Pval | AUC |
|---|---|---|---|---|---|---|---|---|---|
| SEQ ID NO: 860 | hsa-miR-1265 | caggauguggucaaguguguu | 42,469 | 37,375 | 1,136 | 0,128 | 0,24 | 0,41 | 0,554 |
| SEQ ID NO: 40 | hsa-miR-363* | cggguggaucacgaugaauuu | 156,781 | 126,813 | 1,236 | 0,212 | 0,23 | 0,41 | 0,599 |
| SEQ ID NO: 849 | hsa-miR-664* | acuggcuaggggaaaaugauuggau | 103,047 | 128,313 | 0,803 | -0,219 | 0,24 | 0,41 | 0,375 |
| SEQ ID NO: 142 | hsa-miR-554 | gcuagccugacucagccagu | 167,799 | 204,109 | 0,822 | -0,196 | 0,24 | 0,41 | 0,380 |
| SEQ ID NO: 295 | hsa-miR-411* | uauguaacacgguccacuaacc | 102,938 | 114,469 | 0,899 | -0,106 | 0,24 | 0,41 | 0,401 |
| SEQ ID NO: 329 | hsa-miR-219-1-3p | agaguugaguccggacguccg | 79,438 | 93,281 | 0,852 | -0,161 | 0,24 | 0,41 | 0,396 |
| SEQ ID NO: 678 | hsa-miR-671-3p | uccgguccucagggccuccacc | 81,156 | 75,656 | 1,073 | 0,070 | 0,24 | 0,41 | 0,634 |
| SEQ ID NO: 680 | hsa-miR-19b-2* | aguuuugcagguuugcauuuca | 27,875 | 38,906 | 0,716 | -0,333 | 0,24 | 0,42 | 0,416 |
| SEQ ID NO: 759 | hsa-miR-30a* | cuuucagucggauuguugcagc | 78,516 | 91,156 | 0,861 | -0,149 | 0,24 | 0,42 | 0,395 |
| SEQ ID NO: 736 | hsa-miR-10b | uacccuguagaaccgaauuugug | 105,375 | 114,391 | 0,921 | -0,082 | 0,24 | 0,42 | 0,417 |
| SEQ ID NO: 440 | hsa-miR-520d-3p | aaagugcuucucuuugguggu | 18,094 | 15,547 | 1,164 | 0,152 | 0,24 | 0,42 | 0,585 |
| SEQ ID NO: 478 | hsa-miR-29a* | acugauuucuuuuguguucag | 42,266 | 46,188 | 0,915 | -0,089 | 0,25 | 0,42 | 0,377 |
| SEQ ID NO: 610 | hsa-miR-135b* | auuagggcuaaaagccaugg | 90,969 | 98,391 | 0,925 | -0,078 | 0,25 | 0,42 | 0,394 |
| SEQ ID NO: 732 | hsa-miR-150 | cugguacaggccugggggacag | 167,844 | 135,609 | 1,238 | 0,213 | 0,25 | 0,42 | 0,603 |
| SEQ ID NO: 203 | hsa-miR-569 | aguuaaugaauccuggaaagu | 60,938 | 63,109 | 0,966 | -0,035 | 0,25 | 0,42 | 0,415 |
| SEQ ID NO: 38 | hsa-miR-339-3p | ugagcgccucgacgacagaggcg | 409,547 | 375,109 | 1,092 | 0,088 | 0,25 | 0,42 | 0,539 |
| SEQ ID NO: 833 | hsa-miR-1208 | ucacguucagacaggcgga | 158,344 | 169,891 | 0,932 | -0,070 | 0,25 | 0,42 | 0,392 |
| SEQ ID NO: 797 | hsa-miR-203 | gugaaauguuuaggaccacuag | 52,719 | 60,438 | 0,872 | -0,137 | 0,25 | 0,43 | 0,365 |
| SEQ ID NO: 776 | hsa-miR-614 | gaaccgccuguuccuugccaggugg | 82,719 | 98,422 | 0,840 | -0,174 | 0,25 | 0,43 | 0,413 |
| SEQ ID NO: 664 | hsa-miR-381 | uauacaagggcaagcucucugu | 169,063 | 171,109 | 0,988 | -0,012 | 0,25 | 0,43 | 0,419 |
| SEQ ID NO: 426 | hsa-miR-31 | aggcaagaugcuggcauagcu | 238,875 | 240,156 | 0,995 | -0,005 | 0,26 | 0,43 | 0,413 |
| SEQ ID NO: 536 | hsa-miR-138 | agcuggugugugaaucaggccg | 99,000 | 89,000 | 1,112 | 0,106 | 0,26 | 0,43 | 0,597 |
| SEQ ID NO: 721 | hsa-miR-886-3p | cgcgguugcuuuacgaccccu | 66,438 | 53,719 | 1,237 | 0,212 | 0,26 | 0,43 | 0,558 |
| SEQ ID NO: 735 | hsa-miR-320d | aaaagcuggguugagagga | 923,578 | 845,186 | 1,093 | 0,089 | 0,26 | 0,43 | 0,495 |
| SEQ ID NO: 189 | hsa-miR-520b | aaagugcuuccuuuuagaggg | 61,297 | 57,219 | 1,071 | 0,069 | 0,26 | 0,43 | 0,583 |
| SEQ ID NO: 29 | hsa-miR-1248 | accuucuuguauaagcacacugugcuaaa | 106,594 | 88,094 | 1,210 | 0,191 | 0,26 | 0,43 | 0,626 |
| SEQ ID NO: 223 | hsa-let-7g* | uagaguuacaccgggagaua | 82,875 | 67,438 | 1,229 | 0,206 | 0,26 | 0,43 | 0,595 |
| SEQ ID NO: 829 | hsa-miR-608 | aggggugguuggacagcugccgu | 120,422 | 102,344 | 1,177 | 0,163 | 0,26 | 0,43 | 0,620 |
| SEQ ID NO: 506 | hsa-miR-26a-1* | ccuauucuggaguuacucugcacg | 40,094 | 53,563 | 0,749 | -0,290 | 0,27 | 0,44 | 0,382 |
| SEQ ID NO: 393 | hsa-miR-876-5p | uggauuucuuuguguaaucacca | 66,438 | 80,156 | 0,829 | -0,188 | 0,27 | 0,45 | 0,398 |
| SEQ ID NO: 310 | hsa-miR-520h | acaaagugcuuccccuuuagagu | 88,031 | 76,375 | 1,153 | 0,142 | 0,27 | 0,45 | 0,613 |

FIG. 10A (Continued)

| SEQ ID NO | miRNA | Sequence | median_q1 | median_avg2 | median | log median | raw_var | adj_Pval | AUC |
|---|---|---|---|---|---|---|---|---|---|
| SEQ ID NO: 346 | hsa-miR-645* | ucaguaaauguuuauuagauga | 61,844 | 76,625 | 0,807 | -0,214 | 0,28 | 0,45 | 0,387 |
| SEQ ID NO: 8 | hsa-miR-19a | ugugcaaaucuaugcaaaacuga | 3109,006 | 2951,227 | 1,053 | 0,052 | 0,28 | 0,45 | 0,607 |
| SEQ ID NO: 535 | hsa-miR-1276 | uaaagagcccguggagaca | 84,625 | 95,781 | 0,884 | -0,124 | 0,28 | 0,45 | 0,411 |
| SEQ ID NO: 238 | hsa-miR-15b | uagcagcacaucaugguuuaca | 13747,000 | 14869,586 | 0,925 | -0,078 | 0,28 | 0,45 | 0,387 |
| SEQ ID NO: 226 | hsa-miR-514 | auugacacuucugugaguaga | 87,891 | 100,813 | 0,872 | -0,137 | 0,28 | 0,45 | 0,364 |
| SEQ ID NO: 373 | hsa-miR-520d-5p | cuacaaaggaagcccuuuc | 120,156 | 123,688 | 0,971 | -0,029 | 0,28 | 0,45 | 0,400 |
| SEQ ID NO: 319 | hsa-miR-220b | ccaccaccgugucugacauu | 96,828 | 75,875 | 1,276 | 0,244 | 0,28 | 0,45 | 0,622 |
| SEQ ID NO: 312 | hsa-miR-551b* | gaaaucaagcguggugagacc | 118,969 | 108,250 | 1,099 | 0,094 | 0,28 | 0,46 | 0,572 |
| SEQ ID NO: 382 | hsa-miR-372 | uauggcugcgacauuugagcgu | 70,859 | 84,141 | 0,842 | -0,172 | 0,28 | 0,46 | 0,384 |
| SEQ ID NO: 683 | hsa-miR-135a | uauggcuuuuuauuccuaguga | 18,469 | 24,953 | 0,740 | -0,301 | 0,28 | 0,46 | 0,474 |
| SEQ ID NO: 296 | hsa-miR-424 | cagcagcaaucaugguuugaa | 366,547 | 329,953 | 1,111 | 0,105 | 0,29 | 0,46 | 0,589 |
| SEQ ID NO: 113 | hsa-miR-517a | aucgugcauccuuuagagugu | 78,188 | 94,375 | 0,828 | -0,188 | 0,29 | 0,46 | 0,366 |
| SEQ ID NO: 471 | hsa-miR-936 | acaguagaggaagaaucgcag | 97,406 | 92,250 | 1,056 | 0,054 | 0,29 | 0,46 | 0,430 |
| SEQ ID NO: 317 | hsa-miR-211 | uuccuuugucauccuucgccu | 13,375 | 23,500 | 0,569 | -0,564 | 0,29 | 0,46 | 0,411 |
| SEQ ID NO: 802 | hsa-miR-526b* | gaaagcuuccugugugcauuuagagc | 41,078 | 51,281 | 0,801 | -0,222 | 0,29 | 0,46 | 0,411 |
| SEQ ID NO: 783 | hsa-miR-941 | cacccggcugugugcacaugug | 173,906 | 181,688 | 0,957 | -0,044 | 0,29 | 0,47 | 0,569 |
| SEQ ID NO: 863 | hsa-miR-150 | ucucccaacccuuugaccagug | 2736,684 | 2186,016 | 1,252 | 0,225 | 0,29 | 0,47 | 0,632 |
| SEQ ID NO: 46 | hsa-miR-374a | uuauaauacaaccugauaagug | 472,641 | 533,855 | 0,885 | -0,122 | 0,29 | 0,47 | 0,429 |
| SEQ ID NO: 755 | hsa-miR-1306 | acguuggcucuggugug | 39,844 | 47,844 | 0,833 | -0,183 | 0,3 | 0,47 | 0,454 |
| SEQ ID NO: 367 | hsa-miR-653 | guguugaaaucuucucuacg | 71,391 | 88,594 | 0,806 | -0,216 | 0,3 | 0,47 | 0,362 |
| SEQ ID NO: 161 | hsa-miR-181a* | accaucgaccguugauuguacc | 146,813 | 127,813 | 1,149 | 0,139 | 0,3 | 0,47 | 0,579 |
| SEQ ID NO: 252 | hsa-miR-548b-5p | aaaaguaauuguguuuuggcc | 20,172 | 37,625 | 0,536 | -0,623 | 0,3 | 0,47 | 0,346 |
| SEQ ID NO: 262 | hsa-miR-194* | ccaguggggcugcuguuaucug | 115,422 | 100,297 | 1,151 | 0,140 | 0,3 | 0,48 | 0,605 |
| SEQ ID NO: 822 | hsa-miR-875-3p | ccuggaaacacugaggguugu | 81,500 | 87,750 | 0,929 | -0,074 | 0,31 | 0,48 | 0,430 |
| SEQ ID NO: 484 | hsa-miR-519b-5p | cucuagaggaagcgcuuucug | 253,035 | 262,354 | 0,964 | -0,036 | 0,31 | 0,48 | 0,432 |
| SEQ ID NO: 837 | hsa-miR-409-3p | gaauugucggaaccccu | 140,125 | 93,656 | 1,496 | 0,403 | 0,31 | 0,49 | 0,638 |
| SEQ ID NO: 437 | hsa-miR-302a | uaagugcuuccauguuuugguga | 29,328 | 30,313 | 0,968 | -0,033 | 0,31 | 0,49 | 0,447 |
| SEQ ID NO: 553 | hsa-miR-99b | cacccguagaaccgaccuugcg | 230,953 | 195,078 | 1,184 | 0,169 | 0,32 | 0,49 | 0,615 |
| SEQ ID NO: 353 | hsa-miR-876-3p | uggguuuacaaaguaauuca | 49,656 | 50,063 | 0,992 | -0,008 | 0,32 | 0,49 | 0,553 |
| SEQ ID NO: 352 | hsa-miR-455-5p | uaugugccuuuggacuacaucg | 47,344 | 57,281 | 0,827 | -0,191 | 0,32 | 0,49 | 0,392 |
| SEQ ID NO: 815 | hsa-miR-1274b | uccuguucgggcgcca | 1288,578 | 1287,377 | 1,001 | 0,001 | 0,32 | 0,49 | 0,561 |

FIG. 10A (Continued)

| SEQ ID NO | miRNA | sequence | mean.ang.1 | median.a.2 | median | LogMedian | Raw.Pval | adj.Pval | AUC |
|---|---|---|---|---|---|---|---|---|---|
| SEQ ID NO: 265 | hsa-miR-493 | ugaaggucuacuguguccagg | 82,719 | 65,875 | 1,256 | 0,228 | 0,32 | 0,49 | 0,647 |
| SEQ ID NO: 581 | hsa-miR-1281 | ucgccucccucuccc | 247,281 | 126,188 | 1,960 | 0,673 | 0,32 | 0,49 | 0,700 |
| SEQ ID NO: 376 | hsa-miR-921 | cuaguagggacagaaccaggauuc | 133,031 | 120,641 | 1,103 | 0,098 | 0,32 | 0,49 | 0,551 |
| SEQ ID NO: 720 | hsa-miR-146b-5p | ugagaacugaauuccauaggcu | 257,480 | 198,500 | 1,297 | 0,260 | 0,32 | 0,49 | 0,601 |
| SEQ ID NO: 32 | hsa-miR-453 | agguugucgguggugaguccga | 47,438 | 57,938 | 0,819 | -0,200 | 0,32 | 0,49 | 0,425 |
| SEQ ID NO: 739 | hsa-miR-641 | aaagacauaggaugagaguccuc | 90,969 | 105,031 | 0,866 | -0,144 | 0,32 | 0,49 | 0,372 |
| SEQ ID NO: 354 | hsa-miR-373* | acucaaaauggggcguuuc | 59,891 | 64,438 | 0,929 | -0,073 | 0,32 | 0,49 | 0,403 |
| SEQ ID NO: 555 | hsa-miR-200a | uaacacugucuguaagaugu | 164,094 | 184,703 | 0,888 | -0,118 | 0,32 | 0,5 | 0,364 |
| SEQ ID NO: 332 | hsa-miR-323-3p | cacauuacagguccgaccucu | 105,031 | 123,219 | 0,852 | -0,160 | 0,33 | 0,5 | 0,446 |
| SEQ ID NO: 403 | hsa-miR-626 | agcugucugaaaugucau | 67,047 | 73,906 | 0,907 | -0,097 | 0,33 | 0,5 | 0,436 |
| SEQ ID NO: 855 | hsa-miR-519a* | cucuagagggaagcguuucug | 260,965 | 270,137 | 0,966 | -0,035 | 0,33 | 0,5 | 0,419 |
| SEQ ID NO: 222 | hsa-miR-135b | uauggcuuuucauuccuaugagcu | 62,500 | 46,125 | 1,355 | 0,304 | 0,33 | 0,5 | 0,622 |
| SEQ ID NO: 775 | hsa-miR-769-5p | ugagaccucugggguucgagcu | 61,266 | 42,594 | 1,438 | 0,364 | 0,34 | 0,51 | 0,589 |
| SEQ ID NO: 26 | hsa-miR-423-3p | agcucgguucgaggcccccagu | 1582,602 | 1677,063 | 0,944 | -0,058 | 0,34 | 0,51 | 0,427 |
| SEQ ID NO: 258 | hsa-miR-624 | cacaagguauuggguauuaccu | 129,813 | 124,344 | 1,044 | 0,043 | 0,34 | 0,52 | 0,555 |
| SEQ ID NO: 676 | hsa-miR-596 | aagccugccggucgucucggg | 155,469 | 144,609 | 1,075 | 0,072 | 0,35 | 0,52 | 0,566 |
| SEQ ID NO: 663 | hsa-miR-299-3p | uauguggauguguaaaccgccuu | 34,266 | 37,906 | 0,904 | -0,101 | 0,35 | 0,52 | 0,407 |
| SEQ ID NO: 318 | hsa-miR-1304 | uuugaggcuacagugagaugug | 101,609 | 122,313 | 0,831 | -0,185 | 0,35 | 0,52 | 0,311 |
| SEQ ID NO: 515 | hsa-miR-539 | ggagaauuaucccuuggugugu | 41,000 | 44,125 | 0,929 | -0,073 | 0,35 | 0,52 | 0,527 |
| SEQ ID NO: 830 | hsa-miR-1279 | ucauaaugcuucuuucu | 39,391 | 40,531 | 0,972 | -0,029 | 0,35 | 0,53 | 0,437 |
| SEQ ID NO: 330 | hsa-miR-220a | ccacaccguaucgacacuu | 111,391 | 105,625 | 1,055 | 0,053 | 0,35 | 0,53 | 0,580 |
| SEQ ID NO: 406 | hsa-miR-9 | ucuuuggguuaucuagcuguaga | 54,844 | 59,672 | 0,919 | -0,084 | 0,35 | 0,53 | 0,416 |
| SEQ ID NO: 661 | hsa-miR-26b* | ccuguucuccauuacuuggcuc | 60,422 | 47,125 | 1,282 | 0,249 | 0,35 | 0,53 | 0,565 |
| SEQ ID NO: 765 | hsa-miR-196a | uaggiaguuucauguuguuggg | 9,750 | 21,781 | 0,448 | -0,804 | 0,36 | 0,54 | 0,354 |
| SEQ ID NO: 362 | hsa-miR-513a-5p | uucacaggagggugcau | 66,422 | 81,906 | 0,811 | -0,210 | 0,36 | 0,54 | 0,420 |
| SEQ ID NO: 247 | hsa-miR-193a-3p | aacuggccuacaagucccagu | 275,766 | 242,801 | 1,136 | 0,127 | 0,37 | 0,55 | 0,612 |
| SEQ ID NO: 117 | hsa-miR-411 | uaguagaccguauagcguacg | 111,719 | 118,422 | 0,943 | -0,058 | 0,38 | 0,55 | 0,430 |
| SEQ ID NO: 162 | hsa-miR-218-2* | cauguucgugagaucgaauuugug | 121,156 | 129,188 | 0,938 | -0,064 | 0,38 | 0,55 | 0,417 |
| SEQ ID NO: 689 | hsa-miR-10a | uacccuguagauccgaauuugug | 70,734 | 89,344 | 0,792 | -0,234 | 0,38 | 0,56 | 0,399 |
| SEQ ID NO: 271 | hsa-miR-198 | gguccagggguagauaggguuc | 104,781 | 91,094 | 1,150 | 0,140 | 0,38 | 0,56 | 0,614 |
| SEQ ID NO: 109 | hsa-miR-652 | aauggcgccacuaggguugug | 2146,648 | 2399,334 | 0,895 | -0,111 | 0,39 | 0,57 | 0,411 |

FIG. 10A (Continued)

| SEQ ID NO | miRNA | Sequence | median_H | median_K | gmedian_H | gmedian_K | FWER_adj_pval | AUC |
|---|---|---|---|---|---|---|---|---|
| SEQ ID NO: 459 | hsa-miR-802 | caguaacaaagauucaucccuugu | 131,906 | 164,594 | 0,801 | -0,221 | 0,39 | 0,57 | 0,383 |
| SEQ ID NO: 516 | hsa-miR-520a-3p | aaagugcuucccuuuggacugu | 34,813 | 30,469 | 1,143 | 0,133 | 0,39 | 0,57 | 0,570 |
| SEQ ID NO: 853 | hsa-miR-129* | aagcccuuaccccaaaaaguau | 96,828 | 114,969 | 0,842 | -0,172 | 0,39 | 0,57 | 0,409 |
| SEQ ID NO: 496 | hsa-miR-330-5p | ucucggcccguguguguaggc | 82,219 | 60,500 | 1,359 | 0,307 | 0,4 | 0,58 | 0,585 |
| SEQ ID NO: 139 | hsa-miR-378 | acuggacuggagucagaagg | 524,176 | 410,141 | 1,278 | 0,245 | 0,4 | 0,58 | 0,605 |
| SEQ ID NO: 590 | hsa-miR-301b | cagugcaaugauauugucaaagc | 229,281 | 261,775 | 0,876 | -0,133 | 0,4 | 0,58 | 0,405 |
| SEQ ID NO: 339 | hsa-miR-888 | uacucaaaaagcugucaguca | 108,719 | 131,438 | 0,827 | -0,190 | 0,4 | 0,58 | 0,427 |
| SEQ ID NO: 368 | hsa-miR-767-3p | ucugcucuaaccccaugguuucu | 69,781 | 86,625 | 0,806 | -0,216 | 0,4 | 0,58 | 0,394 |
| SEQ ID NO: 83 | hsa-miR-611 | gcgaggaccccucgggucugac | 154,656 | 139,344 | 1,110 | 0,104 | 0,4 | 0,58 | 0,566 |
| SEQ ID NO: 27 | hsa-miR-93* | acugcagcuagcacuuccg | 1645,012 | 1322,637 | 1,244 | 0,218 | 0,4 | 0,58 | 0,532 |
| SEQ ID NO: 199 | hsa-miR-19b-1* | aguuuugcagguuugcauccagc | 110,469 | 128,453 | 0,860 | -0,151 | 0,41 | 0,59 | 0,417 |
| SEQ ID NO: 397 | hsa-miR-199a-3p | acaguagucugcacauggua | 180,750 | 165,688 | 1,091 | 0,087 | 0,41 | 0,59 | 0,587 |
| SEQ ID NO: 693 | hsa-miR-510 | uacucaggagagugcaaucac | 124,328 | 135,859 | 0,915 | -0,089 | 0,41 | 0,59 | 0,469 |
| SEQ ID NO: 351 | hsa-miR-200b | uaauacugccugguaaugauga | 100,688 | 106,547 | 0,945 | -0,057 | 0,41 | 0,59 | 0,430 |
| SEQ ID NO: 5 | hsa-miR-22 | aagcugccaguugaagaacugu | 5683,617 | 6505,273 | 0,874 | -0,135 | 0,41 | 0,59 | 0,413 |
| SEQ ID NO: 684 | hsa-miR-331-5p | cuagguauggucccagggaucc | 107,016 | 93,813 | 1,141 | 0,132 | 0,41 | 0,59 | 0,552 |
| SEQ ID NO: 207 | hsa-miR-506 | uaaggcaccccuucgaguaga | 109,719 | 115,969 | 0,946 | -0,055 | 0,41 | 0,59 | 0,436 |
| SEQ ID NO: 375 | hsa-miR-374a* | cuuaucagauuguauuguaauu | 100,281 | 107,609 | 0,932 | -0,071 | 0,42 | 0,59 | 0,413 |
| SEQ ID NO: 292 | hsa-miR-1827 | ugaggcaguagauugaau | 73,094 | 74,734 | 0,978 | -0,022 | 0,42 | 0,59 | 0,430 |
| SEQ ID NO: 652 | hsa-miR-593 | ugucucugccugggguuucu | 20,875 | 25,391 | 0,822 | -0,196 | 0,42 | 0,6 | 0,423 |
| SEQ ID NO: 810 | hsa-miR-1236 | ccuaucccccuugucucuccag | 65,969 | 53,594 | 1,231 | 0,208 | 0,42 | 0,6 | 0,585 |
| SEQ ID NO: 167 | hsa-miR-1277 | uacguagauauauaugguauuu | 114,969 | 108,719 | 1,057 | 0,056 | 0,42 | 0,6 | 0,587 |
| SEQ ID NO: 766 | hsa-miR-1296 | uuaagggcccuggcuccaucc | 126,453 | 104,219 | 1,213 | 0,193 | 0,42 | 0,6 | 0,649 |
| SEQ ID NO: 764 | hsa-miR-7-1* | caacaaaucacagucugccaua | 417,656 | 398,828 | 1,047 | 0,046 | 0,42 | 0,6 | 0,509 |
| SEQ ID NO: 700 | hsa-miR-890 | uacuuggaaggcucagaguug | 77,688 | 71,063 | 1,093 | 0,089 | 0,43 | 0,6 | 0,452 |
| SEQ ID NO: 811 | hsa-miR-495 | aaacaaacaugguugcacuuu | 145,938 | 167,500 | 0,871 | -0,138 | 0,43 | 0,6 | 0,421 |
| SEQ ID NO: 191 | hsa-miR-520g | acaaagugcuucccuuuagagugu | 103,781 | 115,969 | 0,895 | -0,111 | 0,43 | 0,6 | 0,415 |
| SEQ ID NO: 246 | hsa-miR-181c* | aaccaucgaccguugagaggac | 136,016 | 125,281 | 1,086 | 0,082 | 0,43 | 0,6 | 0,595 |
| SEQ ID NO: 150 | hsa-miR-302b* | acuuuaacauggaagucuuuc | 84,797 | 84,453 | 1,004 | 0,004 | 0,43 | 0,6 | 0,497 |
| SEQ ID NO: 132 | hsa-miR-147b | gugugggaaaugcuucugca | 104,125 | 96,328 | 1,081 | 0,078 | 0,43 | 0,6 | 0,455 |
| SEQ ID NO: 105 | hsa-miR-1204 | ucguggccuggucccauuau | 36,875 | 40,047 | 0,921 | -0,083 | 0,43 | 0,6 | 0,519 |

FIG. 10A (Continued)

| SEQ ID NO | miRNA | Sequence | median_gr1 | median_gr2 | qmedian | logqmedian | raw_p.val | adj_p.val | AUC |
|---|---|---|---|---|---|---|---|---|---|
| SEQ ID NO: 474 | hsa-miR-182* | ugguucuagacuugccaacua | 127,938 | 108,219 | 1,182 | 0,167 | 0,43 | 0,6 | 0,594 |
| SEQ ID NO: 282 | hsa-miR-384 | auuccuagaaauuguucaua | 182,375 | 154,563 | 1,180 | 0,165 | 0,44 | 0,6 | 0,586 |
| SEQ ID NO: 686 | hsa-miR-640 | augauccaggaaccugcccuu | 188,531 | 200,547 | 0,940 | -0,062 | 0,44 | 0,6 | 0,431 |
| SEQ ID NO: 752 | hsa-miR-518d-3p | caaagcgcuuccouuuggagc | 138,328 | 146,813 | 0,942 | -0,060 | 0,44 | 0,61 | 0,471 |
| SEQ ID NO: 276 | hsa-miR-586 | uaugcauuguauuuuuaggucc | 54,000 | 77,375 | 0,698 | -0,360 | 0,44 | 0,61 | 0,330 |
| SEQ ID NO: 270 | hsa-miR-523* | cucuagaggaagcgcuuucug | 235,594 | 250,195 | 0,942 | -0,060 | 0,45 | 0,61 | 0,419 |
| SEQ ID NO: 366 | hsa-miR-369-5p | agaucgacgguguauauucgc | 55,438 | 64,578 | 0,858 | -0,153 | 0,45 | 0,61 | 0,435 |
| SEQ ID NO: 215 | hsa-miR-632 | gugucugcuuccugugga | 72,813 | 74,813 | 0,973 | -0,027 | 0,45 | 0,62 | 0,494 |
| SEQ ID NO: 163 | hsa-miR-371-3p | aagugccgccaucuuuugagugu | 84,453 | 88,078 | 0,959 | -0,042 | 0,45 | 0,62 | 0,435 |
| SEQ ID NO: 604 | hsa-miR-496 | ugaguauacauggccaaucuc | 176,703 | 174,781 | 1,011 | 0,011 | 0,45 | 0,62 | 0,468 |
| SEQ ID NO: 412 | hsa-miR-7-2* | caacaaauccagucuacuaa | 70,953 | 63,500 | 1,117 | 0,111 | 0,45 | 0,62 | 0,580 |
| SEQ ID NO: 157 | hsa-miR-665 | acaggggcugaggcccou | 199,156 | 195,625 | 1,018 | 0,018 | 0,46 | 0,62 | 0,562 |
| SEQ ID NO: 672 | hsa-miR-1267 | ccuguguaaguguaauccca | 72,281 | 80,141 | 0,902 | -0,103 | 0,47 | 0,64 | 0,438 |
| SEQ ID NO: 670 | hsa-miR-627 | gugacucucuaagaaaagagga | 370,391 | 288,438 | 1,284 | 0,250 | 0,47 | 0,64 | 0,774 |
| SEQ ID NO: 12 | hsa-miR-25 | cauugcacuuguucucuga | 8255,773 | 6994,664 | 1,180 | 0,166 | 0,48 | 0,65 | 0,631 |
| SEQ ID NO: 614 | hsa-miR-485-3p | gucauacacggcuucucucu | 111,844 | 130,438 | 0,857 | -0,154 | 0,48 | 0,65 | 0,531 |
| SEQ ID NO: 391 | hsa-miR-548d-5p | aaaaguaauugugguuuuugcc | 20,438 | 20,438 | 1,000 | 0,000 | 0,48 | 0,65 | 0,543 |
| SEQ ID NO: 567 | hsa-miR-371-5p | acucaacugugggggcacu | 81,156 | 75,547 | 1,074 | 0,072 | 0,48 | 0,65 | 0,539 |
| SEQ ID NO: 712 | hsa-miR-548c-5p | aaaaguaauugcguuuuugc | 39,391 | 43,719 | 0,901 | -0,104 | 0,48 | 0,65 | 0,441 |
| SEQ ID NO: 4 | hsa-let-7d | agagguaguaggguugcauagu | 4027,828 | 4193,930 | 0,960 | -0,040 | 0,49 | 0,65 | 0,459 |
| SEQ ID NO: 326 | hsa-miR-887 | gugaacgggcgccauccegagg | 213,625 | 186,953 | 1,143 | 0,133 | 0,49 | 0,65 | 0,574 |
| SEQ ID NO: 328 | hsa-miR-1537 | aaaacgcucuaguuacaguugu | 94,281 | 79,688 | 1,183 | 0,168 | 0,49 | 0,66 | 0,592 |
| SEQ ID NO: 190 | hsa-miR-449b | aggcaguguauugguuagcugc | 92,656 | 95,188 | 0,973 | -0,027 | 0,5 | 0,67 | 0,534 |
| SEQ ID NO: 174 | hsa-miR-522* | cucuagaggaagcgcuuucug | 239,188 | 249,070 | 0,960 | -0,040 | 0,5 | 0,67 | 0,480 |
| SEQ ID NO: 423 | hsa-miR-518d-5p | cucuagaggaagcacuuuucug | 261,387 | 292,324 | 0,894 | -0,112 | 0,5 | 0,67 | 0,462 |
| SEQ ID NO: 278 | hsa-miR-517b | ucgugcauccuuuagagugu | 70,906 | 62,797 | 1,129 | 0,121 | 0,5 | 0,67 | 0,576 |
| SEQ ID NO: 240 | hsa-miR-125b-2* | ucacaagucaggcucuuggac | 60,484 | 80,906 | 0,748 | -0,291 | 0,5 | 0,67 | 0,388 |
| SEQ ID NO: 173 | hsa-miR-302f | uaauugcuccauguuu | 24,813 | 24,281 | 1,022 | 0,022 | 0,5 | 0,67 | 0,436 |
| SEQ ID NO: 251 | hsa-miR-545 | ucagcaaacauuuauugugc | 177,250 | 195,344 | 0,907 | -0,097 | 0,51 | 0,67 | 0,413 |
| SEQ ID NO: 808 | hsa-miR-197 | uucaccaccuucuccaccagc | 761,898 | 644,236 | 1,183 | 0,168 | 0,51 | 0,67 | 0,581 |
| SEQ ID NO: 587 | hsa-miR-218 | uugugcuugaucuaaccaugu | 61,297 | 74,625 | 0,821 | -0,197 | 0,51 | 0,68 | 0,395 |

FIG. 10A (Continued)

| SEQ ID NO | miRNA | Sequence | median_g1 | median_g2 | qmedian | logmedian | rawPval | aucPval | AUC |
|---|---|---|---|---|---|---|---|---|---|
| SEQ ID NO: 460 | hsa-miR-542-5p | ucggggaucaucauguucacagaga | 183,719 | 190,500 | 0,964 | -0,036 | 0,51 | 0,68 | 0,442 |
| SEQ ID NO: 589 | hsa-miR-16-2* | ccaauauuacugugcugcuuua | 195,906 | 176,594 | 1,109 | 0,104 | 0,51 | 0,68 | 0,574 |
| SEQ ID NO: 655 | hsa-let-7e* | cuauacgccuccuagcuuucc | 60,063 | 51,547 | 1,165 | 0,153 | 0,51 | 0,68 | 0,460 |
| SEQ ID NO: 621 | hsa-miR-935 | ccaguuaccgcuucgcuuaccgc | 72,031 | 84,094 | 0,857 | -0,155 | 0,52 | 0,68 | 0,436 |
| SEQ ID NO: 529 | hsa-miR-1914* | ggaggguccgcacugggagg | 290,328 | 283,406 | 1,024 | 0,024 | 0,52 | 0,68 | 0,533 |
| SEQ ID NO: 631 | hsa-miR-610 | ugagcuaaaugugugcuggga | 77,875 | 85,391 | 0,912 | -0,092 | 0,53 | 0,7 | 0,428 |
| SEQ ID NO: 573 | hsa-miR-643 | acuuguaugcuagcucagguag | 123,500 | 134,594 | 0,918 | -0,086 | 0,53 | 0,7 | 0,408 |
| SEQ ID NO: 57 | hsa-miR-519c-3p | aaagugcaucuuuuuagcaggau | 95,859 | 101,688 | 0,943 | -0,059 | 0,54 | 0,7 | 0,439 |
| SEQ ID NO: 345 | hsa-miR-521 | aacgcacuucccuuuagagugu | 87,813 | 88,375 | 0,994 | -0,006 | 0,54 | 0,71 | 0,459 |
| SEQ ID NO: 284 | hsa-miR-1185 | agaggauacccuuugauaguu | 45,844 | 48,172 | 0,952 | -0,050 | 0,54 | 0,71 | 0,417 |
| SEQ ID NO: 832 | hsa-miR-661 | ugccuggguucugcuggcugcgcgu | 79,750 | 71,719 | 1,112 | 0,106 | 0,54 | 0,71 | 0,479 |
| SEQ ID NO: 605 | hsa-miR-1323 | ucaaaacugagggcauuuucu | 93,656 | 96,188 | 0,974 | -0,027 | 0,55 | 0,72 | 0,452 |
| SEQ ID NO: 532 | hsa-miR-377* | agaguugcccuugguguaauc | 26,328 | 33,391 | 0,788 | -0,238 | 0,55 | 0,72 | 0,498 |
| SEQ ID NO: 569 | hsa-miR-758 | uuugauugaccugguccacuaacc | 105,031 | 110,719 | 0,949 | -0,053 | 0,56 | 0,72 | 0,438 |
| SEQ ID NO: 106 | hsa-miR-106b* | ccgcacuguggguacuugcugc | 281,828 | 286,531 | 0,984 | -0,017 | 0,55 | 0,72 | 0,556 |
| SEQ ID NO: 253 | hsa-miR-549 | ugacaacuauggaugagcucu | 119,469 | 117,297 | 1,019 | 0,018 | 0,55 | 0,72 | 0,490 |
| SEQ ID NO: 439 | hsa-miR-206 | uggaauuaagaagugugg | 38,219 | 31,719 | 1,205 | 0,186 | 0,56 | 0,72 | 0,558 |
| SEQ ID NO: 263 | hsa-miR-299-5p | uguuuuaccgucccacauacau | 75,625 | 78,969 | 0,958 | -0,043 | 0,56 | 0,73 | 0,413 |
| SEQ ID NO: 422 | hsa-miR-498 | uuucaagccaggggcguuuuuc | 83,047 | 78,125 | 1,063 | 0,061 | 0,56 | 0,73 | 0,536 |
| SEQ ID NO: 6 | hsa-miR-15a | uagcagcacauaauggugug | 3475,531 | 3470,055 | 1,002 | 0,002 | 0,56 | 0,73 | 0,518 |
| SEQ ID NO: 152 | hsa-miR-1289 | uggaguccaggaaucugcauuuu | 182,813 | 175,219 | 1,043 | 0,042 | 0,57 | 0,73 | 0,562 |
| SEQ ID NO: 405 | hsa-miR-617 | agacuuccauuugaaggugc | 70,734 | 73,297 | 0,965 | -0,036 | 0,57 | 0,73 | 0,539 |
| SEQ ID NO: 198 | hsa-miR-101 | uacaguacugugauaaacuga | 987,070 | 1008,195 | 0,979 | -0,021 | 0,57 | 0,73 | 0,526 |
| SEQ ID NO: 787 | hsa-miR-557 | guuugcacgggugggccuugucu | 66,406 | 75,047 | 0,885 | -0,122 | 0,57 | 0,73 | 0,467 |
| SEQ ID NO: 668 | hsa-miR-125b-1* | acgggguuaggcucuuggcagcu | 36,125 | 39,938 | 0,905 | -0,100 | 0,57 | 0,73 | 0,499 |
| SEQ ID NO: 582 | hsa-miR-337-5p | gaacggcuucauacaggaguu | 98,500 | 93,656 | 1,052 | 0,050 | 0,57 | 0,73 | 0,477 |
| SEQ ID NO: 17 | hsa-let-7a | ugagguaguagguuguauaguu | 2421,387 | 1845,953 | 1,312 | 0,271 | 0,58 | 0,74 | 0,617 |
| SEQ ID NO: 101 | hsa-miR-30b | uguaaacauccuacacucagcu | 8969,791 | 6561,965 | 1,367 | 0,313 | 0,58 | 0,74 | 0,561 |
| SEQ ID NO: 660 | hsa-miR-452 | aacuguuugcagaggaaacuga | 116,047 | 106,406 | 1,091 | 0,087 | 0,58 | 0,74 | 0,507 |
| SEQ ID NO: 94 | hsa-miR-548d-3p | caaaaaccacaguuucuuugc | 95,219 | 99,172 | 0,960 | -0,041 | 0,59 | 0,75 | 0,502 |
| SEQ ID NO: 769 | hsa-miR-92a-1* | agguggaucgguugcaaugcu | 57,813 | 58,313 | 0,991 | -0,009 | 0,59 | 0,75 | 0,463 |

FIG. 10A (Continued)

| SEQ ID NO | miRNA | Sequence | median_g | median_c | median | logmedian | cwPval.adj.val | AUC |
|---|---|---|---|---|---|---|---|---|
| SEQ ID NO: 554 | hsa-miR-200b* | caucuuacugggcagcauugga | 109,797 | 135,281 | 0,812 | -0,209 | 0,59 | 0,75 | 0,421 |
| SEQ ID NO: 583 | hsa-miR-133b | uuuguccccuucaaccagcua | 74,703 | 66,719 | 1,120 | 0,113 | 0,59 | 0,75 | 0,558 |
| SEQ ID NO: 396 | hsa-miR-187 | ucgugucuuguugugcagccg | 61,297 | 53,859 | 1,138 | 0,129 | 0,59 | 0,75 | 0,572 |
| SEQ ID NO: 112 | hsa-miR-424* | caaaacgugaggcgcugcuau | 237,781 | 213,875 | 1,112 | 0,106 | 0,6 | 0,75 | 0,584 |
| SEQ ID NO: 464 | hsa-miR-450a | uuuugcgauguguuccuaauau | 53,156 | 43,438 | 1,224 | 0,202 | 0,6 | 0,75 | 0,560 |
| SEQ ID NO: 66 | hsa-miR-519c-5p | cucuagagguaagcgcuuucg | 249,180 | 220,500 | 1,130 | 0,122 | 0,6 | 0,76 | 0,570 |
| SEQ ID NO: 249 | hsa-miR-486-5p | agaggcuggccgugaugaauuc | 77,750 | 78,813 | 0,987 | -0,014 | 0,6 | 0,76 | 0,463 |
| SEQ ID NO: 349 | hsa-miR-571 | ugauuggcaucugagugag | 111,844 | 107,656 | 1,039 | 0,038 | 0,6 | 0,76 | 0,504 |
| SEQ ID NO: 402 | hsa-miR-1183 | cacuguaguguaugugagugggca | 136,063 | 141,219 | 0,963 | -0,037 | 0,61 | 0,76 | 0,456 |
| SEQ ID NO: 231 | hsa-miR-128 | ucacaguaaccggucucuuu | 753,641 | 803,486 | 0,938 | -0,064 | 0,61 | 0,76 | 0,473 |
| SEQ ID NO: 861 | hsa-miR-92a | uauugcacuugucccggccugu | 18271,367 | 15553,496 | 1,175 | 0,161 | 0,61 | 0,76 | 0,647 |
| SEQ ID NO: 502 | hsa-miR-1915* | accuugccuugcugccggcc | 63,938 | 64,859 | 0,986 | -0,014 | 0,61 | 0,76 | 0,539 |
| SEQ ID NO: 175 | hsa-miR-548j | aaaaguaauugcggucuuuggu | 31,438 | 29,219 | 1,076 | 0,073 | 0,61 | 0,76 | 0,512 |
| SEQ ID NO: 711 | hsa-miR-513c | uucucaaggagugucguuuau | 42,859 | 45,969 | 0,932 | -0,070 | 0,62 | 0,77 | 0,420 |
| SEQ ID NO: 37 | hsa-miR-425 | aaugacacgaucacuucccguuga | 12784,891 | 11122,227 | 1,149 | 0,139 | 0,62 | 0,77 | 0,563 |
| SEQ ID NO: 534 | hsa-miR-548c-3p | caaaaauccuccaauuacuuuga | 98,813 | 97,859 | 1,010 | 0,010 | 0,62 | 0,77 | 0,491 |
| SEQ ID NO: 121 | hsa-miR-548f | aaaaacugcuaauuacuuuu | 77,219 | 95,406 | 0,809 | -0,212 | 0,62 | 0,77 | 0,405 |
| SEQ ID NO: 657 | hsa-miR-18b* | ugccccuaaaugcccccuuuggc | 147,813 | 143,000 | 1,034 | 0,033 | 0,62 | 0,77 | 0,562 |
| SEQ ID NO: 211 | hsa-miR-23b* | uggguccuggcaugcugauuu | 85,969 | 84,906 | 1,013 | 0,012 | 0,62 | 0,77 | 0,508 |
| SEQ ID NO: 749 | hsa-miR-191 | caacggaauccaaaagcagcag | 11122,227 | 10769,656 | 1,033 | 0,032 | 0,63 | 0,77 | 0,541 |
| SEQ ID NO: 255 | hsa-miR-577 | uagauaaaauauugguaccug | 50,875 | 57,266 | 0,888 | -0,118 | 0,63 | 0,78 | 0,443 |
| SEQ ID NO: 16 | hsa-let-7f | ugagguaguagauuguauaguu | 1170,113 | 827,930 | 1,413 | 0,346 | 0,63 | 0,78 | 0,569 |
| SEQ ID NO: 448 | hsa-miR-615-3p | uccgagcgcugguguccccucuu | 70,422 | 72,938 | 0,966 | -0,035 | 0,63 | 0,78 | 0,479 |
| SEQ ID NO: 442 | hsa-miR-511 | gugucuuuugcucugcaguca | 84,125 | 89,156 | 0,944 | -0,058 | 0,64 | 0,78 | 0,471 |
| SEQ ID NO: 821 | hsa-miR-134 | ugugacuggguugaccagaggg | 83,563 | 89,344 | 0,935 | -0,067 | 0,64 | 0,78 | 0,450 |
| SEQ ID NO: 1 | hsa-miR-126 | ucguaccgugaguaauaaugcg | 2576,535 | 2966,773 | 0,868 | -0,141 | 0,64 | 0,78 | 0,460 |
| SEQ ID NO: 168 | hsa-miR-130a* | uuucacauugugcuacugucugc | 146,938 | 172,391 | 0,852 | -0,160 | 0,64 | 0,79 | 0,478 |
| SEQ ID NO: 230 | hsa-miR-488 | uugaaaggcuauuuucuuggu | 32,203 | 25,500 | 1,263 | 0,233 | 0,65 | 0,79 | 0,593 |
| SEQ ID NO: 245 | hsa-miR-141 | uaacacugucugguaaagaugg | 113,266 | 116,875 | 0,969 | -0,031 | 0,65 | 0,79 | 0,440 |
| SEQ ID NO: 411 | hsa-miR-122 | uggagugugacaauggguguuug | 54,094 | 51,063 | 1,059 | 0,058 | 0,65 | 0,79 | 0,540 |
| SEQ ID NO: 792 | hsa-miR-30c-1* | cuggagagggguuguuuacucc | 120,422 | 100,875 | 1,194 | 0,177 | 0,66 | 0,8 | 0,502 |

FIG. 10A (Continued)

| SEQ ID NO | miRNA | Sequence | median q2 | median | median q4 | log(median) | raw P-val | Adj. P-val | AUC |
|---|---|---|---|---|---|---|---|---|---|
| SEQ ID NO: 225 | hsa-miR-374b* | cuuagcaguuguauuaucauu | 76,875 | 79,313 | 0,969 | -0,031 | 0,66 | 0,8 | 0,472 |
| SEQ ID NO: 578 | hsa-miR-581 | ucuuguguccuuagaucagu | 44,578 | 51,438 | 0,867 | -0,143 | 0,66 | 0,8 | 0,381 |
| SEQ ID NO: 599 | hsa-miR-744* | cuguugccacuaaccucaaccu | 123,438 | 109,906 | 1,123 | 0,116 | 0,66 | 0,8 | 0,483 |
| SEQ ID NO: 39 | hsa-miR-668 | ugucacucggcucgcccaacuac | 106,031 | 96,313 | 1,101 | 0,096 | 0,67 | 0,8 | 0,569 |
| SEQ ID NO: 301 | hsa-miR-1197 | uaggacauggcucuacuucu | 90,625 | 95,000 | 0,954 | -0,047 | 0,67 | 0,8 | 0,520 |
| SEQ ID NO: 414 | hsa-miR-181d | aacauucauguugucgguggu | 52,438 | 58,484 | 0,897 | -0,109 | 0,67 | 0,81 | 0,447 |
| SEQ ID NO: 120 | hsa-miR-449a | uggcaguguauuguuagcuggu | 22,688 | 32,969 | 0,688 | -0,374 | 0,67 | 0,81 | 0,417 |
| SEQ ID NO: 689 | hsa-miR-30c-2* | cugggagaaggcuguuuacucu | 59,578 | 53,938 | 1,105 | 0,099 | 0,68 | 0,81 | 0,513 |
| SEQ ID NO: 115 | hsa-miR-199b-3p | acaguagucugcacauugguua | 212,641 | 212,672 | 1,000 | 0,000 | 0,68 | 0,81 | 0,455 |
| SEQ ID NO: 248 | hsa-miR-302c | uaagugcuuccauguuucagugg | 61,141 | 66,281 | 0,922 | -0,081 | 0,68 | 0,81 | 0,439 |
| SEQ ID NO: 160 | hsa-miR-10a* | caaauucguaucuaggggauaua | 102,531 | 96,594 | 1,061 | 0,060 | 0,68 | 0,81 | 0,543 |
| SEQ ID NO: 451 | hsa-miR-770-5p | uccaguaccacgguacagggcca | 100,016 | 92,406 | 1,082 | 0,079 | 0,68 | 0,81 | 0,561 |
| SEQ ID NO: 681 | hsa-miR-1308 | gcaugguggguucagugg | 79,625 | 92,281 | 0,863 | -0,148 | 0,68 | 0,81 | 0,448 |
| SEQ ID NO: 146 | hsa-miR-28-5p | aaggagcuacaguucagucauugag | 426,203 | 422,703 | 1,008 | 0,008 | 0,69 | 0,81 | 0,549 |
| SEQ ID NO: 275 | hsa-miR-548b-3p | caagaaccucagugcuuuuugu | 97,234 | 95,000 | 1,024 | 0,023 | 0,69 | 0,82 | 0,537 |
| SEQ ID NO: 273 | hsa-miR-30d* | cuuucagcagaugugaugcugc | 126,203 | 132,375 | 0,953 | -0,048 | 0,69 | 0,82 | 0,507 |
| SEQ ID NO: 193 | hsa-miR-518f | gaaagcgcuucucucuuuagagg | 118,281 | 118,438 | 0,999 | -0,001 | 0,69 | 0,82 | 0,510 |
| SEQ ID NO: 122 | hsa-miR-597 | ugugucaccgaugaccacugu | 143,000 | 149,500 | 0,957 | -0,044 | 0,7 | 0,82 | 0,498 |
| SEQ ID NO: 730 | hsa-miR-421 | aucaacagacauuaauugggcgc | 272,063 | 215,926 | 1,260 | 0,231 | 0,7 | 0,82 | 0,587 |
| SEQ ID NO: 266 | hsa-miR-497* | caaaccacacugugugugua | 181,563 | 195,156 | 0,930 | -0,072 | 0,7 | 0,82 | 0,446 |
| SEQ ID NO: 210 | hsa-miR-579 | uucauuugguauaaaccgcgauu | 88,891 | 90,125 | 0,986 | -0,014 | 0,7 | 0,82 | 0,471 |
| SEQ ID NO: 606 | hsa-miR-548e | aaaaacugagacuacuuuugca | 93,203 | 90,969 | 1,025 | 0,024 | 0,7 | 0,82 | 0,564 |
| SEQ ID NO: 281 | hsa-miR-431* | caggucucuugcagggccuucu | 60,781 | 65,359 | 0,930 | -0,073 | 0,7 | 0,83 | 0,471 |
| SEQ ID NO: 742 | hsa-miR-520a-5p | cuccagagggaaguacuuucu | 188,531 | 172,438 | 1,093 | 0,089 | 0,7 | 0,83 | 0,537 |
| SEQ ID NO: 315 | hsa-miR-26a | uucaaguaauccaggauaggcu | 6989,555 | 7855,156 | 0,890 | -0,117 | 0,7 | 0,83 | 0,388 |
| SEQ ID NO: 401 | hsa-miR-509-3p | ugauugguacgucuguggaug | 33,484 | 32,453 | 1,032 | 0,031 | 0,71 | 0,83 | 0,515 |
| SEQ ID NO: 435 | hsa-miR-219-2-3p | agaauugcuggacaucugu | 44,578 | 37,375 | 1,193 | 0,176 | 0,71 | 0,83 | 0,530 |
| SEQ ID NO: 809 | hsa-miR-27b | uucacaguggcuaaguucugc | 281,047 | 277,281 | 1,014 | 0,013 | 0,72 | 0,83 | 0,539 |
| SEQ ID NO: 795 | hsa-miR-323-5p | agguccguggcguucgc | 63,313 | 58,922 | 1,075 | 0,072 | 0,72 | 0,84 | 0,541 |
| SEQ ID NO: 642 | hsa-let-7g* | cuguacaggccacugccuugc | 233,219 | 234,938 | 0,993 | -0,007 | 0,72 | 0,84 | 0,538 |
| SEQ ID NO: 612 | hsa-miR-95 | uucaacgggauauuaugagca | 50,500 | 55,375 | 0,912 | -0,092 | 0,72 | 0,84 | 0,466 |

FIG. 10A (Continued)

| SEQ ID NO | miRNA | sequence | median g1 | median g2 | fc median | log median | raw Pval | adj Pval | AUC |
|---|---|---|---|---|---|---|---|---|---|
| SEQ ID NO: 519 | hsa-miR-943 | cugacuguugccguccuccag | 97,234 | 91,438 | 1,063 | 0,061 | 0,73 | 0,84 | 0,565 |
| SEQ ID NO: 741 | hsa-miR-616* | acucaaaacccuucagugacuu | 101,906 | 90,297 | 1,129 | 0,121 | 0,73 | 0,85 | 0,537 |
| SEQ ID NO: 41 | hsa-miR-15b* | cgaaucauuauuugcugcucu | 130,250 | 121,516 | 1,072 | 0,069 | 0,73 | 0,85 | 0,534 |
| SEQ ID NO: 793 | hsa-miR-200c* | cgucuuaccagcagugullugg | 99,281 | 100,688 | 0,986 | -0,014 | 0,74 | 0,85 | 0,452 |
| SEQ ID NO: 488 | hsa-miR-888* | gacugacaaccucuuuugguugaa | 69,766 | 79,438 | 0,878 | -0,130 | 0,74 | 0,85 | 0,471 |
| SEQ ID NO: 782 | hsa-miR-518b | caaaggcguccccuuuagaggu | 198,984 | 190,797 | 1,043 | 0,042 | 0,74 | 0,85 | 0,552 |
| SEQ ID NO: 489 | hsa-miR-205 | uccuucauuccaccgagucug | 139,656 | 125,547 | 1,112 | 0,107 | 0,74 | 0,85 | 0,541 |
| SEQ ID NO: 531 | hsa-miR-515-3p | gaguggcuucuuuuggagcgua | 37,391 | 29,875 | 1,252 | 0,224 | 0,74 | 0,85 | 0,535 |
| SEQ ID NO: 673 | hsa-miR-507 | uuuugcaccuuuuggagugaa | 72,813 | 80,125 | 0,909 | -0,096 | 0,74 | 0,85 | 0,465 |
| SEQ ID NO: 556 | hsa-miR-518e | aaagggcuuccccuucagagug | 146,813 | 139,500 | 1,052 | 0,051 | 0,74 | 0,85 | 0,554 |
| SEQ ID NO: 626 | hsa-miR-1225-3p | ugagcccgugcgccgcccag | 234,969 | 213,891 | 1,099 | 0,094 | 0,75 | 0,85 | 0,553 |
| SEQ ID NO: 864 | hsa-miR-335 | ucaagagcaauaacgaaaaaugu | 573,906 | 667,367 | 0,860 | -0,151 | 0,75 | 0,85 | 0,435 |
| SEQ ID NO: 645 | hsa-miR-34b* | uaggcaguguucauuagcugauug | 97,922 | 99,625 | 0,983 | -0,017 | 0,74 | 0,85 | 0,500 |
| SEQ ID NO: 348 | hsa-miR-920 | gggagcugugaagcagua | 77,219 | 71,375 | 1,082 | 0,079 | 0,75 | 0,85 | 0,546 |
| SEQ ID NO: 824 | hsa-miR-660 | uacccauugcauaucggagug | 668,680 | 665,008 | 1,006 | 0,006 | 0,75 | 0,86 | 0,503 |
| SEQ ID NO: 254 | hsa-miR-576-5p | auucuaauuucccacgucuuu | 40,938 | 40,359 | 1,014 | 0,014 | 0,75 | 0,86 | 0,526 |
| SEQ ID NO: 785 | hsa-miR-195* | ccaauauuggcugugcugcucc | 101,719 | 105,563 | 0,964 | -0,037 | 0,76 | 0,86 | 0,476 |
| SEQ ID NO: 98 | hsa-miR-186* | gcccaaaggugaauuuuuggg | 169,344 | 197,266 | 0,858 | -0,153 | 0,76 | 0,86 | 0,477 |
| SEQ ID NO: 52 | hsa-miR-1269 | cuggacugagccgugcuacug | 100,219 | 97,969 | 1,023 | 0,023 | 0,76 | 0,86 | 0,528 |
| SEQ ID NO: 507 | hsa-miR-567 | aguaguuucuuccaggacagaac | 138,609 | 139,563 | 0,993 | -0,007 | 0,77 | 0,87 | 0,482 |
| SEQ ID NO: 634 | hsa-miR-10b* | acagaucgauucuagggaau | 161,094 | 151,563 | 1,063 | 0,061 | 0,77 | 0,87 | 0,560 |
| SEQ ID NO: 434 | hsa-miR-548m | caaaggcauauugugguuuug | 22,719 | 27,453 | 0,828 | -0,189 | 0,77 | 0,87 | 0,500 |
| SEQ ID NO: 617 | hsa-miR-329 | aacacccuggullaaccucucu | 158,438 | 145,000 | 1,093 | 0,089 | 0,78 | 0,87 | 0,493 |
| SEQ ID NO: 486 | hsa-miR-147 | guguuggaaaugcuucugc | 86,172 | 77,375 | 1,114 | 0,108 | 0,78 | 0,87 | 0,579 |
| SEQ ID NO: 237 | hsa-miR-194 | uguaacagcaaccaugugga | 5810,586 | 6505,273 | 0,893 | -0,113 | 0,78 | 0,87 | 0,412 |
| SEQ ID NO: 322 | hsa-miR-1205 | ucugcagggulugcuuuag | 142,141 | 131,469 | 1,081 | 0,078 | 0,78 | 0,88 | 0,500 |
| SEQ ID NO: 545 | hsa-miR-127-3p | ucggaugcgucgagcuuggcu | 115,969 | 130,375 | 0,890 | -0,117 | 0,79 | 0,88 | 0,475 |
| SEQ ID NO: 187 | hsa-miR-551b | gcgacccauacuuugguuucag | 118,547 | 88,031 | 1,347 | 0,298 | 0,79 | 0,88 | 0,499 |
| SEQ ID NO: 416 | hsa-miR-302d | uaagugcuuccauguuuugagauu | 32,719 | 40,875 | 0,800 | -0,223 | 0,79 | 0,89 | 0,444 |
| SEQ ID NO: 58 | hsa-miR-1244 | aaguaguuuguuauagagauggu | 6,500 | 3,875 | 1,677 | 0,517 | 0,8 | 0,89 | 0,529 |
| SEQ ID NO: 430 | hsa-miR-21* | caacaccagucgauggggcugu | 167,625 | 184,641 | 0,908 | -0,097 | 0,8 | 0,89 | 0,458 |

FIG. 10A (Continued)

| SEQ ID NO | miRNA | Sequence | median gr | median g2 | qmedian | logmedian | raw P-val | adj P-val | AUC |
|---|---|---|---|---|---|---|---|---|---|
| SEQ ID NO: 615 | hsa-miR-541* | aaaggauucugcugucgguccacu | 40,906 | 40,203 | 1,017 | 0,017 | 0,8 | 0,89 | 0,462 |
| SEQ ID NO: 508 | hsa-miR-184 | uggacgagaacugauaagggu | 47,219 | 51,281 | 0,921 | -0,083 | 0,8 | 0,89 | 0,489 |
| SEQ ID NO: 325 | hsa-miR-555 | aggguaagcugaaccucugau | 95,219 | 87,406 | 1,089 | 0,086 | 0,8 | 0,89 | 0,540 |
| SEQ ID NO: 338 | hsa-miR-591 | agaccauggugucaugu | 122,844 | 116,844 | 1,051 | 0,050 | 0,8 | 0,89 | 0,542 |
| SEQ ID NO: 194 | hsa-miR-649 | aaaccuguguguucaagaguc | 54,281 | 60,813 | 0,893 | -0,114 | 0,8 | 0,89 | 0,442 |
| SEQ ID NO: 656 | hsa-miR-1237 | uccucucgcuccgucccccag | 152,094 | 152,156 | 1,000 | 0,000 | 0,81 | 0,89 | 0,483 |
| SEQ ID NO: 600 | hsa-miR-520c-5p | cucuagagggaagcacuuucug | 235,219 | 218,563 | 1,076 | 0,073 | 0,81 | 0,89 | 0,531 |
| SEQ ID NO: 127 | hsa-miR-325 | ccuaguaggugucagguagugu | 117,188 | 108,906 | 1,076 | 0,073 | 0,81 | 0,89 | 0,519 |
| SEQ ID NO: 65 | hsa-miR-520f | aagugcuuccuuuuuagagggu | 28,906 | 29,219 | 0,989 | -0,011 | 0,82 | 0,9 | 0,502 |
| SEQ ID NO: 93 | hsa-miR-136 | acuccauuuguuuugaugauga | 94,625 | 85,422 | 1,108 | 0,102 | 0,82 | 0,9 | 0,527 |
| SEQ ID NO: 666 | hsa-miR-132 | uaacagucuacagccaugucg | 174,750 | 168,688 | 1,036 | 0,035 | 0,82 | 0,9 | 0,579 |
| SEQ ID NO: 852 | hsa-miR-324-5p | cgcauccccuagggcauugugu | 588,781 | 613,781 | 0,959 | -0,042 | 0,82 | 0,9 | 0,491 |
| SEQ ID NO: 557 | hsa-miR-612 | gcuggcaggccuucugagcuccuu | 144,719 | 133,859 | 1,081 | 0,078 | 0,83 | 0,9 | 0,564 |
| SEQ ID NO: 658 | hsa-miR-630 | aguauucguaccagggaagu | 91,500 | 89,938 | 1,017 | 0,017 | 0,83 | 0,9 | 0,539 |
| SEQ ID NO: 458 | hsa-miR-548g | aaaacuguaauuacuuuuguac | 99,094 | 96,875 | 1,023 | 0,023 | 0,83 | 0,91 | 0,492 |
| SEQ ID NO: 394 | hsa-miR-508-3p | ugauguagccuuuugagcuaga | 33,484 | 36,625 | 0,914 | -0,090 | 0,83 | 0,91 | 0,474 |
| SEQ ID NO: 428 | hsa-miR-296-3p | gagguuggguggaggcucucc | 127,000 | 121,594 | 1,044 | 0,044 | 0,83 | 0,91 | 0,512 |
| SEQ ID NO: 674 | hsa-miR-188-5p | caucccuugcauggguggagg | 215,844 | 212,844 | 1,014 | 0,014 | 0,83 | 0,91 | 0,500 |
| SEQ ID NO: 179 | hsa-miR-222 | agcuacauucggcuacugggu | 655,146 | 661,336 | 0,991 | -0,009 | 0,84 | 0,91 | 0,521 |
| SEQ ID NO: 804 | hsa-miR-181a | aacauucaacgcugucggugagu | 1197,650 | 855,281 | 1,400 | 0,337 | 0,84 | 0,91 | 0,634 |
| SEQ ID NO: 510 | hsa-miR-124* | cguguuacacagcggaccuugau | 180,563 | 183,594 | 0,983 | -0,017 | 0,84 | 0,91 | 0,461 |
| SEQ ID NO: 763 | hsa-miR-532-5p | caugccuugagugaggaccgu | 437,328 | 347,672 | 1,258 | 0,229 | 0,84 | 0,91 | 0,574 |
| SEQ ID NO: 72 | hsa-miR-563 | agguugacauacguuuccc | 63,953 | 61,344 | 1,043 | 0,042 | 0,84 | 0,91 | 0,487 |
| SEQ ID NO: 128 | hsa-miR-409-5p | agguuauccgagcaacuuugcau | 158,750 | 149,625 | 1,061 | 0,059 | 0,84 | 0,91 | 0,556 |
| SEQ ID NO: 424 | hsa-miR-556-3p | auauuaccauuagcucaucauu | 29,672 | 25,563 | 1,161 | 0,149 | 0,84 | 0,91 | 0,519 |
| SEQ ID NO: 470 | hsa-miR-526a | cucuagagggaagcacuuucug | 221,047 | 255,043 | 0,867 | -0,143 | 0,84 | 0,91 | 0,393 |
| SEQ ID NO: 613 | hsa-miR-133a | uuuggucccuucaaccagcug | 126,813 | 118,578 | 1,069 | 0,067 | 0,85 | 0,91 | 0,549 |
| SEQ ID NO: 364 | hsa-miR-873 | gcaggaacugugagucuccu | 121,094 | 126,813 | 0,955 | -0,046 | 0,85 | 0,91 | 0,443 |
| SEQ ID NO: 714 | hsa-miR-320c | aaaagcugggUugagagggu | 886,344 | 790,391 | 1,121 | 0,115 | 0,85 | 0,91 | 0,549 |
| SEQ ID NO: 499 | hsa-miR-141* | cauccucaguacagugugga | 166,281 | 168,531 | 0,987 | -0,013 | 0,85 | 0,91 | 0,504 |
| SEQ ID NO: 380 | hsa-miR-200a* | caucuuaccggacagugugga | 171,348 | 159,844 | 1,072 | 0,069 | 0,85 | 0,91 | 0,466 |

FIG. 10A (Continued)

| SEQ ID NO | miRNA | sequence | median ng | median p2 | median | log median | raw Pval | adj Pval | AUC |
|---|---|---|---|---|---|---|---|---|---|
| SEQ ID NO: 807 | hsa-miR-152 | ucagugcaugacagaacuugg | 334,141 | 306,234 | 1,091 | 0,087 | 0,86 | 0,92 | 0,531 |
| SEQ ID NO: 355 | hsa-miR-146a* | ccucugaaauucaguucuucag | 189,938 | 185,766 | 1,022 | 0,022 | 0,86 | 0,92 | 0,527 |
| SEQ ID NO: 862 | hsa-miR-29b-1* | gcuguucauaugguguuuaga | 33,797 | 37,906 | 0,892 | -0,115 | 0,86 | 0,92 | 0,485 |
| SEQ ID NO: 472 | hsa-miR-548n | caaaaguaauguggauuugu | 82,906 | 88,375 | 0,938 | -0,064 | 0,87 | 0,93 | 0,469 |
| SEQ ID NO: 186 | hsa-miR-16-1* | ccaguauaacugugcugcuga | 168,393 | 158,484 | 1,063 | 0,061 | 0,87 | 0,93 | 0,558 |
| SEQ ID NO: 204 | hsa-miR-636 | ugugcuugcucgucccgccgca | 306,016 | 300,641 | 1,018 | 0,018 | 0,87 | 0,93 | 0,567 |
| SEQ ID NO: 294 | hsa-miR-302e | uaagugcuuccaugcuu | 59,938 | 53,719 | 1,116 | 0,110 | 0,87 | 0,93 | 0,543 |
| SEQ ID NO: 386 | hsa-miR-1264 | caagucuuauuugagcaccuguu | 68,313 | 74,563 | 0,916 | -0,088 | 0,88 | 0,93 | 0,482 |
| SEQ ID NO: 415 | hsa-miR-219-5p | ugauugucccaaacgcaauucu | 106,281 | 91,719 | 1,159 | 0,147 | 0,88 | 0,93 | 0,587 |
| SEQ ID NO: 461 | hsa-miR-190 | ugauauguuugauauauuaggu | 27,969 | 37,375 | 0,748 | -0,290 | 0,88 | 0,93 | 0,467 |
| SEQ ID NO: 538 | hsa-miR-494 | ugaaacauuacacgggaaaccuc | 126,813 | 122,313 | 1,037 | 0,036 | 0,89 | 0,94 | 0,506 |
| SEQ ID NO: 521 | hsa-miR-93 | caaagugcugcuugugcagguag | 6179,910 | 6647,320 | 0,930 | -0,073 | 0,89 | 0,94 | 0,510 |
| SEQ ID NO: 566 | hsa-miR-373 | gaagugcuucgauuuggggugu | 18,844 | 14,688 | 1,283 | 0,249 | 0,89 | 0,94 | 0,586 |
| SEQ ID NO: 384 | hsa-miR-548k | aaaaguacuuggcgauuuugcu | 55,500 | 68,688 | 0,808 | -0,213 | 0,9 | 0,94 | 0,464 |
| SEQ ID NO: 82 | hsa-miR-185 | uggagagaaaggcaguccuga | 30296,156 | 27473,492 | 1,103 | 0,098 | 0,9 | 0,95 | 0,509 |
| SEQ ID NO: 144 | hsa-miR-609 | agggguuuucucucucucu | 12,625 | 16,703 | 0,756 | -0,280 | 0,9 | 0,95 | 0,476 |
| SEQ ID NO: 104 | hsa-miR-129-5p | cuuuucggguucuggcaugc | 100,000 | 97,156 | 1,029 | 0,029 | 0,91 | 0,95 | 0,514 |
| SEQ ID NO: 170 | hsa-miR-193b | aacuggccuucaaaguaccgcu | 146,969 | 139,719 | 1,052 | 0,051 | 0,91 | 0,95 | 0,540 |
| SEQ ID NO: 88 | hsa-miR-1207-3p | ucagcugggaggaagcaug | 69,250 | 75,547 | 0,917 | -0,087 | 0,91 | 0,95 | 0,479 |
| SEQ ID NO: 784 | hsa-miR-376c | aacauagaggaaauuccacgu | 155,625 | 161,250 | 0,965 | -0,036 | 0,91 | 0,95 | 0,502 |
| SEQ ID NO: 336 | hsa-miR-302a* | acuuaaacguggauguacugu | 96,828 | 99,844 | 0,970 | -0,031 | 0,91 | 0,95 | 0,485 |
| SEQ ID NO: 728 | hsa-miR-1910 | ccagccuguugcucgccgcu | 68,000 | 88,828 | 0,766 | -0,267 | 0,91 | 0,95 | 0,419 |
| SEQ ID NO: 514 | hsa-let-7b* | cuauacaaccuacugccuccc | 45,688 | 38,625 | 1,183 | 0,168 | 0,92 | 0,95 | 0,520 |
| SEQ ID NO: 86 | hsa-miR-335* | uuuuuuccauuauugucccugacc | 35,141 | 42,563 | 0,826 | -0,192 | 0,92 | 0,96 | 0,469 |
| SEQ ID NO: 533 | hsa-miR-504 | agaccccuggucugucacuauc | 76,453 | 73,031 | 1,047 | 0,046 | 0,92 | 0,96 | 0,498 |
| SEQ ID NO: 95 | hsa-miR-561 | caaagguuaagauccuugaagu | 96,828 | 104,891 | 0,923 | -0,080 | 0,92 | 0,96 | 0,487 |
| SEQ ID NO: 341 | hsa-miR-618 | aaacucuacuugucccuucgagu | 70,344 | 68,625 | 1,025 | 0,025 | 0,93 | 0,96 | 0,523 |
| SEQ ID NO: 758 | hsa-miR-642 | guccucuccaaaugugucug | 84,500 | 77,844 | 1,086 | 0,082 | 0,93 | 0,96 | 0,500 |
| SEQ ID NO: 268 | hsa-miR-99a* | caagcucuuauggucug | 72,328 | 73,375 | 0,986 | -0,014 | 0,93 | 0,96 | 0,487 |
| SEQ ID NO: 777 | hsa-miR-578 | cuucuugugucuaggauugu | 38,781 | 38,094 | 1,018 | 0,018 | 0,93 | 0,96 | 0,496 |
| SEQ ID NO: 691 | hsa-miR-492 | aggaccugcgggacaagauucu | 159,969 | 155,484 | 1,029 | 0,028 | 0,94 | 0,97 | 0,491 |

FIG. 10A (Continued)

| SEQ ID NO | miRNA | Sequence | median g1 | median g2 | qmedian | logqmedian | raw.Pval | adj.Pval | AUC |
|---|---|---|---|---|---|---|---|---|---|
| SEQ ID NO: 715 | hsa-miR-320b | aaaagcuggguugagagggcaa | 3376,021 | 2522,371 | 1,338 | 0,291 | 0,94 | 0,97 | 0,544 |
| SEQ ID NO: 244 | hsa-miR-105 | ucaaaugcucagacuccugggu | 89,656 | 96,563 | 0,928 | -0,074 | 0,94 | 0,97 | 0,476 |
| SEQ ID NO: 490 | hsa-miR-1257 | agugaaugauggguucugacc | 36,297 | 42,156 | 0,861 | -0,150 | 0,94 | 0,97 | 0,464 |
| SEQ ID NO: 138 | hsa-miR-552 | aacaggugacugguuagacaa | 70,719 | 61,797 | 1,144 | 0,135 | 0,95 | 0,97 | 0,525 |
| SEQ ID NO: 126 | hsa-miR-1911 | ugaguacgccaugucuguuggg | 96,641 | 98,453 | 0,982 | -0,019 | 0,95 | 0,98 | 0,512 |
| SEQ ID NO: 387 | hsa-miR-551a | gcgaccacucuuguuucca | 88,938 | 94,719 | 0,939 | -0,063 | 0,95 | 0,98 | 0,496 |
| SEQ ID NO: 308 | hsa-miR-708 | aaggagcuuacaaucuagcuggg | 102,313 | 108,063 | 0,947 | -0,055 | 0,96 | 0,98 | 0,495 |
| SEQ ID NO: 825 | hsa-miR-526b | cucuugagggaagcacuuucugu | 89,766 | 85,891 | 1,045 | 0,044 | 0,96 | 0,98 | 0,487 |
| SEQ ID NO: 595 | hsa-miR-519d | caaagugcuccccuuuagagug | 106,438 | 116,688 | 0,912 | -0,092 | 0,96 | 0,98 | 0,487 |
| SEQ ID NO: 47 | hsa-miR-145* | ggauccugaaauacuguucu | 151,969 | 160,000 | 0,950 | -0,051 | 0,97 | 0,99 | 0,492 |
| SEQ ID NO: 771 | hsa-miR-518f* | cucuagagggaagcacuuucuc | 227,875 | 190,703 | 1,195 | 0,178 | 0,97 | 0,99 | 0,565 |
| SEQ ID NO: 147 | hsa-miR-23a | aucacauugccagggauuucc | 4776,795 | 4344,961 | 1,099 | 0,095 | 0,97 | 0,99 | 0,565 |
| SEQ ID NO: 695 | hsa-miR-518c* | ucucuggagggaagcacuuucug | 119,125 | 123,906 | 0,961 | -0,039 | 0,97 | 0,99 | 0,462 |
| SEQ ID NO: 816 | hsa-miR-139-3p | ggagacgcggcccuguuggagu | 140,125 | 128,500 | 1,090 | 0,087 | 0,97 | 0,99 | 0,572 |
| SEQ ID NO: 306 | hsa-miR-553 | aaaaggugagauuuuguuuu | 49,469 | 40,938 | 1,208 | 0,189 | 0,97 | 0,99 | 0,529 |
| SEQ ID NO: 509 | hsa-miR-376a | aucagaggaaaauccacgu | 172,391 | 162,938 | 1,058 | 0,056 | 0,98 | 0,99 | 0,503 |
| SEQ ID NO: 803 | hsa-miR-148b* | aaguucuguauacacucaggc | 84,625 | 82,125 | 1,030 | 0,030 | 0,98 | 0,99 | 0,525 |
| SEQ ID NO: 812 | hsa-miR-143 | ugagaugaagcacguagcuc | 361,125 | 304,734 | 1,185 | 0,170 | 0,98 | 0,99 | 0,602 |
| SEQ ID NO: 309 | hsa-miR-892b | cacuggcuccuuucugguaga | 84,125 | 76,625 | 1,098 | 0,093 | 0,98 | 0,99 | 0,534 |
| SEQ ID NO: 444 | hsa-miR-1224-3p | ccccaccuccucucucucccag | 243,566 | 159,594 | 1,526 | 0,423 | 0,99 | 1 | 0,614 |
| SEQ ID NO: 840 | hsa-miR-1238 | cuuccucgucugucugcccc | 54,766 | 51,781 | 1,058 | 0,056 | 0,99 | 1 | 0,563 |
| SEQ ID NO: 154 | hsa-miR-513a-3p | uaaauuucaccuuuccugagagg | 119,828 | 111,813 | 1,072 | 0,069 | 0,99 | 1 | 0,551 |
| SEQ ID NO: 500 | hsa-miR-517c | aucgugcauccuuuuagagugu | 50,875 | 44,969 | 1,131 | 0,123 | 0,99 | 1 | 0,509 |
| SEQ ID NO: 73 | hsa-miR-663b | gguggcccggccggugcgagg | 141,750 | 143,000 | 0,991 | -0,009 | 1 | 1 | 0,498 |
| SEQ ID NO: 647 | hsa-miR-382 | gaaguugucguggguggauucg | 43,688 | 50,750 | 0,861 | -0,150 | 1 | 1 | 0,502 |
| SEQ ID NO: 665 | hsa-miR-340 | uuauaaagcaaugagagacugauu | 286,125 | 289,609 | 0,988 | -0,012 | 1 | 1 | 0,498 |
| SEQ ID NO: 487 | hsa-miR-487b | aaucguacagggucauccacuu | 134,344 | 124,344 | 1,080 | 0,077 | 1 | 1 | 0,512 |

FIG. 10B

| SEQ ID NO | Seq ID | Name microRNA (miRNA) | Sequence | test significance |
|---|---|---|---|---|
| SEQ ID NO: 99 | Tab1-1 | hsa-miR-145 | GUCCAGUUUUCCCAGGAAUCCCU | 1,46E-07 |
| SEQ ID NO: 313 | Tab1-2 | hsa-miR-186 | CAAAGAAUUCUCCUUUUGGGCU | 2,89E-07 |
| SEQ ID NO: 456 | Tab1-3 | hsa-miR-684 | UAUUCAUUAUCCCCAGCCUACA | 5,25E-05 |
| SEQ ID NO: 11 | Tab1-4 | hsa-miR-20b | CAAAGUGCUCAUAGUGCAGGUAG | 0,000148065 |
| SEQ ID NO: 826 | Tab1-5 | hsa-miR-422a | ACUGGACUUAGGGUCAGAAGGC | 0,000148065 |
| SEQ ID NO: 667 | Tab1-6 | hsa-miR-142-3p | UGUAGUGUUUCCUACUUUAUGGA | 0,000154481 |
| SEQ ID NO: 609 | Tab1-7 | hsa-miR-584 | UUAUGGUUUGCCUGGGACUGAG | 0,000156461 |
| SEQ ID NO: 51 | Tab1-8 | hsa-miR-223 | UGUCAGUUUGUCAAAUACCCCA | 0,00016217 |
| SEQ ID NO: 495 | Tab1-9 | hsa-miR-1275 | GUGGGGGAGAGGCUGUC | 0,000163285 |
| SEQ ID NO: 690 | Tab1-10 | hsa-miR-491-5p | AGUGGGGAACCCUUCCAUGAGG | 0,000283444 |
| SEQ ID NO: 196 | Tab1-11 | hsa-miR-151-3p | CUAGACUGAAGCUCCUUGAGG | 0,000461766 |
| SEQ ID NO: 823 | Tab1-12 | hsa-miR-92b* | AGGGACGGGACGCGGUGCAGUG | 0,000499915 |
| SEQ ID NO: 15 | Tab1-13 | hsa-let-7c | UGAGGUAGUAGGUUGUAUGGUU | 0,000626377 |
| SEQ ID NO: 635 | Tab1-14 | hsa-miR-216a | UAAUCUCAGCUGGCAACUGUGA | 0,000697573 |
| SEQ ID NO: 465 | Tab1-15 | hsa-miR-367 | AAUUGCACUUUAGCAAUGGUGA | 0,000736487 |
| SEQ ID NO: 505 | Tab1-16 | hsa-miR-942 | UCUUCUCGUUUUGGCCAUGUG | 0,000736487 |
| SEQ ID NO: 49 | Tab1-17 | hsa-miR-106a | AAAAGUGCUUACAGUGCAGGUAG | 0,000843844 |
| SEQ ID NO: 48 | Tab1-18 | hsa-miR-302b | UAAGUGCUUCCAUGUUUUAGUAG | 0,001057227 |
| SEQ ID NO: 552 | Tab1-19 | hsa-miR-385 | UAAUGCCCCUAAAAAUCCUUAU | 0,001057227 |
| SEQ ID NO: 165 | Tab1-20 | hsa-miR-140-5p | CAGUGGUUUUACCCUAUGGUAG | 0,001139983 |
| SEQ ID NO: 50 | Tab1-21 | hsa-miR-30e | UGUAAACAUCCUUGACUGGAAG | 0,001187881 |
| SEQ ID NO: 789 | Tab1-22 | hsa-miR-22* | AGUUCUUCAGUGGCAAGCUUUA | 0,001302256 |
| SEQ ID NO: 594 | Tab1-23 | hsa-miR-185* | AGGGGCUGGCUUUCCUCUGGUC | 0,001302256 |
| SEQ ID NO: 60 | Tab1-24 | hsa-miR-361-3p | UCCCCCAGGUGUGAUUCUGAUU | 0,001372655 |
| SEQ ID NO: 778 | Tab1-25 | hsa-miR-1301 | UUGCAGCUGCCUGGGAGUGACUUC | 0,001391723 |
| SEQ ID NO: 687 | Tab1-26 | hsa-miR-1909 | CGCAGGGGCCGGGUGCUCACCG | 0,001553322 |
| SEQ ID NO: 750 | Tab1-27 | hsa-miR-107 | AGCAGCAUUGUACAGGGCUAUCA | 0,002210862 |
| SEQ ID NO: 23 | Tab1-28 | hsa-miR-18a* | ACUGCCCUAAGUGCUCCUUCUGG | 0,00263885 |
| SEQ ID NO: 800 | Tab1-29 | hsa-miR-146a | UGAGAACUGAAUUCCAUGGGUU | 0,00263885 |
| SEQ ID NO: 748 | Tab1-30 | hsa-miR-501-5p | AAUCCUUUGUCCCUGGGUGAGA | 0,00273563 |
| SEQ ID NO: 320 | Tab1-31 | hsa-miR-891a | UGCAACGAACCUGAGCCACUGA | 0,00282418 |
| SEQ ID NO: 774 | Tab1-32 | hsa-miR-598 | UACGUCAUCGUUGUCAUCGUCA | 0,002982077 |
| SEQ ID NO: 84 | Tab1-33 | hsa-miR-1272 | GAUGAUGAUGGCAGCAAAUUCUGAAA | 0,00298827 |
| SEQ ID NO: 854 | Tab1-34 | hsa-miR-625 | AGGGGGAAAGUUCUAUAGUCC | 0,003045666 |
| SEQ ID NO: 463 | Tab1-35 | hsa-miR-367* | ACUGUUGCUAAUAUGCAACUCU | 0,003045666 |
| SEQ ID NO: 523 | Tab1-36 | hsa-miR-613 | AGGAAUGUUCCUUCUUUGCC | 0,003045666 |
| SEQ ID NO: 560 | Tab1-37 | hsa-miR-103 | AGCAGCAUUGUACAGGGCUAUGA | 0,00348231 |
| SEQ ID NO: 75 | Tab1-38 | hsa-miR-199a-5p | CCCAGUGUUCAGACUACCUGUUC | 0,003507036 |
| SEQ ID NO: 404 | Tab1-39 | hsa-miR-513b | UUCACAAGGAGGUGUCAUUUAU | 0,003974635 |
| SEQ ID NO: 443 | Tab1-40 | hsa-miR-30a | UGUAAACAUCCUCGACUGGAAG | 0,003974635 |
| SEQ ID NO: 806 | Tab1-41 | hsa-miR-125a-5p | UCCCUGAGACCCUUUAACCUGUGA | 0,003974635 |
| SEQ ID NO: 602 | Tab1-42 | hsa-miR-212 | UAACAGUCUCCAGUCACGGCC | 0,004251563 |
| SEQ ID NO: 232 | Tab1-43 | hsa-miR-362-5p | AAUCCUUGGAACCUAGGUGUGAGU | 0,00477326 |
| SEQ ID NO: 409 | Tab1-44 | hsa-miR-29c | UAGCACCAUUUGAAAUCGGUUA | 0,00492113 |
| SEQ ID NO: 250 | Tab1-45 | hsa-miR-499-3p | AACAUCACAGCAAGUCUGUGCU | 0,00492113 |
| SEQ ID NO: 398 | Tab1-46 | hsa-miR-96* | AAUCAUGUGCAGUGCCAAUAUG | 0,005326734 |
| SEQ ID NO: 455 | Tab1-47 | hsa-miR-1251 | ACUCUAGCUGCCAAAGGCGCU | 0,005593262 |
| SEQ ID NO: 56 | Tab1-48 | hsa-miR-451 | AAACCGUUACCAUUACUGAGUU | 0,006594945 |
| SEQ ID NO: 734 | Tab1-49 | hsa-miR-17* | ACUGCAGUGAAGGCACUUGUAG | 0,006594945 |
| SEQ ID NO: 814 | Tab1-50 | hsa-miR-675 | UGGUGCGGAGAGGGCCCACAGUG | 0,006594945 |

FIG. 10B (Continued)

| SEQ ID NO | Seq ID | Name (microRNA miRNA) | Sequence | test significance |
|---|---|---|---|---|
| SEQ ID NO: 365 | Tab1-51 | hsa-miR-556-5p | GAUGAGCUCAUUGUAAUAUGAG | 0,006594945 |
| SEQ ID NO: 74 | Tab1-52 | hsa-let-7d* | CUAUACGACCUGCUGCCUUUCU | 0,006594945 |
| SEQ ID NO: 482 | Tab1-53 | hsa-miR-559 | UAAAGUAAAUAUGCACCAAAA | 0,006594945 |
| SEQ ID NO: 819 | Tab1-54 | hsa-miR-1180 | UUUCCGGCUCGCGUGGGUGUGU | 0,006594945 |
| SEQ ID NO: 379 | Tab1-55 | hsa-miR-525-5p | CUCCAGAGGGAUGCACUUUCU | 0,006594945 |
| SEQ ID NO: 151 | Tab1-56 | hsa-miR-607 | GUUCAAAUCCAGAUCUAUAAC | 0,006594945 |
| SEQ ID NO: 135 | Tab1-57 | hsa-miR-221* | ACCUGGCAUACAAUGUAGAUUU | 0,006878721 |
| SEQ ID NO: 228 | Tab1-58 | hsa-miR-606 | AAACUACUGAAAAUCAAAGAU | 0,007108129 |
| SEQ ID NO: 155 | Tab1-59 | hsa-miR-939 | UGGGGAGCUGAGGCUCUGGGGGUG | 0,007227517 |
| SEQ ID NO: 632 | Tab1-60 | hsa-miR-574-3p | CACGCUCAUGCACACACCCACA | 0,007227517 |
| SEQ ID NO: 644 | Tab1-61 | hsa-miR-214 | ACAGCAGGCACAGACAGGCAGU | 0,00766807 |
| SEQ ID NO: 185 | Tab1-62 | hsa-miR-208b | AUAAGACGAACAAAAGGUUUGU | 0,00766807 |
| SEQ ID NO: 34 | Tab1-63 | hsa-miR-188-3p | CUCCCACAUGCAGGGUUUGCA | 0,00766807 |
| SEQ ID NO: 299 | Tab1-64 | hsa-miR-491-3p | CUUAUGCAAGAUUCCCUUCUAC | 0,00766807 |
| SEQ ID NO: 43 | Tab1-65 | hsa-miR-550* | UGUCUUACUCCCUCAGGCACAU | 0,007676623 |
| SEQ ID NO: 703 | Tab1-66 | hsa-miR-1227 | CGUGCCACCCUUUCCCCAG | 0,008145006 |
| SEQ ID NO: 277 | Tab1-67 | hsa-miR-92b | UAUUGCACUCGUCCGGCCUCC | 0,008146137 |
| SEQ ID NO: 641 | Tab1-68 | hsa-miR-330-3p | GCAAAGCACACGGCCUGCAGAGA | 0,008687984 |
| SEQ ID NO: 817 | Tab1-69 | hsa-miR-130b* | ACUCUUUCCCUGUUGCACUAC | 0,008846701 |
| SEQ ID NO: 260 | Tab1-70 | hsa-miR-655 | AUAAUACAUGGUUAACCUCUUU | 0,008894239 |
| SEQ ID NO: 513 | Tab1-71 | hsa-miR-580 | UUGAGAAUGAUGAAUCAUUAGG | 0,010153347 |
| SEQ ID NO: 134 | Tab1-72 | hsa-miR-378* | CUCCUGACUCCAGGUCCUGUGU | 0,01028601 |
| SEQ ID NO: 688 | Tab1-73 | hsa-miR-629 | UGGGUUUACGUUGGGAGAACU | 0,01028601 |
| SEQ ID NO: 45 | Tab1-74 | hsa-miR-20a | UAAAGUGCUUAUAGUGCAGGUAG | 0,01028601 |
| SEQ ID NO: 498 | Tab1-75 | hsa-miR-136* | CAUCAUCGUCUCAAAUGAGUCU | 0,01028601 |
| SEQ ID NO: 97 | Tab1-76 | hsa-miR-331-3p | GCCCCUGGGCCUAUCCUAGAA | 0,010690643 |
| SEQ ID NO: 584 | Tab1-77 | hsa-miR-92a-2* | GGGUGGGGAUUUGUUGCAUUAC | 0,011065082 |
| SEQ ID NO: 13 | Tab1-78 | hsa-miR-195 | UAGCAGCACAGAAAUAUUGGC | 0,011648579 |
| SEQ ID NO: 494 | Tab1-79 | hsa-miR-380* | UGGUUGACCAUAGAACAUGCGC | 0,012487876 |
| SEQ ID NO: 433 | Tab1-80 | hsa-miR-765 | UGGAGGAGAAGGAAGGUGAUG | 0,012565569 |
| SEQ ID NO: 87 | Tab1-81 | hsa-miR-497 | CAGCAGCACACUGUGGUUUGU | 0,013190076 |
| SEQ ID NO: 547 | Tab1-82 | hsa-miR-148a | UCAGUGCACUACAGAACUUUGU | 0,013799137 |
| SEQ ID NO: 528 | Tab1-83 | hsa-miR-20a* | ACUGCAUUAUGAGCACUUAAAG | 0,014433595 |
| SEQ ID NO: 671 | Tab1-84 | hsa-miR-1908 | CGGCGGGGACGGCGAUUGGUC | 0,014433595 |
| SEQ ID NO: 280 | Tab1-85 | hsa-miR-875-5p | UAUACCUCAGUUUUAUCAGGUG | 0,014489428 |
| SEQ ID NO: 130 | Tab1-86 | hsa-miR-658 | GGCGGAGGGAAGUAGGUCCGUUGGU | 0,015447027 |
| SEQ ID NO: 491 | Tab1-87 | hsa-miR-7 | UGGAAGACUAGUGAUUUUGUUGU | 0,015501759 |
| SEQ ID NO: 137 | Tab1-88 | hsa-miR-593* | AGGCACCAGCCAGGCAUUGCUCAGC | 0,015927763 |
| SEQ ID NO: 344 | Tab1-89 | hsa-miR-181b | AACAUUCAUUGCUGUCGGUGGGU | 0,016362518 |
| SEQ ID NO: 799 | Tab1-90 | hsa-miR-99a | AACCCGUAGAUCCGAUCUUGUG | 0,016362518 |
| SEQ ID NO: 22 | Tab1-91 | hsa-miR-1283 | UCUACAAAGGAAAGCGCUUUCU | 0,016953767 |
| SEQ ID NO: 813 | Tab1-92 | hsa-miR-362-3p | AACACCUAUUCAAGGAUUCA | 0,016953767 |
| SEQ ID NO: 726 | Tab1-93 | hsa-miR-601 | UGGUCUAGGAUUGUUGGAGGAG | 0,016953767 |
| SEQ ID NO: 274 | Tab1-94 | hsa-miR-452* | CUCAUCUGCAAAGAAGUAAGUG | 0,016953767 |
| SEQ ID NO: 31 | Tab1-95 | hsa-miR-19b | UGUGCAAAUCCAUGCAAAACUGA | 0,01746741 |
| SEQ ID NO: 358 | Tab1-96 | hsa-miR-24 | UGGCUCAGUUCAGCAGGAACAG | 0,017528239 |
| SEQ ID NO: 172 | Tab1-97 | hsa-miR-216b | AAAUCUCUGCAGGCAAAUGUGA | 0,017530497 |
| SEQ ID NO: 511 | Tab1-98 | hsa-miR-1254 | AGCCUGGAAGCUGGAGCCUGCAGU | 0,017530497 |
| SEQ ID NO: 176 | Tab1-99 | hsa-miR-568 | AUGUAUAAAUGUAUACACAC | 0,017530497 |
| SEQ ID NO: 659 | Tab1-100 | hsa-miR-519e* | UUCUCCAAAAGGGAGCACUUUC | 0,018441588 |

FIG. 10B (Continued)

| SEQ ID NO | Seq-ID | Name (microRNA/miRNA) | Sequence | Test significance |
|---|---|---|---|---|
| SEQ ID NO: 501 | Tab1-101 | hsa-miR-621 | GGCUAGCAACAGCGCUUACCU | 0,018759484 |
| SEQ ID NO: 526 | Tab1-102 | hsa-miR-500 | UAAUCCUUGCUACCUGGGUGAGA | 0,018759484 |
| SEQ ID NO: 28 | Tab1-103 | hsa-miR-29a | UAGCACCAUCUGAAAUCGGUUA | 0,019371611 |
| SEQ ID NO: 698 | Tab1-104 | hsa-miR-744 | UGCGGGGCUAGGGCUAACAGCA | 0,019371611 |
| SEQ ID NO: 753 | Tab1-105 | hsa-miR-106b | UAAAGUGCUGACAGUGCAGAU | 0,019881348 |
| SEQ ID NO: 512 | Tab1-106 | hsa-miR-1207-5p | UGGCAGGGAGGCUGGGAGGGG | 0,020439781 |
| SEQ ID NO: 856 | Tab1-107 | hsa-miR-181a-2* | ACCACUGACCGUUGACUGUACC | 0,020549704 |
| SEQ ID NO: 410 | Tab1-108 | hsa-miR-1268 | CGGGCGUGGUGGUGGGGG | 0,020810512 |
| SEQ ID NO: 790 | Tab1-109 | hsa-miR-1234 | UCGGCCUGACCACCCACCCCAC | 0,021434867 |
| SEQ ID NO: 377 | Tab1-110 | hsa-miR-1206 | UGUUCAUGUAGAUGUUUAAGC | 0,023397664 |
| SEQ ID NO: 9 | Tab1-111 | hsa-miR-574-5p | UGAGUGUGUGUGUGUGAGUGUGU | 0,023404017 |
| SEQ ID NO: 390 | Tab1-112 | hsa-miR-33a | GUGCAUUGUAGUUGCAUUGCA | 0,023541941 |
| SEQ ID NO: 389 | Tab1-113 | hsa-miR-32* | CAAUUUAGUGUGUGUGAUAUUU | 0,023572686 |
| SEQ ID NO: 347 | Tab1-114 | hsa-miR-9* | AUAAAGCUAGAUAACCGAAAGU | 0,023572686 |
| SEQ ID NO: 651 | Tab1-115 | hsa-miR-544 | AUUCUGCAUUUUUAGCAAGUUC | 0,023572686 |
| SEQ ID NO: 607 | Tab1-116 | hsa-miR-628-3p | UCUAGUAAGAGUGGCAGUCGA | 0,023858088 |
| SEQ ID NO: 483 | Tab1-117 | hsa-miR-217 | UACUGCAUCAGGAACUGAUUGGA | 0,023858088 |
| SEQ ID NO: 169 | Tab1-118 | hsa-miR-1912 | UACCCAGAGCAUGCAGUGUGAA | 0,023858088 |
| SEQ ID NO: 259 | Tab1-119 | hsa-miR-646 | AAGCAGCUGCCUCUGAGGC | 0,023858088 |
| SEQ ID NO: 90 | Tab1-120 | hsa-miR-1 | UGGAAUGUAAAGAAGUAUGUAU | 0,025157317 |
| SEQ ID NO: 141 | Tab1-121 | hsa-miR-1266 | CCUCAGGGCUGUAGAACAGGGCU | 0,025157317 |
| SEQ ID NO: 457 | Tab1-122 | hsa-miR-488* | CCCAGAUAAUGGCACUCUCAA | 0,025320273 |
| SEQ ID NO: 559 | Tab1-123 | hsa-miR-148b | UCAGUGCAUCACAGAACUUUGU | 0,02642468 |
| SEQ ID NO: 363 | Tab1-124 | hsa-miR-509-3-5p | UACUGCAGACGUGGCAAUCAUG | 0,02642468 |
| SEQ ID NO: 71 | Tab1-125 | hsa-miR-503 | UAGCAGCGGGAACAGUUCUGCAG | 0,027387368 |
| SEQ ID NO: 42 | Tab1-126 | hsa-miR-29c* | UGACCGAUUUCUCCUGGUGUUC | 0,027434153 |
| SEQ ID NO: 385 | Tab1-127 | hsa-miR-1300 | UUGAGAAGGAGGCUGCUG | 0,028179038 |
| SEQ ID NO: 159 | Tab1-128 | hsa-miR-1224-5p | GUGAGGACUCGGGAGGUGG | 0,028544926 |
| SEQ ID NO: 446 | Tab1-129 | hsa-miR-1225-5p | GUGGGUACGGCCCAGUGGGGGG | 0,029265392 |
| SEQ ID NO: 558 | Tab1-130 | hsa-miR-183* | GUGAAUUACCGAAGGGCCAUAA | 0,029478737 |
| SEQ ID NO: 177 | Tab1-131 | hsa-miR-648 | AAGUGUGCAGGGCACUGGU | 0,029600689 |
| SEQ ID NO: 100 | Tab1-132 | hsa-miR-17 | CAAAGUGCUUACAGUGCAGGUAG | 0,029636086 |
| SEQ ID NO: 129 | Tab1-133 | hsa-miR-182 | UUUGGCAAUGGUAGAACUCACACU | 0,029636086 |
| SEQ ID NO: 419 | Tab1-134 | hsa-miR-33a* | CAAUGUUUCCACAGUGCAUCAC | 0,031805111 |
| SEQ ID NO: 522 | Tab1-135 | hsa-miR-27a* | AGGGCUUAGCUGCUUGUGAGCA | 0,032378715 |
| SEQ ID NO: 383 | Tab1-136 | hsa-miR-548a-5p | AAAAGUAAUUGCGAGUUUUACC | 0,033678224 |
| SEQ ID NO: 630 | Tab1-137 | hsa-miR-1271 | CUUGGCACCUAGCAAGCACUCA | 0,033894671 |
| SEQ ID NO: 844 | Tab1-138 | hsa-miR-1258 | AGUUAGGAUUAGGUCGUGGAA | 0,034205811 |
| SEQ ID NO: 119 | Tab1-139 | hsa-miR-1302 | UUGGGACAUACUUAUGCUAAA | 0,034708746 |
| SEQ ID NO: 620 | Tab1-140 | hsa-let-7i* | CUGCGCAAGCUACUGCCUUGCU | 0,036510983 |
| SEQ ID NO: 418 | Tab1-141 | hsa-miR-410 | AAUAUAACACAGAUGGCCUGU | 0,036612975 |
| SEQ ID NO: 269 | Tab1-142 | hsa-miR-1280 | UCCCACCGCUGCCACCC | 0,037250015 |
| SEQ ID NO: 201 | Tab1-143 | hsa-miR-144 | UACAGUAUAGAUGAUGUACU | 0,037250015 |
| SEQ ID NO: 719 | Tab1-144 | hsa-miR-328 | CUGGCCCUCUCUGCCCUUCCGU | 0,038220527 |
| SEQ ID NO: 624 | Tab1-145 | hsa-miR-1226 | UCACCAGCCCUGUGUUCCCUAG | 0,039816047 |
| SEQ ID NO: 449 | Tab1-146 | hsa-miR-570 | CGAAAACAGCAAUUACCUUUGC | 0,040473359 |
| SEQ ID NO: 541 | Tab1-147 | hsa-miR-487a | AAUCAUACAGGGACAUCCAGUU | 0,041006357 |
| SEQ ID NO: 304 | Tab1-148 | hsa-miR-132* | ACCGUGGCUUUCGAUUGUUACU | 0,041006357 |
| SEQ ID NO: 805 | Tab1-149 | hsa-miR-622 | ACAGUCUGCUGAGGUUGGAGC | 0,041006357 |
| SEQ ID NO: 616 | Tab1-150 | hsa-miR-374b | AUAUAAUACAACCUGCUAAGUG | 0,041006357 |

FIG. 10B (Continued)

| SEQ ID NO | Seq ID | Name (microRNA miRNA) | Sequence | t-test significance |
|---|---|---|---|---|
| SEQ ID NO: 766 | Tab1-151 | hsa-miR-221 | AGCUACAUUGUCUGCUGGGUUUC | 0,041006357 |
| SEQ ID NO: 337 | Tab1-152 | hsa-miR-27b* | AGAGCUUAGCUGAUUGGUGAAC | 0,041971145 |
| SEQ ID NO: 85 | Tab1-153 | hsa-miR-1299 | UUCUGGAAUUCUGUGUGAGGGA | 0,04237911 |
| SEQ ID NO: 619 | Tab1-154 | hsa-miR-885-3p | AGGCAGCGGGGUGUAGUGGAUA | 0,04237911 |
| SEQ ID NO: 279 | Tab1-155 | hsa-miR-548a-3p | CAAAACUGGCAAUUACUUUUGC | 0,043261584 |
| SEQ ID NO: 53 | Tab1-156 | hsa-let-7b | UGAGGUAGUAGGUUGUGUGGUU | 0,043953954 |
| SEQ ID NO: 438 | Tab1-157 | hsa-miR-202* | UUCCUAUGCAUAUACUUCUUUG | 0,045126664 |
| SEQ ID NO: 143 | Tab1-158 | hsa-miR-631 | AGACCUGGCCCAGACCUCAGC | 0,045544732 |
| SEQ ID NO: 44 | Tab1-159 | hsa-miR-34c-3p | AAUCACUAACCACACGGCCAGG | 0,046793089 |
| SEQ ID NO: 217 | Tab1-160 | hsa-miR-31* | UGCUAUGCCAACAUAUUGCCAU | 0,046921038 |
| SEQ ID NO: 124 | Tab1-161 | hsa-miR-1247 | ACCCGUCCGUUCGUCCCCGGA | 0,047209787 |
| SEQ ID NO: 68 | Tab1-162 | hsa-miR-1245 | AAGUGAUCUAAAGGCCUACAU | 0,048608753 |
| SEQ ID NO: 779 | Tab1-163 | hsa-miR-515-5p | UUCUCCAAAAGAAAGCACUUUCUG | 0,048831114 |
| SEQ ID NO: 333 | Tab1-164 | hsa-miR-376b | AUCAUAGAGGAAAAUCCAUGUU | 0,048930534 |
| SEQ ID NO: 293 | Tab1-165 | hsa-miR-192* | CUGCCAAUUCCAUAGGUCACAG | 0,049319483 |
| SEQ ID NO: 372 | Tab1-166 | hsa-miR-924 | AGAGUCUUGUGAUGCUUGC | 0,050350013 |
| SEQ ID NO: 133 | Tab1-167 | hsa-miR-30d | UGUAAACAUCCCCGACUGGAAG | 0,050591776 |
| SEQ ID NO: 18 | Tab1-168 | hsa-let-7g | UGAGGUAGUAGUUUGUACAGUU | 0,050591776 |
| SEQ ID NO: 202 | Tab1-169 | hsa-miR-508-5p | UACUCCAGAGGGCGUCACUCAUG | 0,050591776 |
| SEQ ID NO: 166 | Tab1-170 | hsa-miR-29b | UAGCACCAUUUGAAAUCAGUGUU | 0,051169589 |
| SEQ ID NO: 417 | Tab1-171 | hsa-miR-34a | UGGCAGUGUCUUAGCUGGUUGU | 0,052910562 |
| SEQ ID NO: 485 | Tab1-172 | hsa-miR-30e* | CUUUCAGUCGGAUGUUUACAGC | 0,05376323 |
| SEQ ID NO: 780 | Tab1-173 | hsa-miR-564 | AGGCACGGUGUCAGCAGGC | 0,053923696 |
| SEQ ID NO: 286 | Tab1-174 | hsa-miR-489 | GUGACAUCACAUAUACGGCAGC | 0,053923696 |
| SEQ ID NO: 760 | Tab1-175 | hsa-miR-139-5p | UCUACAGUGCACGUGUCUCCAG | 0,053923696 |
| SEQ ID NO: 234 | Tab1-176 | hsa-miR-874 | CUGCCCUGGCCCGAGGGACCGA | 0,053923696 |
| SEQ ID NO: 716 | Tab1-177 | hsa-miR-654-5p | UGGUGGGCCGCAGAACAUGUGC | 0,053923696 |
| SEQ ID NO: 327 | Tab1-178 | hsa-miR-363 | AAUUGCACGGUAUCCAUCUGUA | 0,054156699 |
| SEQ ID NO: 243 | Tab1-179 | hsa-miR-493* | UUGUACAUGGUAGGCUUUCAUU | 0,054156699 |
| SEQ ID NO: 708 | Tab1-180 | hsa-miR-345 | GCUGACUCCUAGUCCAGGGCUC | 0,054314773 |
| SEQ ID NO: 543 | Tab1-181 | hsa-miR-300 | UAUACAAGGGCAGACUCUCUCU | 0,054314773 |
| SEQ ID NO: 323 | Tab1-182 | hsa-miR-137 | UUAUUGCUUAAGAAUACGCGUAG | 0,054314773 |
| SEQ ID NO: 733 | Tab1-183 | hsa-miR-1229 | CUCUCACCACUGCCCUCCCACAG | 0,05448776 |
| SEQ ID NO: 378 | Tab1-184 | hsa-miR-1259 | AUAUAUGAUGACUUAGCUUUU | 0,05485668 |
| SEQ ID NO: 467 | Tab1-185 | hsa-miR-767-5p | UGCACCAUGGUUGUCUGAGCAUG | 0,05485668 |
| SEQ ID NO: 218 | Tab1-186 | hsa-miR-33b* | CAGUGCCUCGGCAGUGCAGCCC | 0,056466966 |
| SEQ ID NO: 33 | Tab1-187 | hsa-miR-126* | CAUUAUUACUUUUGGUACGCG | 0,056466966 |
| SEQ ID NO: 697 | Tab1-188 | hsa-miR-25* | AGGCGGAGACUUGGGCAAUUG | 0,057237751 |
| SEQ ID NO: 192 | Tab1-189 | hsa-miR-24-2* | UGCCUACUGAGCUGAAACACAG | 0,059014671 |
| SEQ ID NO: 593 | Tab1-190 | hsa-miR-548p | UAGCAAAAACUGCAGUUACUUU | 0,060600928 |
| SEQ ID NO: 717 | Tab1-191 | hsa-miR-326 | CCUCUGGGCCCUUCCUCCAG | 0,06228617 |
| SEQ ID NO: 611 | Tab1-192 | hsa-miR-1295 | UUAGGCCGCAGAUCUGGGUGA | 0,063344113 |
| SEQ ID NO: 586 | Tab1-193 | hsa-miR-589 | UGAGAACCACGUCUGCUCUGAG | 0,065346969 |
| SEQ ID NO: 272 | Tab1-194 | hsa-miR-934 | UGUCUACUACUGGAGACACUGG | 0,065346969 |
| SEQ ID NO: 737 | Tab1-195 | hsa-miR-766 | ACUCCAGCCCCACAGCCUCAGC | 0,065674214 |
| SEQ ID NO: 123 | Tab1-196 | hsa-miR-603 | CACACACUGCAAUUACUUUUGC | 0,067215048 |
| SEQ ID NO: 835 | Tab1-197 | hsa-miR-450b-5p | UUUUGCAAUAUGUUCCUGAAUA | 0,068231645 |
| SEQ ID NO: 425 | Tab1-198 | hsa-miR-502-5p | AUCCUUGCUAUCUGGGUGCUA | 0,06879968 |
| SEQ ID NO: 772 | Tab1-199 | hsa-miR-1233 | UGAGCCCUGUCCUCCCGCAG | 0,072408565 |
| SEQ ID NO: 851 | Tab1-200 | hsa-miR-105* | ACGGAUGUUUGAGCAUGUGCUA | 0,072566994 |

FIG. 10B (Continued)

| SEQ ID NO | Seq ID | Name (microRNA miRNA) | Sequence | test significance |
|---|---|---|---|---|
| SEQ ID NO: 350 | Tab1-201 | hsa-miR-635 | ACUUGGGCACUGAAACAAUGCC | 0,073440463 |
| SEQ ID NO: 303 | Tab1-202 | hsa-miR-1286 | UGCAGGACCAAGAUGAGCCCU | 0,073440463 |
| SEQ ID NO: 638 | Tab1-203 | hsa-miR-499-5p | UUAAGACUUGCAGUGAUGUUU | 0,074311961 |
| SEQ ID NO: 798 | Tab1-204 | hsa-miR-302c* | UUUAACAUGGGGGUACCUGCUG | 0,075099522 |
| SEQ ID NO: 290 | Tab1-205 | hsa-let-7f-2* | CUAUACAGUCUACUGUCUUUCC | 0,075395505 |
| SEQ ID NO: 633 | Tab1-206 | hsa-miR-1282 | UCGUUUGCCUUUUUCUGCUU | 0,083275792 |
| SEQ ID NO: 723 | Tab1-207 | hsa-miR-1469 | CUCGGCGCGGGCGCGGGCUCC | 0,083930302 |
| SEQ ID NO: 63 | Tab1-208 | hsa-miR-1200 | CUCCUGAGCCAUUCUGAGCCUC | 0,086375453 |
| SEQ ID NO: 35 | Tab1-209 | hsa-miR-624* | UAGUACCAGUACCUUGUGUUCA | 0,086375453 |
| SEQ ID NO: 91 | Tab1-210 | hsa-miR-1291 | UGGCCCUGACUGAAGGACCAGU | 0,086375453 |
| SEQ ID NO: 239 | Tab1-211 | hsa-miR-342-5p | AGGGGUGCUAUCUGUGAUUGA | 0,086548673 |
| SEQ ID NO: 200 | Tab1-212 | hsa-miR-509-5p | UACUGCAGACAGUGGCAAUCA | 0,089271772 |
| SEQ ID NO: 70 | Tab1-213 | hsa-miR-1288 | UGGACUGCCUGAUCUGGAGA | 0,094543349 |
| SEQ ID NO: 628 | Tab1-214 | hsa-miR-196a* | CGGCAACAAGAAACUGCCUGAG | 0,095837993 |
| SEQ ID NO: 140 | Tab1-215 | hsa-miR-143* | GGUGCAGUGCUGCAUCUCUGGU | 0,096157896 |
| SEQ ID NO: 649 | Tab1-216 | hsa-miR-1202 | GUGCCAGCUGCAGUGGGGAG | 0,098703462 |
| SEQ ID NO: 677 | Tab1-217 | hsa-miR-193a-5p | UGGGUCUUUGCGGGCGAGAUGA | 0,098703462 |
| SEQ ID NO: 572 | Tab1-218 | hsa-miR-589* | UCAGAACAAAUGCCGGUUCCAGA | 0,098703462 |
| SEQ ID NO: 233 | Tab1-219 | hsa-miR-671-5p | AGGAAGCCCUGGAGGGGCUGGAG | 0,099228864 |
| SEQ ID NO: 847 | Tab1-220 | hsa-miR-588 | UUGGCCACAAUGGGUUAGAAC | 0,09947915 |
| SEQ ID NO: 493 | Tab1-221 | hsa-miR-1255a | AGGAUGAGCAAAGAAAGUAGAUU | 0,103097462 |
| SEQ ID NO: 747 | Tab1-222 | hsa-miR-138-1* | GCUACUUCACAACACCAGGGCC | 0,104240406 |
| SEQ ID NO: 527 | Tab1-223 | hsa-miR-1201 | AGCCUGAUUAAACACAUGCUCUGA | 0,108839833 |
| SEQ ID NO: 738 | Tab1-224 | hsa-miR-600 | ACUUACAGACAAGAGCCUUGCUC | 0,111467992 |
| SEQ ID NO: 497 | Tab1-225 | hsa-miR-1243 | AACUGGAUCAAUUAUAGGGAGUG | 0,113572086 |
| SEQ ID NO: 195 | Tab1-226 | hsa-miR-32 | UAUUGCACAUUACUAAGUUGCA | 0,113572086 |
| SEQ ID NO: 359 | Tab1-227 | hsa-miR-484 | UCAGGCUCAGUCCCUCCCGAU | 0,113991637 |
| SEQ ID NO: 622 | Tab1-228 | hsa-miR-130b | CAGUGCAAUGAUGAAAGGGCAU | 0,114412538 |
| SEQ ID NO: 108 | Tab1-229 | hsa-miR-34a* | CAAUCAGCAAGUAUACUGCCCU | 0,11971985 |
| SEQ ID NO: 574 | Tab1-230 | hsa-miR-592 | UUGUGUCAAUAUGCGAUGAUGU | 0,120627634 |
| SEQ ID NO: 675 | Tab1-231 | hsa-miR-486-3p | CGGGGCAGCUCAGUACAGGAU | 0,120627634 |
| SEQ ID NO: 305 | Tab1-232 | hsa-miR-33b | GUGCAUUGCUGUUGCAUUGC | 0,120627634 |
| SEQ ID NO: 539 | Tab1-233 | hsa-miR-448 | UUGCAUAUGUAGGAUGUCCCAU | 0,120627634 |
| SEQ ID NO: 577 | Tab1-234 | hsa-miR-576-3p | AAGAUGUGGAAAAAUUGGAAUC | 0,120627634 |
| SEQ ID NO: 81 | Tab1-235 | hsa-miR-922 | GCAGCAGAGAAUAGGACUACGUC | 0,120627634 |
| SEQ ID NO: 866 | Tab1-236 | hsa-miR-562 | AAAGUAGCUGGUUGAACUUUGC | 0,120627634 |
| SEQ ID NO: 54 | Tab1-237 | hsa-miR-542-3p | UGUGACAGAUUGAUAACUGAAA | 0,120627634 |
| SEQ ID NO: 746 | Tab1-238 | hsa-miR-155* | CUCCUACAUAUUAGCAUUAACA | 0,123726223 |
| SEQ ID NO: 149 | Tab1-239 | hsa-miR-647 | GUGGCUGCACUCACUUCCUUC | 0,124342172 |
| SEQ ID NO: 551 | Tab1-240 | hsa-miR-889 | UUAAUAUCGGACAACCAUUGU | 0,124454817 |
| SEQ ID NO: 311 | Tab1-241 | hsa-miR-500* | AUGCACCUGGGCAAGGAUUCUG | 0,125602142 |
| SEQ ID NO: 788 | Tab1-242 | hsa-miR-1228* | GUGGGCGGGGGCAGGUGUGUG | 0,125602142 |
| SEQ ID NO: 828 | Tab1-243 | hsa-miR-938 | UGCCCUUAAAGGUGAACCCAGU | 0,125602142 |
| SEQ ID NO: 360 | Tab1-244 | hsa-miR-103-as | UCAUAGCCCUGUACAAUGCUGCU | 0,125746226 |
| SEQ ID NO: 19 | Tab1-245 | hsa-miR-140-3p | UACCACAGGGUAGAACCACGG | 0,127736191 |
| SEQ ID NO: 356 | Tab1-246 | hsa-miR-122* | AACGCCAUUAUCACACUAAAUA | 0,127736191 |
| SEQ ID NO: 704 | Tab1-247 | hsa-miR-595 | GAAGUGUGCCGUGGUGUGUCU | 0,131738431 |
| SEQ ID NO: 701 | Tab1-248 | hsa-miR-1303 | UUUAGAGACGGGGUCUUGCUCU | 0,133160819 |
| SEQ ID NO: 637 | Tab1-249 | hsa-miR-23a* | GGGGUUCCUGGGGAUGGGAUUU | 0,133247268 |
| SEQ ID NO: 361 | Tab1-250 | hsa-miR-380 | UAUGUAAUAUGGUCCACAUCUU | 0,13436639 |

FIG. 10B (Continued)

| SEQ ID NO. | SeqID | Name (microRNA/miRNA) | Sequence | p-test significance |
|---|---|---|---|---|
| SEQ ID NO: 503 | Tab1-251 | hsa-miR-541 | UGGUGGGCACAGAAUCUGGACU | 0.140533368 |
| SEQ ID NO: 229 | Tab1-252 | hsa-miR-369-3p | AAUAAUACAUGGUUGAUCUUU | 0.141905308 |
| SEQ ID NO: 839 | Tab1-253 | hsa-miR-877* | UCCUCUUCUCCCUCCUCCCAG | 0.141905308 |
| SEQ ID NO: 158 | Tab1-254 | hsa-miR-18a | UAAGGUGCAUCUAGUGCAGAUAG | 0.144828637 |
| SEQ ID NO: 427 | Tab1-255 | hsa-miR-100 | AACCCGUAGAUCCGAACUUGUG | 0.145916876 |
| SEQ ID NO: 287 | Tab1-256 | hsa-miR-566 | GGGCGCCUGUGAUCCCAAC | 0.14716172 |
| SEQ ID NO: 756 | Tab1-257 | hsa-miR-187* | GGCUACAACACAGGACCCGGGC | 0.149917174 |
| SEQ ID NO: 705 | Tab1-258 | hsa-miR-1255b | CGGAUGAGCAAAGAAAGUGGUU | 0.150146074 |
| SEQ ID NO: 682 | Tab1-259 | hsa-miR-208a | AUAAGACGAGCAAAAAGCUUGU | 0.153053938 |
| SEQ ID NO: 3 | Tab1-260 | hsa-let-7i | UGAGGUAGUAGUUUGUGCUGUU | 0.155584098 |
| SEQ ID NO: 865 | Tab1-261 | hsa-miR-638 | AGGGAUCGCGGGCGGGUGCGGCU | 0.155685705 |
| SEQ ID NO: 447 | Tab1-262 | hsa-miR-223* | CGUGUAUUUGACAAGCUGAGUU | 0.158227157 |
| SEQ ID NO: 103 | Tab1-263 | hsa-miR-1305 | UUUUCAACUCUAAUGGGAGAGA | 0.158277678 |
| SEQ ID NO: 540 | Tab1-264 | hsa-miR-633 | CUAAUAGUAUCUACCACAAUAAA | 0.158861635 |
| SEQ ID NO: 837 | Tab1-265 | hsa-miR-409-3p | GAAUGUUGCUCGGUGAACCCCU | 0.158861635 |
| SEQ ID NO: 429 | Tab1-266 | hsa-miR-615-5p | GGGGGUCCCCGGUGCUCGGAUC | 0.159074635 |
| SEQ ID NO: 183 | Tab1-267 | hsa-miR-512-3p | AAGUGCUGUCAUAGCUGAGGUC | 0.159074635 |
| SEQ ID NO: 517 | Tab1-268 | hsa-miR-585 | UGGGCGUAUCUGUAUGCUA | 0.159838843 |
| SEQ ID NO: 291 | Tab1-269 | hsa-miR-1322 | GAUGAUGCUGCUGAUGCUG | 0.159838843 |
| SEQ ID NO: 636 | Tab1-270 | hsa-miR-144* | GGAUAUCAUCAUAUACUGUAAG | 0.161061186 |
| SEQ ID NO: 504 | Tab1-271 | hsa-miR-543 | AAACAUUCGCGGUGCACUCUU | 0.161061186 |
| SEQ ID NO: 178 | Tab1-272 | hsa-miR-662 | UCCCACGUUGUGGCCCAGCAG | 0.161061186 |
| SEQ ID NO: 530 | Tab1-273 | hsa-miR-425* | AUCGGGAAUGUCGUGUCCGCCC | 0.161061186 |
| SEQ ID NO: 576 | Tab1-274 | hsa-miR-944 | AAAUUAUUGUACAUCGGAUGAG | 0.161436981 |
| SEQ ID NO: 357 | Tab1-275 | hsa-miR-450b-3p | UUGGGAUCAUUUUGCAUCCAUA | 0.161436981 |
| SEQ ID NO: 181 | Tab1-276 | hsa-miR-891b | UGCAACUUACCUGAGUCAUUGA | 0.16360492 |
| SEQ ID NO: 524 | Tab1-277 | hsa-miR-220c | ACACAGGGCUGUUGUGAAGACU | 0.16360492 |
| SEQ ID NO: 707 | Tab1-278 | hsa-miR-455-3p | GCAGUCCAUGGGCAUAUACAC | 0.16360492 |
| SEQ ID NO: 145 | Tab1-279 | hsa-miR-30c | UGUAAACAUCCUACACUCUCAGC | 0.16360492 |
| SEQ ID NO: 548 | Tab1-280 | hsa-miR-1294 | UGUGAGGUUGGCAUUGUUGUCU | 0.164265257 |
| SEQ ID NO: 727 | Tab1-281 | hsa-miR-1298 | UUCAUUCGGCUGUCCAGAUGUA | 0.16708942 |
| SEQ ID NO: 857 | Tab1-282 | hsa-miR-199b-5p | CCCAGUGUUUAGACUAUCUGUUC | 0.1671671 |
| SEQ ID NO: 214 | Tab1-283 | hsa-miR-520e | AAAGUGCUUCCUUUUUGAGGG | 0.1671671 |
| SEQ ID NO: 818 | Tab1-284 | hsa-miR-1228 | UCACACCUGCCUCGCCCCCC | 0.169045179 |
| SEQ ID NO: 597 | Tab1-285 | hsa-miR-877 | GUAGAGGAGAUGGCGCAGGG | 0.169045179 |
| SEQ ID NO: 537 | Tab1-286 | hsa-miR-431 | UGUCUUGCAGGCCGUCAUGCA | 0.171256018 |
| SEQ ID NO: 662 | Tab1-287 | hsa-miR-516b | AUCGGAGGUAAGAAGCACUUU | 0.171330477 |
| SEQ ID NO: 562 | Tab1-288 | hsa-miR-1203 | CCCGGAGCCAGGAUGCAGCUC | 0.174507788 |
| SEQ ID NO: 757 | Tab1-289 | hsa-miR-125b | UCCCUGAGACCCUAACUUGUGA | 0.1765915 |
| SEQ ID NO: 850 | Tab1-290 | hsa-miR-1470 | GCCCUCCGCCCGUGCACCCG | 0.177102193 |
| SEQ ID NO: 575 | Tab1-291 | hsa-miR-892a | CACUGUGUCCUUUCUGCGUAG | 0.177102193 |
| SEQ ID NO: 596 | Tab1-292 | hsa-miR-605 | UAAAUCCCAUGGUGCCUUCUCCU | 0.177440007 |
| SEQ ID NO: 297 | Tab1-293 | hsa-miR-582-3p | UAACUGGUUGAACAACUGAACC | 0.177440007 |
| SEQ ID NO: 285 | Tab1-294 | hsa-miR-29b-2* | CUGGUUUCACAUGGUGGCUUAG | 0.177440007 |
| SEQ ID NO: 314 | Tab1-295 | hsa-miR-558 | UGAGCUGCUGUACCAAAAU | 0.177440007 |
| SEQ ID NO: 725 | Tab1-296 | hsa-miR-886-5p | CGGGUCGGAGUUAGCUCAAGCGG | 0.178116551 |
| SEQ ID NO: 849 | Tab1-297 | hsa-miR-664* | ACUGGCUAGGGAAAAUGAUUGGAU | 0.188436337 |
| SEQ ID NO: 791 | Tab1-298 | hsa-miR-149* | AGGGAGGGACGGGGCGUGUGC | 0.188436337 |
| SEQ ID NO: 550 | Tab1-299 | hsa-miR-142-5p | CAUAAAGUAGAAAGCACUACU | 0.193859516 |
| SEQ ID NO: 420 | Tab1-300 | hsa-miR-502-3p | AAUGCACCUGGGCAAGGAUUCA | 0.193859516 |

FIG. 10B (Continued)

| SEQ ID NO | Seq ID | Name (microRNA/miRNA) | Sequence | t-test significance |
|---|---|---|---|---|
| SEQ ID NO: 188 | Tab1-301 | hsa-miR-146b-3p | UGCCCUGUGGACUCAGUUCUGG | 0,193859516 |
| SEQ ID NO: 603 | Tab1-302 | hsa-miR-505 | CGUCAACACUUGCUGGUUUCCU | 0,193859516 |
| SEQ ID NO: 400 | Tab1-303 | hsa-miR-432* | CUGGAUGGCUCCUCCAUGUCU | 0,194166922 |
| SEQ ID NO: 477 | Tab1-304 | hsa-miR-628-5p | AUGCUGACAUAUUUACUAGAGG | 0,196879788 |
| SEQ ID NO: 646 | Tab1-305 | hsa-miR-302d* | ACUUUAACAUGGAGGCACUUGC | 0,196879788 |
| SEQ ID NO: 307 | Tab1-306 | hsa-miR-620 | AUGGAGAUAGAUAUGAAAU | 0,198281114 |
| SEQ ID NO: 80 | Tab1-307 | hsa-miR-1261 | AUGGAUAAGGCUUUGGCUU | 0,19909011 |
| SEQ ID NO: 573 | Tab1-308 | hsa-miR-643 | ACUUGUAUGCUAGCUCAGGUAG | 0,200122644 |
| SEQ ID NO: 476 | Tab1-309 | hsa-miR-429 | UAAUACUGUCUGGUAAAACCGU | 0,200164698 |
| SEQ ID NO: 36 | Tab1-310 | hsa-miR-505* | GGGAGCCAGGAAGUAUUGAUGU | 0,200164698 |
| SEQ ID NO: 216 | Tab1-311 | hsa-miR-106a* | CUGCAAUGUAAGCACUUCUUAC | 0,201432258 |
| SEQ ID NO: 841 | Tab1-312 | hsa-miR-517* | CCUCUAGAUGGAAGCACUGUCU | 0,206009053 |
| SEQ ID NO: 601 | Tab1-313 | hsa-miR-148a* | AAAGUUCUGAGACACUCCGACU | 0,206009053 |
| SEQ ID NO: 102 | Tab1-314 | hsa-let-7f-1* | CUAUACAAUCUAUUGCCUUCC | 0,20830304 |
| SEQ ID NO: 553 | Tab1-315 | hsa-miR-99b | CACCCGUAGAACCGACCUUGCG | 0,20830304 |
| SEQ ID NO: 650 | Tab1-316 | hsa-miR-202 | AGAGGUAUAGGGCAUGGGAA | 0,20830304 |
| SEQ ID NO: 76 | Tab1-317 | hsa-miR-720 | UCUCGCUGGGGCCUCCA | 0,20830304 |
| SEQ ID NO: 564 | Tab1-318 | hsa-miR-383 | AGAUCAGAAGGUGAUUGUGGCU | 0,20830304 |
| SEQ ID NO: 227 | Tab1-319 | hsa-miR-590-3p | UAAUUUUAUGUAUAAGCUAGU | 0,20830304 |
| SEQ ID NO: 729 | Tab1-320 | hsa-miR-1226* | GUGAGGGCAUGCAGGCCUGGAUGGGG | 0,210087753 |
| SEQ ID NO: 842 | Tab1-321 | hsa-miR-193b* | CGGGGUUUUGAGGGCGAGAUGA | 0,210087753 |
| SEQ ID NO: 718 | Tab1-322 | hsa-miR-1825 | UCCAGUGCCCUCCUCUCC | 0,21111594 |
| SEQ ID NO: 370 | Tab1-323 | hsa-miR-520c-3p | AAAGUGCUUCCUUUUAGAGGGU | 0,21111594 |
| SEQ ID NO: 740 | Tab1-324 | hsa-miR-340* | UCCGUCUCAGUUACUUUAUAGC | 0,21111594 |
| SEQ ID NO: 475 | Tab1-325 | hsa-miR-34c-5p | AGGCAGUGUAGUUAGCUGAUUGC | 0,211386507 |
| SEQ ID NO: 164 | Tab1-326 | hsa-miR-377 | AUCACACAAAGGCAACUUUUGU | 0,211896525 |
| SEQ ID NO: 340 | Tab1-327 | hsa-miR-376a* | GUAGAUUCUCCUUCUAUGAGUA | 0,211896525 |
| SEQ ID NO: 561 | Tab1-328 | hsa-miR-548o | CCAAAACUGCAGUUACUUUUGC | 0,212680979 |
| SEQ ID NO: 445 | Tab1-329 | hsa-miR-525-3p | GAAGGCGCUUCCCUUUAGAGCG | 0,213227096 |
| SEQ ID NO: 212 | Tab1-330 | hsa-miR-1262 | AUGGGUGAAUUUGUAGAAGGAU | 0,21721339 |
| SEQ ID NO: 466 | Tab1-331 | hsa-miR-124 | UAAGGCACGCGGUGAAUGCC | 0,220220099 |
| SEQ ID NO: 618 | Tab1-332 | hsa-miR-483-5p | AAGACGGGAGGAAAGAAGGGAG | 0,220910651 |
| SEQ ID NO: 431 | Tab1-333 | hsa-miR-657 | GGCAGGUUCUCACCCUCUCUAGG | 0,221053377 |
| SEQ ID NO: 335 | Tab1-334 | hsa-miR-523 | GAACGCGCUUCCCUAUAGAGGGU | 0,221053377 |
| SEQ ID NO: 7 | Tab1-335 | hsa-miR-98 | UGAGGUAGUAAGUUGUAUUGUU | 0,22261375 |
| SEQ ID NO: 264 | Tab1-336 | hsa-miR-337-3p | CUCCUAUAUGAUGCCUUUCUUC | 0,22261375 |
| SEQ ID NO: 242 | Tab1-337 | hsa-miR-933 | UGUGCGCAGGGAGACCUCUCCC | 0,226590856 |
| SEQ ID NO: 452 | Tab1-338 | hsa-miR-582-5p | UUACAGUUGUUCAACCAGUUACU | 0,227821919 |
| SEQ ID NO: 588 | Tab1-339 | hsa-miR-224 | CAAGUCACUAGUGGUUCCGUU | 0,229624448 |
| SEQ ID NO: 441 | Tab1-340 | hsa-miR-548i | AAAAGUAAUUGCGGAUUUUGCC | 0,234720663 |
| SEQ ID NO: 685 | Tab1-341 | hsa-miR-181c | AACAUUCAACCUGUCGGUGAGU | 0,234720663 |
| SEQ ID NO: 221 | Tab1-342 | hsa-miR-1278 | UAGUACUGUGCAUAUCAUCUAU | 0,238939335 |
| SEQ ID NO: 481 | Tab1-343 | hsa-miR-101* | CAGUUAUCACAGUGCUGAUGCU | 0,239144648 |
| SEQ ID NO: 834 | Tab1-344 | hsa-miR-130a | CAGUGCAAUGUUAAAAGGGCAU | 0,239144648 |
| SEQ ID NO: 289 | Tab1-345 | hsa-miR-28-3p | CACUAGAUUGUGAGCUCCUGGA | 0,239144648 |
| SEQ ID NO: 480 | Tab1-346 | hsa-let-7a* | CUAUACAAUCUACUGUCUUUC | 0,239144648 |
| SEQ ID NO: 468 | Tab1-347 | hsa-miR-200c | UAAUACUGCCGGGUAAUGAUGGA | 0,239144648 |
| SEQ ID NO: 845 | Tab1-348 | hsa-miR-154 | UAGGUUAUCCGUGUUGCCUUCG | 0,239144648 |
| SEQ ID NO: 858 | Tab1-349 | hsa-miR-27a | UUCACAGUGGCUAAGUUCCGC | 0,239144648 |
| SEQ ID NO: 220 | Tab1-350 | hsa-miR-99b* | CAAGCUCGUGUCUGUGGGUCCG | 0,239144648 |

FIG. 10B (Continued)

| SEQ ID NO | Seq ID | Name (microRNA/miRNA) | Sequence | t-test significance |
|---|---|---|---|---|
| SEQ ID NO: 525 | Tab1-351 | hsa-miR-524-3p | GAAGGCGCUUCCCUUUGGAGU | 0,239236378 |
| SEQ ID NO: 118 | Tab1-352 | hsa-miR-23b | AUCACAUUGCCAGGGAUUACC | 0,239236378 |
| SEQ ID NO: 241 | Tab1-353 | hsa-miR-1297 | UUCAAGUAAUUCAGGUG | 0,242177174 |
| SEQ ID NO: 743 | Tab1-354 | hsa-miR-1179 | AAGCAUUCUUUCAUUGGUUGG | 0,242259609 |
| SEQ ID NO: 261 | Tab1-355 | hsa-miR-885-5p | UCCAUUACACUACCCUGCCUCU | 0,245878592 |
| SEQ ID NO: 713 | Tab1-356 | hsa-miR-663 | AGGCGGGGCGCCGCGGGACCGC | 0,24900771 |
| SEQ ID NO: 473 | Tab1-357 | hsa-miR-21 | UAGCUUAUCAGACUGAUGUUGA | 0,251460511 |
| SEQ ID NO: 610 | Tab1-358 | hsa-miR-135b* | AUGUAGGGCUAAAAGCCAUGGG | 0,253113558 |
| SEQ ID NO: 205 | Tab1-359 | hsa-miR-937 | AUCCGCGCUCUGACUCUCUGCC | 0,253997054 |
| SEQ ID NO: 136 | Tab1-360 | hsa-miR-34b | CAAUCACUAACUCCACUGCCAU | 0,254258845 |
| SEQ ID NO: 89 | Tab1-361 | hsa-miR-16 | UAGCAGCACGUAAAUAUUGGCG | 0,25438781 |
| SEQ ID NO: 544 | Tab1-362 | hsa-miR-1826 | AUUGAUCAUCGACACUUCGAACGCAAU | 0,256862278 |
| SEQ ID NO: 324 | Tab1-363 | hsa-miR-154* | AAUCAUACACGGUUGACCUAUU | 0,257604511 |
| SEQ ID NO: 654 | Tab1-364 | hsa-miR-940 | AAGGCAGGGCCCCCGCUCCCC | 0,258972955 |
| SEQ ID NO: 454 | Tab1-365 | hsa-miR-659 | CUUGGUUCAGGGAGGGUCCCA | 0,258972955 |
| SEQ ID NO: 298 | Tab1-366 | hsa-miR-629* | GUUCUCCCAACGUAAGCCCAGC | 0,259713934 |
| SEQ ID NO: 759 | Tab1-367 | hsa-miR-30a* | CUUUCAGUCGGAUGUUUGCAGC | 0,259713934 |
| SEQ ID NO: 478 | Tab1-368 | hsa-miR-29a* | ACUGAUUUCUUUUGGUGUUCAG | 0,260164521 |
| SEQ ID NO: 781 | Tab1-369 | hsa-miR-634 | AACCAGCACCCCAACUUUGGAC | 0,260164521 |
| SEQ ID NO: 640 | Tab1-370 | hsa-miR-490-3p | CAACCUGGAGGACUCCAUGCUG | 0,260164521 |
| SEQ ID NO: 24 | Tab1-371 | hsa-miR-26b | UUCAAGUAAUUCAGGAUAGGU | 0,264400976 |
| SEQ ID NO: 61 | Tab1-372 | hsa-miR-19a* | AGUUUUGCAUAGUUGCACUACA | 0,264567923 |
| SEQ ID NO: 182 | Tab1-373 | hsa-miR-342-3p | UCUCACACAGAAAUCGCACCCGU | 0,264567923 |
| SEQ ID NO: 679 | Tab1-374 | hsa-miR-24-1* | UGCCUACUGAGCUGAUAUCAGU | 0,264890121 |
| SEQ ID NO: 20 | Tab1-375 | hsa-miR-339-5p | UCCCUGUCCUCCAGGAGCUCACG | 0,266489431 |
| SEQ ID NO: 699 | Tab1-376 | hsa-miR-550 | AGUGCCUGAGGGAGUAAGAGCCC | 0,266995739 |
| SEQ ID NO: 14 | Tab1-377 | hsa-let-7e | UGAGGUAGGAGGUUGUAUAGUU | 0,268841801 |
| SEQ ID NO: 21 | Tab1-378 | hsa-miR-361-5p | UUAUCAGAAUCUCCAGGGGUAC | 0,268841801 |
| SEQ ID NO: 710 | Tab1-379 | hsa-miR-1321 | CAGGGAGGUGAAUGUGAU | 0,273455554 |
| SEQ ID NO: 166 | Tab1-380 | hsa-miR-301a | CAGUGCAAUAGUAUUGUCAAAGC | 0,273455554 |
| SEQ ID NO: 565 | Tab1-381 | hsa-miR-1913 | UCUGCCCCCUCCGCUGCUGCCA | 0,274833654 |
| SEQ ID NO: 219 | Tab1-382 | hsa-miR-654-3p | UAUGUCUGCUGACCAUCACCUU | 0,275703435 |
| SEQ ID NO: 267 | Tab1-383 | hsa-miR-519a | AAAGUGCAUCCUUUUAGAGUGU | 0,277196408 |
| SEQ ID NO: 579 | Tab1-384 | hsa-miR-625* | GACUAUAGAACUUUCCCCCUCA | 0,277196408 |
| SEQ ID NO: 623 | Tab1-385 | hsa-miR-1274a | GUCCCUGUUCAGGCGCCA | 0,277196408 |
| SEQ ID NO: 773 | Tab1-386 | hsa-miR-1290 | UGGAUUUUUGGAUCAGGGA | 0,279227266 |
| SEQ ID NO: 506 | Tab1-387 | hsa-miR-26a-1* | CCUAUUCUUGGUUACUUGCACG | 0,283847021 |
| SEQ ID NO: 331 | Tab1-388 | hsa-miR-222* | CUCAGUAGCCAGUGUAGAUCCU | 0,286671943 |
| SEQ ID NO: 479 | Tab1-389 | hsa-miR-370 | GCCUGCUGGGGUGGAACCUGGU | 0,291662183 |
| SEQ ID NO: 453 | Tab1-390 | hsa-miR-590-5p | GAGCUUAUUCAUAAAAGUGCAG | 0,298436524 |
| SEQ ID NO: 678 | Tab1-391 | hsa-miR-671-3p | UCCGGUUCUCAGGGCUCCACC | 0,298436524 |
| SEQ ID NO: 843 | Tab1-392 | hsa-miR-524-5p | CUACAAAGGGAAGCACUUUCUC | 0,308517636 |
| SEQ ID NO: 4 | Tab1-393 | hsa-let-7d | AGAGGUAGUAGGUUGCAUAGUU | 0,308759989 |
| SEQ ID NO: 257 | Tab1-394 | hsa-miR-587 | UUUCCAUAGGUGAUGAGUCAC | 0,311658225 |
| SEQ ID NO: 639 | Tab1-395 | hsa-miR-183 | UAUGGCACUGGUAGAAUUCACU | 0,311762874 |
| SEQ ID NO: 302 | Tab1-396 | hsa-miR-127-5p | CUGAAGCUCAGAGGGCUCUGAU | 0,311762874 |
| SEQ ID NO: 30 | Tab1-397 | hsa-miR-210 | CUGUGCGUGUGACAGCGGCUGA | 0,312879774 |
| SEQ ID NO: 107 | Tab1-398 | hsa-miR-619 | GACCUGGACAUGUUUGUGCCCAGU | 0,315454067 |
| SEQ ID NO: 542 | Tab1-399 | hsa-miR-149 | UCUGGCUCCGUGUCUUCACUCCC | 0,315454067 |
| SEQ ID NO: 571 | Tab1-400 | hsa-miR-518c | CAAAGCGCUUCUCUUUAGAGUGU | 0,315454067 |

FIG. 10B (Continued)

| SEQ ID NO | SeqID | Name (microRNA/miRNA) | Sequence | Test significance |
|---|---|---|---|---|
| SEQ ID NO: 114 | Tab1-401 | hsa-miR-1284 | UCUAUACAGACCCUGGCUUUUC | 0.315454067 |
| SEQ ID NO: 184 | Tab1-402 | hsa-miR-623 | AUCCCUUGCAGGGGCUGUUGGGU | 0.315591256 |
| SEQ ID NO: 407 | Tab1-403 | hsa-miR-519e | AAGUGCCUCCUUUUAGAGUGUU | 0.319657836 |
| SEQ ID NO: 213 | Tab1-404 | hsa-miR-153 | UUGCAUAGUCACAAAAGUGAUC | 0.32006095 |
| SEQ ID NO: 116 | Tab1-405 | hsa-miR-599 | GUUGUGUCAGUUUAUCAAAC | 0.320979054 |
| SEQ ID NO: 295 | Tab1-406 | hsa-miR-411* | UAUGUAACACGGUCCACUAACC | 0.320979054 |
| SEQ ID NO: 859 | Tab1-407 | hsa-miR-518a-3p | GAAAGCGCUUCCCUUUGCUGGA | 0.324308422 |
| SEQ ID NO: 55 | Tab1-408 | hsa-miR-516b* | UGCUUCCUUUCAGAGGGU | 0.324372505 |
| SEQ ID NO: 392 | Tab1-409 | hsa-miR-616 | AGUCAUUGGAGGGUUUGAGCAG | 0.324748713 |
| SEQ ID NO: 608 | Tab1-410 | hsa-miR-1914 | CCCUGUGCCCGGCCCACUUCUG | 0.326381759 |
| SEQ ID NO: 247 | Tab1-411 | hsa-miR-193a-3p | AACUGGCCUACAAAGUCCCAGU | 0.326381759 |
| SEQ ID NO: 224 | Tab1-412 | hsa-miR-1468 | CUCCGUUUGCCUGUUUCGCUG | 0.326594517 |
| SEQ ID NO: 643 | Tab1-413 | hsa-miR-483-3p | UCACUCCUCUCCUCCCGUCUU | 0.328858287 |
| SEQ ID NO: 64 | Tab1-414 | hsa-miR-522 | AAAAUGGUUCCCUUUAGAGUGU | 0.330220519 |
| SEQ ID NO: 77 | Tab1-415 | hsa-miR-1246 | AAUGGAUUUUUGGAGCAGG | 0.330414212 |
| SEQ ID NO: 794 | Tab1-416 | hsa-miR-1181 | CCGUCGCCGCCACCCGAGCCG | 0.330414212 |
| SEQ ID NO: 585 | Tab1-417 | hsa-miR-100* | CAAGCUUGUAUCUAUAGGUAUG | 0.330836904 |
| SEQ ID NO: 629 | Tab1-418 | hsa-miR-1270 | CUGGAGAUAUGGAAGAGCUGUGU | 0.331309957 |
| SEQ ID NO: 827 | Tab1-419 | hsa-miR-1250 | ACGGUGCUGGAUGUGGCCUUU | 0.331309957 |
| SEQ ID NO: 125 | Tab1-420 | hsa-miR-1539 | UCCUGCGCGUCCCAGAUGCCC | 0.331309957 |
| SEQ ID NO: 413 | Tab1-421 | hsa-miR-15a* | CAGGCCAUAUUGGUGCUGCUCA | 0.331309957 |
| SEQ ID NO: 369 | Tab1-422 | hsa-miR-516a-3p | UGCUUCCUUUCAGAGGGU | 0.331945413 |
| SEQ ID NO: 388 | Tab1-423 | hsa-miR-196b | UAGGUAGUUUCCUGUUGUUGGG | 0.331945413 |
| SEQ ID NO: 676 | Tab1-424 | hsa-miR-596 | AAGCCUGCCCGGCUCCUCGGG | 0.332241443 |
| SEQ ID NO: 382 | Tab1-425 | hsa-miR-372 | AAAGUGCUGCGACAUUUGAGCGU | 0.338337546 |
| SEQ ID NO: 696 | Tab1-426 | hsa-miR-1273 | GGGCGACAAAGCAAGACUCUUUCUU | 0.34131865 |
| SEQ ID NO: 563 | Tab1-427 | hsa-miR-135a* | UAUAGGGAUUGGAGCCGUGGCG | 0.341540665 |
| SEQ ID NO: 751 | Tab1-428 | hsa-miR-639 | AUCGCUGCGGUUGCGAGCGCUGU | 0.341540665 |
| SEQ ID NO: 722 | Tab1-429 | hsa-miR-1909* | UGAGUGCCGGUGCCUGCCCUG | 0.341540665 |
| SEQ ID NO: 492 | Tab1-430 | hsa-miR-296-5p | AGGGCCCCCCCUCAAUCCUGU | 0.341540665 |
| SEQ ID NO: 801 | Tab1-431 | hsa-miR-656 | AAUAUUAUACAGUCAACCUCU | 0.34325022 |
| SEQ ID NO: 67 | Tab1-432 | hsa-miR-192 | CUGACCUAUGAAUUGACAGCC | 0.354100965 |
| SEQ ID NO: 549 | Tab1-433 | hsa-miR-548l | AAAAGUAUUGCGGGUUUUGUC | 0.354497159 |
| SEQ ID NO: 367 | Tab1-434 | hsa-miR-653 | GUGUUGAAACAAUCUCUACUG | 0.354642247 |
| SEQ ID NO: 296 | Tab1-435 | hsa-miR-424 | CAGCAGCAAUUCAUGUUUUGAA | 0.355052546 |
| SEQ ID NO: 321 | Tab1-436 | hsa-miR-1253 | AGAGAAGAAGAUCAGCCUGCA | 0.357014754 |
| SEQ ID NO: 625 | Tab1-437 | hsa-miR-518e* | CUCUAGAGGGAAGCGCUUUCUG | 0.362045451 |
| SEQ ID NO: 591 | Tab1-438 | hsa-miR-190b | UGAUAUGUUUGAUAUGGGUU | 0.362820484 |
| SEQ ID NO: 776 | Tab1-439 | hsa-miR-614 | GAACGCCUGUUCUUGCCAGGUGG | 0.362820484 |
| SEQ ID NO: 598 | Tab1-440 | hsa-miR-125a-3p | ACAGGUGAGGUUCUUGGGAGCC | 0.362820484 |
| SEQ ID NO: 432 | Tab1-441 | hsa-miR-651 | UUUAGGAUAAGCUUGACUUUUG | 0.363753509 |
| SEQ ID NO: 197 | Tab1-442 | hsa-miR-454 | UAGUGCAAUAUUGCAAUAGGGU | 0.366097513 |
| SEQ ID NO: 283 | Tab1-443 | hsa-miR-644 | AGUGUGGCUUUCUUAGAGC | 0.368756685 |
| SEQ ID NO: 745 | Tab1-444 | hsa-miR-30b* | CUGGGAGGUGGAUGUUUACUUC | 0.369278576 |
| SEQ ID NO: 209 | Tab1-445 | hsa-miR-1184 | CCUGCAGCGACUUGAUGGCUUCC | 0.369769198 |
| SEQ ID NO: 310 | Tab1-446 | hsa-miR-520h | ACAAAGUGCUUCCCUUUAGAGU | 0.37157953 |
| SEQ ID NO: 79 | Tab1-447 | hsa-miR-297 | AUGUAUGUGUGCAUGUGCAUG | 0.37157953 |
| SEQ ID NO: 860 | Tab1-448 | hsa-miR-1265 | CAGGAUGUGGUCAAGUGUUGUU | 0.372890395 |
| SEQ ID NO: 256 | Tab1-449 | hsa-miR-583 | CAAAGAGGAAGGUCCCAUUAC | 0.375142139 |
| SEQ ID NO: 399 | Tab1-450 | hsa-miR-18b | UAAGGUGCAUCUAGUGCAGUUAG | 0.375142139 |

FIG. 10B (Continued)

| SEQ ID NO | Seq ID | Name (microRNA miRNA) | Sequence | t-test significance |
|---|---|---|---|---|
| SEQ ID NO: 471 | Tab1-451 | hsa-miR-936 | ACAGUAGAGGGAGGAAUCGCAG | 0,375142139 |
| SEQ ID NO: 316 | Tab1-452 | hsa-miR-1263 | AUGGUACCCUGGCAUACUGAGU | 0,375142139 |
| SEQ ID NO: 469 | Tab1-453 | hsa-miR-572 | GUCCGCUCGGCGGUGGCCCA | 0,375142139 |
| SEQ ID NO: 450 | Tab1-454 | hsa-miR-320a | AAAAGCUGGGUUGAGAGGGCGA | 0,375142139 |
| SEQ ID NO: 831 | Tab1-455 | hsa-miR-1249 | ACGCCCUUCCCCCCCUUCUUCA | 0,375265231 |
| SEQ ID NO: 761 | Tab1-456 | hsa-miR-1307 | ACUCGGCGUGGCGUCGGUCGUG | 0,377013669 |
| SEQ ID NO: 546 | Tab1-457 | hsa-miR-486-5p | UCCUGUACUGAGCUGCCCCGAG | 0,378689797 |
| SEQ ID NO: 334 | Tab1-458 | hsa-miR-490-5p | CCAUGGAUCUCCAGGUGGGU | 0,378689797 |
| SEQ ID NO: 797 | Tab1-459 | hsa-miR-203 | GUGAAAUGUUUAGGACCACUAG | 0,378689797 |
| SEQ ID NO: 754 | Tab1-460 | hsa-miR-129-3p | AAGCCCUUACCCCAAAAAGCAU | 0,378689797 |
| SEQ ID NO: 820 | Tab1-461 | hsa-miR-575 | GAGCCAGUUGGACAGGAGC | 0,378689797 |
| SEQ ID NO: 395 | Tab1-462 | hsa-miR-26a-2* | CCUAUUCUUGAUUACUUGUUUC | 0,378689797 |
| SEQ ID NO: 568 | Tab1-463 | hsa-miR-298 | AGCAGAAGCAGGGAGGUUCUCCCA | 0,378689797 |
| SEQ ID NO: 436 | Tab1-464 | hsa-miR-501-3p | AAUGCACCCGGGCAAGGAUUCU | 0,382606427 |
| SEQ ID NO: 40 | Tab1-465 | hsa-miR-363* | CGGGUGGAUCACGAUGCAAUUU | 0,387972126 |
| SEQ ID NO: 732 | Tab1-466 | hsa-miR-150* | CUGGUACAGGCCUGGGGGACAG | 0,38963321 |
| SEQ ID NO: 653 | Tab1-467 | hsa-miR-760 | CGGCUCUGGGUCUGUGGGGA | 0,389646374 |
| SEQ ID NO: 393 | Tab1-468 | hsa-miR-876-5p | UGGAUUUCUUUGUGAAUCACCA | 0,391926575 |
| SEQ ID NO: 403 | Tab1-469 | hsa-miR-626 | AGCUGUCUGAAAAUGUCUU | 0,395413561 |
| SEQ ID NO: 59 | Tab1-470 | hsa-miR-602 | GACACGGGCGACAGCUGCGGCCC | 0,396803101 |
| SEQ ID NO: 371 | Tab1-471 | hsa-miR-708* | CAACUAGACUGUGAGCUUCUAG | 0,397410101 |
| SEQ ID NO: 381 | Tab1-472 | hsa-miR-1293 | UGGGUGGUCUGGAGAUUUGUGC | 0,397410101 |
| SEQ ID NO: 683 | Tab1-473 | hsa-miR-135a | UAUGGCUUUUUAUUCCUAUGUGA | 0,397852695 |
| SEQ ID NO: 317 | Tab1-474 | hsa-miR-211 | UUCCCUUUGUCAUCCUUCGCCU | 0,399198327 |
| SEQ ID NO: 153 | Tab1-475 | hsa-miR-1324 | CCAGACAGAAUUCUAUGCACUUUC | 0,399198327 |
| SEQ ID NO: 762 | Tab1-476 | hsa-miR-769-3p | CUGGGAUCUCCGGGGUCUUGGUU | 0,400664102 |
| SEQ ID NO: 421 | Tab1-477 | hsa-miR-379 | UGGUAGACUAUGGAACGUAGG | 0,401906727 |
| SEQ ID NO: 440 | Tab1-478 | hsa-miR-520d-3p | AAAGUGCUUCUCUUUGGUGGGU | 0,401906727 |
| SEQ ID NO: 786 | Tab1-479 | hsa-miR-518a-5p | CUGCAAAGGGAAGCCCUUUC | 0,402813063 |
| SEQ ID NO: 652 | Tab1-480 | hsa-miR-593 | UGUCUCUGCUGGGGUUUCU | 0,410733773 |
| SEQ ID NO: 838 | Tab1-481 | hsa-miR-527 | CUGCAAAGGGAAGCCCUUUC | 0,411425252 |
| SEQ ID NO: 692 | Tab1-482 | hsa-miR-516a-5p | UUCUCGAGGAAAGAAGCACUUUC | 0,412047849 |
| SEQ ID NO: 702 | Tab1-483 | hsa-miR-650 | AGGAGGCAGCGCUCUCAGGAC | 0,412792045 |
| SEQ ID NO: 744 | Tab1-484 | hsa-miR-1178 | UUGCUCACUGUUCUUCCCUAG | 0,413823037 |
| SEQ ID NO: 796 | Tab1-485 | hsa-miR-1231 | GUGUCUGGGCGGACAGCUGC | 0,414294389 |
| SEQ ID NO: 46 | Tab1-486 | hsa-miR-374a | UUAUAAUACAACCUGAUAAGUG | 0,417875814 |
| SEQ ID NO: 110 | Tab1-487 | hsa-miR-1256 | AGGCAUUGACUUCUCACUAGCU | 0,422404938 |
| SEQ ID NO: 783 | Tab1-488 | hsa-miR-941 | CACCCGGCUGUGUGCACAUGUGC | 0,423233999 |
| SEQ ID NO: 235 | Tab1-489 | hsa-miR-1911* | CACCAGGCAUUGUGGUCUCC | 0,424076618 |
| SEQ ID NO: 581 | Tab1-490 | hsa-miR-1281 | UCGCCUCCUCCUCUCCC | 0,426525923 |
| SEQ ID NO: 706 | Tab1-491 | hsa-miR-1252 | AGAAGGAAAUUGAAUUCAUUUA | 0,42807231 |
| SEQ ID NO: 83 | Tab1-492 | hsa-miR-611 | GCGAGGACCCCUCGGGGUCUGAC | 0,434004119 |
| SEQ ID NO: 592 | Tab1-493 | hsa-miR-375 | UUUGUUCGUUCGGCUCGCGUGA | 0,434020339 |
| SEQ ID NO: 115 | Tab1-494 | hsa-miR-199b-3p | ACAGUAGUCUGCACAUUGGUUA | 0,437090287 |
| SEQ ID NO: 131 | Tab1-495 | hsa-miR-215 | AUGACCUAUGAAUUGACAGAC | 0,439973637 |
| SEQ ID NO: 206 | Tab1-496 | hsa-miR-346 | UGUCUGCCCGCAUGCCUGCCUCU | 0,440177538 |
| SEQ ID NO: 271 | Tab1-497 | hsa-miR-198 | GGUCCAGAGGGGAGAUAGGUUC | 0,44024154 |
| SEQ ID NO: 246 | Tab1-498 | hsa-miR-181c* | AACCAUCGACCGUUGAUUGGAC | 0,44024154 |
| SEQ ID NO: 775 | Tab1-499 | hsa-miR-769-5p | UGAGACCUCGGGGUUCUGAGCU | 0,446525942 |
| SEQ ID NO: 767 | Tab1-500 | hsa-miR-191* | GCUGCGCUUGGAUUUCGUCCCC | 0,446573004 |

FIG. 10B (Continued)

| SEQ ID NO | Seq ID | Name (microRNA/miRNA) | Sequence | t-test significance |
|---|---|---|---|---|
| SEQ ID NO: 374 | Tab1-501 | hsa-miR-512-5p | CACUCAGCCUUGAGGGCACUUUC | 0,446601179 |
| SEQ ID NO: 319 | Tab1-502 | hsa-miR-220b | CCACCACCGUGUCUGACACUU | 0,446608937 |
| SEQ ID NO: 721 | Tab1-503 | hsa-miR-886-3p | CGCGGGUGCUUACUGACCCUU | 0,4500346 |
| SEQ ID NO: 111 | Tab1-504 | hsa-miR-20b* | ACUGUAGUAUGGGCACUUCCAG | 0,452108102 |
| SEQ ID NO: 437 | Tab1-505 | hsa-miR-302a | UAAGUGCUUCCAUGUUUUGGUGA | 0,454000804 |
| SEQ ID NO: 106 | Tab1-506 | hsa-miR-106b* | CCGCACUGUGGGUACUUGCUGC | 0,459710333 |
| SEQ ID NO: 764 | Tab1-507 | hsa-miR-7-1* | CAACAAAUCACAGUCUGCCAUA | 0,460376321 |
| SEQ ID NO: 25 | Tab1-508 | hsa-miR-604 | AGGCUGCGGAAUUCAGGAC | 0,460376321 |
| SEQ ID NO: 92 | Tab1-509 | hsa-miR-138-2* | GCUAUUUCACGACACCAGGGUU | 0,461435075 |
| SEQ ID NO: 604 | Tab1-510 | hsa-miR-496 | UGAGUAUUACAUGGCCAAUCUC | 0,461695951 |
| SEQ ID NO: 735 | Tab1-511 | hsa-miR-320d | AAAAGCUGGGUUGAGAGGA | 0,468379686 |
| SEQ ID NO: 811 | Tab1-512 | hsa-miR-495 | AAACAAACAUGGUGCACUUCUU | 0,468379686 |
| SEQ ID NO: 836 | Tab1-513 | hsa-miR-432 | UCUUGGAGUAGGUCAUUGGGUGG | 0,468802712 |
| SEQ ID NO: 802 | Tab1-514 | hsa-miR-526b* | GAAAGUGCUUCCUUUUAGAGGC | 0,474699836 |
| SEQ ID NO: 536 | Tab1-515 | hsa-miR-138 | AGCUGGUGUUGUGAAUCAGGCCG | 0,475071987 |
| SEQ ID NO: 462 | Tab1-516 | hsa-miR-218-1* | AUGGUUCCGUCAAGCACCAUGG | 0,475596861 |
| SEQ ID NO: 207 | Tab1-517 | hsa-miR-506 | UAAGGCACCCUUCUGAGUAGA | 0,483842553 |
| SEQ ID NO: 236 | Tab1-518 | hsa-miR-1292 | UGGGAACGGGUUCCGGCAGACGCUG | 0,483842553 |
| SEQ ID NO: 351 | Tab1-519 | hsa-miR-200b | UAAUACUGCCUGGUAAUGAUGA | 0,488956479 |
| SEQ ID NO: 366 | Tab1-520 | hsa-miR-369-5p | AGAUCGACCGUGUUAUAUUCGC | 0,491381288 |
| SEQ ID NO: 731 | Tab1-521 | hsa-miR-1471 | GCCCGCGUGUGGAGCCAGGUGU | 0,493639719 |
| SEQ ID NO: 680 | Tab1-522 | hsa-miR-19b-2* | AGUUUUGCAGGUUUGCAUUUCA | 0,496570991 |
| SEQ ID NO: 406 | Tab1-523 | hsa-miR-9 | UCUUUGGUUAUCUAGCUGUAUGA | 0,500011514 |
| SEQ ID NO: 190 | Tab1-524 | hsa-miR-449b | AGGCAGUGUAUUGUUAGCUGGC | 0,502446002 |
| SEQ ID NO: 12 | Tab1-525 | hsa-miR-25 | CAUUGCACUUGUCUCGGUCUGA | 0,505665104 |
| SEQ ID NO: 672 | Tab1-526 | hsa-miR-1267 | CCUGUUGAAGUGUAAUCCCCA | 0,509629962 |
| SEQ ID NO: 189 | Tab1-527 | hsa-miR-520b | AAAGUGCUUCCUUUUAGAGGG | 0,509979611 |
| SEQ ID NO: 661 | Tab1-528 | hsa-miR-26b* | CCUGUUCUCCAUUACUUGGCUC | 0,512172529 |
| SEQ ID NO: 142 | Tab1-529 | hsa-miR-554 | GCUAGUCCUGACUCAGCCAGU | 0,515829635 |
| SEQ ID NO: 2 | Tab1-530 | hsa-miR-423-5p | UGAGGGGCAGAGAGCGAGACUUU | 0,519402593 |
| SEQ ID NO: 62 | Tab1-531 | hsa-miR-433 | AUCAUGAUGGGCUCCUCGGUGU | 0,519402593 |
| SEQ ID NO: 755 | Tab1-532 | hsa-miR-1306 | ACGUUGGCUCUGGUGGUG | 0,519402593 |
| SEQ ID NO: 148 | Tab1-533 | hsa-miR-645 | UCUAGGCUGGUACUGCUGA | 0,519402593 |
| SEQ ID NO: 534 | Tab1-534 | hsa-miR-548c-3p | CAAAAAUCUCAAUUACUUUUGC | 0,521228772 |
| SEQ ID NO: 96 | Tab1-535 | hsa-miR-548h | AAAAGUAAUCGCGGUUUUUGUC | 0,525614604 |
| SEQ ID NO: 712 | Tab1-536 | hsa-miR-548c-5p | AAAAGUAAUUGCGGUUUUUGCC | 0,531224088 |
| SEQ ID NO: 180 | Tab1-537 | hsa-miR-1287 | UGCUGGAUCAGUGGUUCGAGUC | 0,531854468 |
| SEQ ID NO: 570 | Tab1-538 | hsa-miR-412 | ACUUCACCUGGUCCACUAGCCGU | 0,534911351 |
| SEQ ID NO: 318 | Tab1-539 | hsa-miR-1304 | UUUGAGGCUACAGUGAGAUGUG | 0,541471772 |
| SEQ ID NO: 171 | Tab1-540 | hsa-miR-214* | UGCCUGUCUACACUUGCUGUGC | 0,544692491 |
| SEQ ID NO: 146 | Tab1-541 | hsa-miR-28-5p | AAGGAGCUCACAGUCUAUUGAG | 0,545336294 |
| SEQ ID NO: 29 | Tab1-542 | hsa-miR-1248 | ACCUUCUUGUAUAAGCACUGUGCUAAA | 0,547251927 |
| SEQ ID NO: 332 | Tab1-543 | hsa-miR-323-3p | CACAUUACACGGUCGACCUCU | 0,547251927 |
| SEQ ID NO: 343 | Tab1-544 | hsa-miR-532-3p | CCUCCCACACCCAAGGCUUGCA | 0,548448982 |
| SEQ ID NO: 329 | Tab1-545 | hsa-miR-219-1-3p | AGAGUUGAGUCUGGACGUCCCG | 0,549136112 |
| SEQ ID NO: 846 | Tab1-546 | hsa-miR-637 | ACUGGGGGCUUUCGGGCUCUGCGU | 0,552482272 |
| SEQ ID NO: 300 | Tab1-547 | hsa-miR-519b-3p | AAAGUGCAUCCUUUUAGAGGUU | 0,554013697 |
| SEQ ID NO: 689 | Tab1-548 | hsa-miR-10a | UACCCUGUAGAUCCGAAUUUGUG | 0,554013697 |
| SEQ ID NO: 222 | Tab1-549 | hsa-miR-135b | UAUGGCUUUUCAUUCCUAUGUGA | 0,554013697 |
| SEQ ID NO: 173 | Tab1-550 | hsa-miR-302f | UAAUUGCUUCCAUGUUU | 0,556112545 |

FIG. 10B (Continued)

| SEQ ID NO | SeqID | Name microRNA (miRNA) | Sequence | total significance |
|---|---|---|---|---|
| SEQ ID NO: 109 | Tab1-551 | hsa-miR-652 | AAUGGCGCCACUAGGGUUGUG | 0,556112545 |
| SEQ ID NO: 262 | Tab1-552 | hsa-miR-194* | CCAGUGGGGCUGCUGUUAUCUG | 0,556112545 |
| SEQ ID NO: 765 | Tab1-553 | hsa-miR-196a | UAGGUAGUUUCAUGUUGUUGGG | 0,556112545 |
| SEQ ID NO: 223 | Tab1-554 | hsa-let-7c* | UAGAGUUACACCCUGGGAGUUA | 0,556112545 |
| SEQ ID NO: 439 | Tab1-555 | hsa-miR-206 | UGGAAUGUAAGGAAGUGUGUGG | 0,556112545 |
| SEQ ID NO: 655 | Tab1-556 | hsa-let-7e* | CUAUACGGCCUCCUAGCUUUCC | 0,556112545 |
| SEQ ID NO: 132 | Tab1-557 | hsa-miR-147b | GUGUGCGGAAAUGCUUCUGCUA | 0,556112545 |
| SEQ ID NO: 556 | Tab1-558 | hsa-miR-518e | AAAGCGCUUCCCUUCAGAGUG | 0,556112545 |
| SEQ ID NO: 152 | Tab1-559 | hsa-miR-1289 | UGGAGUCCAGGAAUCUGCAUUUU | 0,561548903 |
| SEQ ID NO: 833 | Tab1-560 | hsa-miR-1208 | UCACUGUUCAGACAGGCGGA | 0,563707633 |
| SEQ ID NO: 163 | Tab1-561 | hsa-miR-371-3p | AAGUGCCGCCAUCUUUUGAGUGU | 0,564921522 |
| SEQ ID NO: 32 | Tab1-562 | hsa-miR-453 | AGGUUGUCCGUGGUGAGUUCGCA | 0,567377405 |
| SEQ ID NO: 426 | Tab1-563 | hsa-miR-31 | AGGCAAGAUGCUGGCAUAGCU | 0,567377405 |
| SEQ ID NO: 694 | Tab1-564 | hsa-miR-1915 | CCCCAGGGCGACGCGGCGGG | 0,567503712 |
| SEQ ID NO: 830 | Tab1-565 | hsa-miR-1279 | UCAUAUUGCUUCUUUCU | 0,571092246 |
| SEQ ID NO: 684 | Tab1-566 | hsa-miR-381 | UAUACAAGGGCAAGCUCUCUGU | 0,571523437 |
| SEQ ID NO: 770 | Tab1-567 | hsa-miR-1285 | UCUGGGCAACAAAGUGAGACCU | 0,571523437 |
| SEQ ID NO: 69 | Tab1-568 | hsa-miR-151-5p | UCGAGGAGCUCACAGUCUAGU | 0,573198276 |
| SEQ ID NO: 41 | Tab1-569 | hsa-miR-15b* | CGAAUCAUUAUUUGCUGCUCUA | 0,57359824 |
| SEQ ID NO: 37 | Tab1-570 | hsa-miR-425 | AAUGACACGAUCACUCCCGUUGA | 0,577510466 |
| SEQ ID NO: 724 | Tab1-571 | hsa-miR-338-3p | UCCAGCAUCAGUGAUUUUGUUG | 0,580169863 |
| SEQ ID NO: 353 | Tab1-572 | hsa-miR-876-3p | UGGUGGUUUACAAAGUAAUUCA | 0,580169863 |
| SEQ ID NO: 668 | Tab1-573 | hsa-miR-125b-1* | ACGGGUUAGGCUCUUGGGAGCU | 0,580169863 |
| SEQ ID NO: 521 | Tab1-574 | hsa-miR-93 | CAAAGUGCUGUUCGUGCAGGUAG | 0,580169863 |
| SEQ ID NO: 265 | Tab1-575 | hsa-miR-493 | UGAAGGUCUACUGUGUGCCAGG | 0,580169863 |
| SEQ ID NO: 614 | Tab1-576 | hsa-miR-485-3p | GUCAUACACGGCUCUCCUCUCU | 0,581097836 |
| SEQ ID NO: 161 | Tab1-577 | hsa-miR-181a* | ACCAUCGACCGUUGAUUGUACC | 0,585714021 |
| SEQ ID NO: 605 | Tab1-578 | hsa-miR-1323 | UCAAAACUGAGGGGCAUUUUCU | 0,591370567 |
| SEQ ID NO: 657 | Tab1-579 | hsa-miR-18b* | UGCCCUAAAUGCCCCUUCUGGC | 0,591370567 |
| SEQ ID NO: 263 | Tab1-580 | hsa-miR-299-5p | UGGUUUACCGUCCCACAUACAU | 0,592146368 |
| SEQ ID NO: 167 | Tab1-581 | hsa-miR-1277 | UACGUAGAUAUAUAUGUAUUUU | 0,592146368 |
| SEQ ID NO: 863 | Tab1-582 | hsa-miR-150 | UCUCCCAACCCUUGUACCAGUG | 0,592146368 |
| SEQ ID NO: 354 | Tab1-583 | hsa-miR-373* | ACUCAAAAUGGGGGCGCUUUCC | 0,592146368 |
| SEQ ID NO: 855 | Tab1-584 | hsa-miR-519a* | CUCUAGAGGGAAGCGCUUUCUG | 0,592146368 |
| SEQ ID NO: 621 | Tab1-585 | hsa-miR-935 | CCAGUUACCGCUUCCGCUACCGC | 0,595432308 |
| SEQ ID NO: 589 | Tab1-586 | hsa-miR-16-2* | CCAAUAUUACUGUGCUGCUUUA | 0,595432308 |
| SEQ ID NO: 352 | Tab1-587 | hsa-miR-455-5p | UAUGUGCCUUUGGACUACAUCG | 0,595432308 |
| SEQ ID NO: 666 | Tab1-588 | hsa-miR-132 | UAACAGUCUACAGCCAUGGUCG | 0,595432308 |
| SEQ ID NO: 648 | Tab1-589 | hsa-miR-454* | ACCCUAUCAAUAUUGUCUCUGC | 0,595432308 |
| SEQ ID NO: 346 | Tab1-590 | hsa-miR-545* | UCAGUAAAUGUUUAUUAGAUGA | 0,595543256 |
| SEQ ID NO: 408 | Tab1-591 | hsa-miR-204 | UUCCCUUUGUCAUCCUAUGCCU | 0,598928408 |
| SEQ ID NO: 252 | Tab1-592 | hsa-miR-548b-5p | AAAAGUAAUUGUGGUUUUGGCC | 0,601885514 |
| SEQ ID NO: 451 | Tab1-593 | hsa-miR-770-5p | UCCAGUACCACGUGUCAGGGCCA | 0,605158716 |
| SEQ ID NO: 720 | Tab1-594 | hsa-miR-146b-5p | UGAGAACUGAAUUCCAUAGGCU | 0,605158716 |
| SEQ ID NO: 423 | Tab1-595 | hsa-miR-518d-5p | CUCUAGAGGGAAGCACUUUCUG | 0,607320615 |
| SEQ ID NO: 238 | Tab1-596 | hsa-miR-15b | UAGCAGCACAUCAUGGUUUACA | 0,611319842 |
| SEQ ID NO: 199 | Tab1-597 | hsa-miR-19b-1* | AGUUUUGCAGGUUUGCAUCCAGC | 0,611319842 |
| SEQ ID NO: 139 | Tab1-598 | hsa-miR-378 | ACUGGACUUGGAGUCAGAAGG | 0,612379274 |
| SEQ ID NO: 104 | Tab1-599 | hsa-miR-129-5p | CUUUUUGCGGUCUGGGCUUGC | 0,612998945 |
| SEQ ID NO: 693 | Tab1-600 | hsa-miR-510 | UACUCAGGAGAGUGGCAAUCAC | 0,612998945 |

FIG. 10B (Continued)

| SEQ ID NO | Seq ID | Name microRNA (miRNA) | Sequence | Qaal significance |
|---|---|---|---|---|
| SEQ ID NO: 78 | Tab1-601 | hsa-miR-338-5p | AACAAUAUCCUGGUGCUGAGUG | 0,614264927 |
| SEQ ID NO: 373 | Tab1-602 | hsa-miR-520d-5p | CUACAAAGGGAAGCCCUUUC | 0,619528052 |
| SEQ ID NO: 711 | Tab1-603 | hsa-miR-513c | UUCUCAAGGAGGUGUCGUUUAU | 0,619598756 |
| SEQ ID NO: 515 | Tab1-604 | hsa-miR-539 | GGAGAAAUUAUCCUUGGUGUGU | 0,620252569 |
| SEQ ID NO: 8 | Tab1-605 | hsa-miR-19a | UGUGCAAAUCUAUGCAAAACUGA | 0,620252569 |
| SEQ ID NO: 555 | Tab1-606 | hsa-miR-200a | UAACACUGUCUGGUAACGAUGU | 0,620252569 |
| SEQ ID NO: 554 | Tab1-607 | hsa-miR-200b* | CAUCUUACUGGGCAGCAUUGGA | 0,620252569 |
| SEQ ID NO: 864 | Tab1-608 | hsa-miR-335 | UCAAGAGCAAUAACGAAAAAUGU | 0,620252569 |
| SEQ ID NO: 203 | Tab1-609 | hsa-miR-569 | AGUUAAUGAAUCCUGGAAAGU | 0,620252569 |
| SEQ ID NO: 529 | Tab1-610 | hsa-miR-1914* | GGAGGGGUCCCGCACUGGGAGG | 0,621973183 |
| SEQ ID NO: 484 | Tab1-611 | hsa-miR-519b-5p | CUCUAGAGGGAAGCGCUUUCUG | 0,627550294 |
| SEQ ID NO: 771 | Tab1-612 | hsa-miR-518f* | CUCUAGAGGGAAGCACUUUCUC | 0,628289927 |
| SEQ ID NO: 520 | Tab1-613 | hsa-miR-573 | CUGAAGUGAUGUGUAACUGAUCAG | 0,628289927 |
| SEQ ID NO: 312 | Tab1-614 | hsa-miR-551b* | GAAAUCAAGCGUGGGUGAGACC | 0,628289927 |
| SEQ ID NO: 822 | Tab1-615 | hsa-miR-875-3p | CCUGGAAACACUGAGGUUGUG | 0,629452457 |
| SEQ ID NO: 288 | Tab1-616 | hsa-miR-1538 | CGGCCGGGCUGCUGCUGUUCCU | 0,631620045 |
| SEQ ID NO: 191 | Tab1-617 | hsa-miR-520g | ACAAAGUGCUUCCCUUUAGAGUGU | 0,638581862 |
| SEQ ID NO: 204 | Tab1-618 | hsa-miR-638 | UGUGCUUGCUCGUCCCGCCCGCA | 0,639310876 |
| SEQ ID NO: 6 | Tab1-619 | hsa-miR-15a | UAGCAGCACAUAAUGGUUUGUG | 0,643794056 |
| SEQ ID NO: 670 | Tab1-620 | hsa-miR-627 | GUGAGUCUCUAAGAAAAGAGGA | 0,643794056 |
| SEQ ID NO: 225 | Tab1-621 | hsa-miR-374b* | CUUAGCAGGUUGUAUUAUCAUU | 0,645024259 |
| SEQ ID NO: 709 | Tab1-622 | hsa-miR-96 | UUUGGCACUAGCACAUUUUUGCU | 0,651179502 |
| SEQ ID NO: 117 | Tab1-623 | hsa-miR-411 | UAGUAGACCGUAUAGCGUACG | 0,652371304 |
| SEQ ID NO: 349 | Tab1-624 | hsa-miR-571 | UGAGUUGGCCAUCUGAGUGAG | 0,652815994 |
| SEQ ID NO: 342 | Tab1-625 | hsa-miR-1182 | GAGGGUCUUGGGAGGGAUGUGAC | 0,652815994 |
| SEQ ID NO: 150 | Tab1-626 | hsa-miR-302b* | ACUUUAACAUGGAAGUGCUUUC | 0,652815994 |
| SEQ ID NO: 208 | Tab1-627 | hsa-miR-379* | UAUGUAACAUGGUCCACUAACU | 0,652815994 |
| SEQ ID NO: 330 | Tab1-628 | hsa-miR-220a | CCACACCGUAUCUGACACUUU | 0,657009528 |
| SEQ ID NO: 1 | Tab1-629 | hsa-miR-126 | UCGUACCGUGAGUAAUAAUGCG | 0,657009528 |
| SEQ ID NO: 226 | Tab1-630 | hsa-miR-514 | AUUGACACUUCUGUGAGUAGA | 0,657009528 |
| SEQ ID NO: 580 | Tab1-631 | hsa-miR-1260 | AUCCCACCUCUGCCACCA | 0,657844854 |
| SEQ ID NO: 793 | Tab1-632 | hsa-miR-200c* | CGUCUUACCCAGCAGUGUUUGG | 0,657844854 |
| SEQ ID NO: 10 | Tab1-633 | hsa-miR-324-3p | ACUGCCCCAGGUGCUGCUGG | 0,66185069 |
| SEQ ID NO: 251 | Tab1-634 | hsa-miR-545 | UCAGCAAACAUUUAUUGUGUGC | 0,661950447 |
| SEQ ID NO: 362 | Tab1-635 | hsa-miR-513a-5p | UUCACAGGGAGGUGUCAU | 0,664274223 |
| SEQ ID NO: 502 | Tab1-636 | hsa-miR-1915* | ACCUUGCCUUGCUGCCCGGCC | 0,664274223 |
| SEQ ID NO: 739 | Tab1-637 | hsa-miR-641 | AAAGACAUAGGAUAGAGUCACCUC | 0,665742723 |
| SEQ ID NO: 339 | Tab1-638 | hsa-miR-888 | UACUCAAAAAGCUGUCAGUCA | 0,668569181 |
| SEQ ID NO: 162 | Tab1-639 | hsa-miR-218-2* | CAUGGUUCUGUCAAGCACCGCG | 0,672838942 |
| SEQ ID NO: 673 | Tab1-640 | hsa-miR-507 | UUUUGCACCUUUUGGAGUGAA | 0,672838942 |
| SEQ ID NO: 282 | Tab1-641 | hsa-miR-384 | AUUCCUAGAAAUUGUUCAUA | 0,681686382 |
| SEQ ID NO: 587 | Tab1-642 | hsa-miR-218 | UUGUGCUUGAUCUAACCAUGU | 0,687308342 |
| SEQ ID NO: 848 | Tab1-643 | hsa-miR-155 | UUAAUGCUAAUCGUGAUAGGGGU | 0,687308342 |
| SEQ ID NO: 396 | Tab1-644 | hsa-miR-187 | UCGUGUCUUGUGUUGCAGCCGG | 0,688911345 |
| SEQ ID NO: 422 | Tab1-645 | hsa-miR-498 | UUUCAAGCCAGGGGGCGUUUUC | 0,691825163 |
| SEQ ID NO: 861 | Tab1-646 | hsa-miR-92a | UAUUGCACUUGUCCCGGCCUGU | 0,699502459 |
| SEQ ID NO: 752 | Tab1-647 | hsa-miR-518d-3p | CAAAGCGCUUCCCUUUGGAGC | 0,699502459 |
| SEQ ID NO: 375 | Tab1-648 | hsa-miR-374a* | CUUAUCAGAUUGUAUUGUAAUU | 0,701120366 |
| SEQ ID NO: 292 | Tab1-649 | hsa-miR-1827 | UGAGGCAGUAGAUUGAAU | 0,704329351 |
| SEQ ID NO: 634 | Tab1-650 | hsa-miR-10b* | ACAGAUUCGAUUCUAGGGGAAU | 0,709330539 |

FIG. 10B (Continued)

| SEQ ID NO | Seq ID | Name microRNA (miRNA) | Sequence | t-test significance |
|---|---|---|---|---|
| SEQ ID NO: 730 | Tab1-651 | hsa-miR-421 | AUCAACAGACAUUAAUUGGGCGC | 0.709330539 |
| SEQ ID NO: 615 | Tab1-652 | hsa-miR-541* | AAAGGAUUCUGCUGUCGGUCCCACU | 0.709330539 |
| SEQ ID NO: 245 | Tab1-653 | hsa-miR-141 | UAACACUGUCUGGUAAAGAUGG | 0.710634011 |
| SEQ ID NO: 278 | Tab1-654 | hsa-miR-517b | UCGUGCAUCCCUUUAGAGUGUU | 0.711881595 |
| SEQ ID NO: 101 | Tab1-655 | hsa-miR-30b | UGUAAACAUCCUACACUCAGCU | 0.718740147 |
| SEQ ID NO: 175 | Tab1-656 | hsa-miR-548j | AAAAGUAAUUGCGGUCUUUGGU | 0.720045031 |
| SEQ ID NO: 258 | Tab1-657 | hsa-miR-624 | CACAAGGUAUUGGUAUUACCU | 0.720045031 |
| SEQ ID NO: 749 | Tab1-658 | hsa-miR-191 | CAACGGAAUCCCAAAAGCAGCUG | 0.721716233 |
| SEQ ID NO: 459 | Tab1-659 | hsa-miR-802 | CAGUAACAAAGAUUCAUCCUUGU | 0.721759568 |
| SEQ ID NO: 460 | Tab1-660 | hsa-miR-542-5p | UCGGGGAUCAUCAUGUCACGAGA | 0.721759568 |
| SEQ ID NO: 154 | Tab1-661 | hsa-miR-513a-3p | UAAAUUUCACCUUUCUGAGAAGG | 0.722960963 |
| SEQ ID NO: 829 | Tab1-662 | hsa-miR-608 | AGGGGUGGUGUUGGGACAGCUCCGU | 0.728749257 |
| SEQ ID NO: 128 | Tab1-663 | hsa-miR-409-5p | AGGUUACCCGAGCAACUUUGCAU | 0.731671228 |
| SEQ ID NO: 113 | Tab1-664 | hsa-miR-517a | AUCGUGCAUCCCUUUAGAGUGU | 0.73479974 |
| SEQ ID NO: 27 | Tab1-665 | hsa-miR-93* | ACUGCUGAGCUAGCACUUCCCG | 0.742283122 |
| SEQ ID NO: 17 | Tab1-666 | hsa-let-7a | UGAGGUAGUAGGUUGUAUAGUU | 0.742283122 |
| SEQ ID NO: 508 | Tab1-667 | hsa-miR-184 | UGGACGGAGAACUGAUAAGGGU | 0.742283122 |
| SEQ ID NO: 397 | Tab1-668 | hsa-miR-199a-3p | ACAGUAGUCUGCACAUUGGUUA | 0.74447289 |
| SEQ ID NO: 472 | Tab1-669 | hsa-miR-548n | CAAAAGUAAUUGUGGAUUUUGU | 0.748072189 |
| SEQ ID NO: 328 | Tab1-670 | hsa-miR-1537 | AAAAACGCUCUAGUUACAGUUGU | 0.750397294 |
| SEQ ID NO: 414 | Tab1-671 | hsa-miR-181d | AACAUUCAUUGUUGUCGGUGGGU | 0.750397294 |
| SEQ ID NO: 582 | Tab1-672 | hsa-miR-337-5p | GAACGGCUUCAUACAGGAGUU | 0.757344712 |
| SEQ ID NO: 168 | Tab1-673 | hsa-miR-130a* | UUCACAUUGUGCUACUGUCUGC | 0.758994236 |
| SEQ ID NO: 590 | Tab1-674 | hsa-miR-301b | CAGUGCAAUGAUAUUGUCAAAGC | 0.761640489 |
| SEQ ID NO: 567 | Tab1-675 | hsa-miR-371-5p | ACUCAAACUGUGGGGGCACU | 0.767436325 |
| SEQ ID NO: 94 | Tab1-676 | hsa-miR-548d-3p | CAAAAACCACAGUUUCUUUUGC | 0.769306239 |
| SEQ ID NO: 815 | Tab1-677 | hsa-miR-1274b | UCCCUGUUCGGGCGCCA | 0.769306239 |
| SEQ ID NO: 210 | Tab1-678 | hsa-miR-579 | UUCAUUUGGUAUAAACCGCGAUU | 0.773050164 |
| SEQ ID NO: 215 | Tab1-679 | hsa-miR-632 | GUGUCUGCUUCCUGUGGGA | 0.774794391 |
| SEQ ID NO: 412 | Tab1-680 | hsa-miR-7-2* | CAACAAAUCCCAGUCUACCUAA | 0.775709011 |
| SEQ ID NO: 105 | Tab1-681 | hsa-miR-1204 | UCGUGGCCUGGUCUCCAUUAU | 0.775709011 |
| SEQ ID NO: 376 | Tab1-682 | hsa-miR-921 | CUAGUGAGGGACAGAACCAGGAUUC | 0.775709011 |
| SEQ ID NO: 742 | Tab1-683 | hsa-miR-520a-5p | CUCCAGAGGGAAGUACUUUCU | 0.775709011 |
| SEQ ID NO: 39 | Tab1-684 | hsa-miR-668 | UGUCACUCGGCUCGGCCCACUAC | 0.775709011 |
| SEQ ID NO: 486 | Tab1-685 | hsa-miR-147 | GUGUGUGGAAAUGCUUCUGC | 0.775709011 |
| SEQ ID NO: 566 | Tab1-686 | hsa-miR-373 | GAAGUGCUUCGAUUUUGGGGUGU | 0.775709011 |
| SEQ ID NO: 766 | Tab1-687 | hsa-miR-1296 | UUAGGGCCCUGGCUCCAUCUCC | 0.775709011 |
| SEQ ID NO: 663 | Tab1-688 | hsa-miR-299-3p | UAUGUGGGAUGGUAAACCGCUU | 0.785026312 |
| SEQ ID NO: 507 | Tab1-689 | hsa-miR-567 | AGUAUGUUCUUCCAGGACAGAAC | 0.786493938 |
| SEQ ID NO: 631 | Tab1-690 | hsa-miR-610 | UGAGCUAAAUGUGUGCUGGGA | 0.788520251 |
| SEQ ID NO: 270 | Tab1-691 | hsa-miR-523* | CUCUAGAGGGAAGCGCUUUCUG | 0.788783622 |
| SEQ ID NO: 448 | Tab1-692 | hsa-miR-615-3p | UCCGAGCCUGGGUCUCCCUCUU | 0.788783622 |
| SEQ ID NO: 231 | Tab1-693 | hsa-miR-128 | UCACAGUGAACCGGUCUCUUU | 0.78975234 |
| SEQ ID NO: 642 | Tab1-694 | hsa-let-7g* | CUGUACAGGCCACUGCCUUGC | 0.792669588 |
| SEQ ID NO: 121 | Tab1-695 | hsa-miR-548f | AAAAACUGUAAUUACUUUU | 0.792669588 |
| SEQ ID NO: 489 | Tab1-696 | hsa-miR-205 | UCCUUCAUUCCACCGGAGUCUG | 0.792669588 |
| SEQ ID NO: 496 | Tab1-697 | hsa-miR-330-5p | UCUCUGGGCCUGUGUCUUAGGC | 0.792669588 |
| SEQ ID NO: 444 | Tab1-698 | hsa-miR-1224-3p | CCCCACCUCCUCUCUCCUCAG | 0.792669588 |
| SEQ ID NO: 249 | Tab1-699 | hsa-miR-485-5p | AGAGGCUGGCCGUGAUGAAUUC | 0.792669588 |
| SEQ ID NO: 807 | Tab1-700 | hsa-miR-152 | UCAGUGCAUGACAGAACUUGG | 0.792669588 |

FIG. 10B (Continued)

| SEQ ID NO | Seq ID | Name (microRNA) miRNA | Sequence | cross significance |
|---|---|---|---|---|
| SEQ ID NO: 474 | Tab1-701 | hsa-miR-182* | UGGUUCUAGACUUGCCAACUA | 0,792669588 |
| SEQ ID NO: 66 | Tab1-702 | hsa-miR-519c-5p | CUCUAGAGGGAAGCGCUUUCUG | 0,797511408 |
| SEQ ID NO: 253 | Tab1-703 | hsa-miR-549 | UGACAACUAUGGAUGAGCUCU | 0,797511408 |
| SEQ ID NO: 95 | Tab1-704 | hsa-miR-561 | CAAAGUUUAAGAUCCUUGAAGU | 0,7984642 |
| SEQ ID NO: 281 | Tab1-705 | hsa-miR-431* | CAGGUCGUCUUGCAGGGCUUCU | 0,799246708 |
| SEQ ID NO: 810 | Tab1-706 | hsa-miR-1236 | CCUCUUCCCCUUGUCUCUCCAG | 0,799246708 |
| SEQ ID NO: 681 | Tab1-707 | hsa-miR-1308 | GCAUGGGUGGUUCAGUGG | 0,799246708 |
| SEQ ID NO: 276 | Tab1-708 | hsa-miR-586 | UAUGCAUUGUAUUUUAGGUCC | 0,800314761 |
| SEQ ID NO: 569 | Tab1-709 | hsa-miR-758 | UUUGUGACCGGUCCACUAACC | 0,80582552 |
| SEQ ID NO: 684 | Tab1-710 | hsa-miR-331-5p | CUAGGUAUGGUCCCAGGGAUCC | 0,806071461 |
| SEQ ID NO: 112 | Tab1-711 | hsa-miR-424* | CAAAACGUGAGGCGCUGCUAU | 0,807375071 |
| SEQ ID NO: 147 | Tab1-712 | hsa-miR-23a | AUCACAUUGCCAGGGAUUUCC | 0,807448834 |
| SEQ ID NO: 301 | Tab1-713 | hsa-miR-1197 | UAGGACACAUGGUCUACUUCU | 0,810196672 |
| SEQ ID NO: 341 | Tab1-714 | hsa-miR-618 | AAACUCUACUUGUCCUUCUGAGU | 0,813971435 |
| SEQ ID NO: 832 | Tab1-715 | hsa-miR-661 | UGCCUGGGUCUCUGGCCUGCGCGU | 0,813971435 |
| SEQ ID NO: 386 | Tab1-716 | hsa-miR-1264 | CAAGUCUUAUUUGAGCACCUGUU | 0,815546928 |
| SEQ ID NO: 660 | Tab1-717 | hsa-miR-452 | AACUGUUUGCAGAGGAAACUGA | 0,815546928 |
| SEQ ID NO: 824 | Tab1-718 | hsa-miR-660 | UACCCAUUGCAUAUCGGAGUUG | 0,815546928 |
| SEQ ID NO: 198 | Tab1-719 | hsa-miR-101 | UACAGUACUGUGAUAACUGAA | 0,818290788 |
| SEQ ID NO: 516 | Tab1-720 | hsa-miR-520a-3p | AAAGUGCUUCCCUUUGGACUGU | 0,818290788 |
| SEQ ID NO: 98 | Tab1-721 | hsa-miR-186* | GCCCAAAGGUGAAUUUUUUGGG | 0,818290788 |
| SEQ ID NO: 557 | Tab1-722 | hsa-miR-612 | GCUGGGCAGGGCUUCUGAGCUCCUU | 0,822137456 |
| SEQ ID NO: 72 | Tab1-723 | hsa-miR-563 | AGGUUGACAUACGUUUCCC | 0,824341004 |
| SEQ ID NO: 16 | Tab1-724 | hsa-let-7f | UGAGGUAGUAGAUUGUAUAGUU | 0,824494104 |
| SEQ ID NO: 816 | Tab1-725 | hsa-miR-139-3p | GGAGACGCGGCCCUGUUGGAGU | 0,825308686 |
| SEQ ID NO: 144 | Tab1-726 | hsa-miR-609 | AGGGUGUUUCUCUCAUCUCU | 0,825989592 |
| SEQ ID NO: 38 | Tab1-727 | hsa-miR-339-3p | UGAGCGCCUCGACGACAGAGCCG | 0,828936411 |
| SEQ ID NO: 535 | Tab1-728 | hsa-miR-1276 | UAAAGAGCCCUGUGGAGACA | 0,829563183 |
| SEQ ID NO: 384 | Tab1-729 | hsa-miR-548k | AAAAGUACUUGCGGAUUUUGCU | 0,831337059 |
| SEQ ID NO: 193 | Tab1-730 | hsa-miR-518f | GAAAGCGCUUCUCUUUAGAGG | 0,831337059 |
| SEQ ID NO: 157 | Tab1-731 | hsa-miR-665 | ACCAGGAGGCUGAGGCCCCU | 0,831337059 |
| SEQ ID NO: 777 | Tab1-732 | hsa-miR-578 | CUUCUUGUGCUCUAGGAUUGU | 0,831337059 |
| SEQ ID NO: 52 | Tab1-733 | hsa-miR-1269 | CUGGACUGAGCCGUGCUACUGG | 0,831337059 |
| SEQ ID NO: 617 | Tab1-734 | hsa-miR-329 | AACACACCUGGUUAACCUCUUU | 0,832130588 |
| SEQ ID NO: 345 | Tab1-735 | hsa-miR-521 | AACGCACUUCCCUUUAGAGUGU | 0,832130588 |
| SEQ ID NO: 211 | Tab1-736 | hsa-miR-23b* | UGGGUUCCUGGCAUGCUGAUUU | 0,832130588 |
| SEQ ID NO: 248 | Tab1-737 | hsa-miR-302c | UAAGUGCUUCCAUGUUUCAGUGG | 0,834010232 |
| SEQ ID NO: 499 | Tab1-738 | hsa-miR-141* | CAUCUUCCAGUACAGUGUUGGA | 0,834010232 |
| SEQ ID NO: 825 | Tab1-739 | hsa-miR-526b | CUCUUGAGGGAAGCACUUUCUGU | 0,83442217 |
| SEQ ID NO: 787 | Tab1-740 | hsa-miR-567 | GUUUGCACGGGUGGGCCUUGUCU | 0,83442217 |
| SEQ ID NO: 509 | Tab1-741 | hsa-miR-376a | AUCAUAGAGGAAAAUCCACGU | 0,83442217 |
| SEQ ID NO: 240 | Tab1-742 | hsa-miR-125b-2* | UCACAAGUCAGGCUCUUGGGAC | 0,835148073 |
| SEQ ID NO: 368 | Tab1-743 | hsa-miR-767-3p | UCUGCUCAUACCCCAUGGUUUCU | 0,837311353 |
| SEQ ID NO: 273 | Tab1-744 | hsa-miR-30d* | CUUUCAGUCAGAUGUUUGCUGC | 0,84316404 |
| SEQ ID NO: 519 | Tab1-745 | hsa-miR-943 | CUGACUGUUGCCGUCCUCCAG | 0,84316404 |
| SEQ ID NO: 500 | Tab1-746 | hsa-miR-517c | AUCGUGCAUCCUUUUAGAGUGU | 0,860000686 |
| SEQ ID NO: 416 | Tab1-747 | hsa-miR-302d | UAAGUGCUUCCAUGUUUGAGUGU | 0,861406109 |
| SEQ ID NO: 821 | Tab1-748 | hsa-miR-134 | UGUGACUGGUUGACCAGAGGGG | 0,86160008 |
| SEQ ID NO: 464 | Tab1-749 | hsa-miR-450a | UUUUGCGAUGUGUUCCUAAUAU | 0,862347398 |
| SEQ ID NO: 852 | Tab1-750 | hsa-miR-324-5p | CGCAUCCCCUAGGGCAUUGGUGU | 0,862492671 |

FIG. 10B (Continued)

| SEQ ID NO: | Seq ID | Name microRNA (miRNA) | Sequence | t-test significance |
|---|---|---|---|---|
| SEQ ID NO: 230 | Tab1-751 | hsa-miR-488 | UUGAAAGGCUAUUUCUUGGUC | 0,865866588 |
| SEQ ID NO: 695 | Tab1-752 | hsa-miR-518c* | UCUCUGGAGGGAAGCACUUUCUG | 0,865866588 |
| SEQ ID NO: 424 | Tab1-753 | hsa-miR-556-3p | AUAUUACCAUUAGCUCAUCUUU | 0,865866588 |
| SEQ ID NO: 294 | Tab1-754 | hsa-miR-302e | UAAGUGCUUCCAUGCUU | 0,86721168 |
| SEQ ID NO: 853 | Tab1-755 | hsa-miR-129* | AAGCCCUUACCCCAAAAAGUAU | 0,86880513 |
| SEQ ID NO: 47 | Tab1-756 | hsa-miR-145* | GGAUUCCUGGAAAUACUGUUCU | 0,86880513 |
| SEQ ID NO: 380 | Tab1-757 | hsa-miR-200e* | CAUCUUACCGGACAGUGCUGGA | 0,870825969 |
| SEQ ID NO: 736 | Tab1-758 | hsa-miR-10b | UACCCUGUAGAACCGAAUUUGUG | 0,871953638 |
| SEQ ID NO: 160 | Tab1-759 | hsa-miR-10a* | CAAAUUCGUAUCUAGGGGAAUA | 0,871953638 |
| SEQ ID NO: 348 | Tab1-760 | hsa-miR-920 | GGGGAGCUGUGGAAGCAGUA | 0,872075585 |
| SEQ ID NO: 461 | Tab1-761 | hsa-miR-190 | UGAUAUGUUUGAUAUAUUAGGU | 0,872156739 |
| SEQ ID NO: 792 | Tab1-762 | hsa-miR-30c-1* | CUGGGAGAGGGUUGUUUACUCC | 0,875624561 |
| SEQ ID NO: 402 | Tab1-763 | hsa-miR-1183 | CACUGUAGGUGAUGGUGAGAGUGGGCA | 0,876832201 |
| SEQ ID NO: 583 | Tab1-764 | hsa-miR-133b | UUUGGUCCCCUUCAACCAGCUA | 0,87724303 |
| SEQ ID NO: 808 | Tab1-765 | hsa-miR-197 | UUCACCACCUUCUCCACCCAGC | 0,87977382 |
| SEQ ID NO: 57 | Tab1-766 | hsa-miR-519c-3p | AAAGUGCAUCUUUUUAGAGGAU | 0,87977382 |
| SEQ ID NO: 578 | Tab1-767 | hsa-miR-581 | UCUUGUGUUCUCUAGAUCAGU | 0,87977382 |
| SEQ ID NO: 88 | Tab1-768 | hsa-miR-1207-3p | UCAGCUGGCCCUCAUUUC | 0,881969477 |
| SEQ ID NO: 669 | Tab1-769 | hsa-miR-30c-2* | CUGGGAGAAGGCUGUUUACUCU | 0,882006154 |
| SEQ ID NO: 120 | Tab1-770 | hsa-miR-449a | UGGCAGUGUAUUGUUAGCUGGU | 0,88738286 |
| SEQ ID NO: 533 | Tab1-771 | hsa-miR-504 | AGACCCUGGUCUGCACUCUAUC | 0,887654613 |
| SEQ ID NO: 490 | Tab1-772 | hsa-miR-1257 | AGUGAAUGAUGGGUUCUGACC | 0,888605891 |
| SEQ ID NO: 254 | Tab1-773 | hsa-miR-576-5p | AUUCUAAUUUCUCCACGUCUUU | 0,889196695 |
| SEQ ID NO: 326 | Tab1-774 | hsa-miR-887 | GUGAACGGGCGCCAUCCCGAGG | 0,892039618 |
| SEQ ID NO: 405 | Tab1-775 | hsa-miR-617 | AGACUUCCCAUUUGAAGGUGGC | 0,892039618 |
| SEQ ID NO: 309 | Tab1-776 | hsa-miR-892b | CACUGGCUCCUUUCUGGGUAGA | 0,89282672 |
| SEQ ID NO: 812 | Tab1-777 | hsa-miR-143 | UGAGAUGAAGCACUGUAGCUC | 0,89282672 |
| SEQ ID NO: 65 | Tab1-778 | hsa-miR-520f | AAGUGCUUCCUUUUAGAGGGUU | 0,89282672 |
| SEQ ID NO: 862 | Tab1-779 | hsa-miR-29b-1* | GCUGGUUUCAUAUGGUGGUUUAGA | 0,89282672 |
| SEQ ID NO: 187 | Tab1-780 | hsa-miR-551b | GCGACCCAUACUUGGUUUCAG | 0,907405605 |
| SEQ ID NO: 600 | Tab1-781 | hsa-miR-520c-5p | CUCUAGAGGGAAGCACUUUCUG | 0,907598391 |
| SEQ ID NO: 338 | Tab1-782 | hsa-miR-591 | AGACCAUGGGUUCUCAUUGU | 0,907598391 |
| SEQ ID NO: 715 | Tab1-783 | hsa-miR-320b | AAAAGCUGGGUUGAGAGGGCAA | 0,909262403 |
| SEQ ID NO: 538 | Tab1-784 | hsa-miR-494 | UGAAACAUACACGGGAAACCUC | 0,909862556 |
| SEQ ID NO: 769 | Tab1-785 | hsa-miR-92a-1* | AGGUUGGGAUCGGUUGCAAUGCU | 0,911189217 |
| SEQ ID NO: 186 | Tab1-786 | hsa-miR-16-1* | CCAGUAUUAACUGUGCUGCUGA | 0,913014432 |
| SEQ ID NO: 26 | Tab1-787 | hsa-miR-423-3p | AGCUCGGUCUGAGGCCCCUCAGU | 0,920112393 |
| SEQ ID NO: 804 | Tab1-788 | hsa-miR-181a | AACAUUCAACGCUGUCGGUGAGU | 0,920112393 |
| SEQ ID NO: 194 | Tab1-789 | hsa-miR-649 | AAACCUGUUGUUCAAGAGUC | 0,920112393 |
| SEQ ID NO: 174 | Tab1-790 | hsa-miR-522* | CUCUAGAGGGAAGCGCUUUCUG | 0,9264405 |
| SEQ ID NO: 322 | Tab1-791 | hsa-miR-1205 | UCUGCAGGGUUUGCUUUGAG | 0,928532034 |
| SEQ ID NO: 435 | Tab1-792 | hsa-miR-219-2-3p | AGAAUUGUGGCUGGACAUCUGU | 0,928532034 |
| SEQ ID NO: 391 | Tab1-793 | hsa-miR-548d-5p | AAAAGUAAUUGUGGUUUUUGCC | 0,928532034 |
| SEQ ID NO: 255 | Tab1-794 | hsa-miR-577 | UAGAUAAAAUAUUGGUACCUG | 0,928532034 |
| SEQ ID NO: 5 | Tab1-795 | hsa-miR-22 | AAGCUGCCAGUUGAAGAACUGU | 0,932423244 |
| SEQ ID NO: 728 | Tab1-796 | hsa-miR-1910 | CCAGUCCUGUGCCUGCCGCCU | 0,938411573 |
| SEQ ID NO: 415 | Tab1-797 | hsa-miR-219-5p | UGAUUGUCCAAACGCAAUUCU | 0,94096824 |
| SEQ ID NO: 470 | Tab1-798 | hsa-miR-526a | CUCUAGAGGGAAGCACUUUCUG | 0,943387843 |
| SEQ ID NO: 510 | Tab1-799 | hsa-miR-124* | CGUGUUCACAGCGGACCUUGAU | 0,943387843 |
| SEQ ID NO: 612 | Tab1-800 | hsa-miR-95 | UUCAACGGGUAUUUAUUGAGCA | 0,943387843 |

FIG. 10B (Continued)

| SEQ ID NO | Seq ID | Name microRNA miRNA | Sequence | t-test significance |
|---|---|---|---|---|
| SEQ ID NO: 686 | Tab1-801 | hsa-miR-640 | AUGAUCCAGGAACCUGCCUCU | 0,946088391 |
| SEQ ID NO: 595 | Tab1-802 | hsa-miR-519d | CAAAGUGCCUCCCUUUAGAGUG | 0,94617422 |
| SEQ ID NO: 93 | Tab1-803 | hsa-miR-136 | ACUCCAUUUGUUUUGAUGAUGGA | 0,946781524 |
| SEQ ID NO: 488 | Tab1-804 | hsa-miR-888* | GACUGACACCUCUUUGGGUGAA | 0,946781524 |
| SEQ ID NO: 658 | Tab1-805 | hsa-miR-630 | AGUAUUCUGUACCAGGGAAGGU | 0,947028321 |
| SEQ ID NO: 656 | Tab1-806 | hsa-miR-1237 | UCCUUCUGCUCCGUCCCCAG | 0,949368934 |
| SEQ ID NO: 315 | Tab1-807 | hsa-miR-26a | UUCAAGUAAUCCAGGAUAGGCU | 0,949368934 |
| SEQ ID NO: 127 | Tab1-808 | hsa-miR-325 | CCUAGUAGGUGUCCAGUAAGUGU | 0,949368934 |
| SEQ ID NO: 170 | Tab1-809 | hsa-miR-193b | AACUGGCCCUCAAAGUCCCGCU | 0,951430819 |
| SEQ ID NO: 647 | Tab1-810 | hsa-miR-382 | GAAGUUGUUCGUGGUGGAUUCG | 0,953697694 |
| SEQ ID NO: 532 | Tab1-811 | hsa-miR-377* | AGAGGUUGCCCUUGGUGAAUUC | 0,954382372 |
| SEQ ID NO: 179 | Tab1-812 | hsa-miR-222 | AGCUACAUCUGGCUACUGGGU | 0,954382372 |
| SEQ ID NO: 308 | Tab1-813 | hsa-miR-708 | AAGGAGCUUACAAUCUAGCUGGG | 0,954382372 |
| SEQ ID NO: 411 | Tab1-814 | hsa-miR-122 | UGGAGUGUGACAAUGGUGUUUG | 0,954382372 |
| SEQ ID NO: 237 | Tab1-815 | hsa-miR-194 | UGUAACAGCAACUCCAUGUGGA | 0,954382372 |
| SEQ ID NO: 763 | Tab1-816 | hsa-miR-532-5p | CAUGCCUUGAGUGUAGGACCGU | 0,954382372 |
| SEQ ID NO: 86 | Tab1-817 | hsa-miR-335* | UUUUUCAUUAUUGCUCCUGACC | 0,954382372 |
| SEQ ID NO: 428 | Tab1-818 | hsa-miR-296-3p | GAGGGUUGGGUGGAGGCUCUCC | 0,954382372 |
| SEQ ID NO: 430 | Tab1-819 | hsa-miR-21* | CAACACCAGUCGAUGGGCUGU | 0,958924949 |
| SEQ ID NO: 606 | Tab1-820 | hsa-miR-548e | AAAAACUGAGACUACUUUUGCA | 0,958924949 |
| SEQ ID NO: 599 | Tab1-821 | hsa-miR-744* | CUGUUGCCACUAACCUCAACCU | 0,958924949 |
| SEQ ID NO: 387 | Tab1-822 | hsa-miR-551a | GCGACCCACUCUUGGUUUCCA | 0,959289953 |
| SEQ ID NO: 531 | Tab1-823 | hsa-miR-515-3p | GAGUGCCUUCUUUUGGAGCGUU | 0,959289953 |
| SEQ ID NO: 645 | Tab1-824 | hsa-miR-34b* | UAGGCAGUGUCAUUAGCUGAUUG | 0,963053434 |
| SEQ ID NO: 758 | Tab1-825 | hsa-miR-642 | GUCCCUCUCCAAAUGUGUCUUG | 0,963053434 |
| SEQ ID NO: 284 | Tab1-826 | hsa-miR-1185 | AGAGGAUACCCUUUGUAUGUU | 0,96606999 |
| SEQ ID NO: 691 | Tab1-827 | hsa-miR-492 | AGGACCUGCGGGACAAGAUUCUU | 0,96606999 |
| SEQ ID NO: 795 | Tab1-828 | hsa-miR-323-5p | AGGUGGUCCGUGGCGCGUUCGC | 0,96606999 |
| SEQ ID NO: 714 | Tab1-829 | hsa-miR-320c | AAAAGCUGGGUUGAGAGGGU | 0,96606999 |
| SEQ ID NO: 434 | Tab1-830 | hsa-miR-548m | CAAAGGUAUUGUGGUUUUUG | 0,96606999 |
| SEQ ID NO: 244 | Tab1-831 | hsa-miR-105 | UCAAAUGCUCAGACUCCUGUGGU | 0,96606999 |
| SEQ ID NO: 122 | Tab1-832 | hsa-miR-597 | UGUGUCACUCGAUGACCACUGU | 0,966704103 |
| SEQ ID NO: 58 | Tab1-833 | hsa-miR-1244 | AAGUAGUUGGUUUGUAGAGAUGGUU | 0,966704103 |
| SEQ ID NO: 275 | Tab1-834 | hsa-miR-548b-3p | CAAGAACCUCAGUUGCUUUUGU | 0,969921147 |
| SEQ ID NO: 700 | Tab1-835 | hsa-miR-890 | UACUUGGAAAGGCAUCAGUUG | 0,972999091 |
| SEQ ID NO: 803 | Tab1-836 | hsa-miR-148b* | AAGUUCUGUUAUACACUCAGGC | 0,972999091 |
| SEQ ID NO: 613 | Tab1-837 | hsa-miR-133a | UUUGGUCCCCUUCAACCAGCUG | 0,972999091 |
| SEQ ID NO: 73 | Tab1-838 | hsa-miR-663b | GGUGGCCCGGCCGUGCCUGAGG | 0,975482077 |
| SEQ ID NO: 785 | Tab1-839 | hsa-miR-195* | CCAAUAUUGGCUGUGCUGCUCC | 0,975482077 |
| SEQ ID NO: 401 | Tab1-840 | hsa-miR-509-3p | UGAUUGGUACGUCUGUGGGUAG | 0,975482077 |
| SEQ ID NO: 364 | Tab1-841 | hsa-miR-873 | GCAGGAACUUGUGAGUCUCCU | 0,975482077 |
| SEQ ID NO: 514 | Tab1-842 | hsa-let-7b* | CUAUACAACCUACUGCCUUCCC | 0,975482077 |
| SEQ ID NO: 306 | Tab1-843 | hsa-miR-553 | AAAACGGUGAGAUUUUGUUUU | 0,977944702 |
| SEQ ID NO: 782 | Tab1-844 | hsa-miR-518b | CAAAGCGCUCCCCUUUAGAGGU | 0,981049422 |
| SEQ ID NO: 126 | Tab1-845 | hsa-miR-1911 | UGAGUACCGCCAUGUCUGUUGGG | 0,982703187 |
| SEQ ID NO: 545 | Tab1-846 | hsa-miR-127-3p | UCGGAUCCGUCUGAGCUUGGCU | 0,982703187 |
| SEQ ID NO: 665 | Tab1-847 | hsa-miR-340 | UUAUAAAGCAAUGAGACUGAUU | 0,984739991 |
| SEQ ID NO: 355 | Tab1-848 | hsa-miR-146a* | CCUCUGAAAUUCAGUUCUUCAG | 0,984772697 |
| SEQ ID NO: 458 | Tab1-849 | hsa-miR-548g | AAAACUGUAAUUACUUUUGUAC | 0,984772697 |
| SEQ ID NO: 674 | Tab1-850 | hsa-miR-188-5p | CAUCCCUUGCAUGGUGGAGGG | 0,984772697 |

FIG. 10B (Continued)

| SEQ ID No | Seq-ID | Name (microRNA/miRNA) | Sequence | Greatest significance |
|---|---|---|---|---|
| SEQ ID NO: 325 | Tab1-851 | hsa-miR-555 | AGGGUAAGCUGAACCUCUGAU | 0,984772697 |
| SEQ ID NO: 626 | Tab1-852 | hsa-miR-1225-3p | UGAGCCCCUGUGCCGCCCCAG | 0,988620756 |
| SEQ ID NO: 82 | Tab1-853 | hsa-miR-185 | UGGAGAGAAAGGCAGUUCCUGA | 0,988620756 |
| SEQ ID NO: 268 | Tab1-854 | hsa-miR-99a* | CAAGCUCGCUUCUAUGGGUCUG | 0,988620756 |
| SEQ ID NO: 809 | Tab1-855 | hsa-miR-27b | UUCACAGUGGCUAAGUUCUGC | 0,988620756 |
| SEQ ID NO: 266 | Tab1-856 | hsa-miR-497* | CAAACCACACUGUGGUGUUAGA | 0,988620756 |
| SEQ ID NO: 336 | Tab1-857 | hsa-miR-302a* | ACUUAAACGUGGAUGUACUUGCU | 0,988620756 |
| SEQ ID NO: 394 | Tab1-858 | hsa-miR-508-3p | UGAUUGUAGCCUUUUGGAGUAGA | 0,988620756 |
| SEQ ID NO: 138 | Tab1-859 | hsa-miR-552 | AACAGGUGACUGGUUAGACAA | 0,996239894 |
| SEQ ID NO: 840 | Tab1-860 | hsa-miR-1238 | CUUCCUCGUCUGUCUGCCCC | 0,99849342 |
| SEQ ID NO: 487 | Tab1-861 | hsa-miR-487b | AAUCGUACAGGGUCAUCCACUU | 0,99849342 |
| SEQ ID NO: 442 | Tab1-862 | hsa-miR-511 | GUGUCUUUUGCUCUGCAGUCA | 0,99849342 |
| SEQ ID NO: 741 | Tab1-863 | hsa-miR-616* | ACUCAAAACCCUUCAGUGACUU | 0,99849342 |
| SEQ ID NO: 784 | Tab1-864 | hsa-miR-376c | AACAUAGAGGAAAUUCCACGU | 0,999732203 |

FIG. 10C

| SEQ ID NO: | miRNA | median_g1 | median_g2 | qmedian | logmedian | ttest_rawp | ttest_adjp | AUC | limma_rawp | limma_adjp |
|---|---|---|---|---|---|---|---|---|---|---|
| SEQ ID NO: 53 | hsa-let-7b | 902 | 2634 | 0.34 | -1.072 | 1.345E-10 | 1.161E-07 | 0.097 | 1.751E-06 | 1.374E-04 |
| SEQ ID NO: 632 | hsa-miR-574-3p | 2061 | 811 | 2.54 | 0.933 | 2.154E-09 | 5.115E-07 | 0.882 | 2.891E-09 | 1.247E-06 |
| SEQ ID NO: 197 | hsa-miR-454 | 114 | 282 | 0.41 | -0.903 | 1.181E-08 | 1.133E-06 | 0.139 | 3.879E-05 | 1.240E-03 |
| SEQ ID NO: 526 | hsa-miR-500 | 213 | 438 | 0.49 | -0.722 | 2.866E-07 | 1.546E-05 | 0.214 | 1.943E-04 | 4.091E-03 |
| SEQ ID NO: 737 | hsa-miR-766 | 491 | 227 | 2.16 | 0.770 | 1.633E-05 | 3.131E-04 | 0.788 | 3.545E-05 | 1.224E-03 |
| SEQ ID NO: 14 | hsa-let-7e | 141 | 372 | 0.38 | -0.971 | 2.766E-05 | 5.078E-04 | 0.216 | 2.865E-04 | 5.420E-03 |
| SEQ ID NO: 790 | hsa-miR-1234 | 699 | 254 | 2.75 | 1.011 | 7.186E-05 | 8.761E-04 | 0.873 | 2.931E-07 | 4.007E-05 |
| SEQ ID NO: 806 | hsa-miR-125a-5p | 151 | 354 | 0.43 | -0.852 | 1.398E-04 | 1.471E-03 | 0.237 | 2.572E-04 | 5.045E-03 |
| SEQ ID NO: 16 | hsa-let-7f | 418 | 873 | 0.48 | -0.736 | 4.540E-04 | 3.349E-03 | 0.257 | 5.594E-04 | 8.323E-03 |
| SEQ ID NO: 823 | hsa-miR-92b* | 132 | 268 | 0.49 | -0.709 | 2.027E-03 | 9.976E-03 | 0.216 | 7.738E-05 | 1.908E-03 |
| SEQ ID NO: 15 | hsa-let-7c | 423 | 1377 | 0.31 | -1.180 | 2.774E-10 | 1.197E-07 | 0.043 | 1.306E-07 | 2.818E-05 |
| SEQ ID NO: 18 | hsa-let-7g | 294 | 970 | 0.30 | -1.194 | 3.138E-09 | 5.115E-07 | 0.162 | 4.302E-05 | 1.316E-03 |
| SEQ ID NO: 99 | hsa-miR-145 | 131 | 423 | 0.31 | -1.175 | 3.557E-09 | 5.115E-07 | 0.115 | 3.250E-07 | 4.007E-05 |
| SEQ ID NO: 3 | hsa-let-7i | 513 | 1689 | 0.30 | -1.192 | 2.317E-08 | 1.818E-06 | 0.133 | 9.333E-06 | 5.072E-04 |
| SEQ ID NO: 622 | hsa-miR-130b | 1463 | 748 | 1.96 | 0.671 | 2.968E-09 | 5.115E-07 | 0.819 | 4.944E-03 | 3.411E-02 |
| SEQ ID NO: 580 | hsa-miR-1260 | 2587 | 1494 | 1.73 | 0.549 | 5.532E-07 | 2.387E-05 | 0.756 | 2.518E-03 | 2.312E-02 |
| SEQ ID NO: 641 | hsa-miR-330-3p | 377 | 234 | 1.61 | 0.477 | 1.056E-06 | 3.647E-05 | 0.786 | 8.055E-04 | 1.103E-02 |
| SEQ ID NO: 50 | hsa-miR-30e | 241 | 482 | 0.50 | -0.691 | 1.290E-06 | 4.122E-05 | 0.162 | 1.826E-05 | 7.168E-04 |
| SEQ ID NO: 4 | hsa-let-7d | 1987 | 3301 | 0.60 | -0.508 | 4.387E-06 | 1.113E-04 | 0.208 | 4.019E-03 | 3.002E-02 |
| SEQ ID NO: 436 | hsa-miR-501-3p | 372 | 263 | 1.42 | 0.349 | 6.010E-06 | 1.441E-04 | 0.760 | 3.025E-02 | 1.097E-01 |
| SEQ ID NO: 565 | hsa-miR-1913 | 359 | 210 | 1.71 | 0.535 | 8.523E-06 | 1.936E-04 | 0.678 | 5.251E-02 | 1.584E-01 |
| SEQ ID NO: 75 | hsa-miR-199a-5p | 236 | 464 | 0.51 | -0.677 | 1.032E-05 | 2.121E-04 | 0.182 | 1.827E-05 | 7.168E-04 |
| SEQ ID NO: 5 | hsa-miR-22 | 7722 | 5135 | 1.50 | 0.408 | 3.175E-05 | 5.434E-04 | 0.767 | 1.017E-04 | 2.310E-03 |
| SEQ ID NO: 51 | hsa-miR-223 | 2257 | 4200 | 0.54 | -0.621 | 3.135E-05 | 5.434E-04 | 0.163 | 1.117E-05 | 5.072E-04 |
| SEQ ID NO: 13 | hsa-miR-195 | 620 | 477 | 1.30 | 0.262 | 3.211E-05 | 5.434E-04 | 0.720 | 8.910E-02 | 2.231E-01 |
| SEQ ID NO: 343 | hsa-miR-532-3p | 4406 | 2881 | 1.53 | 0.425 | 6.494E-05 | 8.365E-04 | 0.735 | 1.690E-03 | 1.779E-02 |
| SEQ ID NO: 129 | hsa-miR-182 | 4200 | 2208 | 1.90 | 0.643 | 8.322E-05 | 9.839E-04 | 0.769 | 8.014E-03 | 4.770E-02 |
| SEQ ID NO: 67 | hsa-miR-192 | 5652 | 3793 | 1.49 | 0.399 | 2.142E-04 | 1.969E-03 | 0.770 | 1.188E-01 | 2.728E-01 |
| SEQ ID NO: 145 | hsa-miR-30c | 2233 | 1621 | 1.38 | 0.320 | 2.113E-04 | 1.969E-03 | 0.675 | 4.195E-02 | 1.346E-01 |
| SEQ ID NO: 327 | hsa-miR-363 | 3453 | 2208 | 1.56 | 0.447 | 2.674E-04 | 2.267E-03 | 0.697 | 4.408E-01 | 6.257E-01 |
| SEQ ID NO: 750 | hsa-miR-107 | 1305 | 783 | 1.67 | 0.512 | 2.679E-04 | 2.267E-03 | 0.694 | 1.390E-01 | 2.955E-01 |
| SEQ ID NO: 675 | hsa-miR-486-3p | 223 | 158 | 1.41 | 0.343 | 2.806E-04 | 2.351E-03 | 0.660 | 1.249E-01 | 2.794E-01 |
| SEQ ID NO: 87 | hsa-miR-497 | 167 | 138 | 1.20 | 0.186 | 3.052E-04 | 2.508E-03 | 0.665 | 5.713E-02 | 1.650E-01 |

FIG. 10C (Continued)

| | | | | | | | | | |
|---|---|---|---|---|---|---|---|---|---|
| SEQ ID NO: 20 | hsa-miR-339-5p | 693 | 533 | 1.30 | 0.262 | 3,281E-04 | 2,610E-03 | 0.665 | 2,402E-01 | 4,160E-01 |
| SEQ ID NO: 137 | hsa-miR-593* | 288 | 224 | 1.29 | 0.253 | 3,326E-04 | 2,610E-03 | 0.668 | 1,024E-01 | 2,442E-01 |
| SEQ ID NO: 237 | hsa-miR-194 | 6578 | 5135 | 1.28 | 0.248 | 3,723E-04 | 2,840E-03 | 0.737 | 3,328E-01 | 5,147E-01 |
| SEQ ID NO: 670 | hsa-miR-627 | 155 | 243 | 0.64 | -0.450 | 4,709E-04 | 3,444E-03 | 0.166 | 5,482E-04 | 8,301E-03 |
| SEQ ID NO: 521 | hsa-miR-93 | 3453 | 5652 | 0.61 | -0.493 | 5,069E-04 | 3,646E-03 | 0.239 | 2,265E-03 | 2,148E-02 |
| SEQ ID NO: 808 | hsa-miR-197 | 662 | 559 | 1.18 | 0.168 | 5,395E-04 | 3,755E-03 | 0.589 | 1,839E-01 | 3,574E-01 |
| SEQ ID NO: 198 | hsa-miR-101 | 576 | 723 | 0.80 | -0.226 | 5,588E-04 | 3,827E-03 | 0.295 | 1,355E-02 | 6,465E-02 |
| SEQ ID NO: 861 | hsa-miR-92a | 11992 | 17656 | 0.68 | -0.387 | 5,787E-04 | 3,932E-03 | 0.222 | 4,633E-03 | 3,360E-02 |
| SEQ ID NO: 826 | hsa-miR-422a | 139 | 241 | 0.58 | -0.548 | 5,882E-04 | 3,935E-03 | 0.260 | 1,302E-03 | 1,540E-02 |
| SEQ ID NO: 850 | hsa-miR-1470 | 164 | 143 | 1.15 | 0.136 | 6,257E-04 | 4,122E-03 | 0.612 | 2,368E-01 | 4,143E-01 |
| SEQ ID NO: 778 | hsa-miR-1301 | 202 | 149 | 1.35 | 0.302 | 7,201E-04 | 4,536E-03 | 0.712 | 5,832E-01 | 7,401E-01 |
| SEQ ID NO: 43 | hsa-miR-550* | 697 | 477 | 1.46 | 0.380 | 7,265E-04 | 4,543E-03 | 0.600 | 4,806E-01 | 6,594E-01 |
| SEQ ID NO: 232 | hsa-miR-362-5p | 126 | 220 | 0.57 | -0.556 | 8,225E-04 | 5,034E-03 | 0.270 | 1,405E-03 | 1,555E-02 |
| SEQ ID NO: 644 | hsa-miR-214 | 296 | 218 | 1.35 | 0.300 | 8,750E-04 | 5,280E-03 | 0.660 | 1,287E-01 | 2,836E-01 |
| SEQ ID NO: 293 | hsa-miR-192* | 113 | 102 | 1.11 | 0.109 | 9,224E-04 | 5,528E-03 | 0.680 | 2,289E-02 | 8,806E-02 |
| SEQ ID NO: 217 | hsa-miR-31* | 171 | 139 | 1.23 | 0.206 | 9,631E-04 | 5,693E-03 | 0.661 | 2,125E-01 | 3,902E-01 |
| SEQ ID NO: 720 | hsa-miR-146b-5p | 101 | 157 | 0.64 | -0.439 | 1,130E-03 | 6,466E-03 | 0.270 | 5,794E-03 | 3,720E-02 |
| SEQ ID NO: 358 | hsa-miR-24 | 1762 | 1184 | 1.49 | 0.397 | 1,160E-03 | 6,581E-03 | 0.655 | 7,169E-01 | 8,355E-01 |
| SEQ ID NO: 642 | hsa-let-7g* | 109 | 140 | 0.78 | -0.252 | 1,254E-03 | 6,821E-03 | 0.293 | 2,427E-02 | 9,147E-02 |
| SEQ ID NO: 81 | hsa-miR-922 | 126 | 101 | 1.25 | 0.221 | 1,397E-03 | 7,535E-03 | 0.616 | 3,766E-01 | 5,662E-01 |
| SEQ ID NO: 800 | hsa-miR-146a | 193 | 321 | 0.60 | -0.510 | 1,511E-03 | 7,950E-03 | 0.245 | 1,364E-03 | 1,549E-02 |
| SEQ ID NO: 109 | hsa-miR-652 | 1113 | 1621 | 0.69 | -0.376 | 1,742E-03 | 9,041E-03 | 0.302 | 1,508E-02 | 6,922E-02 |
| SEQ ID NO: 182 | hsa-miR-342-3p | 4525 | 2881 | 1.57 | 0.452 | 1,841E-03 | 9,345E-03 | 0.718 | 8,636E-04 | 1,147E-02 |
| SEQ ID NO: 834 | hsa-miR-130a | 1369 | 1621 | 0.84 | -0.169 | 1,951E-03 | 9,731E-03 | 0.287 | 7,842E-03 | 4,709E-02 |
| SEQ ID NO: 544 | hsa-miR-1826 | 195 | 156 | 1.25 | 0.223 | 2,378E-03 | 1,151E-02 | 0.644 | 6,756E-01 | 8,054E-01 |
| SEQ ID NO: 671 | hsa-miR-1908 | 1071 | 1762 | 0.61 | -0.498 | 2,464E-03 | 1,175E-02 | 0.261 | 5,888E-04 | 8,469E-03 |
| SEQ ID NO: 858 | hsa-miR-27a | 259 | 413 | 0.63 | -0.468 | 2,866E-03 | 1,316E-02 | 0.261 | 1,335E-03 | 1,549E-02 |
| SEQ ID NO: 24 | hsa-miR-26b | 316 | 543 | 0.58 | -0.542 | 2,883E-03 | 1,316E-02 | 0.277 | 3,925E-03 | 3,002E-02 |
| SEQ ID NO: 209 | hsa-miR-1184 | 176 | 164 | 1.08 | 0.075 | 3,384E-03 | 1,505E-02 | 0.549 | 4,678E-01 | 6,522E-01 |
| SEQ ID NO: 492 | hsa-miR-296-5p | 237 | 226 | 1.05 | 0.046 | 3,520E-03 | 1,534E-02 | 0.556 | 2,904E-01 | 4,667E-01 |
| SEQ ID NO: 139 | hsa-miR-378 | 259 | 366 | 0.71 | -0.347 | 3,617E-03 | 1,568E-02 | 0.315 | 1,719E-02 | 7,471E-02 |
| SEQ ID NO: 814 | hsa-miR-675 | 138 | 239 | 0.58 | -0.546 | 4,333E-03 | 1,824E-02 | 0.248 | 3,176E-03 | 2,661E-02 |
| SEQ ID NO: 560 | hsa-miR-103 | 6845 | 4200 | 1.63 | 0.488 | 4,883E-03 | 2,007E-02 | 0.673 | 1,477E-01 | 3,095E-01 |
| SEQ ID NO: 274 | hsa-miR-452* | 291 | 269 | 1.08 | 0.077 | 4,919E-03 | 2,012E-02 | 0.552 | 6,562E-01 | 7,920E-01 |

FIG. 10C (Continued)

| | | | | | | | | |
|---|---|---|---|---|---|---|---|---|
| SEQ ID NO: 562 | hsa-miR-1203 | 198 | | 1,19 | 0,171 | 4,949E-03 | 2,015E-02 | 0,606 | 5,153E-01 | 6,927E-01 |
| SEQ ID NO: 234 | hsa-miR-874 | 155 | 167 | 0,83 | -0,191 | 5,037E-03 | 2,041E-02 | 0,287 | 6,531E-03 | 4,026E-02 |
| SEQ ID NO: 847 | hsa-miR-588 | 119 | 188 | 1,19 | 0,174 | 5,682E-03 | 2,202E-02 | 0,636 | 5,066E-01 | 6,852E-01 |
| SEQ ID NO: 49 | hsa-miR-106a | 5928 | 8665 | 0,68 | -0,380 | 5,858E-03 | 2,224E-02 | 0,330 | 1,779E-02 | 7,600E-02 |
| SEQ ID NO: 649 | hsa-miR-1202 | 208 | 194 | 1,07 | 0,072 | 6,019E-03 | 2,234E-02 | 0,582 | 6,022E-01 | 7,529E-01 |
| SEQ ID NO: 305 | hsa-miR-33b | 172 | 139 | 1,24 | 0,217 | 5,989E-03 | 2,234E-02 | 0,608 | 7,537E-01 | 8,558E-01 |
| SEQ ID NO: 17 | hsa-let-7a | 1025 | 1762 | 0,58 | -0,542 | 6,576E-03 | 2,384E-02 | 0,243 | 2,441E-03 | 2,265E-02 |
| SEQ ID NO: 810 | hsa-miR-1228 | 236 | 164 | 1,43 | 0,361 | 6,514E-03 | 2,384E-02 | 0,678 | 1,862E-01 | 3,612E-01 |
| SEQ ID NO: 501 | hsa-miR-621 | 332 | 251 | 1,32 | 0,278 | 6,624E-03 | 2,392E-02 | 0,639 | 3,959E-01 | 5,870E-01 |
| SEQ ID NO: 707 | hsa-miR-455-3p | 169 | 130 | 1,29 | 0,258 | 7,163E-03 | 2,544E-02 | 0,666 | 4,842E-01 | 6,632E-01 |
| SEQ ID NO: 553 | hsa-miR-99b | 167 | 133 | 1,25 | 0,225 | 7,238E-03 | 2,560E-02 | 0,598 | 4,896E-01 | 6,696E-01 |
| SEQ ID NO: 714 | hsa-miR-320c | 783 | 675 | 1,16 | 0,148 | 7,758E-03 | 2,700E-02 | 0,593 | 2,990E-01 | 4,743E-01 |
| SEQ ID NO: 455 | hsa-miR-1251 | 128 | 109 | 1,17 | 0,157 | 7,813E-03 | 2,708E-02 | 0,648 | 2,473E-01 | 4,208E-01 |
| SEQ ID NO: 247 | hsa-miR-193a-3p | 123 | 173 | 0,71 | -0,339 | 7,950E-03 | 2,735E-02 | 0,292 | 1,922E-02 | 7,976E-02 |
| SEQ ID NO: 56 | hsa-miR-451 | 1604 | 2881 | 0,56 | -0,505 | 8,476E-03 | 2,871E-02 | 0,288 | 1,197E-03 | 1,454E-02 |
| SEQ ID NO: 528 | hsa-miR-20a* | 139 | 118 | 1,19 | 0,170 | 8,548E-03 | 2,876E-02 | 0,612 | 7,580E-01 | 8,562E-01 |
| SEQ ID NO: 735 | hsa-miR-320d | 908 | 697 | 1,30 | 0,263 | 8,735E-03 | 2,922E-02 | 0,593 | 2,809E-01 | 4,591E-01 |
| SEQ ID NO: 286 | hsa-miR-489 | 155 | 145 | 1,07 | 0,066 | 8,938E-03 | 2,955E-02 | 0,612 | 2,187E-01 | 3,991E-01 |
| SEQ ID NO: 200 | hsa-miR-509-5p | 213 | 210 | 1,01 | 0,013 | 9,055E-03 | 2,980E-02 | 0,526 | 8,125E-01 | 8,955E-01 |
| SEQ ID NO: 628 | hsa-miR-196a* | 139 | 122 | 1,14 | 0,128 | 9,082E-03 | 2,980E-02 | 0,570 | 4,546E-01 | 6,411E-01 |
| SEQ ID NO: 616 | hsa-miR-374b | 493 | 352 | 1,40 | 0,338 | 9,159E-03 | 2,994E-02 | 0,594 | 8,125E-01 | 8,955E-01 |
| SEQ ID NO: 780 | hsa-miR-564 | 157 | 129 | 1,21 | 0,195 | 9,547E-03 | 3,074E-02 | 0,619 | 6,265E-01 | 7,746E-01 |
| SEQ ID NO: 413 | hsa-miR-15a* | 112 | 135 | 0,83 | -0,182 | 1,051E-02 | 3,322E-02 | 0,290 | 3,593E-02 | 1,207E-01 |
| SEQ ID NO: 259 | hsa-miR-646 | 206 | 203 | 1,02 | 0,018 | 1,073E-02 | 3,380E-02 | 0,535 | 8,306E-01 | 9,085E-01 |
| SEQ ID NO: 619 | hsa-miR-885-3p | 177 | 268 | 0,66 | -0,412 | 1,139E-02 | 3,561E-02 | 0,292 | 3,297E-03 | 2,736E-02 |
| SEQ ID NO: 311 | hsa-miR-500* | 250 | 222 | 1,13 | 0,119 | 1,143E-02 | 3,561E-02 | 0,612 | 4,720E-01 | 6,539E-01 |
| SEQ ID NO: 770 | hsa-miR-1285 | 264 | 189 | 1,39 | 0,331 | 1,138E-02 | 3,561E-02 | 0,689 | 7,878E-02 | 2,042E-01 |
| SEQ ID NO: 363 | hsa-miR-509-3-5p | 212 | 194 | 1,09 | 0,089 | 1,182E-02 | 3,668E-02 | 0,540 | 7,614E-01 | 8,587E-01 |
| SEQ ID NO: 169 | hsa-miR-1912 | 152 | 138 | 1,11 | 0,100 | 1,198E-02 | 3,705E-02 | 0,606 | 5,817E-01 | 7,401E-01 |
| SEQ ID NO: 251 | hsa-miR-545 | 116 | 102 | 1,14 | 0,130 | 1,210E-02 | 3,728E-02 | 0,621 | 7,126E-01 | 8,343E-01 |
| SEQ ID NO: 10 | hsa-miR-324-3p | 825 | 655 | 1,26 | 0,231 | 1,266E-02 | 3,892E-02 | 0,576 | 4,340E-01 | 6,201E-01 |
| SEQ ID NO: 820 | hsa-miR-575 | 127 | 112 | 1,13 | 0,122 | 1,381E-02 | 4,181E-02 | 0,601 | 5,249E-01 | 6,958E-01 |
| SEQ ID NO: 11 | hsa-miR-20b | 2820 | 2112 | 1,34 | 0,289 | 1,433E-02 | 4,254E-02 | 0,623 | 8,502E-01 | 9,171E-01 |
| SEQ ID NO: 231 | hsa-miR-128 | 623 | 553 | 1,13 | 0,118 | 1,551E-02 | 4,518E-02 | 0,627 | 4,654E-01 | 6,499E-01 |

FIG. 10C (Continued)

| | | | | | | | | | |
|---|---|---|---|---|---|---|---|---|---|
| SEQ ID NO: 158 | hsa-miR-18a | 1205 | 1762 | 0.68 | -0.380 | 1.620E-02 | 4.677E-02 | 0.294 | 3.983E-03 | 3.002E-02 |
| SEQ ID NO: 9 | hsa-miR-574-5p | 840 | 587 | 1.43 | 0.358 | 1.675E-02 | 4.754E-02 | 0.660 | 1.973E-01 | 3.751E-01 |
| SEQ ID NO: 733 | hsa-miR-1229 | 185 | 164 | 1.13 | 0.124 | 1.722E-02 | 4.856E-02 | 0.612 | 8.303E-01 | 9.085E-01 |
| SEQ ID NO: 812 | hsa-miR-143 | 168 | 232 | 0.73 | -0.321 | 1.779E-02 | 4.984E-02 | 0.325 | 3.118E-02 | 1.103E-01 |
| SEQ ID NO: 481 | hsa-miR-101* | 69 | 140 | 0.50 | -0.703 | 2.462E-07 | 1.416E-05 | 0.161 | 5.439E-04 | 8.301E-03 |
| SEQ ID NO: 768 | hsa-miR-221 | 81 | 164 | 0.49 | -0.704 | 7.761E-06 | 1.810E-04 | 0.159 | 2.889E-04 | 5.420E-03 |
| SEQ ID NO: 552 | hsa-miR-365 | 64 | 132 | 0.48 | -0.728 | 3.896E-05 | 5.899E-04 | 0.191 | 1.140E-02 | 5.789E-02 |
| SEQ ID NO: 789 | hsa-miR-22* | 47 | 101 | 0.46 | -0.776 | 6.863E-05 | 8.710E-04 | 0.223 | 5.851E-04 | 8.469E-03 |
| SEQ ID NO: 495 | hsa-miR-1275 | 60 | 125 | 0.48 | -0.731 | 3.751E-04 | 2.840E-03 | 0.194 | 3.183E-04 | 5.723E-03 |
| SEQ ID NO: 854 | hsa-miR-625 | 59 | 178 | 0.33 | -1.110 | 5.165E-04 | 3.684E-03 | 0.244 | 2.748E-03 | 2.464E-02 |
| SEQ ID NO: 609 | hsa-miR-584 | 84 | 211 | 0.40 | -0.918 | 7.733E-04 | 4.801E-03 | 0.252 | 1.134E-03 | 1.398E-02 |
| SEQ ID NO: 704 | hsa-miR-595 | 103 | 41 | 2.51 | 0.922 | 2.387E-03 | 1.151E-02 | 0.689 | 3.924E-02 | 1.278E-01 |
| SEQ ID NO: 677 | hsa-miR-193a-5p | 55 | 124 | 0.44 | -0.813 | 5.246E-03 | 2.079E-02 | 0.250 | 4.333E-03 | 3.169E-02 |
| SEQ ID NO: 719 | hsa-miR-328 | 57 | 124 | 0.46 | -0.773 | 1.439E-02 | 4.254E-02 | 0.293 | 1.720E-02 | 7.471E-02 |
| SEQ ID NO: 688 | hsa-miR-629 | 58 | 210 | 0.27 | -1.292 | 4.148E-07 | 1.941E-05 | 0.156 | 5.162E-05 | 1.392E-03 |
| SEQ ID NO: 313 | hsa-miR-186 | 34 | 162 | 0.21 | -1.571 | 7.793E-07 | 3.193E-05 | 0.138 | 9.540E-06 | 5.072E-04 |
| SEQ ID NO: 667 | hsa-miR-142-3p | 18 | 127 | 0.14 | -1.941 | 9.396E-06 | 1.978E-04 | 0.131 | 1.146E-07 | 2.818E-05 |
| SEQ ID NO: 491 | hsa-miR-7 | 31 | 127 | 0.25 | -1.406 | 6.070E-05 | 8.060E-04 | 0.171 | 2.564E-05 | 9.620E-04 |
| SEQ ID NO: 320 | hsa-miR-891a | 114 | 71 | 1.60 | 0.471 | 4.274E-07 | 1.941E-05 | 0.791 | 5.642E-05 | 1.475E-03 |
| SEQ ID NO: 611 | hsa-miR-1295 | 113 | 73 | 1.54 | 0.429 | 1.294E-05 | 2.589E-04 | 0.719 | 1.888E-02 | 7.909E-02 |
| SEQ ID NO: 84 | hsa-miR-1272 | 129 | 92 | 1.41 | 0.340 | 5.781E-05 | 7.795E-04 | 0.723 | 1.723E-02 | 7.471E-02 |
| SEQ ID NO: 730 | hsa-miR-421 | 87 | 168 | 0.52 | -0.658 | 9.543E-05 | 1.084E-03 | 0.169 | 5.136E-04 | 8.059E-03 |
| SEQ ID NO: 782 | hsa-miR-518b | 96 | 113 | 0.85 | -0.162 | 1.687E-04 | 1.693E-03 | 0.307 | 1.528E-02 | 6.978E-02 |
| SEQ ID NO: 135 | hsa-miR-221* | 104 | 56 | 1.84 | 0.610 | 1.740E-04 | 1.726E-03 | 0.748 | 1.071E-03 | 1.360E-02 |
| SEQ ID NO: 355 | hsa-miR-146a* | 68 | 109 | 0.62 | -0.471 | 5.993E-04 | 3.979E-03 | 0.248 | 4.070E-03 | 3.002E-02 |
| SEQ ID NO: 239 | hsa-miR-342-5p | 85 | 156 | 0.54 | -0.615 | 1.037E-03 | 6.048E-03 | 0.270 | 4.033E-03 | 3.002E-02 |
| SEQ ID NO: 828 | hsa-miR-938 | 86 | 121 | 0.71 | -0.346 | 1.193E-03 | 6.610E-03 | 0.257 | 8.467E-03 | 4.819E-02 |
| SEQ ID NO: 282 | hsa-miR-384 | 59 | 101 | 0.58 | -0.539 | 2.789E-03 | 1.294E-02 | 0.271 | 3.580E-03 | 2.861E-02 |
| SEQ ID NO: 604 | hsa-miR-496 | 69 | 101 | 0.68 | -0.385 | 3.330E-03 | 1.489E-02 | 0.285 | 2.244E-02 | 8.775E-02 |
| SEQ ID NO: 454 | hsa-miR-659 | 65 | 118 | 0.56 | -0.586 | 4.070E-03 | 1.739E-02 | 0.264 | 1.746E-02 | 7.500E-02 |
| SEQ ID NO: 558 | hsa-miR-183* | 85 | 142 | 0.60 | -0.516 | 4.309E-03 | 1.823E-02 | 0.289 | 3.674E-02 | 1.229E-01 |
| SEQ ID NO: 365 | hsa-miR-556-5p | 117 | 86 | 1.37 | 0.313 | 5.143E-03 | 2.055E-02 | 0.628 | 1.128E-01 | 2.624E-01 |
| SEQ ID NO: 690 | hsa-miR-491-5p | 92 | 143 | 0.64 | -0.444 | 5.715E-03 | 2.202E-02 | 0.268 | 8.714E-03 | 4.883E-02 |
| SEQ ID NO: 761 | hsa-miR-1307 | 57 | 106 | 0.54 | -0.618 | 6.543E-03 | 2.384E-02 | 0.300 | 5.737E-02 | 1.650E-01 |

FIG. 10C (Continued)

| | | | | | | | | | | |
|---|---|---|---|---|---|---|---|---|---|---|
| SEQ ID NO: 503 | hsa-miR-541 | 106 | 85 | 1,25 | 0,221 | 8,288E-03 | 2,827E-02 | 0,621 | 9,286E-01 | 9,656E-01 |
| SEQ ID NO: 572 | hsa-miR-589* | 83 | 102 | 0,82 | -0,197 | 8,769E-03 | 2,922E-02 | 0,330 | 3,183E-02 | 1,112E-01 |
| SEQ ID NO: 115 | hsa-miR-199b-3p | 93 | 118 | 0,79 | -0,236 | 1,487E-02 | 4,322E-02 | 0,338 | 2,247E-02 | 8,775E-02 |
| SEQ ID NO: 717 | hsa-miR-326 | 86 | 107 | 0,80 | -0,224 | 1,555E-02 | 4,518E-02 | 0,392 | 3,491E-02 | 1,181E-01 |
| SEQ ID NO: 465 | hsa-miR-367 | 85 | 37 | 2,32 | 0,842 | 1,566E-08 | 1,343E-06 | 0,856 | 2,093E-07 | 3,612E-05 |
| SEQ ID NO: 377 | hsa-miR-1206 | 59 | 23 | 2,59 | 0,952 | 1,784E-07 | 1,087E-05 | 0,806 | 2,826E-05 | 1,016E-03 |
| SEQ ID NO: 631 | hsa-miR-610 | 50 | 21 | 2,34 | 0,849 | 2,381E-06 | 6,629E-05 | 0,740 | 9,909E-04 | 1,296E-02 |
| SEQ ID NO: 659 | hsa-miR-519e* | 60 | 23 | 2,64 | 0,970 | 2,836E-06 | 7,648E-05 | 0,784 | 1,036E-05 | 5,072E-04 |
| SEQ ID NO: 488 | hsa-miR-888* | 47 | 18 | 2,67 | 0,984 | 9,351E-06 | 1,978E-04 | 0,728 | 5,913E-03 | 3,725E-02 |
| SEQ ID NO: 822 | hsa-miR-875-3p | 52 | 25 | 2,07 | 0,729 | 7,615E-05 | 9,127E-04 | 0,728 | 2,263E-02 | 8,796E-02 |
| SEQ ID NO: 249 | hsa-miR-485-5p | 47 | 21 | 2,29 | 0,828 | 1,288E-04 | 1,372E-03 | 0,715 | 9,724E-03 | 5,278E-02 |
| SEQ ID NO: 601 | hsa-miR-148a* | 25 | 56 | 0,44 | -0,824 | 2,073E-04 | 1,969E-03 | 0,237 | 4,775E-04 | 7,838E-03 |
| SEQ ID NO: 285 | hsa-miR-29b-2* | 36 | 79 | 0,45 | -0,788 | 2,642E-04 | 2,267E-03 | 0,228 | 3,743E-04 | 6,593E-03 |
| SEQ ID NO: 403 | hsa-miR-626 | 33 | 14 | 2,39 | 0,873 | 2,919E-04 | 2,422E-03 | 0,682 | 3,732E-02 | 1,243E-01 |
| SEQ ID NO: 306 | hsa-miR-553 | 3 | 1 | 2,86 | 1,049 | 3,316E-04 | 2,610E-03 | 0,615 | 1,160E-01 | 2,676E-01 |
| SEQ ID NO: 368 | hsa-miR-767-3p | 44 | 21 | 2,06 | 0,721 | 6,828E-04 | 4,398E-03 | 0,715 | 1,533E-03 | 1,669E-02 |
| SEQ ID NO: 393 | hsa-miR-876-5p | 36 | 14 | 2,61 | 0,959 | 9,829E-04 | 5,770E-03 | 0,670 | 2,781E-02 | 1,017E-01 |
| SEQ ID NO: 177 | hsa-miR-648 | 47 | 19 | 2,45 | 0,896 | 1,257E-03 | 6,821E-03 | 0,713 | 1,946E-03 | 1,953E-02 |
| SEQ ID NO: 241 | hsa-miR-1297 | 44 | 21 | 2,07 | 0,729 | 1,552E-03 | 8,120E-03 | 0,692 | 7,558E-02 | 1,989E-01 |
| SEQ ID NO: 92 | hsa-miR-138-2* | 54 | 27 | 2,03 | 0,706 | 2,673E-03 | 1,254E-02 | 0,684 | 1,570E-02 | 7,058E-02 |
| SEQ ID NO: 831 | hsa-miR-1249 | 68 | 27 | 2,47 | 0,905 | 2,810E-03 | 1,297E-02 | 0,693 | 1,368E-02 | 6,465E-02 |
| SEQ ID NO: 588 | hsa-miR-224 | 47 | 21 | 2,23 | 0,801 | 3,027E-03 | 1,361E-02 | 0,678 | 5,690E-02 | 1,650E-01 |
| SEQ ID NO: 543 | hsa-miR-300 | 48 | 19 | 2,57 | 0,942 | 4,872E-03 | 2,007E-02 | 0,668 | 7,587E-02 | 1,990E-01 |
| SEQ ID NO: 523 | hsa-miR-613 | 2 | 7 | 0,33 | -1,107 | 7,271E-03 | 2,561E-02 | 0,541 | 5,782E-01 | 7,401E-01 |
| SEQ ID NO: 701 | hsa-miR-1303 | 29 | 63 | 0,47 | -0,757 | 8,564E-03 | 2,876E-02 | 0,279 | 1,719E-02 | 7,471E-02 |
| SEQ ID NO: 629 | hsa-miR-1270 | 20 | 8 | 2,64 | 0,970 | 1,508E-02 | 4,426E-02 | 0,605 | 2,480E-01 | 4,208E-01 |
| SEQ ID NO: 121 | hsa-miR-548f | 48 | 20 | 2,46 | 0,899 | 1,636E-02 | 4,707E-02 | 0,706 | 9,627E-03 | 5,258E-02 |
| SEQ ID NO: 411 | hsa-miR-122 | 20 | 8 | 2,41 | 0,881 | 1,710E-02 | 4,838E-02 | 0,624 | 8,385E-02 | 2,131E-01 |
| SEQ ID NO: 183 | hsa-miR-512-3p | 36 | 1 | 36,06 | 3,585 | 5,059E-09 | 6,236E-07 | 0,809 | 9,063E-07 | 8,690E-05 |
| SEQ ID NO: 307 | hsa-miR-620 | 13 | 1 | 13,28 | 2,586 | 7,565E-09 | 8,161E-07 | 0,768 | 1,233E-05 | 5,319E-04 |
| SEQ ID NO: 110 | hsa-miR-1256 | 67 | 11 | 5,93 | 1,779 | 9,667E-08 | 6,952E-06 | 0,821 | 7,897E-07 | 8,519E-05 |
| SEQ ID NO: 755 | hsa-miR-1306 | 24 | 1 | 23,64 | 3,163 | 3,794E-07 | 1,926E-05 | 0,773 | 1,058E-05 | 5,072E-04 |
| SEQ ID NO: 102 | hsa-let-7f-1* | 34 | 1 | 33,91 | 3,524 | 8,509E-07 | 3,193E-05 | 0,793 | 4,996E-06 | 3,593E-04 |
| SEQ ID NO: 404 | hsa-miR-513b | 46 | 7 | 6,86 | 1,926 | 9,913E-07 | 3,565E-05 | 0,807 | 5,542E-06 | 3,679E-04 |

FIG. 10C (Continued)

| | | | | | | | | |
|---|---|---|---|---|---|---|---|---|
| SEQ ID NO: 650 | hsa-miR-202 | 21 | 1 | 21,29 | 3,058 | 1,257E-06 | 4,122E-05 | 0,753 | 4,719E-05 | 1,357E-03 |
| SEQ ID NO: 663 | hsa-miR-299-3p | 14 | 1 | 13,83 | 2,627 | 1,358E-06 | 4,186E-05 | 0,732 | 6,539E-05 | 1,660E-03 |
| SEQ ID NO: 602 | hsa-miR-212 | 55 | 11 | 5,06 | 1,621 | 1,851E-06 | 5,326E-05 | 0,868 | 1,766E-11 | 1,524E-08 |
| SEQ ID NO: 668 | hsa-miR-125b-1* | 10 | 1 | 9,79 | 2,281 | 3,822E-06 | 9,995E-05 | 0,717 | 3,896E-04 | 6,725E-03 |
| SEQ ID NO: 652 | hsa-miR-593 | 14 | 1 | 13,77 | 2,622 | 5,028E-06 | 1,240E-04 | 0,758 | 6,225E-06 | 3,837E-04 |
| SEQ ID NO: 421 | hsa-miR-379 | 8 | 1 | 8,39 | 2,127 | 1,990E-05 | 3,733E-04 | 0,629 | 4,845E-02 | 1,504E-01 |
| SEQ ID NO: 769 | hsa-miR-92a-1* | 15 | 4 | 3,25 | 1,179 | 3,090E-05 | 5,434E-04 | 0,675 | 1,284E-02 | 6,223E-02 |
| SEQ ID NO: 414 | hsa-miR-181d | 30 | 1 | 30,09 | 3,404 | 3,355E-05 | 5,568E-04 | 0,729 | 7,026E-04 | 9,940E-03 |
| SEQ ID NO: 255 | hsa-miR-577 | 20 | 1 | 19,57 | 2,974 | 3,790E-05 | 5,859E-04 | 0,708 | 4,026E-03 | 3,002E-02 |
| SEQ ID NO: 372 | hsa-miR-924 | 18 | 1 | 17,53 | 2,864 | 3,802E-05 | 5,859E-04 | 0,761 | 4,423E-05 | 1,316E-03 |
| SEQ ID NO: 229 | hsa-miR-369-3p | 16 | 1 | 16,17 | 2,783 | 3,684E-05 | 5,859E-04 | 0,736 | 4,814E-04 | 7,83BE-03 |
| SEQ ID NO: 548 | hsa-miR-1294 | 9 | 1 | 9,16 | 2,215 | 4,640E-05 | 6,636E-04 | 0,669 | 9,143E-03 | 5,091E-02 |
| SEQ ID NO: 662 | hsa-miR-516b | 35 | 10 | 3,64 | 1,291 | 7,208E-05 | 8,761E-04 | 0,715 | 1,491E-02 | 6,881E-02 |
| SEQ ID NO: 290 | hsa-let-7f-2* | 4 | 1 | 4,42 | 1,486 | 9,227E-05 | 1,062E-03 | 0,689 | 2,835E-03 | 2,471E-02 |
| SEQ ID NO: 802 | hsa-miR-526b* | 13 | 1 | 13,27 | 2,585 | 9,732E-05 | 1,091E-03 | 0,694 | 5,271E-03 | 3,526E-02 |
| SEQ ID NO: 354 | hsa-miR-373* | 29 | 5 | 5,57 | 1,718 | 1,679E-04 | 1,693E-03 | 0,738 | 1,092E-03 | 1,366E-02 |
| SEQ ID NO: 517 | hsa-miR-585 | 13 | 1 | 12,98 | 2,563 | 1,951E-04 | 1,913E-03 | 0,716 | 1,350E-03 | 1,549E-02 |
| SEQ ID NO: 840 | hsa-miR-1238 | 30 | 1 | 29,83 | 3,396 | 2,092E-04 | 1,969E-03 | 0,686 | 1,549E-02 | 7,000E-02 |
| SEQ ID NO: 795 | hsa-miR-323-5p | 48 | 8 | 5,64 | 1,730 | 2,581E-04 | 2,267E-03 | 0,706 | 1,747E-02 | 7,500E-02 |
| SEQ ID NO: 612 | hsa-miR-95 | 16 | 1 | 16,19 | 2,784 | 2,663E-04 | 2,267E-03 | 0,695 | 1,051E-02 | 5,495E-02 |
| SEQ ID NO: 283 | hsa-miR-644 | 25 | 1 | 24,92 | 3,215 | 3,093E-04 | 2,518E-03 | 0,679 | 1,435E-02 | 6,696E-02 |
| SEQ ID NO: 32 | hsa-miR-453 | 21 | 1 | 20,52 | 3,021 | 3,207E-04 | 2,587E-03 | 0,680 | 1,264E-02 | 6,187E-02 |
| SEQ ID NO: 638 | hsa-miR-499-5p | 21 | 2 | 9,52 | 2,253 | 3,501E-04 | 2,722E-03 | 0,693 | 5,798E-03 | 3,720E-02 |
| SEQ ID NO: 743 | hsa-miR-1179 | 27 | 1 | 27,05 | 3,298 | 4,994E-04 | 3,622E-03 | 0,701 | 2,769E-03 | 2,464E-02 |
| SEQ ID NO: 647 | hsa-miR-382 | 15 | 1 | 15,02 | 2,710 | 5,232E-04 | 3,701E-03 | 0,647 | 3,830E-02 | 1,257E-01 |
| SEQ ID NO: 362 | hsa-miR-513a-5p | 48 | 14 | 3,45 | 1,237 | 5,511E-04 | 3,805E-03 | 0,707 | 2,286E-02 | 8,806E-02 |
| SEQ ID NO: 447 | hsa-miR-223* | 28 | 8 | 3,59 | 1,277 | 5,872E-04 | 3,935E-03 | 0,708 | 2,121E-03 | 2,034E-02 |
| SEQ ID NO: 669 | hsa-miR-30c-2* | 22 | 7 | 3,34 | 1,205 | 6,770E-04 | 4,393E-03 | 0,635 | 9,294E-02 | 2,305E-01 |
| SEQ ID NO: 280 | hsa-miR-875-5p | 27 | 1 | 27,14 | 3,301 | 7,030E-04 | 4,488E-03 | 0,725 | 2,180E-04 | 4,376E-03 |
| SEQ ID NO: 851 | hsa-miR-105* | 8 | 1 | 8,28 | 2,114 | 9,331E-04 | 5,554E-03 | 0,757 | 9,455E-05 | 2,205E-03 |
| SEQ ID NO: 366 | hsa-miR-369-5p | 31 | 1 | 31,08 | 3,436 | 1,167E-03 | 6,581E-03 | 0,690 | 6,782E-03 | 4,151E-02 |
| SEQ ID NO: 525 | hsa-miR-524-3p | 19 | 4 | 4,24 | 1,444 | 1,231E-03 | 6,765E-03 | 0,679 | 1,031E-02 | 5,424E-02 |
| SEQ ID NO: 284 | hsa-miR-1185 | 11 | 1 | 10,99 | 2,397 | 1,420E-03 | 7,582E-03 | 0,680 | 4,830E-03 | 3,381E-02 |
| SEQ ID NO: 500 | hsa-miR-517c | 7 | 1 | 6,86 | 1,926 | 1,766E-03 | 9,074E-03 | 0,606 | 1,394E-01 | 2,956E-01 |

FIG. 10C (Continued)

| | | | | | | | | |
|---|---|---|---|---|---|---|---|---|
| SEQ ID NO: 105 | hsa-miR-1204 | 18 | 1 | 18,30 | 2,907 | 2,035E-03 | 9,976E-03 | 0,661 | 1,002E-02 | 5,373E-02 |
| SEQ ID NO: 90 | hsa-miR-1 | 13 | 1 | 13,05 | 2,569 | 2,713E-03 | 1,266E-02 | 0,646 | 2,919E-02 | 1,063E-01 |
| SEQ ID NO: 369 | hsa-miR-516a-3p | 6 | 1 | 6,13 | 1,813 | 3,514E-03 | 1,534E-02 | 0,651 | 3,151E-02 | 1,105E-01 |
| SEQ ID NO: 608 | hsa-miR-1914 | 52 | 8 | 6,12 | 1,811 | 3,873E-03 | 1,671E-02 | 0,715 | 1,609E-03 | 1,714E-02 |
| SEQ ID NO: 227 | hsa-miR-590-3p | 4 | 1 | 4,18 | 1,431 | 4,754E-03 | 1,973E-02 | 0,670 | 1,689E-02 | 7,471E-02 |
| SEQ ID NO: 340 | hsa-miR-376a* | 1 | 5 | 0,19 | -1,648 | 5,089E-03 | 2,049E-02 | 0,543 | 6,448E-01 | 7,835E-01 |
| SEQ ID NO: 506 | hsa-miR-26a-1* | 9 | 1 | 9,28 | 2,228 | 5,106E-03 | 2,049E-02 | 0,625 | 6,209E-02 | 1,734E-01 |
| SEQ ID NO: 353 | hsa-miR-876-3p | 10 | 1 | 9,84 | 2,287 | 5,693E-03 | 2,202E-02 | 0,658 | 2,130E-02 | 8,432E-02 |
| SEQ ID NO: 569 | hsa-miR-758 | 12 | 46 | 0,27 | -1,304 | 5,995E-03 | 2,234E-02 | 0,293 | 3,751E-05 | 1,240E-03 |
| SEQ ID NO: 240 | hsa-miR-125b-2* | 32 | 8 | 4,10 | 1,412 | 6,032E-03 | 2,234E-02 | 0,664 | 4,547E-02 | 1,432E-01 |
| SEQ ID NO: 352 | hsa-miR-455-5p | 11 | 1 | 11,35 | 2,429 | 6,570E-03 | 2,384E-02 | 0,650 | 2,661E-02 | 9,857E-02 |
| SEQ ID NO: 243 | hsa-miR-493* | 33 | 10 | 3,19 | 1,161 | 8,157E-03 | 2,793E-02 | 0,667 | 5,649E-02 | 1,647E-01 |
| SEQ ID NO: 798 | hsa-miR-302c* | 23 | 1 | 23,49 | 3,157 | 1,038E-02 | 3,293E-02 | 0,732 | 1,021E-03 | 1,315E-02 |
| SEQ ID NO: 392 | hsa-miR-616 | 17 | 2 | 9,48 | 2,250 | 1,403E-02 | 4,232E-02 | 0,634 | 6,019E-02 | 1,708E-01 |
| SEQ ID NO: 276 | hsa-miR-586 | 30 | 2 | 13,50 | 2,603 | 1,516E-02 | 4,436E-02 | 0,713 | 2,339E-03 | 2,194E-02 |
| SEQ ID NO: 485 | hsa-miR-30e* | 39 | 78 | 0,51 | -0,681 | 1,840E-06 | 5,326E-05 | 0,169 | 1,878E-04 | 4,052E-03 |
| SEQ ID NO: 477 | hsa-miR-628-5p | 78 | 48 | 1,61 | 0,479 | 9,046E-06 | 1,978E-04 | 0,751 | 1,936E-03 | 1,953E-02 |
| SEQ ID NO: 337 | hsa-miR-27b* | 61 | 36 | 1,70 | 0,530 | 1,320E-05 | 2,589E-04 | 0,759 | 2,152E-04 | 4,376E-03 |
| SEQ ID NO: 173 | hsa-miR-302f | 1 | 1 | 1,46 | 0,376 | 3,526E-05 | 5,742E-04 | 0,726 | 3,181E-03 | 5,723E-03 |
| SEQ ID NO: 149 | hsa-miR-647 | 68 | 38 | 1,79 | 0,584 | 3,982E-05 | 5,924E-04 | 0,772 | 1,426E-06 | 1,230E-04 |
| SEQ ID NO: 513 | hsa-miR-580 | 43 | 22 | 1,95 | 0,667 | 4,163E-05 | 6,089E-04 | 0,729 | 5,064E-03 | 3,441E-02 |
| SEQ ID NO: 431 | hsa-miR-657 | 59 | 34 | 1,71 | 0,538 | 4,691E-05 | 6,636E-04 | 0,737 | 5,482E-02 | 1,609E-01 |
| SEQ ID NO: 480 | hsa-let-7a* | 1 | 1 | 1,00 | 0,000 | 5,009E-05 | 6,972E-04 | 0,692 | 8,398E-04 | 1,132E-02 |
| SEQ ID NO: 482 | hsa-miR-559 | 48 | 27 | 1,81 | 0,593 | 5,409E-05 | 7,409E-04 | 0,746 | 2,613E-03 | 2,373E-02 |
| SEQ ID NO: 424 | hsa-miR-556-3p | 1 | 1 | 1,00 | 0,000 | 6,217E-05 | 8,129E-04 | 0,664 | 3,440E-03 | 2,800E-02 |
| SEQ ID NO: 107 | hsa-miR-619 | 54 | 85 | 0,63 | -0,459 | 7,025E-05 | 8,761E-04 | 0,239 | 4,044E-03 | 3,002E-02 |
| SEQ ID NO: 387 | hsa-miR-551a | 51 | 30 | 1,70 | 0,528 | 8,947E-05 | 1,043E-03 | 0,707 | 3,343E-02 | 1,154E-01 |
| SEQ ID NO: 471 | hsa-miR-936 | 64 | 39 | 1,63 | 0,491 | 1,104E-04 | 1,221E-03 | 0,722 | 2,098E-02 | 8,381E-02 |
| SEQ ID NO: 268 | hsa-miR-99a* | 34 | 18 | 1,87 | 0,626 | 1,117E-04 | 1,221E-03 | 0,693 | 2,780E-02 | 1,017E-01 |
| SEQ ID NO: 230 | hsa-miR-488 | 1 | 1 | 1,00 | 0,000 | 1,155E-04 | 1,246E-03 | 0,630 | 1,634E-02 | 7,307E-02 |
| SEQ ID NO: 63 | hsa-miR-1200 | 75 | 48 | 1,56 | 0,446 | 1,514E-04 | 1,575E-03 | 0,740 | 4,919E-04 | 7,861E-03 |
| SEQ ID NO: 591 | hsa-miR-190b | 1 | 1 | 1,00 | 0,000 | 1,547E-04 | 1,590E-03 | 0,657 | 5,902E-03 | 3,725E-02 |
| SEQ ID NO: 233 | hsa-miR-671-5p | 62 | 33 | 1,84 | 0,611 | 2,103E-04 | 1,969E-03 | 0,744 | 3,377E-03 | 2,776E-02 |
| SEQ ID NO: 571 | hsa-miR-518c | 63 | 99 | 0,63 | -0,455 | 2,484E-04 | 2,233E-03 | 0,239 | 3,491E-03 | 2,815E-02 |

FIG. 10C (Continued)

| | | | | | | | | |
|---|---|---|---|---|---|---|---|---|
| SEQ ID NO: 624 | hsa-miR-1226 | 49 | 80 | 0.62 | -0.485 | 2.469E-04 | 2.233E-03 | 0.220 | 1.794E-03 | 1.843E-02 |
| SEQ ID NO: 634 | hsa-miR-10b* | 51 | 88 | 0.58 | -0.541 | 2.669E-04 | 2.267E-03 | 0.254 | 7.070E-03 | 4.297E-02 |
| SEQ ID NO: 469 | hsa-miR-572 | 57 | 94 | 0.60 | -0.506 | 3.701E-04 | 2.840E-03 | 0.246 | 3.131E-03 | 2.649E-02 |
| SEQ ID NO: 188 | hsa-miR-146b-3p | 55 | 41 | 1.32 | 0.281 | 4.178E-04 | 3.135E-03 | 0.669 | 7.535E-02 | 1.989E-01 |
| SEQ ID NO: 187 | hsa-miR-551b | 73 | 56 | 1.31 | 0.271 | 4.487E-04 | 3.338E-03 | 0.678 | 1.911E-02 | 7.967E-02 |
| SEQ ID NO: 615 | hsa-miR-541* | 1 | 1 | 1.00 | 0.000 | 5.292E-04 | 3.713E-03 | 0.673 | 5.633E-03 | 3.685E-02 |
| SEQ ID NO: 739 | hsa-miR-641 | 58 | 35 | 1.68 | 0.517 | 6.420E-04 | 4.197E-03 | 0.752 | 4.813E-04 | 7.838E-03 |
| SEQ ID NO: 754 | hsa-miR-129-3p | 77 | 69 | 1.13 | 0.118 | 7.072E-04 | 4.488E-03 | 0.667 | 3.966E-03 | 3.002E-02 |
| SEQ ID NO: 208 | hsa-miR-379* | 54 | 31 | 1.77 | 0.570 | 8.058E-04 | 4.967E-03 | 0.697 | 5.466E-03 | 3.628E-02 |
| SEQ ID NO: 844 | hsa-miR-1258 | 1 | 1 | 1.00 | 0.000 | 8.407E-04 | 5.109E-03 | 0.641 | 1.086E-02 | 5.580E-02 |
| SEQ ID NO: 380 | hsa-miR-200a* | 62 | 96 | 0.65 | -0.437 | 1.047E-03 | 6.063E-03 | 0.270 | 4.831E-03 | 3.381E-02 |
| SEQ ID NO: 821 | hsa-miR-134 | 56 | 33 | 1.66 | 0.509 | 1.131E-03 | 6.466E-03 | 0.692 | 1.540E-02 | 6.995E-02 |
| SEQ ID NO: 700 | hsa-miR-890 | 37 | 20 | 1.82 | 0.597 | 1.177E-03 | 6.595E-03 | 0.666 | 2.334E-01 | 4.143E-01 |
| SEQ ID NO: 672 | hsa-miR-1267 | 41 | 21 | 1.98 | 0.684 | 1.195E-03 | 6.610E-03 | 0.671 | 1.280E-01 | 2.833E-01 |
| SEQ ID NO: 785 | hsa-miR-195* | 69 | 43 | 1.58 | 0.458 | 1.423E-03 | 7.502E-03 | 0.664 | 3.321E-01 | 5.146E-01 |
| SEQ ID NO: 178 | hsa-miR-662 | 52 | 88 | 0.58 | -0.538 | 1.436E-03 | 7.601E-03 | 0.256 | 1.123E-02 | 5.733E-02 |
| SEQ ID NO: 25 | hsa-miR-604 | 89 | 63 | 1.42 | 0.350 | 1.750E-03 | 9.041E-03 | 0.669 | 5.027E-02 | 1.544E-01 |
| SEQ ID NO: 457 | hsa-miR-488* | 72 | 59 | 1.22 | 0.197 | 1.813E-03 | 9.260E-03 | 0.651 | 9.967E-02 | 2.403E-01 |
| SEQ ID NO: 531 | hsa-miR-515-3p | 1 | 1 | 1.00 | 0.000 | 1.852E-03 | 9.345E-03 | 0.617 | 5.114E-02 | 1.565E-01 |
| SEQ ID NO: 759 | hsa-miR-30a* | 40 | 25 | 1.59 | 0.465 | 1.923E-03 | 9.649E-03 | 0.673 | 2.016E-02 | 8.240E-02 |
| SEQ ID NO: 836 | hsa-miR-432 | 1 | 1 | 1.00 | 0.000 | 1.971E-03 | 9.776E-03 | 0.617 | 2.200E-02 | 8.668E-02 |
| SEQ ID NO: 291 | hsa-miR-1322 | 77 | 57 | 1.36 | 0.306 | 2.106E-03 | 1.027E-02 | 0.621 | 1.931E-01 | 3.703E-01 |
| SEQ ID NO: 402 | hsa-miR-1183 | 90 | 73 | 1.24 | 0.212 | 2.453E-03 | 1.175E-02 | 0.645 | 4.858E-03 | 3.381E-02 |
| SEQ ID NO: 835 | hsa-miR-450b-5p | 61 | 43 | 1.41 | 0.340 | 2.522E-03 | 1.191E-02 | 0.684 | 7.913E-04 | 1.101E-02 |
| SEQ ID NO: 451 | hsa-miR-770-5p | 54 | 39 | 1.39 | 0.331 | 2.525E-03 | 1.191E-02 | 0.667 | 9.380E-03 | 5.160E-02 |
| SEQ ID NO: 610 | hsa-miR-1355b* | 53 | 33 | 1.60 | 0.469 | 2.922E-03 | 1.320E-02 | 0.708 | 1.713E-03 | 1.781E-02 |
| SEQ ID NO: 144 | hsa-miR-609 | 1 | 1 | 1.00 | 0.000 | 2.914E-03 | 1.320E-02 | 0.660 | 4.030E-03 | 3.002E-02 |
| SEQ ID NO: 70 | hsa-miR-1288 | 55 | 91 | 0.60 | -0.506 | 3.408E-03 | 1.508E-02 | 0.323 | 1.002E-02 | 5.373E-02 |
| SEQ ID NO: 570 | hsa-miR-412 | 51 | 42 | 1.19 | 0.175 | 3.993E-03 | 1.714E-02 | 0.667 | 6.196E-03 | 3.847E-02 |
| SEQ ID NO: 96 | hsa-miR-548h | 1 | 1 | 1.00 | 0.000 | 4.189E-03 | 1.781E-02 | 0.643 | 2.096E-02 | 8.381E-02 |
| SEQ ID NO: 738 | hsa-miR-600 | 73 | 56 | 1.29 | 0.257 | 4.588E-03 | 1.922E-02 | 0.600 | 9.602E-01 | 9.806E-01 |
| SEQ ID NO: 774 | hsa-miR-598 | 52 | 71 | 0.72 | -0.326 | 4.652E-03 | 1.940E-02 | 0.315 | 1.010E-02 | 5.381E-02 |
| SEQ ID NO: 651 | hsa-miR-544 | 37 | 22 | 1.65 | 0.502 | 5.251E-03 | 2.079E-02 | 0.646 | 6.853E-02 | 1.866E-01 |
| SEQ ID NO: 777 | hsa-miR-578 | 1 | 1 | 1.00 | 0.000 | 5.379E-03 | 2.120E-02 | 0.586 | 1.495E-01 | 3.116E-01 |

FIG. 10C (Continued)

| | | | | | | | | |
|---|---|---|---|---|---|---|---|---|
| SEQ ID NO: 741 | hsa-miR-616* | 57 | 42 | 1,36 | 0,306 | 5,413E-03 | 2,123E-02 | 0,642 | 2,698E-01 | 4,477E-01 |
| SEQ ID NO: 810 | hsa-miR-1236 | 23 | 14 | 1,62 | 0,479 | 5,522E-03 | 2,156E-02 | 0,576 | 5,857E-01 | 7,412E-01 |
| SEQ ID NO: 681 | hsa-miR-1308 | 44 | 27 | 1,62 | 0,483 | 5,801E-03 | 2,215E-02 | 0,605 | 4,347E-01 | 6,201E-01 |
| SEQ ID NO: 533 | hsa-miR-504 | 31 | 20 | 1,55 | 0,440 | 5,798E-03 | 2,215E-02 | 0,638 | 7,391E-02 | 1,969E-01 |
| SEQ ID NO: 597 | hsa-miR-877 | 60 | 94 | 0,63 | -0,455 | 5,901E-03 | 2,224E-02 | 0,285 | 1,154E-02 | 5,826E-02 |
| SEQ ID NO: 185 | hsa-miR-208b | 60 | 46 | 1,31 | 0,272 | 5,899E-03 | 2,224E-02 | 0,642 | 6,131E-02 | 1,718E-01 |
| SEQ ID NO: 520 | hsa-miR-573 | 51 | 31 | 1,66 | 0,508 | 6,132E-03 | 2,261E-02 | 0,682 | 2,811E-03 | 2,471E-02 |
| SEQ ID NO: 567 | hsa-miR-371-5p | 43 | 26 | 1,65 | 0,500 | 6,917E-03 | 2,487E-02 | 0,659 | 3,095E-02 | 1,099E-01 |
| SEQ ID NO: 370 | hsa-miR-520c-3p | 1 | 1 | 1,00 | 0,000 | 6,988E-03 | 2,502E-02 | 0,597 | 4,974E-02 | 1,533E-01 |
| SEQ ID NO: 273 | hsa-miR-30d* | 50 | 66 | 0,76 | -0,275 | 7,090E-03 | 2,528E-02 | 0,338 | 1,174E-02 | 5,892E-02 |
| SEQ ID NO: 541 | hsa-miR-487a | 64 | 58 | 1,10 | 0,092 | 7,450E-03 | 2,614E-02 | 0,629 | 8,395E-03 | 4,798E-02 |
| SEQ ID NO: 640 | hsa-miR-490-3p | 87 | 72 | 1,21 | 0,189 | 7,750E-03 | 2,700E-02 | 0,666 | 8,239E-03 | 4,795E-02 |
| SEQ ID NO: 256 | hsa-miR-583 | 47 | 33 | 1,40 | 0,335 | 7,954E-03 | 2,735E-02 | 0,671 | 1,547E-03 | 1,669E-02 |
| SEQ ID NO: 212 | hsa-miR-1262 | 1 | 1 | 1,00 | 0,000 | 8,484E-03 | 2,871E-02 | 0,625 | 6,543E-02 | 1,798E-01 |
| SEQ ID NO: 77 | hsa-miR-1246 | 1 | 1 | 1,00 | 0,000 | 8,893E-03 | 2,952E-02 | 0,639 | 3,076E-02 | 1,098E-01 |
| SEQ ID NO: 437 | hsa-miR-302a | 1 | 1 | 1,00 | 0,000 | 9,315E-03 | 3,033E-02 | 0,649 | 8,674E-03 | 4,883E-02 |
| SEQ ID NO: 564 | hsa-miR-383 | 49 | 31 | 1,61 | 0,474 | 9,456E-03 | 3,060E-02 | 0,658 | 1,016E-01 | 2,434E-01 |
| SEQ ID NO: 119 | hsa-miR-1302 | 30 | 18 | 1,71 | 0,537 | 9,514E-03 | 3,074E-02 | 0,629 | 2,482E-01 | 4,208E-01 |
| SEQ ID NO: 432 | hsa-miR-651 | 1 | 1 | 1,14 | 0,128 | 9,743E-03 | 3,114E-02 | 0,635 | 3,421E-02 | 1,167E-01 |
| SEQ ID NO: 224 | hsa-miR-1468 | 1 | 1 | 1,00 | 0,000 | 9,733E-03 | 3,114E-02 | 0,568 | 1,515E-01 | 3,144E-01 |
| SEQ ID NO: 479 | hsa-miR-370 | 48 | 34 | 1,44 | 0,362 | 9,983E-03 | 3,179E-02 | 0,669 | 6,351E-01 | 7,763E-01 |
| SEQ ID NO: 378 | hsa-miR-1259 | 23 | 14 | 1,62 | 0,482 | 1,272E-02 | 3,892E-02 | 0,579 | 3,490E-01 | 5,339E-01 |
| SEQ ID NO: 219 | hsa-miR-654-3p | 30 | 18 | 1,71 | 0,535 | 1,327E-02 | 4,047E-02 | 0,625 | 1,319E-01 | 2,847E-01 |
| SEQ ID NO: 747 | hsa-miR-138-1* | 92 | 72 | 1,28 | 0,245 | 1,359E-02 | 4,129E-02 | 0,637 | 5,819E-01 | 7,401E-01 |
| SEQ ID NO: 506 | hsa-miR-589 | 79 | 93 | 0,85 | -0,167 | 1,412E-02 | 4,246E-02 | 0,338 | 4,518E-02 | 1,428E-01 |
| SEQ ID NO: 168 | hsa-miR-130a* | 53 | 78 | 0,68 | -0,392 | 1,439E-02 | 4,254E-02 | 0,352 | 1,269E-02 | 6,187E-02 |
| SEQ ID NO: 522 | hsa-miR-27a* | 34 | 27 | 1,28 | 0,249 | 1,437E-02 | 4,254E-02 | 0,633 | 1,304E-01 | 2,845E-01 |
| SEQ ID NO: 832 | hsa-miR-661 | 44 | 25 | 1,74 | 0,556 | 1,436E-02 | 4,254E-02 | 0,633 | 2,396E-01 | 4,160E-01 |
| SEQ ID NO: 322 | hsa-miR-1205 | 71 | 75 | 0,95 | -0,048 | 1,566E-02 | 4,535E-02 | 0,577 | 7,557E-02 | 1,989E-01 |
| SEQ ID NO: 345 | hsa-miR-521 | 47 | 33 | 1,39 | 0,331 | 1,663E-02 | 4,753E-02 | 0,630 | 9,387E-03 | 5,160E-02 |
| SEQ ID NO: 478 | hsa-miR-29a* | 1 | 1 | 1,00 | 0,000 | 1,662E-02 | 4,753E-02 | 0,667 | 5,820E-03 | 3,720E-02 |
| SEQ ID NO: 655 | hsa-let-7e* | 10 | 7 | 1,50 | 0,404 | 1,669E-02 | 4,754E-02 | 0,590 | 3,123E-01 | 4,900E-01 |
| SEQ ID NO: 120 | hsa-miR-449a | 1 | 1 | 1,00 | 0,000 | 1,753E-02 | 4,929E-02 | 0,658 | 8,278E-03 | 4,795E-02 |
| SEQ ID NO: 399 | hsa-miR-18b | 166 | 413 | 0,40 | -0,911 | 2,145E-04 | 1,969E-03 | 0,196 | 5,078E-03 | 1,392E-03 |

FIG. 10C (Continued)

| SEQ ID NO: 547 | hsa-miR-148a | 950 | 629 | 1.51 | 0.412 | 1.227E-07 | 8.144E-06 | 0.758 | 2.072E-02 | 8.381E-02 |
| --- | --- | --- | --- | --- | --- | --- | --- | --- | --- | --- |
| SEQ ID NO: 709 | hsa-miR-96 | 156 | 254 | 0.61 | -0.490 | 8.273E-07 | 3.193E-05 | 0.183 | 1.266E-04 | 2.801E-03 |
| SEQ ID NO: 116 | hsa-miR-599 | 29 | 11 | 2.65 | 0.976 | 3.442E-03 | 1.516E-02 | 0.651 | 7.819E-02 | 2.040E-01 |

Figure 11
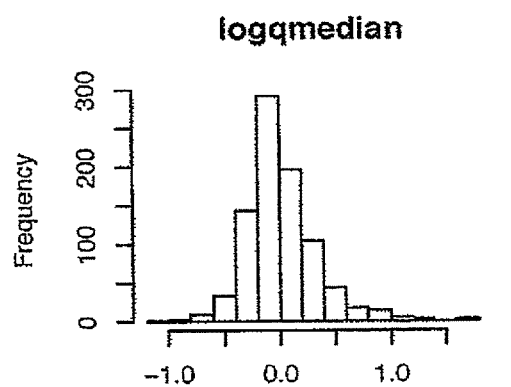
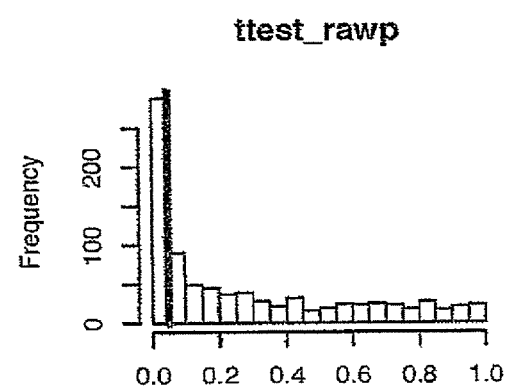
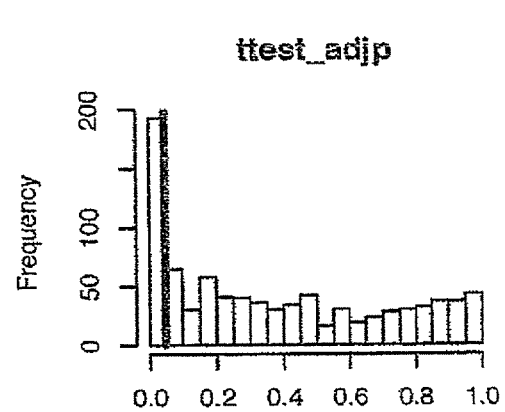

MIRNA FINGERPRINT IN THE DIAGNOSIS OF MULTIPLE SCLEROSIS

This application is a divisional of U.S. Ser. No. 13/376,243, filed Feb. 28, 2012, which is a 35 U.S.C. 371 National Phase Entry Application from PCT/EP2010/057943, filed Jun. 7, 2010, which claims the benefit of U.S. Provisional Applications Nos. 61/184,452 filed Jun. 5, 2009, 61/213,971 filed Aug. 3, 2009, 61/287,521 filed Dec. 17, 2009 and European Patent Application No. 09015668.8 filed on Dec. 17, 2009, the disclosures of which are incorporated herein in their entirety by reference.

BACKGROUND OF THE INVENTION

MicroRNAs (miRNA) are a recently discovered class of small non-coding RNAs (17-14 nucleotides). Due to their function as regulators of gene expression they play a critical role both in physiological and in pathological processes, such as cancer (Calin and Croce 2006; Esquela-Kerscher and Slack 2006; Zhang, Pan et al. 2007; Sassen, Miska et al. 2008).

There is increasing evidence that miRNAs are not only found in tissues but also in human blood both as free circulating nucleic acids (also called circulating miRNAs) and in mononuclear cells. A recent proof-of-principle study demonstrated miRNA expression pattern in pooled blood sera and pooled blood cells, both in healthy individuals and in cancer patients including patients with lung cancer (Chen, Ba et al. 2008). In addition, a remarkable stability of miRNAs in human sera was recently demonstrated (Chen, Ba et al. 2008; Gilad, Meiri et al. 2008). These findings make miRNA a potential tool for diagnostics for various types of diseases based on blood analysis.

Multiple sclerosis (MS), also known as disseminated sclerosis or encephalomyelitis disseminata) is an inflammatory autoimmune disease of the central nervous system (CNS). Causing MS appears to be a combination of immunological, genetic and environmental factors. It is a chronic demyelinating disease, which primarily affects young adults and is characterized by a highly variable course. The heterogeneous presentation of MS is characterized by a variety of clinical problems arising from multiple regions of demyelination and inflammation along axonal pathways. The signs and symptoms of MS are determined by the location of the affected regions.

Mostly, the disease begins in the third or fourth decade of life. Its initial course is characterized by acute episodes of neurological dysfunction, such as decreased vision, followed by subsequent recovery. This course is known as relapsing-remitting MS. Over time, the improvement after attacks may be incomplete and the relapsing-remitting course may evolve into one of increasing progression of disability, termed secondary progressive MS.

The diagnosis of MS generally relies on the presence of a neurological problem that remits and then returns at an unrelated site. This is confirmed by magnetic resonance imaging (MRI) or functional evidence of lesions in a particular pathway by abnormal evoked potentials. The histological hallmark of MS at postmortem exam is multiple lesions at different sites showing loss of myelin and infiltration by a characteristic complement of inflammatory cells.

The key to identifying predictive markers is a deeper understanding of the factors that underlie the therapeutic response. Identification of biomarkers will in turn allow for stratification of MS patients for their response to a specific treatment, ultimately leading to improved therapeutic benefits and a personalized treatment approach for MS patients.

Identification of reliable biomarkers in MS sclerosis patients bears the potential for an improved MS diagnosis, monitoring the disease activity and progression and also to evaluate response to treatments. The field of biomarker discovery has gradually shifted from the aim to find the perfect surrogate marker to the construction of composite markers with higher performances, taking advantage of technologies allowing unbiased screening, including microarray analyses. However, suitable biomarker sets allowing for a non-invasive diagnosis of MS based on peripheral profiles have not been detected, so far.

Various markers have been proposed to indicate specific types of disorders such as cancer or MS. However, there is still a need for more efficient and effective methods and compositions for the diagnosis of diseases.

SUMMARY OF THE INVENTION

The present invention provides novel methods for diagnosing diseases based on the determination of specific miRNAs that have altered expression levels in disease states compared to healthy or other relevant controls. The present invention particularly provides novel methods for the diagnosis and/or prognosis and/or monitoring of multiple sclerosis or related diseases in human individuals based on miRNA analysis from samples derived from blood.

A first subject-matter of the invention is a method for diagnosing multiple sclerosis, comprising the steps
(a) determining an expression profile of a predetermined set of miRNAs in a biological sample from a patient; and
(b) comparing said expression profile to a reference expression profile,
wherein the comparison of said determined expression profile to said reference expression profile allows for the diagnosis of multiple sclerosis.

A "biological sample" in terms of the invention means a sample of biological tissue or fluid. Examples of biological samples are sections of tissues, blood, blood fractions, plasma, serum, etc. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy or other therapeutic treatment. According to the invention, the biological sample preferably is a blood, plasma, or PBMC (peripheral blood mononuclear cell), or a serum sample. Further, it is also preferred to use blood cells, e.g. erythrocytes, leukocytes or thrombocytes.

A biological sample from a patient means a sample from a subject suspected to be affected by a disease. As used herein, the term "subject" refers to any mammal, including both human and other mammals. Preferably, the methods of the present invention are applied to human subjects.

In step (a) of the method of the invention, an expression profile of a predetermined set of miRNAs is determined. The determination may be carried out by any convenient means for determining nucleic acids. For expression profiling, qualitative, semi-quantitative and preferably quantitative detection methods can be used. A variety of techniques are well known to those of skill in the art. In particular, the determination may comprise nucleic acid hybridization and/or nucleic acid amplification steps.

Nucleic acid hybridization may for example be performed using beads, a solid phase nucleic acid biochip array, in particular a microarray, beads, or in situ hybridization. The miRNA microarray technology affords the analysis of a complex biological sample for all expressed miRNAs. Nucleotides with complementarity to the corresponding miRNAs are spotted, or synthesized on coated carriers. E.g., miRNAs isolated from the sample of interest may be labelled, e.g. fluorescently labelled, so that upon hybridization of the miRNAs to the complementary sequences on the carrier the resulting signal indicates the occurrence of a distinct miRNA. Preferably, microarray methods are employed that do not require labeling of the miRNAs prior to hybridization (FIGS. 3-4) and start directly from total RNA input. On one miRNA microarray, preferably the whole predetermined set of miRNAs can be analyzed. Examples of preferred hybridization assays are shown in FIGS. 1-4. The design of exemplary miRNA capture probes for use in hybridization assays is depicted in FIGS. 5 and 6.

Further, quantitative real-time polymerase chain reaction (RT-PCR) can be used to detect also low abandoned miRNAs. Furthermore, bead-based assays, e.g. the luminex platform, are also suitable.

Furthermore, bead-based assays, e.g. the Luminex platform, are also suited to carry out the present invention.

Alternative methods for obtaining expression profiles may also contain sequencing, next generation sequencing or mass spectroscopy.

The predetermined set of miRNAs in step (a) of the method of the invention depends on the disease to be diagnosed. The inventors found out that single miRNA biomarkers lack sufficient accuracy, specificity and sensitivity, and therefore it is preferred to analyze more complex miRNA expression patterns, so-called miRNA signatures. The predetermined set of miRNAs comprises one or more, preferably a larger number of miRNAs (miRNA signatures) that are differentially regulated in samples of a patient affected by a particular disease compared to healthy or other relevant controls.

The expression profile determined in step (a) is subsequently compared to a reference expression profile or a relevant reference in step (b). This reference may be a mathematical function or algorithm that allows for the diagnosis of the disease. This mathematical function or algorithm has been developed on the basis of a plurality of reference expression profiles. The reference expression profile is the expression profile of the same set of miRNAs in a biological sample originating from the same source as the biological sample from a patient but obtained from a healthy subject. Preferably, both the reference expression profile and the expression profile of step (a) are determined in a blood or serum sample including whole blood, plasma, serum or fractions thereof, or in a sample of peripheral blood mononuclear cells, erythrocytes, leukocytes and/or thrombocytes. It is understood that the reference expression profile is not necessarily obtained from a single healthy subject but may be an average expression profile of a plurality of healthy subjects. It is preferred to use a reference expression profile obtained from a person of the same gender, and a similar age as the patient. It is also understood that the reference expression profile is not necessarily determined for each test. Appropriate reference profiles stored in databases may also be used. These stored references profiles may, e.g., be derived from previous tests. The reference profile may also be a mathematical function or algorithm which is developed on a plurality of measured reference profiles.

Figure 9:
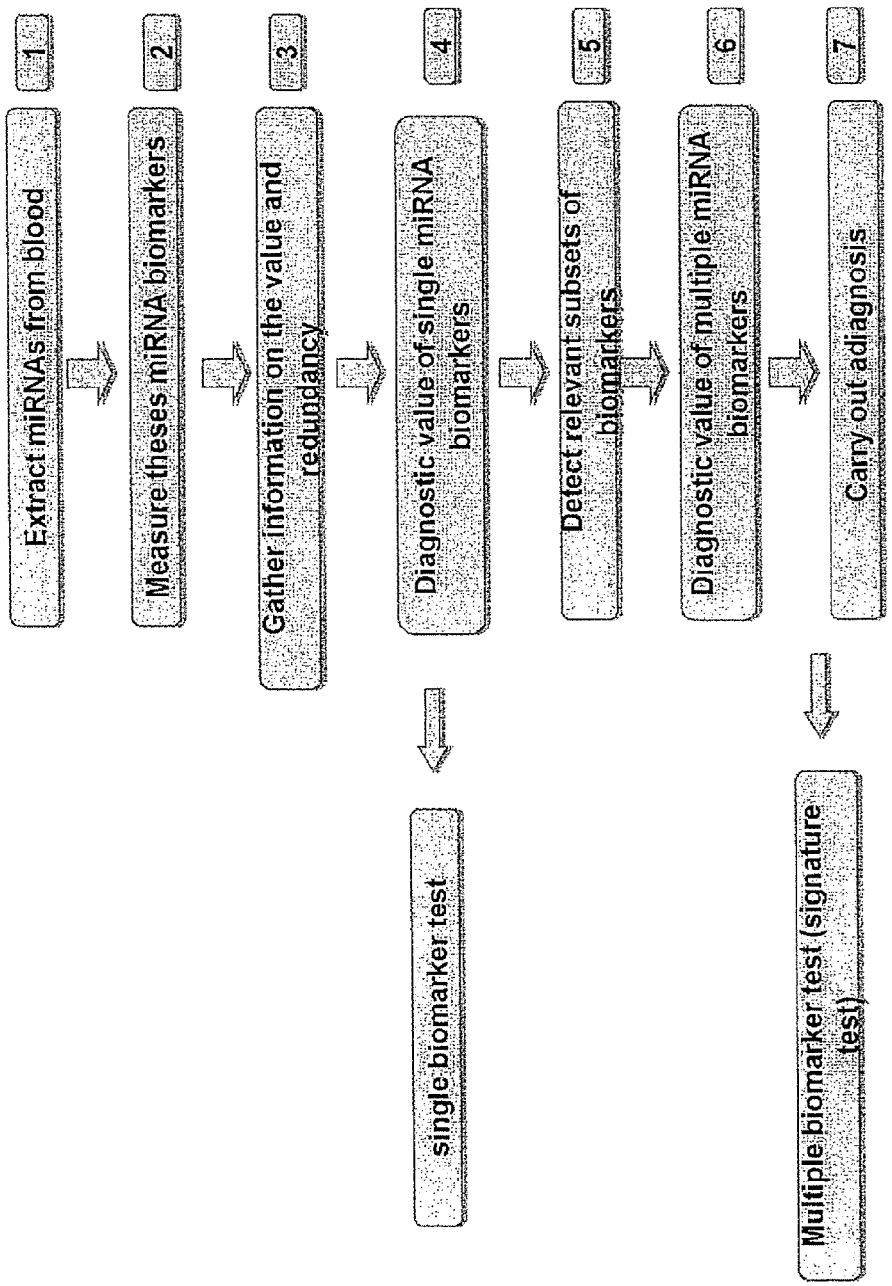

The inventors succeeded in developing a generally applicable approach to arrive at miRNA signatures that are correlated with a particular disease. The general work flow is depicted in FIG. 9. In more detail, the following steps are accomplished:

1. miRNAs are extracted from a biological sample of a patient, preferably a blood or serum sample or a sample comprising erythrocytes, leukocytes or thrombocytes, using suitable kits/purification methods
2. The respective samples are measured using experimental techniques. These techniques include but are not restricted to:
   Array based approaches
   Real time quantitative polymerase chain reaction
   Bead based assays (e.g. Luminex)
   Sequencing
   Next Generation Sequencing
   Mass Spectroscopy
3. Mathematical approaches are applied to gather information on the value and the redundancy of single biomarkers. These methods include, but are not restricted to:
   basic mathematic approaches (e.g. Fold Quotients, Signal to Noise ratios, Correlation)
   statistical methods as hypothesis tests (e.g. t-test, Wilcoxon-Mann-Whitney test), the Area under the Receiver operator Characteristics Curve
   Information Theory approaches, (e.g. the Mutual Information, Cross-entropy)
   Probability theory (e.g. joint and conditional probabilities)
   Combinations and modifications of the previously mentioned examples
4. The information collected in 3) are used to estimate for each biomarker the diagnostic content or value. Usually, however, this diagnostic value is too small to get a highly accurate diagnosis with accuracy rates, specificities and sensitivities beyond the 90% barrier.
   Please note that the diagnostic content for our miRNAs can be found in FIGS. 10A, 10B and 10C. This table includes the miRNAs with the sequences, the fold quotient, the mutual information and the significance value as computed by a t-test.
5. Thus statistical learning/machine learning/bioinformatics/computational approaches are applied to define subsets of biomarkers that are tailored for the detection of diseases. These techniques includes but are not restricted to
   Wrapper subset selection techniques (e.g. forward step-wise, backward step-wise, combinatorial approaches, optimization approaches)
   Filter subset selection methods (e.g. the methods mentioned in 3)
   Principal Component Analysis
   Combinations and modifications of such methods (e.g. hybrid approaches)
6. The diagnostic content of each detected set can be estimated by mathematical and/or computational techniques to define the diagnostic information content of subsets.
7. The subsets, detected in step 5, which may range from only a small number (at least two) to all measured biomarkers is then used to carry out a diagnosis. To this end, statistical learning/machine learning/bioinformatics/computational approaches are applied that include but are not restricted to any type of supervised or unsupervised analysis:
   Classification techniques (e.g. naïve Bayes, Linear Discriminant Analysis, Quadratic Discriminant Analysis Neural Nets, Tree based approaches, Support Vector Machines, Nearest Neighbour Approaches)

Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression)

Clustering techniques (e.g. k-means clustering, hierarchical clustering, PCA)

Adaptations, extensions, and combinations of the previously mentioned approaches The inventors surprisingly found out that the described approach yields in miRNA signatures that provide high diagnostic accuracy, specificity and sensitivity in the determination of multiple sclerosis or related disease states/clinical conditions.

According to a preferred embodiment of the invention, the disease to be determined is multiple sclerosis. Surprisingly, the inventors found out that miRNAs are differentially regulated in samples from MS patients as compared to health controls. A complete overview of all miRNAs that are found to be differentially regulated in blood samples of multiple sclerosis patients is provided in the tables shown in FIGS. 10A, 10B and 10C. In one embodiment, 193 miRNAs were found to be significantly deregulated in blood cells of MS patients as compared to controls (FIG. 10A). In a further embodiment—based on additional information—165 miRNAs were found to be significantly deregulated in blood cells of MS patients as compared to controls (FIG. 10B). In a still further embodiment, 308 miRNAs were found to be significantly deregulated in blood cells of MS patients as compared to controls (FIG. 10C).

Preferably, the predetermined set of miRNAs for the diagnosis of multiple sclerosis comprises one or more nucleic acids selected from the deregulated miRNAs presented in the tables in FIG. 10A, 10B or 10C. The predetermined set of miRNAs should preferably comprise at least 7, preferably at least 10, 15, 20 or 24 of the indicated nucleic acids. It is particularly preferred to include the 24, 20, 15, 10 or at least 7 of the first mentioned miRNAs according to their order in the tables in FIG. 10A, 10B or 10C, preferably except hsa-miR-148a, hsa-miR-18b, hsa-miR-96, hsa-miR-96, hsa-miR-599, hsa-miR-493, hsa-miR-184, hsa-miR-193a.

Thus, preferably the predetermined set of miRNAs for the diagnosis of MS comprises one or more nucleic acids selected from the 24 most deregulated miRNAs hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p. Preferably, the predetermined set of miRNAs comprises at least 7, preferably at least 10, 15, 20 or all of the above-indicated nucleic acids. Most preferably, the predetermined set of miRNAs comprises those miRNAs that were most significantly deregulated: hsa-miR-145, hsa-miR-186, hsa-miR-664, hsa-miR-584, hsa-miR-20b, hsa-miR-223, hsa-miR-422a, hsa-miR-142-3p, hsa-let-7c.

In another embodiment, the predetermined set of miRNAs for the diagnosis of MS comprises at least one preferred signature 1-84 as shown in Table 1. It should be noted that preferred diagnostic sets may also comprise one or more miRNAs of the miRNAs disclosed in Table 1 and any combination of the miRNAs together with one or more further diagnostically relevant miRNA from FIG. 10A, 10B or 10C. Preferred predetermined sets of miRNA based on Table 1 comprise at least 3, 4, 5, 6, 7, 8, 9 or 10 miRNAs and up to 10, 15, or 20 or more miRNAs.

TABLE 1

| Signature | Signature | SEQ-ID Nos | miRNA-identifiers |
|---|---|---|---|
| 1 | A1 | SEQ ID NO: 53, SEQ ID NO: 632, SEQ ID NO: 526 | hsa-let-7b, hsa-miR-574-3p, hsa-miR-500 |
| 2 | A2 | SEQ ID NO: 526, SEQ ID NO: 790, SEQ ID NO: 806 | hsa-miR-500, hsa-miR-1234, hsa-miR-125a-5p |
| 3 | A3 | SEQ ID NO: 806, SEQ ID NO: 823, SEQ ID NO: 15 | hsa-miR-125a-5p, hsa-miR-92b*, hsa-let-7c |
| 4 | A4 | SEQ ID NO: 15, SEQ ID NO: 99, SEQ ID NO: 641 | hsa-let-7c, hsa-miR-145, hsa-miR-330-3p |
| 5 | A5 | SEQ ID NO: 641, SEQ ID NO: 50, SEQ ID NO: 75 | hsa-miR-330-3p, hsa-miR-30e, hsa-miR-199a-5p |
| 6 | A6 | SEQ ID NO: 75, SEQ ID NO: 51, SEQ ID NO: 13 | hsa-miR-199a-5p, hsa-miR-223, hsa-miR-195 |
| 7 | A7 | SEQ ID NO: 13, SEQ ID NO: 129, SEQ ID NO: 750 | hsa-miR-195, hsa-miR-182, hsa-miR-107 |
| 8 | A8 | SEQ ID NO: 750, SEQ ID NO: 87, SEQ ID NO: 137 | hsa-miR-107, hsa-miR-497, hsa-miR-593* |
| 9 | A9 | SEQ ID NO: 137, SEQ ID NO: 826, SEQ ID NO: 778 | hsa-miR-593*, hsa-miR-422a, hsa-miR-1301 |
| 10 | A10 | SEQ ID NO: 778, SEQ ID NO: 232, SEQ ID NO: 644 | hsa-miR-1301, hsa-miR-362-5p, hsa-miR-214 |
| 11 | A11 | SEQ ID NO: 644, SEQ ID NO: 217, SEQ ID NO: 358 | hsa-miR-214, hsa-miR-31*, hsa-miR-24 |
| 12 | A12 | SEQ ID NO: 358, SEQ ID NO: 800, SEQ ID NO: 671 | hsa-miR-24, hsa-miR-146a, hsa-miR-1908 |
| 13 | A13 | SEQ ID NO: 671, SEQ ID NO: 560, SEQ ID NO: 49 | hsa-miR-1908, hsa-miR-103, hsa-miR-106a |
| 14 | A14 | SEQ ID NO: 560, SEQ ID NO: 274, SEQ ID NO: 49 | hsa-miR-103, hsa-miR-452*, hsa-miR-106a |
| 15 | A15 | SEQ ID NO: 49, SEQ ID NO: 501, SEQ ID NO: 455 | hsa-miR-106a, hsa-miR-621, hsa-miR-1251 |
| 16 | A16 | SEQ ID NO: 53, SEQ ID NO: 632, SEQ ID NO: 526, SEQ ID NO: 790, SEQ ID NO: 806 | hsa-let-7b, hsa-miR-574-3p, hsa-miR-500, hsa-miR-1234, hsa-miR-125a-5p |

TABLE 1-continued

| Signature | Signature | SEQ-ID Nos | miRNA-identifiers |
|---|---|---|---|
| 17 | A17 | SEQ ID NO: 526, SEQ ID NO: 790, SEQ ID NO: 806, SEQ ID NO: 823, SEQ ID NO: 15 | hsa-miR-500, hsa-miR-1234, hsa-miR-125a-5p, hsa-miR-92b*, hsa-let-7c |
| 18 | A18 | SEQ ID NO: 806, SEQ ID NO: 823, SEQ ID NO: 15, SEQ ID NO: 99, SEQ ID NO: 641 | hsa-miR-125a-5p, hsa-miR-92b*, hsa-let-7c, hsa-miR-145, hsa-miR-330-3p |
| 19 | A19 | SEQ ID NO: 823, SEQ ID NO: 15, SEQ ID NO: 99, SEQ ID NO: 641, SEQ ID NO: 50 | hsa-miR-92b*, hsa-let-7c, hsa-miR-145, hsa-miR-330-3p, hsa-miR-30e |
| 20 | A20 | SEQ ID NO: 99, SEQ ID NO: 641, SEQ ID NO: 50, SEQ ID NO: 75, SEQ ID NO: 51 | hsa-miR-145, hsa-miR-330-3p, hsa-miR-30e, hsa-miR-199a-5p, hsa-miR-223 |
| 21 | A21 | SEQ ID NO: 50, SEQ ID NO: 75, SEQ ID NO: 51, SEQ ID NO: 13, SEQ ID NO: 129 | hsa-miR-30e, hsa-miR-199a-5p, hsa-miR-223, hsa-miR-195, hsa-miR-182 |
| 22 | A22 | SEQ ID NO: 75, SEQ ID NO: 51, SEQ ID NO: 13, SEQ ID NO: 129, SEQ ID NO: 750, SEQ ID NO: 87 | hsa-miR-199a-5p, hsa-miR-223, hsa-miR-195, hsa-miR-182, hsa-miR-107, hsa-miR-497 |
| 23 | A23 | SEQ ID NO: 129, SEQ ID NO: 750, SEQ ID NO: 87, SEQ ID NO: 137, SEQ ID NO: 826, SEQ ID NO: 778 | hsa-miR-182, hsa-miR-107, hsa-miR-497, hsa-miR-593*, hsa-miR-422a, hsa-miR-1301 |
| 24 | A24 | SEQ ID NO: 137, SEQ ID NO: 826, SEQ ID NO: 778, SEQ ID NO: 232, SEQ ID NO: 644, SEQ ID NO: 217 | hsa-miR-593*, hsa-miR-422a, hsa-miR-1301, hsa-miR-362-5p, hsa-miR-214, hsa-miR-31* |
| 25 | A25 | SEQ ID NO: 232, SEQ ID NO: 644, SEQ ID NO: 217, SEQ ID NO: 358, SEQ ID NO: 800, SEQ ID NO: 671 | hsa-miR-362-5p, hsa-miR-214, hsa-miR-31*, hsa-miR-24, hsa-miR-146a, hsa-miR-1908 |
| 26 | A26 | SEQ ID NO: 358, SEQ ID NO: 800, SEQ ID NO: 671, SEQ ID NO: 814, SEQ ID NO: 560, SEQ ID NO: 274 | hsa-miR-24, hsa-miR-146a, hsa-miR-1908, hsa-miR-675, hsa-miR-103, hsa-miR-452* |
| 27 | A27 | SEQ ID NO: 814, SEQ ID NO: 560, SEQ ID NO: 274, SEQ ID NO: 49, SEQ ID NO: 501, SEQ ID NO: 455 | hsa-miR-675, hsa-miR-103, hsa-miR-452*, hsa-miR-106a, hsa-miR-621, hsa-miR-1251 |
| 28 | A28 | SEQ ID NO: 49, SEQ ID NO: 501, SEQ ID NO: 455, SEQ ID NO: 528, SEQ ID NO: 259, SEQ ID NO: 619 | hsa-miR-106a, hsa-miR-621, hsa-miR-1251, hsa-miR-20a*, hsa-miR-646, hsa-miR-885-3p |
| 29 | A29 | SEQ ID NO: 528, SEQ ID NO: 259, SEQ ID NO: 619, SEQ ID NO: 363, SEQ ID NO: 169, SEQ ID NO: 11 | hsa-miR-20a*, hsa-miR-646, hsa-miR-885-3p, hsa-miR-509-3-5p, hsa-miR-1912, hsa-miR-20b |
| 30 | A30 | SEQ ID NO: 363, SEQ ID NO: 169, SEQ ID NO: 11, SEQ ID NO: 9, SEQ ID NO: 768, SEQ ID NO: 552 | hsa-miR-509-3-5p, hsa-miR-1912, hsa-miR-20b, hsa-miR-574-5p, hsa-miR-221, hsa-miR-365 |
| 31 | A31 | SEQ ID NO: 53, SEQ ID NO: 632, SEQ ID NO: 526, SEQ ID NO: 790, SEQ ID NO: 806, SEQ ID NO: 823, SEQ ID NO: 15, SEQ ID NO: 99, SEQ ID NO: 641, SEQ ID NO: 50 | hsa-let-7b, hsa-miR-574-3p, hsa-miR-500, hsa-miR-1234, hsa-miR-125a-5p, hsa-miR-92b*, hsa-let-7c, hsa-miR-145, hsa-miR-330-3p, hsa-miR-30e |
| 32 | A32 | SEQ ID NO: 823, SEQ ID NO: 15, SEQ ID NO: 99, SEQ ID NO: 641, SEQ ID NO: 50, SEQ ID NO: 75, SEQ ID NO: 51, SEQ ID NO: 13, SEQ ID NO: 129, SEQ ID NO: 750, SEQ ID NO: 87 | hsa-miR-92b*, hsa-let-7c, hsa-miR-145, hsa-miR-330-3p, hsa-miR-30e, hsa-miR-199a-5p, hsa-miR-223, hsa-miR-195, hsa-miR-182, hsa-miR-107, hsa-miR-497 |
| 33 | A33 | SEQ ID NO: 51, SEQ ID NO: 13, SEQ ID NO: 129, SEQ ID NO: 750, SEQ ID NO: 87, SEQ ID NO: 137, SEQ ID NO: 826, SEQ ID NO: 778, SEQ ID NO: 232, SEQ ID NO: 644 | hsa-miR-223, hsa-miR-195, hsa-miR-182, hsa-miR-107, hsa-miR-497, hsa-miR-593*, hsa-miR-422a, hsa-miR-1301, hsa-miR-362-5p, hsa-miR-214 |
| 34 | A34 | SEQ ID NO: 137, SEQ ID NO: 826, SEQ ID NO: 778, SEQ ID NO: 232, SEQ ID NO: 644, SEQ ID NO: 217, SEQ ID NO: 358, SEQ ID NO: 800, SEQ ID NO: 671, SEQ ID NO: 814 | hsa-miR-593*, hsa-miR-422a, hsa-miR-1301, hsa-miR-362-5p, hsa-miR-214, hsa-miR-31*, hsa-miR-24, hsa-miR-146a, hsa-miR-1908, hsa-miR-675 |
| 35 | A35 | SEQ ID NO: 217, SEQ ID NO: 358, SEQ ID NO: 800, SEQ ID NO: 671, SEQ ID NO: 814, SEQ ID NO: 560, SEQ ID NO: 274, SEQ ID NO: 49, SEQ ID NO: 501, SEQ ID NO: 455 | hsa-miR-31*, hsa-miR-24, hsa-miR-146a, hsa-miR-1908, hsa-miR-675, hsa-miR-103, hsa-miR-452*, hsa-miR-106a, hsa-miR-621, hsa-miR-1251 |
| 36 | A36 | SEQ ID NO: 560, SEQ ID NO: 274, SEQ ID NO: 49, SEQ ID NO: 501, SEQ ID NO: 455, SEQ ID NO: 528, SEQ ID NO: 259, SEQ ID NO: 619, SEQ ID NO: 363, SEQ ID NO: 169 | hsa-miR-103, hsa-miR-452*, hsa-miR-106a, hsa-miR-621, hsa-miR-1251, hsa-miR-20a*, hsa-miR-646, hsa-miR-885-3p, hsa-miR-509-3-5p, hsa-miR-1912 |
| 37 | A37 | SEQ ID NO: 528, SEQ ID NO: 259, SEQ ID NO: 619, SEQ ID NO: 363, SEQ ID NO: 169, SEQ ID NO: 11, SEQ ID NO: 9, SEQ ID NO: 768, SEQ ID NO: 552, SEQ ID NO: 789 | hsa-miR-20a*, hsa-miR-646, hsa-miR-885-3p, hsa-miR-509-3-5p, hsa-miR-1912, hsa-miR-20b, hsa-miR-574-5p, hsa-miR-221, hsa-miR-365, hsa-miR-22* |
| 38 | A38 | SEQ ID NO: 11, SEQ ID NO: 9, SEQ ID NO: 768, SEQ ID NO: 552, SEQ ID NO: 789, SEQ ID NO: 495, SEQ ID NO: 854, SEQ ID NO: 609, SEQ ID NO: 719, SEQ ID NO: 688 | hsa-miR-20b, hsa-miR-574-5p, hsa-miR-221, hsa-miR-365, hsa-miR-22*, hsa-miR-1275, hsa-miR-625, hsa-miR-584, hsa-miR-328, hsa-miR-629 |
| 39 | A39 | SEQ ID NO: 495, SEQ ID NO: 854, SEQ ID NO: 609, SEQ ID NO: 719, SEQ ID NO: 688, SEQ ID NO: 313, SEQ ID NO: 667, SEQ ID NO: 491, SEQ ID NO: 320, SEQ ID NO: 84 | hsa-miR-1275, hsa-miR-625, hsa-miR-584, hsa-miR-328, hsa-miR-629, hsa-miR-186, hsa-miR-142-3p, hsa-miR-7, hsa-miR-891a, hsa-miR-1272 |
| 40 | A40 | SEQ ID NO: 53, SEQ ID NO: 526, SEQ ID NO: 806, SEQ ID NO: 15, SEQ ID NO: 641 | hsa-let-7b, hsa-miR-500, hsa-miR-125a-5p, hsa-let-7c, hsa-miR-330-3p |
| 41 | A41 | SEQ ID NO: 790, SEQ ID NO: 823, SEQ ID NO: 99, SEQ ID NO: 50, SEQ ID NO: 51 | hsa-miR-1234, hsa-miR-92b*, hsa-miR-145, hsa-miR-30e, hsa-miR-223 |

TABLE 1-continued

| Signature | Signature | SEQ-ID Nos | miRNA-identifiers |
|---|---|---|---|
| 42 | A42 | SEQ ID NO: 99, SEQ ID NO: 50, SEQ ID NO: 51, SEQ ID NO: 129, SEQ ID NO: 87 | hsa-miR-145, hsa-miR-30e, hsa-miR-223, hsa-miR-182, hsa-miR-497 |
| 43 | B1 | SEQ ID NO: 53, SEQ ID NO: 632, SEQ ID NO: 197 | hsa-let-7b, hsa-miR-574-3p, hsa-miR-454 |
| 44 | B2 | SEQ ID NO: 197, SEQ ID NO: 526, SEQ ID NO: 737 | hsa-miR-454, hsa-miR-500, hsa-miR-766 |
| 45 | B3 | SEQ ID NO: 737, SEQ ID NO: 14, SEQ ID NO: 790 | hsa-miR-766, hsa-let-7e, hsa-miR-1234 |
| 46 | B4 | SEQ ID NO: 790, SEQ ID NO: 806, SEQ ID NO: 16 | hsa-miR-1234, hsa-miR-125a-5p, hsa-let-7f |
| 47 | B5 | SEQ ID NO: 16, SEQ ID NO: 823, SEQ ID NO: 15 | hsa-let-7f, hsa-miR-92b*, hsa-let-7c |
| 48 | B6 | SEQ ID NO: 15, SEQ ID NO: 18, SEQ ID NO: 99 | hsa-let-7c, hsa-let-7g, hsa-miR-145 |
| 49 | B7 | SEQ ID NO: 99, SEQ ID NO: 3, SEQ ID NO: 622 | hsa-miR-145, hsa-let-7i, hsa-miR-130b |
| 50 | B8 | SEQ ID NO: 622, SEQ ID NO: 580, SEQ ID NO: 641 | hsa-miR-130b, hsa-miR-1260, hsa-miR-330-3p |
| 51 | B9 | SEQ ID NO: 641, SEQ ID NO: 50, SEQ ID NO: 4 | hsa-miR-330-3p, hsa-miR-30e, hsa-let-7d |
| 52 | B10 | SEQ ID NO: 4, SEQ ID NO: 436, SEQ ID NO: 565 | hsa-let-7d, hsa-miR-501-3p, hsa-miR-1913 |
| 53 | B11 | SEQ ID NO: 565, SEQ ID NO: 75, SEQ ID NO: 5 | hsa-miR-1913, hsa-miR-199a-5p, hsa-miR-22 |
| 54 | B12 | SEQ ID NO: 5, SEQ ID NO: 51, SEQ ID NO: 13 | hsa-miR-22, hsa-miR-223, hsa-miR-195 |
| 55 | B13 | SEQ ID NO: 13, SEQ ID NO: 129, SEQ ID NO: 145 | hsa-miR-195, hsa-miR-182, hsa-miR-30c |
| 56 | B14 | SEQ ID NO: 129, SEQ ID NO: 67, SEQ ID NO: 145 | hsa-miR-182, hsa-miR-192, hsa-miR-30c |
| 57 | B15 | SEQ ID NO: 145, SEQ ID NO: 327, SEQ ID NO: 750 | hsa-miR-30c, hsa-miR-363, hsa-miR-107 |
| 58 | B16 | SEQ ID NO: 53, SEQ ID NO: 632, SEQ ID NO: 197, SEQ ID NO: 526, SEQ ID NO: 737 | hsa-let-7b, hsa-miR-574-3p, hsa-miR-454, hsa-miR-500, hsa-miR-766 |
| 59 | B17 | SEQ ID NO: 197, SEQ ID NO: 526, SEQ ID NO: 737, SEQ ID NO: 14, SEQ ID NO: 790 | hsa-miR-454, hsa-miR-500, hsa-miR-766, hsa-let-7e, hsa-miR-1234 |
| 60 | B18 | SEQ ID NO: 737, SEQ ID NO: 14, SEQ ID NO: 790, SEQ ID NO: 806, SEQ ID NO: 16 | hsa-miR-766, hsa-let-7e, hsa-miR-1234, hsa-miR-125a-5p, hsa-let-7f |
| 61 | B19 | SEQ ID NO: 14, SEQ ID NO: 790, SEQ ID NO: 806, SEQ ID NO: 16, SEQ ID NO: 823 | hsa-let-7e, hsa-miR-1234, hsa-miR-125a-5p, hsa-let-7f, hsa-miR-92b* |
| 62 | B20 | SEQ ID NO: 806, SEQ ID NO: 16, SEQ ID NO: 823, SEQ ID NO: 15, SEQ ID NO: 18 | hsa-miR-125a-5p, hsa-let-7f, hsa-miR-92b*, hsa-let-7c, hsa-let-7g |
| 63 | B21 | SEQ ID NO: 823, SEQ ID NO: 15, SEQ ID NO: 18, SEQ ID NO: 99, SEQ ID NO: 3 | hsa-miR-92b*, hsa-let-7c, hsa-let-7g, hsa-miR-145, hsa-let-7i |
| 64 | B22 | SEQ ID NO: 15, SEQ ID NO: 18, SEQ ID NO: 99, SEQ ID NO: 3, SEQ ID NO: 622, SEQ ID NO: 580 | hsa-let-7c, hsa-let-7g, hsa-miR-145, hsa-let-7i, hsa-miR-130b, hsa-miR-1260 |
| 65 | B23 | SEQ ID NO: 3, SEQ ID NO: 622, SEQ ID NO: 580, SEQ ID NO: 641, SEQ ID NO: 50, SEQ ID NO: 4 | hsa-let-7i, hsa-miR-130b, hsa-miR-1260, hsa-miR-330-3p, hsa-miR-30e, hsa-let-7d |
| 66 | B24 | SEQ ID NO: 641, SEQ ID NO: 50, SEQ ID NO: 4, SEQ ID NO: 436, SEQ ID NO: 565, SEQ ID NO: 75 | hsa-miR-330-3p, hsa-miR-30e, hsa-let-7d, hsa-miR-501-3p, hsa-miR-1913, hsa-miR-199a-5p |
| 67 | B25 | SEQ ID NO: 436, SEQ ID NO: 565, SEQ ID NO: 75, SEQ ID NO: 5, SEQ ID NO: 51, SEQ ID NO: 13 | hsa-miR-501-3p, hsa-miR-1913, hsa-miR-199a-5p, hsa-miR-22, hsa-miR-223, hsa-miR-195 |
| 68 | B26 | SEQ ID NO: 5, SEQ ID NO: 51, SEQ ID NO: 13, SEQ ID NO: 343, SEQ ID NO: 129, SEQ ID NO: 67 | hsa-miR-22, hsa-miR-223, hsa-miR-195, hsa-miR-532-3p, hsa-miR-182, hsa-miR-192 |
| 69 | B27 | SEQ ID NO: 343, SEQ ID NO: 129, SEQ ID NO: 67, SEQ ID NO: 145, SEQ ID NO: 327, SEQ ID NO: 750 | hsa-miR-532-3p, hsa-miR-182, hsa-miR-192, hsa-miR-30c, hsa-miR-363, hsa-miR-107 |
| 70 | B28 | SEQ ID NO: 145, SEQ ID NO: 327, SEQ ID NO: 750, SEQ ID NO: 675, SEQ ID NO: 87, SEQ ID NO: 20 | hsa-miR-30c, hsa-miR-363, hsa-miR-107, hsa-miR-486-3p, hsa-miR-497, hsa-miR-339-5p |
| 71 | B29 | SEQ ID NO: 675, SEQ ID NO: 87, SEQ ID NO: 20, SEQ ID NO: 137, SEQ ID NO: 237, SEQ ID NO: 670 | hsa-miR-486-3p, hsa-miR-497, hsa-miR-339-5p, hsa-miR-593*, hsa-miR-194, hsa-miR-627 |
| 72 | B30 | SEQ ID NO: 137, SEQ ID NO: 237, SEQ ID NO: 670, SEQ ID NO: 521, SEQ ID NO: 808, SEQ ID NO: 198 | hsa-miR-593*, hsa-miR-194, hsa-miR-627, hsa-miR-93, hsa-miR-197, hsa-miR-101 |
| 73 | B31 | SEQ ID NO: 53, SEQ ID NO: 632, SEQ ID NO: 197, SEQ ID NO: 526, SEQ ID NO: 737, SEQ ID NO: 14, SEQ ID NO: 790, SEQ ID NO: 806, SEQ ID NO: 16, SEQ ID NO: 823 | hsa-let-7b, hsa-miR-574-3p, hsa-miR-454, hsa-miR-500, hsa-miR-766, hsa-let-7e, hsa-miR-1234, hsa-miR-125a-5p, hsa-let-7f, hsa-miR-92b* |

TABLE 1-continued

| Signature | Signature | SEQ-ID Nos | miRNA-identifiers |
|---|---|---|---|
| 74 | B32 | SEQ ID NO: 14, SEQ ID NO: 790, SEQ ID NO: 806, SEQ ID NO: 16, SEQ ID NO: 823, SEQ ID NO: 15, SEQ ID NO: 18, SEQ ID NO: 99, SEQ ID NO: 3, SEQ ID NO: 622, SEQ ID NO: 580 | hsa-let-7e, hsa-miR-1234, hsa-miR-125a-5p, hsa-let-7f, hsa-miR-92b*, hsa-let-7c, hsa-let-7g, hsa-miR-145, hsa-let-7i, hsa-miR-130b, hsa-miR-1260 |
| 75 | B33 | SEQ ID NO: 18, SEQ ID NO: 99, SEQ ID NO: 3, SEQ ID NO: 622, SEQ ID NO: 580, SEQ ID NO: 641, SEQ ID NO: 50, SEQ ID NO: 4, SEQ ID NO: 436, SEQ ID NO: 565 | hsa-let-7g, hsa-miR-145, hsa-let-7i, hsa-miR-130b, hsa-miR-1260, hsa-miR-330-3p, hsa-miR-30e, hsa-let-7d, hsa-miR-501-3p, hsa-miR-1913 |
| 76 | B34 | SEQ ID NO: 641, SEQ ID NO: 50, SEQ ID NO: 4, SEQ ID NO: 436, SEQ ID NO: 565, SEQ ID NO: 75, SEQ ID NO: 5, SEQ ID NO: 51, SEQ ID NO: 13, SEQ ID NO: 343 | hsa-miR-330-3p, hsa-miR-30e, hsa-let-7d, hsa-miR-501-3p, hsa-miR-1913, hsa-miR-199a-5p, hsa-miR-22, hsa-miR-223, hsa-miR-195, hsa-miR-532-3p |
| 77 | B35 | SEQ ID NO: 75, SEQ ID NO: 5, SEQ ID NO: 51, SEQ ID NO: 13, SEQ ID NO: 343, SEQ ID NO: 129, SEQ ID NO: 67, SEQ ID NO: 145, SEQ ID NO: 327, SEQ ID NO: 750 | hsa-miR-199a-5p, hsa-miR-22, hsa-miR-223, hsa-miR-195, hsa-miR-532-3p, hsa-miR-182, hsa-miR-192, hsa-miR-30c, hsa-miR-363, hsa-miR-107 |
| 78 | B36 | SEQ ID NO: 129, SEQ ID NO: 67, SEQ ID NO: 145, SEQ ID NO: 327, SEQ ID NO: 750, SEQ ID NO: 675, SEQ ID NO: 87, SEQ ID NO: 20, SEQ ID NO: 137, SEQ ID NO: 237 | hsa-miR-182, hsa-miR-192, hsa-miR-30c, hsa-miR-363, hsa-miR-107, hsa-miR-486-3p, hsa-miR-497, hsa-miR-339-5p, hsa-miR-593*, hsa-miR-194 |
| 79 | B37 | SEQ ID NO: 675, SEQ ID NO: 87, SEQ ID NO: 20, SEQ ID NO: 137, SEQ ID NO: 237, SEQ ID NO: 670, SEQ ID NO: 521, SEQ ID NO: 808, SEQ ID NO: 198, SEQ ID NO: 861 | hsa-miR-486-3p, hsa-miR-497, hsa-miR-339-5p, hsa-miR-593*, hsa-miR-194, hsa-miR-627, hsa-miR-93, hsa-miR-197, hsa-miR-101, hsa-miR-92a |
| 80 | B38 | SEQ ID NO: 670, SEQ ID NO: 521, SEQ ID NO: 808, SEQ ID NO: 198, SEQ ID NO: 861, SEQ ID NO: 826, SEQ ID NO: 850, SEQ ID NO: 778, SEQ ID NO: 43, SEQ ID NO: 232 | hsa-miR-627, hsa-miR-93, hsa-miR-197, hsa-miR-101, hsa-miR-92a, hsa-miR-422a, hsa-miR-1470, hsa-miR-1301, hsa-miR-550*, hsa-miR-362-5p |
| 81 | B39 | SEQ ID NO: 826, SEQ ID NO: 850, SEQ ID NO: 778, SEQ ID NO: 43, SEQ ID NO: 232, SEQ ID NO: 644, SEQ ID NO: 293, SEQ ID NO: 217, SEQ ID NO: 720, SEQ ID NO: 358 | hsa-miR-422a, hsa-miR-1470, hsa-miR-1301, hsa-miR-550*, hsa-miR-362-5p, hsa-miR-214, hsa-miR-192*, hsa-miR-31*, hsa-miR-146b-5p, hsa-miR-24 |
| 82 | B40 | SEQ ID NO: 53, SEQ ID NO: 197, SEQ ID NO: 737, SEQ ID NO: 790, SEQ ID NO: 16 | hsa-let-7b, hsa-miR-454, hsa-miR-766, hsa-miR-1234, hsa-let-7f |
| 83 | B41 | SEQ ID NO: 526, SEQ ID NO: 14, SEQ ID NO: 806, SEQ ID NO: 823, SEQ ID NO: 18 | hsa-miR-500, hsa-let-7e, hsa-miR-125a-5p, hsa-miR-92b*, hsa-let-7g |
| 84 | B42 | SEQ ID NO: 806, SEQ ID NO: 823, SEQ ID NO: 18, SEQ ID NO: 3, SEQ ID NO: 580 | hsa-miR-125a-5p, hsa-miR-92b*, hsa-let-7g, hsa-let-7i, hsa-miR-1260 |

Another embodiment of the present invention is a kit for diagnosing a disease, comprising means for determining an expression profile of a predetermined set of miRNAs in a biological sample, in particular in a blood, plasma, and/or serum sample including whole blood, plasma, serum or fractions thereof, or in a sample comprising peripheral blood mononuclear cells, erythrocytes, leukocytes and/or thrombocytes. Preferably, one or more reference expression profiles or a relevant reference which may be a mathematical function or algorithm—which allows for the diagnosis of the disease—are also provided which show the expression profile of the same set of miRNAs in the same type of biological sample, in particular in a blood and/or serum sample, obtained from one or more healthy subjects. A comparison to said reference expression profile(s) or relevant reference incl. a mathematical function or algorithm allows for the diagnosis of the disease.

The kit is preferably a test kit for detecting a predetermined set of miRNAs in sample by nucleic acid hybridisation and optionally amplification such as PCR or RT-PCR. The kit preferably comprises probes and/or primers and enzymes and reagents, including also reagent for cDNA-synthesis from miRNAs prior to real-time PCR for detecting a predetermined set of miRNAs. Further, the kit may comprise enzymes and reagents, e.g. for cDNA synthesis from miRNAs prior to RT-PCR.

A preferred embodiment of the present invention is a kit for diagnosing multiple sclerosis, comprising means for determining the expression profile of one or more relevant miRNAs presented in the table in FIG. 10A, 10B or 10C as described above, preferably one or more miRNAs selected from the group consisting of hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p.

In a preferred embodiment the kit comprises means for determining at least seven, preferably at least 10, 15, 20 or all of the indicated miRNAs. It is particularly preferred to include means for determining the 24, 20, 15, 10 or at least 7 first mentioned miRNAs in the order of their diagnostic significance as represented by their order in the table in FIG. 10A, 10B, or 10C. Further, the kit may comprise means for determining the expression profile of a predetermined set of miRNAs based on Table 1 as described above. The kit for diagnosing MS is particularly suitable for diagnosing MS in a blood, plasma, and/or serum sample or in a sample comprising peripheral blood mononuclear cells, erythrocytes, leukocytes and/or thrombocytes.

The means for determining a predetermined set of miRNAs may for example comprise a microarray comprising miRNA-specific oligonucleotide probes. In a preferred embodiment, the microarray comprises miRNA-specific oligonucleotide probes for one or more miRNAs oligonucleotide probes for one or more miRNAs. Depending on the intended use of the microarray in the diagnostic of a particular disease, probes for different miRNAs may be included.

A microarray intended for use in the diagnosis of multiple sclerosis preferably comprises miRNA specific oligonucleotide probes for one or more miRNAs presented in the table in FIG. 10A, 10B or 10C as described above, preferably for one or more miRNAs selected from the group consisting of hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p.

In a preferred embodiment the microarray comprises oligonucleotide probes for determining at least 7, preferably at least 10, 15, 20 or all of the indicated miRNAs. It is particularly preferred to include oligonucleotide probes for determining the most significant miRNAs, which is represented by their order in the table depicted in FIG. 10A, 10B or 10C. In a further embodiment, the microarray comprises oligonucleotide probes for determining miRNA sets based on Table 1 as described above.

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

The invention also relates to sets of oligo- or polynucleotides for diagnosing multiple sclerosis comprising the sequences of at least 7, preferably at least 10, 15, 20 or all of the indicated miRNAs, and/or the complement of such sequences. It is particularly preferred to include oligo- or polynucleotides for detecting the most significant miRNAs, which are represented by their order in the table depicted in FIG. 10A, 10B or 10C. In a further embodiment, the set includes oligo- or polynucleotides for detecting of the miRNA sets based on Table 1 as described above. The oligo- or polynucleotides preferably have a length of 10, 15 or 20 and up to 30, 40, 50, 100 or more nucleotides. The term "oligo- or polynucleotides" includes single- or double-stranded molecules, RNA molecules, DNA molecules or nucleic acid analogs such as PNA or LNA.

Another embodiment of the present invention relates to a method for the assessment of a clinical condition related to multiple sclerosis of a patient.

Recent developments have shown that there is a tendency towards smaller sets of biomarkers for the detection of diseases. However, for single biomarkers and small biomarker sets, there is only a basic understanding whether these biomarkers are specific for only the single diseases or whether they occur in any other disease.

Therefore, the present inventors developed a novel class of diagnostic tests improving the current test scenarios. The inventors found out that a variety of diseases are correlated with a specific expression profile of miRNAs. In case a patient is affected by a particular disease, several miRNAs are present in larger amounts compared to a healthy normal control, whereas the amount of other miRNAs is decreased. Interestingly, the amount of some miRNAs is deregulated, i.e. increased or decreased, in more than one disease. The miRNA profile for a particular disease therefore shows conformity with the miRNA profile of other diseases in regard of individual miRNAs while other miRNAs show significant differences. If the expression profile of a large variety of miRNAs in a biological sample of a patient is measured, the comparison of the expression profile with a variety of reference expression profiles which are each characteristic for different diseases makes it possible to obtain information about the clinical condition of a certain patient and to determine, which disease(s) is/are present in said patient.

A further subject matter of the invention is a method for the assessment of a clinical condition related to multiple sclerosis of a patient comprising the steps
(a) providing a sample from the patient,
(b) determining a predetermined set of miRNAs in said sample to obtain a miRNA expression profile,
(c) comparing said miRNA expression profile with a plurality of miRNA reference expression profiles characteristic for different diseases, and
(d) assessing the clinical condition of the patient based on the comparison of step (c).

The inventors found out that the above method for the assessment of a clinical condition makes it possible to carry out an integrative diagnosis of a wide variety of diseases, particularly including multiple sclerosis. Comparing a miRNA profile obtained from a biological sample of a patient whose clinical condition is not known with a plurality of reference profiles characteristic for different diseases enables the diagnosis of a wide variety of diseases with high specificity and sensitivity.

A "biological sample" in terms of the invention means a sample of biological tissue or fluid as described hereinabove. Examples of biological samples are sections of tissues, blood, blood fractions, plasma, serum, urine or samples from other peripheral sources.

The set of miRNAs determined in step (d) preferably includes a large number of different miRNAs. It is particularly preferred to use at least 10, 20, 30, 50, preferably at least 100, 200, 500 or 1,000 miRNAs. Most preferably, all known miRNAs are included in the set of miRNAs determined in step (b) Such a complex set of miRNA-biomarkers enables a diagnosis with higher specificity and sensitivity compared to single biomarkers or sets of only a few dozens of such markers.

The determination of the set of miRNAs can be done as described herein above. Preferably, the determination is done on an experimental platform which shows a high degree of automation to minimize experimental variations, measure results time- and cost-efficiently, measures results highly reproduceably and be able for measuring more than one sample at once in order to ensure a high throughput.

Step (c) preferably includes a comparison of the miRNA profile measured for a patient with a large number of different reference profiles to provide information about the presence of as many different diseases as possible. The reference expression profiles may be laid down in a database, e.g. an internet database, a centralized or a decentralized database. The reference profiles do not necessarily have to include information about all miRNAs included in step (b), which are determined in the sample of the patient. It is, according to the invention, sufficient if the reference profile provides information on those miRNAs which are altered to a large extent compared to the condition of a healthy individual in case of the presence of a disease. Alternatively, the said relevant reference may be a mathematical function or algorithm.

Preferably, an miRNA reference profile or the relevant reference according to the invention provides information on miRNA expression characteristic for a particular disease in the same type of biological sample as used in step (b) for determining a predetermined set of miRNAs in a sample from a patient. This means that, if a patient with an unknown disease is to be classified with the analysis of a blood sample, the comparison is preferably made with miRNA reference expression profiles, which do also relate to the miRNA expression pattern in a blood sample.

The reference profiles or the relevant reference characteristic for particular diseases provide information on one or more miRNAs, which are, in case of the disease, highly deregulated, for example strongly increased or decreased, as compared to a healthy condition. It is not necessary for the reference profiles to provide information about all miRNAs included in the set of biomarkers determined in step (b). However, the more miRNAs are included in the reference profile or relevant reference, the more precise the diagnosis will be. If, for example, a reference profile for lung cancer is included, it is preferred to include the characteristic miRNAs for lung cancer. Equivalently, it is preferred to include into a reference profile for multiple sclerosis the characteristic miRNAs for multiple sclerosis as described hereinabove as well.

Another embodiment of this aspect of the invention is a kit for the assessment of a clinical condition related to multiple sclerosis of a patient comprising
(a) means for determining a predetermined set of miRNAs in a biological sample from a patient, and
(b) a plurality of miRNA reference expression profiles characteristic for different diseases or a mathematical function that allows for the diagnosis on the basis of the data derived from the miRNA expression profiles of a patient.

The set of miRNAs to be determined in a biological sample from a patient preferably includes a large number of different miRNAs. It is particularly preferred to include all known miRNAs in the set of miRNAs to be determined. In each case, said predetermined set of miRNAs should include those miRNAs for which information is provided in the reference profiles characteristic for particular diseases. It is understood that only in case the set of miRNAs determined in a biological sample from a patient comprises those miRNAs included in the reference profile/reference for a disease, a diagnosis regarding this particular disease can be provided or otherwise the diagnosis may be less informative.

The assessment of a clinical condition of a patient according to the invention is suitable for diagnosing any diseases which are correlated with a characteristic miRNA profile. Accordingly, the kit for the assessment of a clinical condition preferably includes reference profiles/references for a plurality of diseases that are correlated with a characteristic miRNA profile. It is understood that all miRNAs that are significantly deregulated in the disease states for which reference profiles are provided should be included in the set of miRNAs to be determined in a biological sample from a patient. If the kit for the assessment of a clinical condition of a patient should provide information regarding, e.g. lung cancer or multiple sclerosis, a reference profile should be available providing information about the significantly deregulated miRNAs compared to a normal or any other relevant control individual or any other relevant control individual(s). A kit for the assessment of a clinical condition shall provide information on the presence of multiple sclerosis, a reference profile characteristic for multiple sclerosis should be included. Said reference profile preferably includes information on those miRNAs that are most significantly deregulated in the case of MS. The relevant miRNAs are as disclosed hereinabove.

The invention will now be illustrated by the following figures and the non-limiting experimental examples.

FIGURES

FIG. 1:
Scheme of a miRNA hybridization assay for use in the invention.
miRNA capture probes consist of 1 miRNA probe sequence stretch that is linked to support via 3'-end or alternatively by 5'-end (not depicted here)
the miRNA probe sequence stretches are complementary to miRNA target sequences
each miRNA capture probe can bind 1 miRNA target sequences
the miRNA target sequences are labeled prior to hybridisation (e.g. by biotin labeling)

Figure 2:
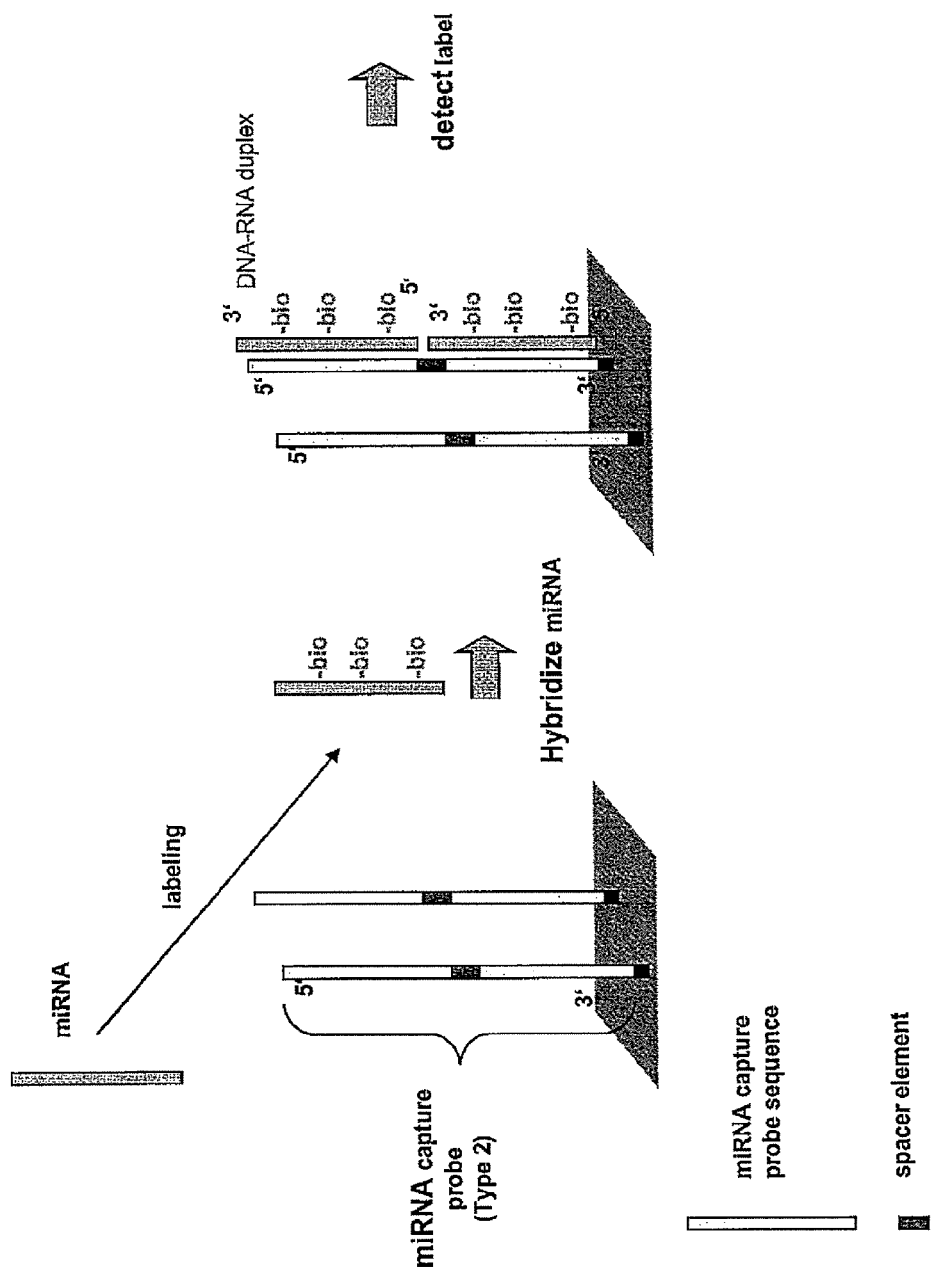

FIG. 2:
Scheme of an miRNA tandem hybridization assay for use in the invention
miRNA capture probes consist of 2 DNA-based miRNA probe sequence stretches that are linked to each other by a spacer element
the miRNA probe sequence stretches are complementary to miRNA target sequences
each miRNA capture probe can bind 2 miRNA target sequences
the spacer sequence consists of 0-8 nucleotides
the miRNA target sequences are labeled prior to hybridisation (e.g. by biotin labeling)

Figure 3:
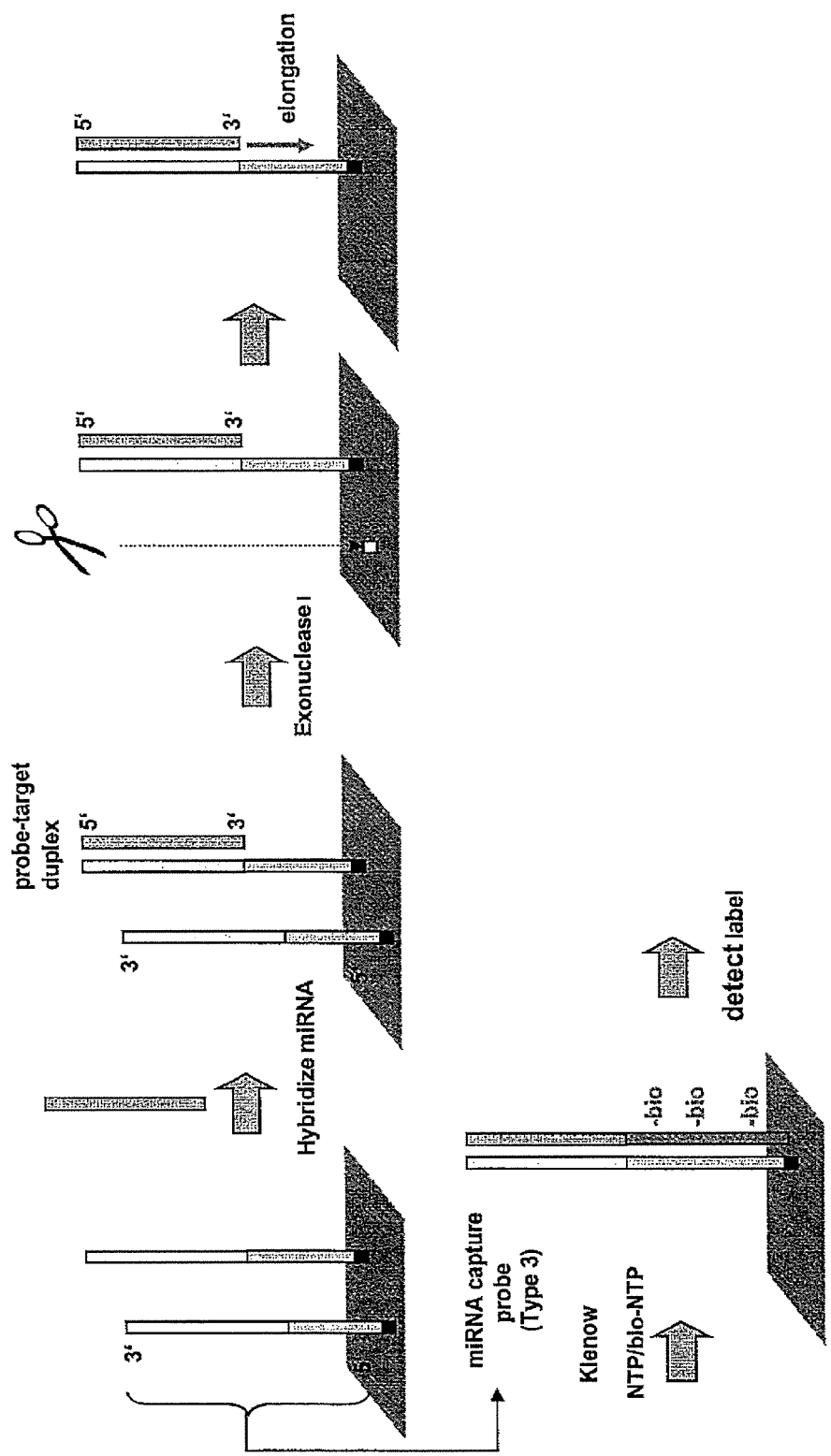
Figure 4:
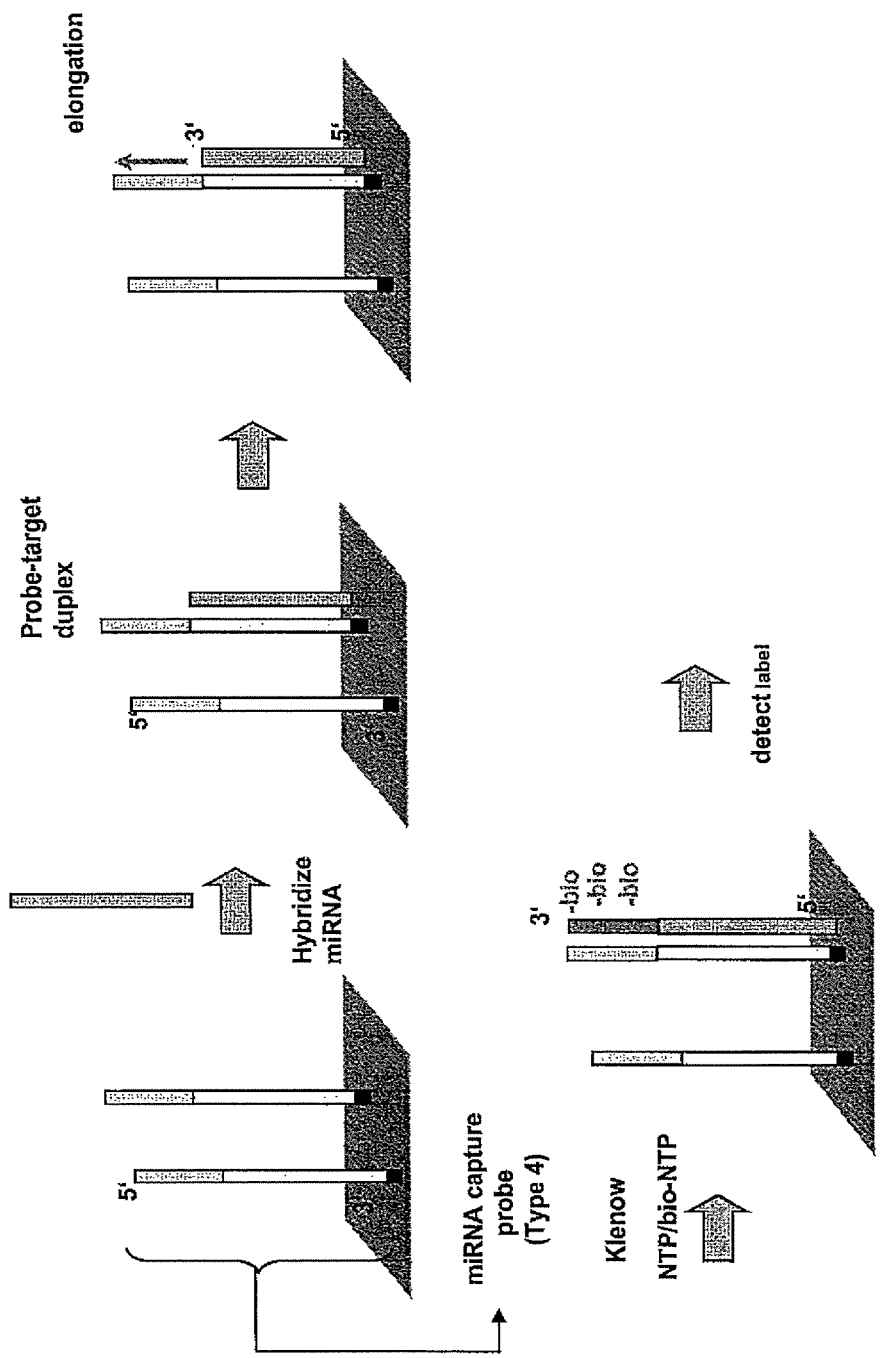
Figure 8:
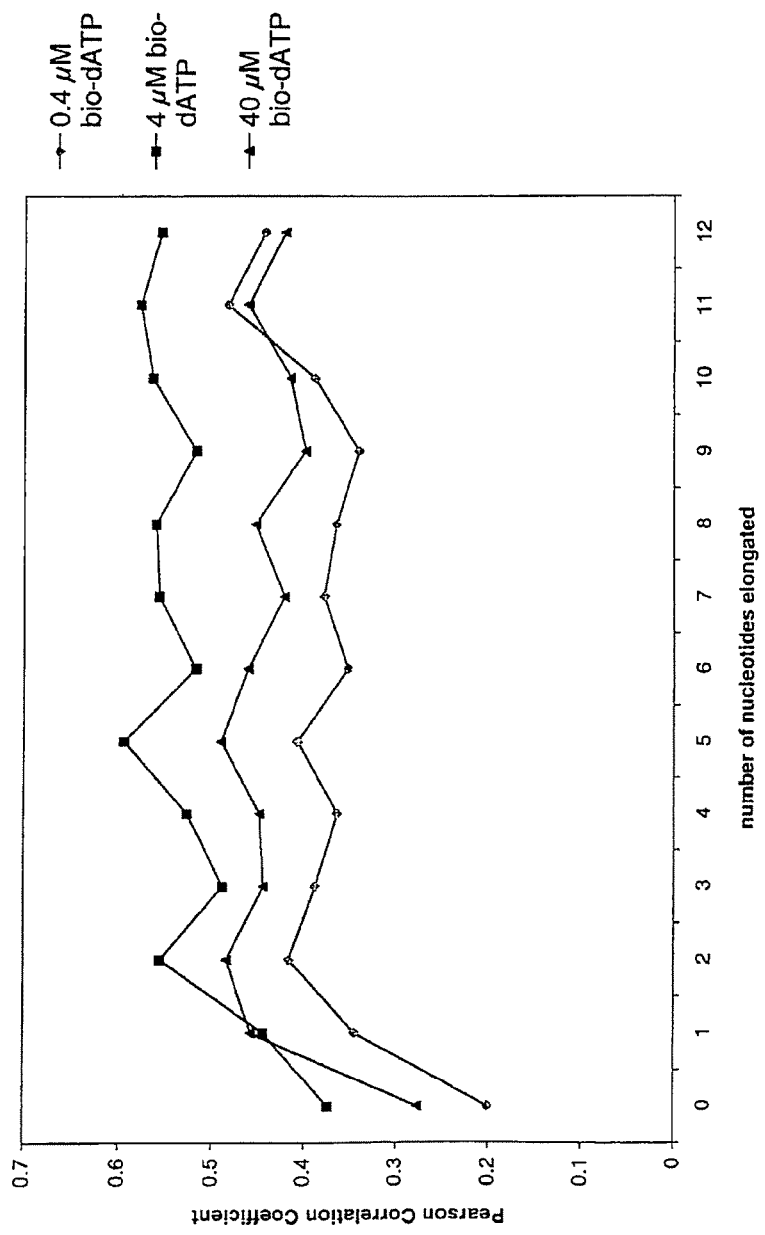

FIG. 3:
miRNA RAKE-Assay for use in the invention (PT Nelson et al., Nature Methods, 2004, 1(2), 1)
the miRNA capture probes consist of one miRNA probe sequence stretch (green) and one elongation element (orange)
probes are oriented 5'→3', presenting a free terminal 3'-OH
the miRNA probe sequence stretch (green) is complementary to miRNA target sequences (dark green)
the elongation sequences (orange) can be freely chosen and is typically between 1-12 nucleotides long, preferably a homomeric sequence
each miRNA capture probe can bind 1 miRNA target sequence
the miRNA target sequences are NOT labeled prior to hybridisation
Labeling occurs after hybridisation during elongation by polymerase extension reaction
Biochip is not reusable due to exonuclease treatment FIG. 4:
miRNA MPEA-Assay for use in the invention (Vorwerk S. et al., Microfluidic-based enzymatic on-chip labeling of miRNAs, N. Biotechnol. 2008; 25(2-3):142-9. Epub 2008 Aug. 20)
the miRNA capture probes consist of one miRNA probe sequence stretch (green) and one elongation element (orange)
probes are oriented 3'→5', presenting a free terminal 5'-OH
the miRNA probe sequence stretch (green) is complementary to miRNA target sequences (dark green)
the elongation sequences (orange) can be freely chosen and is typically between 1-12 nucleotides long, preferably a homomeric sequence each miRNA capture probe can bind 1 miRNA target sequences the miRNA target sequences are NOT labeled prior to hybridisation Labeling occurs after hybridisation during elongation by polymerase extension reaction Biochip is reusable after removal of target/elongated target

FIG. 5:

miRNA capture probe design (design MPEA/RAKE)

Depicted is the design of a capture probe for the exemplary miRNA human mature miRNA let-7a for use in the various types of hybridization assays shown in FIGS. 1-4. SP=spacer element; EL=elongation element

FIG. 6:

Spacer Element.

Capture probes for use in e.g. a tandem hybridization assay as shown in FIG. 2 may comprise a spacer element SP. The spacer element represents a nucleotide sequence with n=0-12 nucleotides chosen on the basis of showing low complementarity to potential target sequences, therefore resulting in no to low degree of crosshybridization to target mixture. Preferably, n=0, i.e. there is no spacer between the 2 miRNA probe sequence stretches.

FIG. 7:

Elongation element (Design Probe MPEA/RAKE)

A capture probe, e.g. for use in a RAKE or MPEA assay as shown in FIGS. 3 and 4 may include an elongation element. The elongation element comprises a nucleotide sequence with N=0-30 nucleotides chosen on the basis of showing low complementarity to potential target sequences, therefore resulting in no to low degree of crosshybridization to target mixture. Preferred is a homomeric sequence stretch $-N_n$- with n=1-30, N=A or C, or T, or G. Especially preferred is a homomeric sequence stretch -Nn- with n=1-12, N=A or C, or T, or G.

FIG. 8:

Pearson Correlation Coefficient depending on the number of elongated nucleotides in capture probes in an MPEA assay.

FIG. 9:

Diagram describing the general approach for determining miRNA signatures for use as biomarkers in disease diagnosis.

FIG. 10A:

Overview of all miRNAs that are found to be differentially regulated in blood samples of MS patients, grouped according to their diagnostic information represented by the respective area under the curve (AUC) value in receiver-operator characteristic curves. The first 193 entries represent miRNAs with t-test p-values <0.05.

FIG. 10B:

Overview of all miRNAs that are found to be differentially regulated in blood samples of MS patients, grouped according to their diagnostic information represented by the t-test significance. The first 165 entries represent miRNAs with t-test p-values<0.05. The grouping is based on additional information derived from further patients (compared to FIG. 10A).

FIG. 10C:

A further list of 308 entries representing miRNAs with t-test p-values<0.05. The grouping is based on additional information derived from further patients (compared to FIGS. 10A and 10B).

FIG. 11:

Histogram plots of the logarithm of fold quotients, the raw t-test p-values and the adjusted p-values. The histogram plots show in the upper part a histogram of logarithmized fold changes, detailing a manifold up-regulated miRNAs in Multiple Sclerosis compared to healthy subjects. The middle and lower part of the Figure describe raw significance values and adjusted significance values providing evidence for a wide variety of deregulated miRNAs that are well suited for MS detection.

Figure 12A:
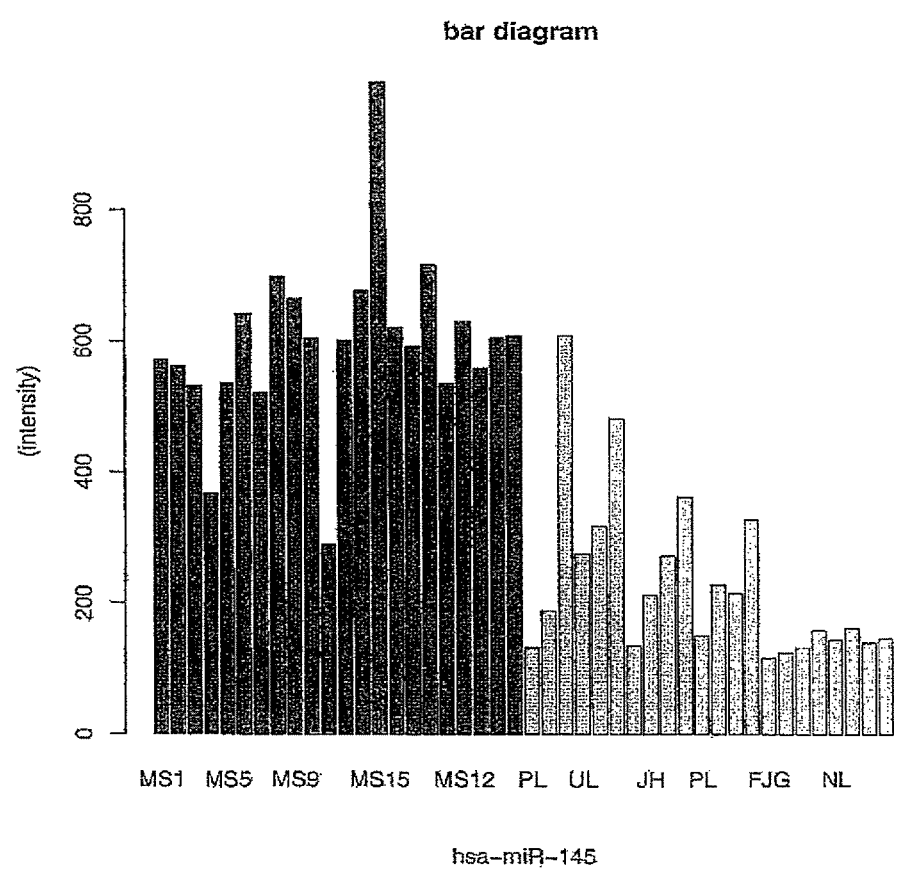
Figure 12B:
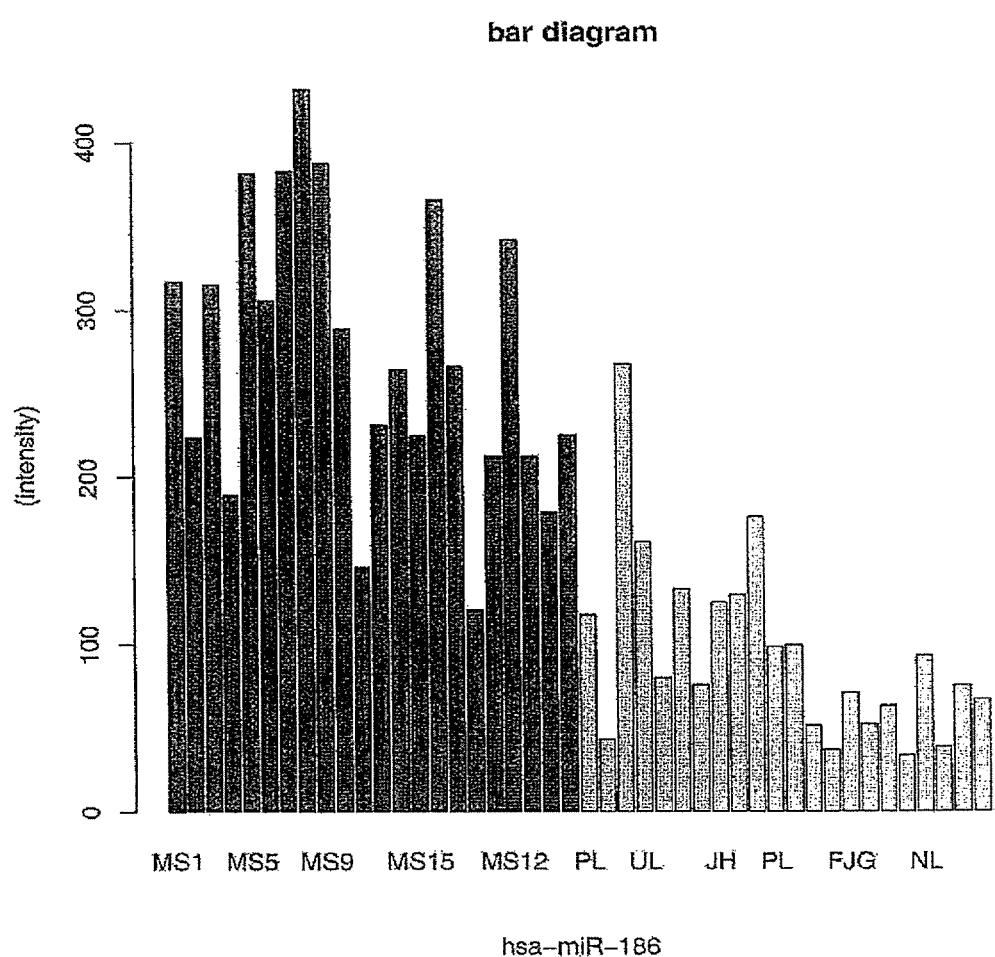

FIGS. 12A and 12B:

This Figure presents for two miRNAs, namely miR-145 and miR-186, the intensity values for all MS (left part) and control (right part) samples.

Both miRNAs show a significant up-regulation in MS.

FIG. 13:

The Box-plots denote the accuracy, specificity and sensitivity of the diagnostic test of the invention. In comparison, random classification results are shown, providing evidence for a decreased classification accuracy of about 50% (corresponding to random guessing). Furthermore, the graphic shows that the true classification scenario is more stable while the random classifications entail high variances.

FIG. 14:

This graph illustrates a disease network containing nodes for each disease as blue-colored rhombs (lung cancer, multiple sclerosis, pancreatic cancer, melanoma and Wilm tumor). Additionally, it contains differentially colored and sized nodes, representing biomarker sets. The size of these nodes represents the number of biomarkers inside the set (additionally the number of biomarkers is given inside the corresponding circles). The color represents the information on the number of diseases that are significant for the biomarkers in the set. The nodes are connected to the respective diseases, e.g., each green colored node contains biomarkers, significant for two diseases and thus each green node is connected to two disease nodes. (blue=significant to one disease, rose=significant for 3 diseases, purple=significant to 5 diseases).

Figure 15A:
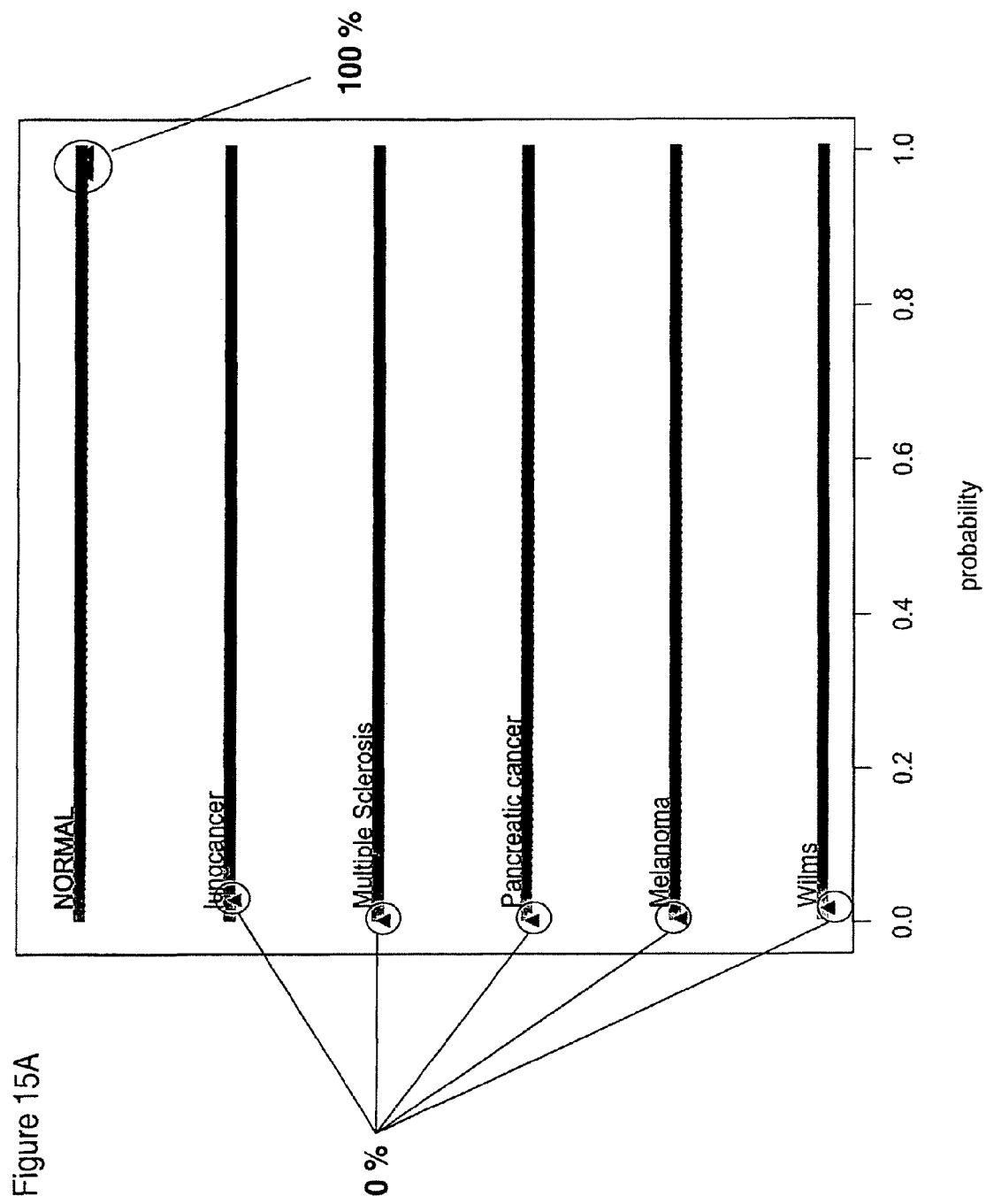
Figure 15B:
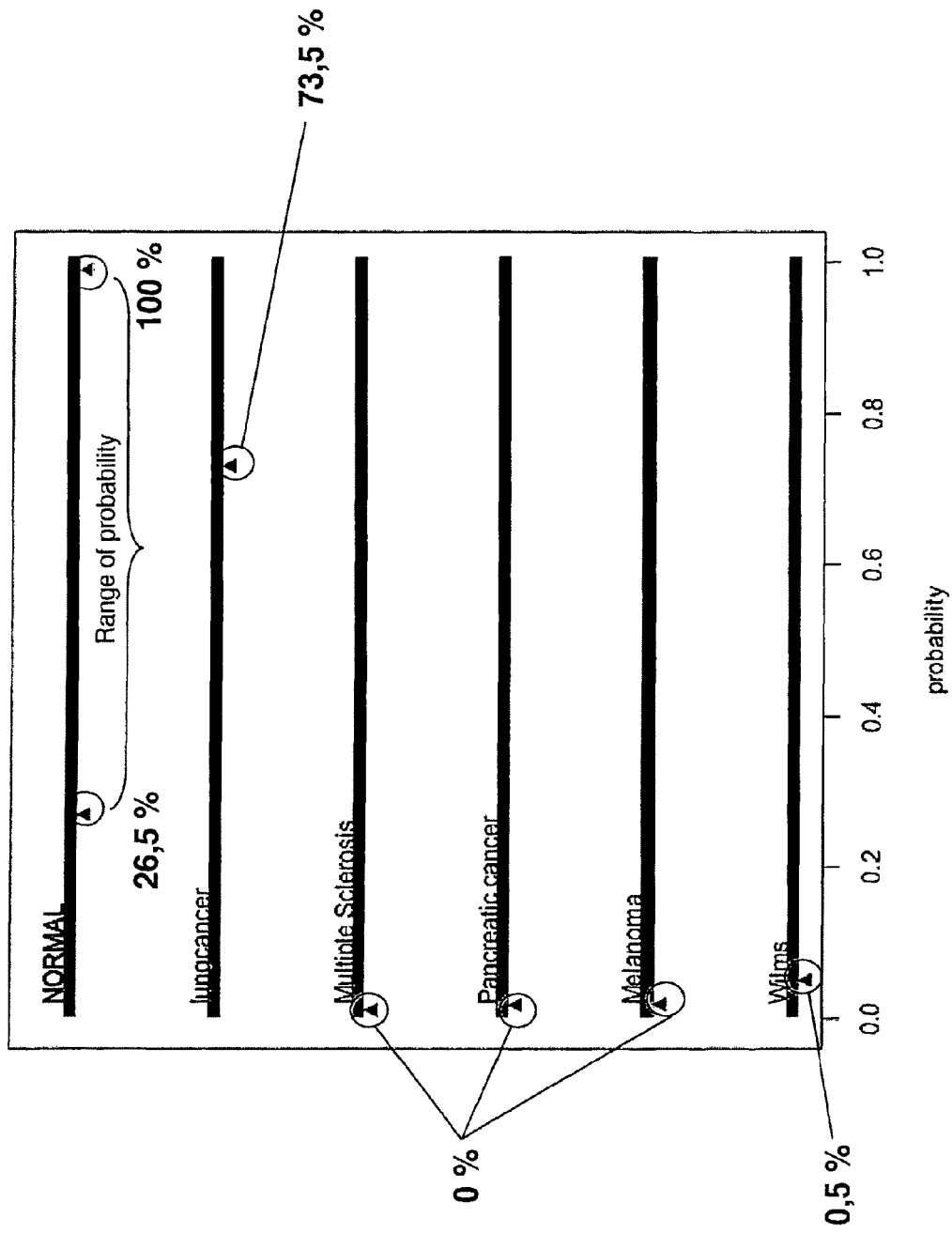
Figure 15C:
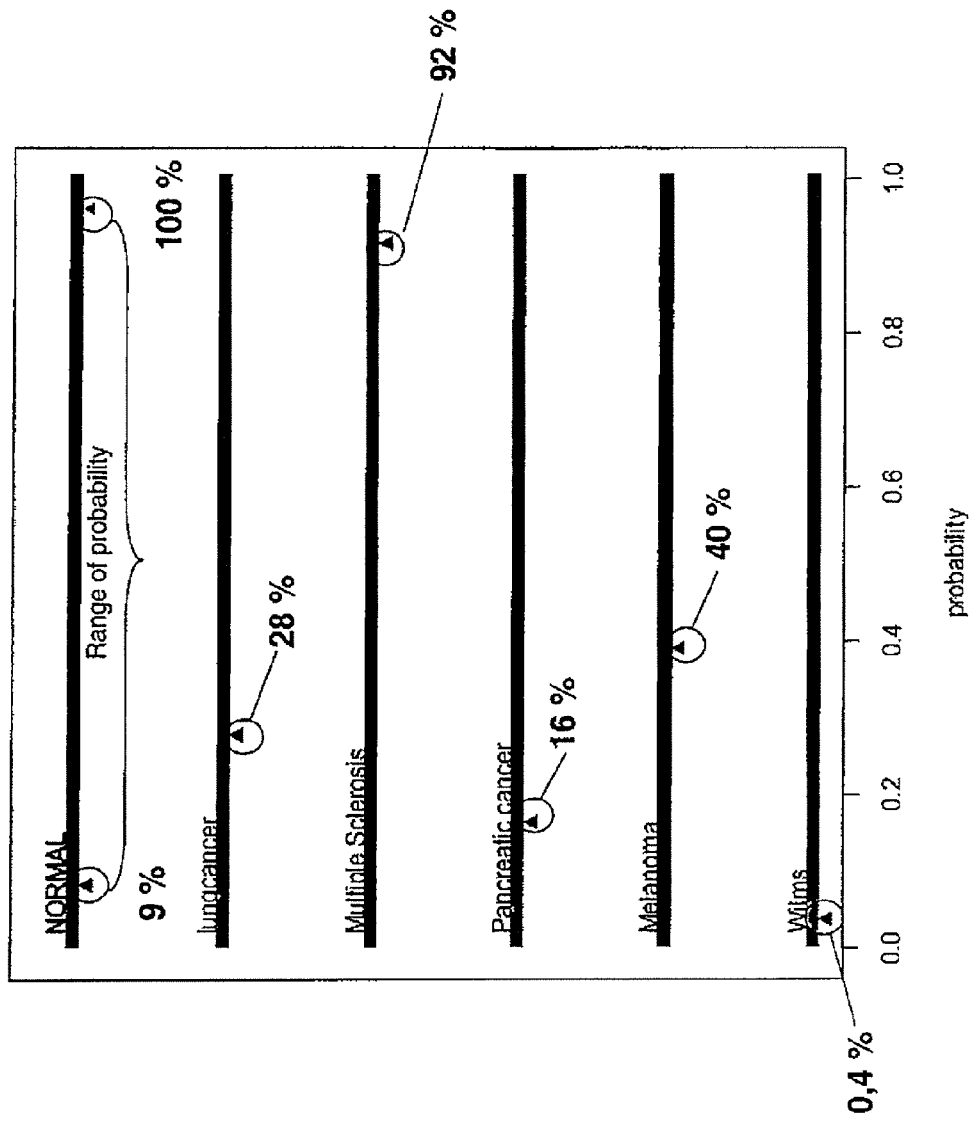

FIGS. 15a)-c):

The bar graphs in FIGS. 15a), b) and c) depict the disease probability for a "normal" individual a), for an individual suffering from lung cancer b) and for an individual suffering from multiple sclerosis c).

EXAMPLES

Example 1

Multiple Sclerosis 1.1 Materials and Methods 1.1.1 Samples

Blood samples were obtained with patients' informed consent.

1.1.2 miRNA Microarray Screening

Blood of MS patients and volunteers without known disease was extracted in PAXgene Blood RNA tubes (BD, Franklin Lakes, N.J. USA). For each blood donor, 5 ml of peripheral blood were obtained. Total RNA was extracted from blood cells using the miRNeasy Mini Kit (Qiagen GmbH, Hilden, Germany) and the RNA has been stored at −70° C. Samples were analyzed with the Geniom Realtime Analyzer (GRTA, febit GmbH, Heidelberg, Germany) using the Geniom Biochip miRNA *homo sapiens*. Each array contains 7 replicates of 866 miRNAs and miRNA star sequences as annotated in the Sanger mirBase 12.0. Sample labelling with Biotine has been carried out by multifluidic-based enzymatic on-chip labelling of miRNAs (MPEA).

Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values have been calculated corresponding to each replicate copy of mirBase on the array. Following background correction, the seven replicate intensity values of each miRNA were summarized by their median value. To normalize the data across different arrays, quantile normalization was applied and all further analyses were carried out using the normalized and background subtracted intensity values.

1.1.3 Statistical Analysis

After having verified the normal distribution of the measured data, a parametric t-test (unpaired, two-tailed) was carried out for each miRNA separately, to detect miRNAs that show a different behavior in different groups of blood donors. The resulting p-values were adjusted for multiple testing by Benjamini-Hochberg adjustment.

To find relations of the detected miRNAs to other diseases the Human miRNA Disease Database was used. In more detail, a bipartite network was built where nodes correspond either to a miRNA or to a diseases. Only edges between miRNA and diseases nodes are allowed, where an edge between miRNA A and disease B means that the miRNA A is differentially regulated in disease B. Since for MS no deregulated miRNAs are known the node "MultipleSclerosis" was added to this network and linked to all miRNAs that were significant in the analysis.

In addition to the single biomarker analysis and network analysis, classification of samples using miRNA patterns was carried out using Support Vector Machines (SVM) as implemented in the R e1071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique we applied a filter approach based on t-test. In detail, the s miRNAs with lowest p-values were computed on the training set in each fold of the cross validation, where s was sampled from 1 to 866. The respective subset was used to train the SVM and to carry out the prediction of the test samples. As result, the mean accuracy, specificity, and sensitivity were calculated together with the 95% Confidence Intervals (95% CI) for each subset size. To check for overtraining permutation tests were applied. Here the class labels were sampled randomly and classifications were carried out using the permuted class labels. All statistical analyzes were performed using R.

1.2 Results 1.2.1 miRNA Experiments

The expression of 866 miRNAs and miRNA star sequences was analyzed in blood cells of 22 patients with MS. As a control blood cells of 22 volunteers without known disease were used.

Following RNA isolation and the novel on-chip labeling technique, the miRNA expression profiles were measured by the Geniom Bioship miRNA *homo sapiens* in the GRTA (febit GmbH, Heidelberg). Following intensity value computation and quantile normalization of the miRNA profiles, a mean correlation value of 0.97 for technical replicates was determined by using purchased total RNA from Ambion (four heart and four liver replicates). For the biological replicates the different tumor samples were compared between each other and the different normal samples were compared between each other. The biological replicates showed a mean correlation of 0.87 and a variance of 0.009.

1.2.2 Ruling Out the Influence of Age and Gender

To cross-check that age and gender do not have an influence on our analysis, t-tests for the normal samples were computed. In the case of males versus females there were no statistically significant deregulated miRNA. The most significant miRNA, hsa-miR-423, showed an adjusted significance level of 0.78.

To test for the influence of donor age the profiles obtained from samples obtained from the oldest versus youngest patients were compared by splitting the group in half based on age. Here, the most significant miRNA, miR-890, obtained an adjusted p-value of 0.87. As for gender, there were no deregulated miRNAs, thus providing evidence that age and gender do not have a substantial influence on the miRNA profiles.

Additionally, we checked the influence of a therapy. Patients were either treated with glatiramer acetate (n=9), or interferon-β (n=10), or did not get a therapy (n=1). We compared the group of patients treated with glatiramer acetate to the group treated with interferon-β. As for the gender and the age we did not find any significant miRNA.

1.2.3 Single Deregulated miRNAs

Hypothesis testing was applied to identify miRNAs deregulated in the blood cells of MS patients as compared to the blood cells of the controls. Following verification of an approximately normal distribution, two-tailed unpaired t-tests were performed for each miRNA. The respective p-values were adjusted for multiple testing by the Benjamini-Hochberg approach. In total 193 miRNAs significantly deregulated in blood cells of MS patients as compared to the controls were detected. Histogram plots of the logarithm of fold quotients, the raw t-test p-values and the adjusted p-values are presented in FIG. 11. A complete list of deregulated miRNAs is given in the Table in FIG. 10A. The miRNAs that were most significantly deregulated included hsa-miR-145 ($5.25*10^{-9}$), hsa-miR-186 ($3.42*10^{-7}$), hsa-miR-664 ($1.20'10^{-5}$), hsa-miR-20b ($1.98*10^{-5}$), hsa-miR-584 ($1.98*10^{-5}$), hsa-miR-223 ($2.14'10^{-5}$), hsa-miR-422a ($2.87*10^{-5}$), hsa-miR-142-3p ($3.01*10^{-5}$) and hsa-let-7c ($7.68*10^{-5}$). For the two best miRNAs, hsa-miR-186 and hsa-miR-145, bar-plots showing the intensity values for all MS and control samples are presented in FIGS. 12a and 12b.

Notably, all the above-mentioned miRNAs showed a significant up-regulation in MS besides miR-20b. Table 2 shows the 24 most deregulated miRNAs. Of these 91.7% were up-regulated in MS while 8.3% were down-regulated, providing evidence for an overall up-regulation of miRNAs in MS.

Additionally for the best miRNAs receiver operator characteristic curves (ROC) and the area under the curve value (AUC) were computed. The higher the AUC, the better the miRNA biomarker is, where a maximal value of 1 for miRNA A would mean that the highest control reactivity would be lower than the lowest MS intensity of miRNA A. For the best miRNA hsa-miR-145 an AUC value of 0.96 was obtained and four of the 44 samples were wrong classified (2 Ms sera as controls, so-called False Negatives, and 2 controls classified as MS samples, so-called False Positives).

TABLE 2

24 most significant miRNAs for MS

| miRNA | median g1 | median g2 | qmedian | Log (qmedian) | raw Pval | adj. Pval | AUC |
|---|---|---|---|---|---|---|---|
| hsa-miR-145 | 602.719 | 174.344 | 3.457 | 1.240 | 6.08E−12 | 5.25E−09 | 0.962 |
| hsa-miR-186 | 265.295 | 77.719 | 3.414 | 1.228 | 7.91E−10 | 3.42E−07 | 0.961 |
| hsa-miR-664 | 707.168 | 285.703 | 2.475 | 0.906 | 4.17E−08 | 1.20E−05 | 0.916 |
| hsa-miR-584 | 332.922 | 106.969 | 3.112 | 1.135 | 1.15E−07 | 1.98E−05 | 0.897 |
| hsa-miR-20b | 2689.207 | 5810.586 | 0.463 | −0.770 | 9.83E−08 | 1.98E−05 | 0.056 |
| hsa-miR-223 | 5118.574 | 2579.250 | 1.985 | 0.685 | 1.49E−07 | 2.14E−05 | 0.964 |
| hsa-miR-422a | 373.953 | 189.219 | 1.976 | 0.681 | 2.32E−07 | 2.87E−05 | 0.870 |
| hsa-miR-142-3p | 215.375 | 40.516 | 5.316 | 1.671 | 2.79E−07 | 3.01E−05 | 0.934 |
| hsa-let-7c | 1948.098 | 950.223 | 2.050 | 0.718 | 8.00E−07 | 7.68E−05 | 0.889 |
| hsa-miR-151-3p | 1021.363 | 571.344 | 1.788 | 0.581 | 1.81E−06 | 0.000156587 | 0.883 |
| hsa-miR-491-5p | 241.000 | 153.563 | 1.569 | 0.451 | 2.05E−06 | 0.000160884 | 0.876 |
| hsa-miR-942 | 112.969 | 38.094 | 2.966 | 1.087 | 5.09E−06 | 0.000366452 | 0.882 |
| hsa-miR-361-3p | 325.766 | 181.375 | 1.796 | 0.586 | 5.77E−06 | 0.000383235 | 0.852 |
| hsa-miR-22* | 178.938 | 103.844 | 1.723 | 0.544 | 6.24E−06 | 0.000385004 | 0.868 |
| hsa-miR-140-5p | 105.063 | 48.250 | 2.177 | 0.778 | 7.99E−06 | 0.000399262 | 0.874 |
| hsa-miR-216a | 202.219 | 315.828 | 0.640 | −0.446 | 8.24E−06 | 0.000399262 | 0.060 |
| hsa-miR-1275 | 210.203 | 116.969 | 1.797 | 0.586 | 7.04E−06 | 0.000399262 | 0.907 |
| hsa-miR-367 | 92.500 | 160.375 | 0.577 | −0.550 | 8.32E−06 | 0.000399262 | 0.138 |
| hsa-miR-146a | 470.359 | 271.342 | 1.733 | 0.550 | 9.61E−06 | 0.000437137 | 0.862 |
| hsa-miR-598 | 140.531 | 91.000 | 1.544 | 0.435 | 1.29E−05 | 0.000556416 | 0.841 |
| hsa-miR-613 | 60.781 | 19.000 | 3.199 | 1.163 | 1.67E−05 | 0.000687276 | 0.862 |
| hsa-miR-18a* | 490.891 | 233.672 | 2.101 | 0.742 | 2.02E−05 | 0.000794863 | 0.876 |
| hsa-miR-302b | 54.469 | 21.406 | 2.545 | 0.934 | 2.23E−05 | 0.000838901 | 0.855 |
| hsa-miR-501-5p | 139.938 | 79.563 | 1.759 | 0.565 | 2.60E−05 | 0.000936279 | 0.866 |

1.2.4 Relation to Other Diseases

Since there is no evidence for de-regulated miRNAs in MS patients in the literature, it was checked whether the detected 193 miRNAs are already related to other human diseases. To this end, the Human microRNA Disease Database (HMDD) was grasped. This comprehensive database contains for over 100 human diseases information on deregulated miRNAs. Altogether, over 2000 relations are included in the HMDD. To analyze the respective data, a bipartite graph was created were nodes are either miRNAs or human diseases, and edges between a miRNA and a disease mean that the respective miRNA is deregulated in the respective disease.

Thereby, a network containing 452 nodes was created, 137 belonging to diseases and 315 to miRNAs. The network also contained 1617 unique edges (some relations between miRNAs and diseases have been published in multiple papers). As mentioned previously, MS is not included as disease in this network. Thus, the network was modified as followings: a disease node "MultipleSclerosis" was added and edges between this node and all significant miRNAs were created. Additionally, all disease nodes that are not linked to any MS miRNA and all miRNAs belonging only to removed disease nodes were removed. The novel network thus contains only those miRNAs that are significant in MS and other diseases and those that are significant in MS, only. This shrunken network contained 77 disease nodes together with the 193 significant miRNAs. Remarkably, only 43 of the 193 (22%) miRNAs were related to a disease other than MS while the remaining 78% miRNAs were only connected to MS. Of these 146 miRNAs, 36 were so-called star sequences.

Altogether, these results provide strong evidence that the detected complex miRNA profile is not disease specific but rather specific for MS.

1.2.5 Evaluating Complex Fingerprints

As discussed in Section 1.2.3, the best miRNA suffices to classify 20 of 22 MS samples and 20 of 22 control samples correctly. This obviously corresponds to a high specificity, sensitivity and accuracy of 90.8%. However, these results are not validated by a re-sampling technique as bootstrapping or cross-validation and are based only on a single marker.

In order to improve the already high classification accuracy and the statistical reliability the predictive power of multiple miRNAs was combined by using statistical learning techniques. In detail, Support Vector Machines with different kernels (linear, polynomial, sigmoid, radial basis function) were applied to the data and a hypothesis test based subset selection was carried out as described in Material and Methods. To gain statistical significance 100 repetitions of 10-fold cross validation were carried out. Likewise, 100 repetitions for the permutation tests were computed where samples with randomly assigned class labels were investigated.

The best results were obtained with radial basis function Support Vector Machines and a subset of 24 miRNAs (see Table 2). These miRNAs allowed for the discrimination between blood samples of MS patients and blood samples of controls with an accuracy of 95.5% a specificity of 95.5%, and a sensitivity of 95.5%.

Figure 13:
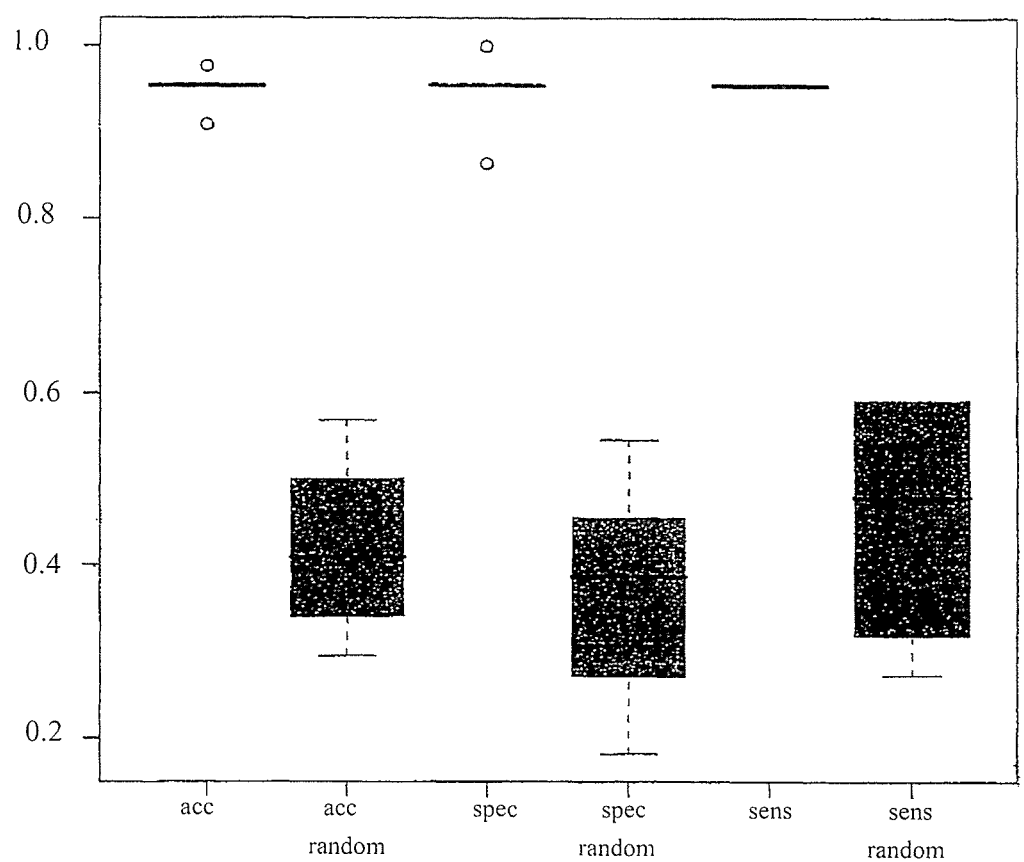
Figure 14:
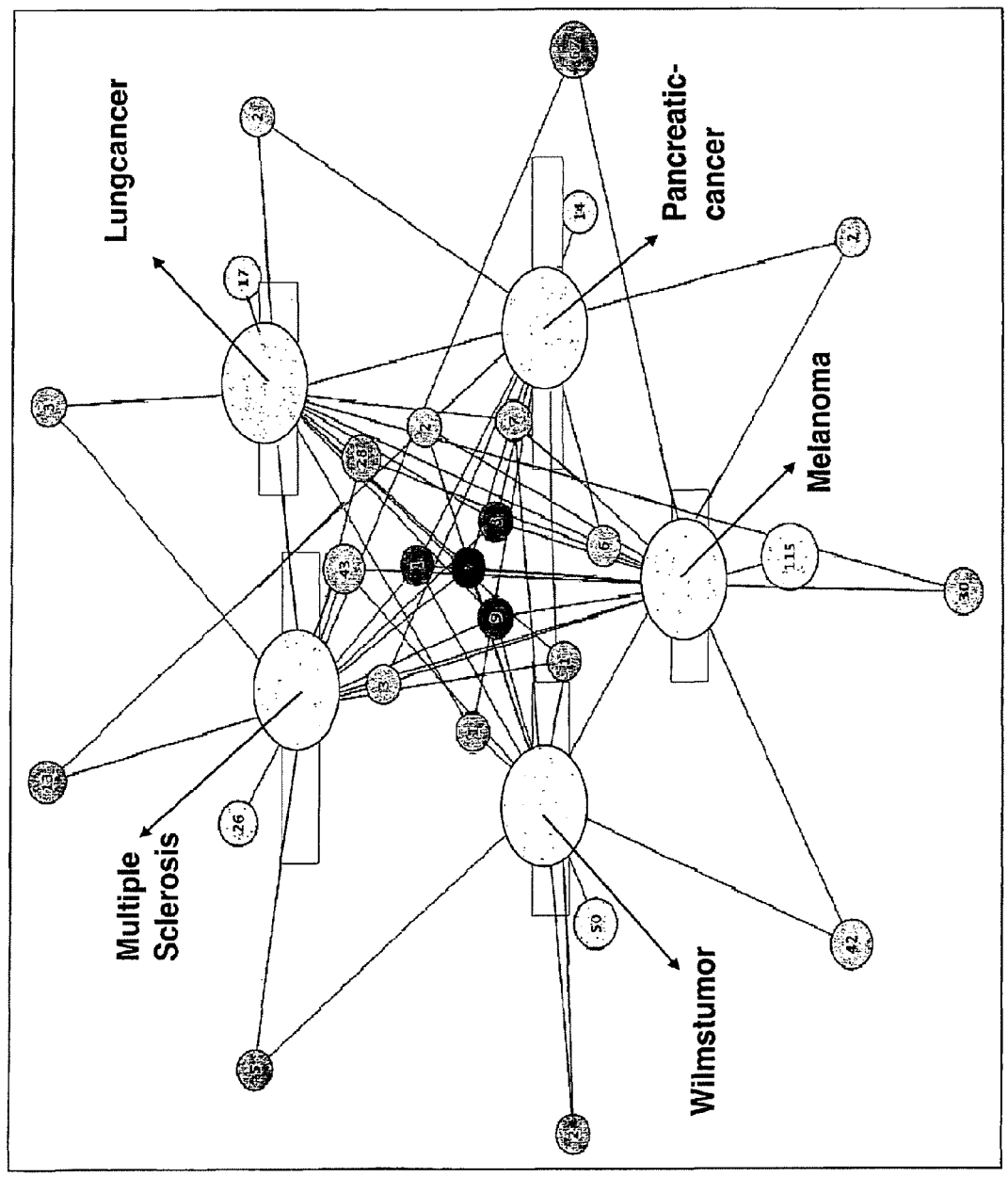

The permutation tests showed significantly decreased accuracy, specificity, and sensitivity rates, as detailed in FIG. 13. These results show that the obtained results are not due to an overfit of the statistical model on the miRNA fingerprints.

Additionally, it was checked whether the relevant miRNAs were linked to one of over 100 other diseases as annotated in the HMDD. Remarkable over 80% of the respective miRNAs have not been linked to other diseases, so far.

Example 2

Molecular Clinical Thermometer

For the molecular clinical thermometer, an arbitrary machine learning (feature extraction/classification/regression/clustering) technique can be applied. The workflow does not depend on the applied method that can be seen as a black box.

First, a sophisticated large set of samples for the diseases to be investigated has to be measured using a larger amount of biomarkers. This set, consisting of a p×n matrix where n is the number of samples and p the number of biomarkers, is commonly denoted as training data set.

Now, a combination of feature extraction and supervised learning techniques (the process can be also carried out with slight modifications using unsupervised techniques) is applied to generate a statistical model, which describes the training data well. Here, it is essential to control the model complexity in order to avoid so-called overtraining of the statistical models. Although, in general, multi-class cases can be carried out, we focus on two class comparisons, i.e., normal versus cancer 1, normal versus cancer 2, cancer 1 versus cancer 2.

Given the trained models and a new biomarker profile, the statistical model can be used to compute the probability for each class and this new sample. Only one example are support vector machines, where the distance of a sample to the separating hyperplane can be used to estimate the class probability via a regression approach. The specificity and sensitivity can be trade-off by shifting the probability threshold (which usually should be 0.5 or 50%).

The probabilities in the previously described step can be used to generate so-called disease probability plots (DPP). These plots contain for each class and a single sample the probabilities to belong to a certain class. In detail, each class is described by a colored line of length 100 (representing a percentage range), where the lower rate is colored green (representing small probabilities) and the higher range red (higher probabilities). For each class, an arrow marks the probability for the patient and the respective disease. For class "normal" the minimal and maximal probability to be normal are shown.

The DPPs thus allow for visualizing the complex statistical evaluation in a simple and well interpretable way.

REFERENCES

Alvarez-Garcia, I. and E. A. Miska (2005). "MicroRNA functions in animal development and human disease." *Development* 132(21): 4653-62.

Benjamini, Y. and Y. Hochberg (1995). "Controlling the false discovery rate: A practical and powerful approach to multiple testing." *J R Statist Soc B* 57: 289-300.

Bolstad, B. M., R. A. Irizarry, et al. (2003). "A comparison of normalization methods for high density oligonucleotide array data based on variance and bias." *Bioinformatics* 19(2): 185-93.

Calin, G. A. and C. M. Croce (2006). "MicroRNA-cancer connection: the beginning of a new tale." *Cancer Res* 66(15): 7390-4.

Calin, G. A. and C. M. Croce (2006). "MicroRNA signatures in human cancers." *Nat Rev Cancer* 6(11): 857-66.

Chen, X., Y. Ba, et al. (2008). "Characterization of microRNAs in serum: a novel class of biomarkers for diagnosis of cancer and other diseases." *Cell Res* 18(10): 997-1006.

Crawford, M., E. Brawner, et al. (2008). "MicroRNA-126 inhibits invasion in non-small cell lung carcinoma cell lines." *Biochem Biophys Res Commun* 373(4): 607-12.

Esquela-Kerscher, A. and F. J. Slack (2006). "Oncomirs—microRNAs with a role in cancer." *Nat Rev Cancer* 6(4): 259-69.

Feitelson, M. A. and J. Lee (2007). "Hepatitis B virus integration, fragile sites, and hepatocarcinogenesis." *Cancer Lett* 252(2): 157-70.

Gilad, S., E. Meiri, et al. (2008). "Serum microRNAs are promising novel biomarkers." *PLoS ONE* 3(9): e3148.

Griffiths-Jones, S., R. J. Grocock, et al. (2006). "miRBase: microRNA sequences, targets and gene nomenclature." *Nucleic Acids Res* 34 (Database issue): D140-4.

Griffiths-Jones, S., S. Moxon, et al. (2005). "Rfam: annotating non-coding RNAs in complete genomes." *Nucleic Acids Res* 33 (Database issue): D121-4.

Griffiths-Jones, S., H. K. Saini, et al. (2008). "miRBase: tools for microRNA genomics." *Nucleic Acids Res* 36 (Database issue): D154-8.

Guo, L., Z. X. Huang, et al. (2008). "Differential Expression Profiles of microRNAs in NIH3T3 Cells in Response to UVB Irradiation." *Photochem Photobiol*.

Harris, T. A., M. Yamakuchi, et al. (2008). "MicroRNA-126 regulates endothelial expression of vascular cell adhesion molecule 1." *Proc Natl Acad Sci USA* 105(5): 1516-21.

Hayashita, Y., H. Osada, et al. (2005). "A polycistronic microRNA cluster, miR-17-92, is overexpressed in human lung cancers and enhances cell proliferation." *Cancer Res* 65(21): 9628-32.

He, L., J. M. Thomson, et al. (2005). "A microRNA polycistron as a potential human oncogene." *Nature* 435 (7043): 828-33.

Henschke, C. I. and D. F. Yankelevitz (2008). "CT screening for lung cancer: update 2007." *Oncologist* 13(1): 65-78.

Hochberg, Y. (1988). "A sharper bonferroni procedure for multiple tests of significance." *Biometrica* 75: 185-193.

Ichimi, T., H. Enokida, et al. (2009). "Identification of novel microRNA targets based on microRNA signatures in bladder cancer." *Int J Cancer*.

Jemal, A., R. Siegel, et al. (2008). "Cancer statistics, 2008." *CA Cancer J Clin* 58(2): 71-96.

Johnson, S. M., H. Grosshans, et al. (2005). "RAS is regulated by the let-7 microRNA family." *Cell* 120(5): 635-47.

Keller, A., N. Ludwig, et al. (2006). "A minimally invasive multiple marker approach allows highly efficient detection of meningioma tumors." *BMC Bioinformatics* 7: 539.

Lee, R. C., R. L. Feinbaum, et al. (1993). "The C. elegans heterochronic gene lin-4 encodes small RNAs with antisense complementarity to lin-14." *Cell* 75(5): 843-54.

Lu, J., G. Getz, et al. (2005). "MicroRNA expression profiles classify human cancers." *Nature* 435(7043): 834-8.

Mann, H. and F. Wilcoxon (1947). "On a test whether one of two random variables is stochastically larger than the other." *Ann Mat Stat* 18: 50-60.

Sassen, S., E. A. Miska, et al. (2008). "MicroRNA: implications for cancer." *Virchows Arch* 452(1): 1-10.

Scott, W. J., J. Howington, et al. (2007). "Treatment of non-small cell lung cancer stage I and stage II: ACCP evidence-based clinical practice guidelines (2nd edition)." *Chest* 132 (3 Suppl): 234S-242S.

Shannon, C. (1984). "A mathematical theory of communication." *The Bell System Technical Journal* 27: 623-656.

Stahlhut Espinosa, C. E. and F. J. Slack (2006). "The role of microRNAs in cancer." Yale *J Biol Med* 79(3-4): 131-40.

Takamizawa, J., H. Konishi, et al. (2004). "Reduced expression of the let-7 microRNAs in human lung cancers in association with shortened postoperative survival." *Cancer Res* 64(11): 3753-6.

Team, R. D. C. (2008). *R: A Language and Environment for Statistical Computing*. Vienna, Austria, R Foundation for Statistical Computing.

Tong, A. W. (2006). "Small RNAs and non-small cell lung cancer." *Curr Mol Med* 6(3): 339-49.

Vapnik, V. (2000). The *Nature of Statistical Learning Theory.*, Springer.

Volinia, S., G. A. Calin, et al. (2006). "A microRNA expression signature of human solid tumors defines cancer gene targets." *Proc Natl Acad Sci USA* 103(7): 2257-61.

Vorwerk, S., K. Ganter, et al. (2008). "Microfluidic-based enzymatic on-chip labeling of miRNAs." *N Biotechnol* 25(2-3): 142-9.

Wilcoxon, F. (1945). "Individual comparisons by ranking methods." *Biometric Bull* 1:80-83.

Williams, A. E. (2008). "Functional aspects of animal microRNAs." *Cell Mol Life Sci* 65(4): 545-62.

Yanaihara, N., N. Caplen, et al. (2006). "Unique microRNA molecular profiles in lung cancer diagnosis and prognosis." *Cancer Cell* 9(3): 189-98.

Zhang, B., X. Pan, et al. (2007). "microRNAs as oncogenes and tumor suppressors." *Dev Biol* 302(1): 1-12.

Zhang, B., Q. Wang, et al. (2007). "MicroRNAs and their regulatory roles in animals and plants." *J Cell Physiol* 210(2): 279-89.

The invention claimed is:

1. A method of diagnosing multiple sclerosis, comprising
   (a) obtaining blood cells from a blood sample from a patient suspected of having multiple sclerosis, wherein said blood cells consists of a mixture of erythrocytes, leukocytes and thrombocytes,
   (b) extracting total RNA from said mixture of blood cells,
   (c) determining an expression profile of a predetermined set of miRNAs in said total RNA, said predetermined set of miRNAs comprising one or more miRNAs is selected from the group consisting of hsa-miR-20b, hsa-miR-145, hsa-miR-186, hsa-miR-664, hsa-miR-584, hsa-miR-223, hsa-miR-422a, hsa-miR-142-3p, and hsa-let-7c, wherein determining said expression profile comprises nucleic acid amplification performed using real-time PCR (RT-PCR), and
   (d) comparing said expression profile to a reference expression profile, wherein said reference expression profile is obtained using a mixture of erythrocytes, leukocytes and thrombocytes from healthy subjects, wherein the comparison of said determined expression profile to said reference expression profile allows for the diagnosis of multiple sclerosis.

2. The method of claim 1, wherein said predetermined set of miRNAs comprises hsa-miR-20b (SEQ ID NO: 11).

3. The method of claim 1, wherein the diagnosis comprises determining survival rate, responsiveness to drugs, and/or monitoring the course of the disease or the therapy, staging of the disease, measuring the response of a patient to therapeutic intervention, segmentation of patients suffering from the disease, identifying of a patient who has a risk to develop the disease, predicting/estimating the occurrence, predicting/estimating the severity of the occurrence of the disease, or predicting the response of a patient with the disease to therapeutic intervention.

4. The method of claim 1, wherein the determination of an expression profile in step (c) comprises qualitative, quantitative or semiquantitative determination of said predetermined set of miRNAs.

5. The method of claim 1, wherein said predetermined set of miRNAs further comprises hsa-miR-186.

6. The method of claim 1, wherein said predetermined set of miRNA comprises at least one miRNA molecule or signature of miRNA molecules as shown in Table 1.

7. The method of claim 5, wherein said predetermined set of miRNAs comprises a signature selected from the group consisting of
   A29: hsa-miR-20a*, hsa-miR-646, hsa-miR-885-3p, hsa-miR-509-3-5p, hsa-miR-1912 and hsa-miR-20b
   A30: hsa-miR-509-3-5p, hsa-miR-1912, hsa-miR-20b, hsa-miR-574-5p, hsa-miR-221 and hsa-miR-365
   A37: hsa-miR-20a*, hsa-miR-646, hsa-miR-885-3p, hsa-miR-509-3-5p, hsa-miR-1912, hsa-miR-20b, hsa-miR-574-5p, hsa-miR-221, hsa-miR-365 and hsa-miR-22*
   A38: hsa-miR-20b, hsa-miR-574-5p, hsa-miR-221, hsa-miR-365, hsa-miR-22*, hsa-miR-1275, hsa-miR-625, hsa-miR-584, hsa-miR-328 and hsa-miR-629.

8. The method of claim 1, wherein said predetermined set of miRNAs comprises at least 7, 10, 15 or 20, and/or all of the indicated miRNAs, particularly at least 1, 7, 10, 15, 20, 25, 30, 35, 40, 50, 75, 100 of the miRNAs selected from the group consisting of:
   (I) the first 193 miRNAs from FIG. 10A,
   (ii) the first 165 miRNAs from FIG. 10B, and
   (iii) the 308 miRNAs from FIG. 10C
   optionally except hsa-miR-148a, hsa-miR-18b, hsa-miR-96, hsa-miR-599, hsa-miR-493, hsa-miR-184, hsa-miR193a.

9. The method of claim 8, wherein said predetermined set of miRNAs comprises the miRNAs hsa-miR-145, hsa-miR-186, hsa-miR-664, hsa-miR-584, hsa-miR-20b, hsa-miR-223 and hsa-miR-422a.

10. The method of claim 8, wherein said predetermined set of miRNAs comprises the miRNAs hsa-miR-145, hsa-miR-186, hsa-miR-664, hsa-miR-584, hsa-miR-20b, hsa-miR-223, hsa-miR-422a, hsa-miR-142-3p, hsa-let-7c, and hsa-miR-151-3p.

11. The method of claim 8, wherein said predetermined set of miRNAs comprises the miRNAs hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22* and hsa-miR-140-5p.

12. The method of claim 8, wherein said predetermined set of miRNAs comprises the miRNAs hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR942, hsa-miR-361-3p, hsa-miR-22*, hsa-miR-140-5p, hsa-miR-216a, hsa-miR-1275, hsa-miR-367, hsa-miR-146a, and hsa-miR-598.

13. The method of claim 3, wherein said therapy is chemotherapy.

14. The method of claim 1, wherein determining the expression profile using real-time PCR (RT-PCR), comprises:
   a) reverse-transcribing the total RNA isolated from the mixture of blood cells into cDNA, and
   (b) quantifying the cDNA, thereby determining the expression profile of said
   miRNAs.

15. The method of claim 8, wherein said predetermined set of miRNAs does not include hsa-miR-148a, hsa-miR-18b, hsa-miR-96, hsa-miR-599, hsa-miR-493, hsa-miR-184, or hsa-miR-193a.

16. The method of claim 2, wherein the severity of the occurrence of the disease is predicted/estimated.

17. A method for the assessment of a clinical condition related to multiple sclerosis of a patient comprising the steps:
   (a) obtaining blood cells from a blood sample from a patient suspected of having multiple sclerosis, wherein said blood cells consists of a mixture of erythrocytes, leukocytes and thrombocytes,
   (b) extracting total RNA from said mixture of blood cells, (c) determining an expression profile of a predetermined set of miRNAs in said total RNA, said predetermined set of miRNAs comprising one or more miRNAs is selected from the group consisting of hsa-miR-20b, hsa-miR-145, hsa-miR-186, hsa-miR-664, hsa-miR-584, hsa-miR-223, hsa-miR-422a, hsa-miR-142-3p, and hsa-let-7c; wherein determining said expression profile comprises nucleic acid amplification performed using real-time PCR (RT-PCR), and (d) providing a plurality of miRNA reference expression profiles characteristic for a plurality of diseases, wherein said reference expression profiles are obtained using a mixture of erythrocytes, leukocytes and thrombocytes (e) comparing said miRNA expression profile (of step (c)) with said plurality of miRNA reference expression, and (f) assessing the clinical condition of the patient based on the comparison of step (e).

18. The method of claim 17, wherein said predetermined set of miRNAs comprises hsa-miR-20b (SEQ ID NO: 11).

19. The method of claim 17, wherein said miRNA reference expression profiles in step (d) are obtained from a database such as an internet database, a centralized or a decentralized database.

20. The method of claim 17, wherein the plurality of reference expression profiles comprise one or more miRNAs that are highly deregulated in said diseases as compared to a healthy condition, and/or said miRNAs are strongly increased or decreased in said diseases as compared to a healthy condition.

* * * * *

UNITED STATES PATENT AND TRADEMARK OFFICE
CERTIFICATE OF CORRECTION

PATENT NO. : 10,000,810 B2
APPLICATION NO. : 14/873385
DATED : June 19, 2018
INVENTOR(S) : Andreas Keller et al.

Page 1 of 1

It is certified that error appears in the above-identified patent and that said Letters Patent is hereby corrected as shown below:

On the Title Page

Item (71) please correct the Applicant from:
"COMPREHENSIVE BIOMARKER CENTER GMBH, Heidelberg, GERMANY;"
To:
"HUMMINGBIRD DIAGNOSTICS GMBH, Heidelberg, GERMANY;"

Signed and Sealed this
Twenty-eighth Day of May, 2019

Andrei Iancu
*Director of the United States Patent and Trademark Office*

SEQUENCE LISTING

```
<160> NUMBER OF SEQ ID NOS: 868

<210> SEQ ID NO 1
<211> LENGTH: 22
<212> TYPE: RNA
<213> ORGANISM: Homo sapiens

<400> SEQUENCE: 1
ucguaccgug aguaauaaug cg                                              22

<210> SEQ ID NO 2
<211> LENGTH: 23
<212> TYPE: RNA
<213> ORGANISM: Homo sapiens

<400> SEQUENCE: 2
ugaggggcag agagcgagac uuu                                             23

<210> SEQ ID NO 3
<211> LENGTH: 22
<212> TYPE: RNA
<213> ORGANISM: Homo sapiens

<400> SEQUENCE: 3
ugagguagua guuugugcug uu                                              22

<210> SEQ ID NO 4
<211> LENGTH: 22
<212> TYPE: RNA
<213> ORGANISM: Homo sapiens

<400> SEQUENCE: 4
agagguagua gguugcauag uu                                              22

<210> SEQ ID NO 5
<211> LENGTH: 22
<212> TYPE: RNA
<213> ORGANISM: Homo sapiens

<400> SEQUENCE: 5
aagcugccag uugaagaacu gu                                              22

<210> SEQ ID NO 6
<211> LENGTH: 22
<212> TYPE: RNA
<213> ORGANISM: Homo sapiens

<400> SEQUENCE: 6
uagcagcaca uaaugguuug ug                                              22
```

```
<210> SEQ ID NO 7
<211> LENGTH: 22
<212> TYPE: RNA
<213> ORGANISM: Homo sapiens

<400> SEQUENCE: 7
ugagguagua aguuguauug uu                                              22

<210> SEQ ID NO 8
<211> LENGTH: 23
<212> TYPE: RNA
<213> ORGANISM: Homo sapiens

<400> SEQUENCE: 8
ugugcaaauc uaugcaaaac uga                                             23

<210> SEQ ID NO 9
<211> LENGTH: 23
<212> TYPE: RNA
<213> ORGANISM: Homo sapiens

<400> SEQUENCE: 9
ugagugugug ugugugagug ugu                                             23

<210> SEQ ID NO 10
<211> LENGTH: 20
<212> TYPE: RNA
<213> ORGANISM: Homo sapiens

<400> SEQUENCE: 10
acugccccag gugcugcugg                                                 20

<210> SEQ ID NO 11
<211> LENGTH: 23
<212> TYPE: RNA
<213> ORGANISM: Homo sapiens

<400> SEQUENCE: 11
caaagugcuc auagugcagg uag                                             23

<210> SEQ ID NO 12
<211> LENGTH: 22
<212> TYPE: RNA
<213> ORGANISM: Homo sapiens

<400> SEQUENCE: 12
cauugcacuu gucucggucu ga                                              22

<210> SEQ ID NO 13
<211> LENGTH: 21
<212> TYPE: RNA
<213> ORGANISM: Homo sapiens

<400> SEQUENCE: 13
uagcagcaca gaaauauugg c                                               21

<210> SEQ ID NO 14
<211> LENGTH: 22
<212> TYPE: RNA
<213> ORGANISM: Homo sapiens

<400> SEQUENCE: 14
ugagguagga gguuguauag uu                                              22
```

```
<210> SEQ ID NO 15
<211> LENGTH: 22
<212> TYPE: RNA
<213> ORGANISM: Homo sapiens

<400> SEQUENCE: 15
ugagguagua gguuguaugg uu                                              22

<210> SEQ ID NO 16
<211> LENGTH: 22
<212> TYPE: RNA
<213> ORGANISM: Homo sapiens

<400> SEQUENCE: 16
ugagguagua gauuguauag uu                                              22

<210> SEQ ID NO 17
<211> LENGTH: 22
<212> TYPE: RNA
<213> ORGANISM: Homo sapiens

<400> SEQUENCE: 17
ugagguagua gguuguauag uu                                              22

<210> SEQ ID NO 18
<211> LENGTH: 22
<212> TYPE: RNA
<213> ORGANISM: Homo sapiens

<400> SEQUENCE: 18
ugagguagua guuuguacag uu                                              22

<210> SEQ ID NO 19
<211> LENGTH: 21
<212> TYPE: RNA
<213> ORGANISM: Homo sapiens

<400> SEQUENCE: 19
uaccacaggg uagaaccacg g                                               21

<210> SEQ ID NO 20
<211> LENGTH: 23
<212> TYPE: RNA
<213> ORGANISM: Homo sapiens

<400> SEQUENCE: 20
ucccuguccu ccaggagcuc acg                                             23

<210> SEQ ID NO 21
<211> LENGTH: 22
<212> TYPE: RNA
<213> ORGANISM: Homo sapiens

<400> SEQUENCE: 21
uuaucagaau cuccaggggu ac                                              22

<210> SEQ ID NO 22
<211> LENGTH: 22
<212> TYPE: RNA
<213> ORGANISM: Homo sapiens

<400> SEQUENCE: 22
ucuacaaagg aaagcgcuuu cu                                              22
```

```
<210> SEQ ID NO 23
<211> LENGTH: 23
<212> TYPE: RNA
<213> ORGANISM: Homo sapiens

<400> SEQUENCE: 23
acugcccuaa gugcuccuuc ugg                                              23

<210> SEQ ID NO 24
<211> LENGTH: 21
<212> TYPE: RNA
<213> ORGANISM: Homo sapiens

<400> SEQUENCE: 24
uucaaguaau ucaggauagg u                                                21

<210> SEQ ID NO 25
<211> LENGTH: 19
<212> TYPE: RNA
<213> ORGANISM: Homo sapiens

<400> SEQUENCE: 25
aggcugcgga auucaggac                                                   19

<210> SEQ ID NO 26
<211> LENGTH: 23
<212> TYPE: RNA
<213> ORGANISM: Homo sapiens

<400> SEQUENCE: 26
agcucggucu gaggccccuc agu                                              23

<210> SEQ ID NO 27
<211> LENGTH: 22
<212> TYPE: RNA
<213> ORGANISM: Homo sapiens

<400> SEQUENCE: 27
acugcugagc uagcacuucc cg                                               22

<210> SEQ ID NO 28
<211> LENGTH: 22
<212> TYPE: RNA
<213> ORGANISM: Homo sapiens

<400> SEQUENCE: 28
uagcaccauc ugaaaucggu ua                                               22

<210> SEQ ID NO 29
<211> LENGTH: 27
<212> TYPE: RNA
<213> ORGANISM: Homo sapiens

<400> SEQUENCE: 29
accuucuugu auaagcacug ugcuaaa                                          27

<210> SEQ ID NO 30
<211> LENGTH: 22
<212> TYPE: RNA
<213> ORGANISM: Homo sapiens

<400> SEQUENCE: 30
```

```
cugugcgugu gacagcggcu ga                                              22

<210> SEQ ID NO 31
<211> LENGTH: 23
<212> TYPE: RNA
<213> ORGANISM: Homo sapiens

<400> SEQUENCE: 31
ugugcaaauc caugcaaaac uga                                             23

<210> SEQ ID NO 32
<211> LENGTH: 23
<212> TYPE: RNA
<213> ORGANISM: Homo sapiens

<400> SEQUENCE: 32
agguuguccg uggugaguuc gca                                             23

<210> SEQ ID NO 33
<211> LENGTH: 21
<212> TYPE: RNA
<213> ORGANISM: Homo sapiens

<400> SEQUENCE: 33
cauuauuacu uuugguacgc g                                               21

<210> SEQ ID NO 34
<211> LENGTH: 21
<212> TYPE: RNA
<213> ORGANISM: Homo sapiens

<400> SEQUENCE: 34
cucccacaug caggguuugc a                                               21

<210> SEQ ID NO 35
<211> LENGTH: 22
<212> TYPE: RNA
<213> ORGANISM: Homo sapiens

<400> SEQUENCE: 35
uaguaccagu accuuguguu ca                                              22

<210> SEQ ID NO 36
<211> LENGTH: 22
<212> TYPE: RNA
<213> ORGANISM: Homo sapiens

<400> SEQUENCE: 36
gggagccagg aaguauugau gu                                              22

<210> SEQ ID NO 37
<211> LENGTH: 23
<212> TYPE: RNA
<213> ORGANISM: Homo sapiens

<400> SEQUENCE: 37
aaugacacga ucacucccgu uga                                             23

<210> SEQ ID NO 38
<211> LENGTH: 23
<212> TYPE: RNA
<213> ORGANISM: Homo sapiens

<400> SEQUENCE: 38
```
ugagcgccuc gacgacagag ccg                                    23

<210> SEQ ID NO 39
<211> LENGTH: 23
<212> TYPE: RNA
<213> ORGANISM: Homo sapiens

<400> SEQUENCE: 39
ugucacucgg cucggcccac uac                                    23

<210> SEQ ID NO 40
<211> LENGTH: 22
<212> TYPE: RNA
<213> ORGANISM: Homo sapiens

<400> SEQUENCE: 40
cggguggauc acgaugcaau uu                                     22

<210> SEQ ID NO 41
<211> LENGTH: 22
<212> TYPE: RNA
<213> ORGANISM: Homo sapiens

<400> SEQUENCE: 41
cgaaucauua uuugcugcuc ua                                     22

<210> SEQ ID NO 42
<211> LENGTH: 22
<212> TYPE: RNA
<213> ORGANISM: Homo sapiens

<400> SEQUENCE: 42
ugaccgauuu cuccuggugu uc                                     22

<210> SEQ ID NO 43
<211> LENGTH: 22
<212> TYPE: RNA
<213> ORGANISM: Homo sapiens

<400> SEQUENCE: 43
ugucuuacuc ccucaggcac au                                     22

<210> SEQ ID NO 44
<211> LENGTH: 22
<212> TYPE: RNA
<213> ORGANISM: Homo sapiens

<400> SEQUENCE: 44
aaucacuaac cacacggcca gg                                     22

<210> SEQ ID NO 45
<211> LENGTH: 23
<212> TYPE: RNA
<213> ORGANISM: Homo sapiens

<400> SEQUENCE: 45
uaaagugcuu auagugcagg uag                                    23

<210> SEQ ID NO 46
<211> LENGTH: 22
<212> TYPE: RNA
<213> ORGANISM: Homo sapiens

```
<400> SEQUENCE: 46
uuauaauaca accugauaag ug                                              22

<210> SEQ ID NO 47
<211> LENGTH: 22
<212> TYPE: RNA
<213> ORGANISM: Homo sapiens

<400> SEQUENCE: 47
ggauuccugg aaauacuguu cu                                              22

<210> SEQ ID NO 48
<211> LENGTH: 23
<212> TYPE: RNA
<213> ORGANISM: Homo sapiens

<400> SEQUENCE: 48
uaagugcuuc cauguuuuag uag                                             23

<210> SEQ ID NO 49
<211> LENGTH: 23
<212> TYPE: RNA
<213> ORGANISM: Homo sapiens

<400> SEQUENCE: 49
aaaagugcuu acagugcagg uag                                             23

<210> SEQ ID NO 50
<211> LENGTH: 22
<212> TYPE: RNA
<213> ORGANISM: Homo sapiens

<400> SEQUENCE: 50
uguaaacauc cuugacugga ag                                              22

<210> SEQ ID NO 51
<211> LENGTH: 22
<212> TYPE: RNA
<213> ORGANISM: Homo sapiens

<400> SEQUENCE: 51
ugucaguuug ucaaauaccc ca                                              22

<210> SEQ ID NO 52
<211> LENGTH: 22
<212> TYPE: RNA
<213> ORGANISM: Homo sapiens

<400> SEQUENCE: 52
cuggacugag ccgugcuacu gg                                              22

<210> SEQ ID NO 53
<211> LENGTH: 22
<212> TYPE: RNA
<213> ORGANISM: Homo sapiens

<400> SEQUENCE: 53
ugagguagua gguugugugg uu                                              22

<210> SEQ ID NO 54
<211> LENGTH: 22
<212> TYPE: RNA
<213> ORGANISM: Homo sapiens
```

-continued

<400> SEQUENCE: 54
ugugacagau ugauaacuga aa                                            22

<210> SEQ ID NO 55
<211> LENGTH: 18
<212> TYPE: RNA
<213> ORGANISM: Homo sapiens

<400> SEQUENCE: 55
ugcuuccuuu cagagggu                                                 18

<210> SEQ ID NO 56
<211> LENGTH: 22
<212> TYPE: RNA
<213> ORGANISM: Homo sapiens

<400> SEQUENCE: 56
aaaccguuac cauuacugag uu                                            22

<210> SEQ ID NO 57
<211> LENGTH: 22
<212> TYPE: RNA
<213> ORGANISM: Homo sapiens

<400> SEQUENCE: 57
aaagugcauc uuuuuagagg au                                            22

<210> SEQ ID NO 58
<211> LENGTH: 26
<212> TYPE: RNA
<213> ORGANISM: Homo sapiens

<400> SEQUENCE: 58
aaguaguugg uuuguaugag augguu                                        26

<210> SEQ ID NO 59
<211> LENGTH: 23
<212> TYPE: RNA
<213> ORGANISM: Homo sapiens

<400> SEQUENCE: 59
gacacgggcg acagcugcgg ccc                                           23

<210> SEQ ID NO 60
<211> LENGTH: 23
<212> TYPE: RNA
<213> ORGANISM: Homo sapiens

<400> SEQUENCE: 60 uccccaggu gugauucuga uuu                                            23

<210> SEQ ID NO 61
<211> LENGTH: 22
<212> TYPE: RNA
<213> ORGANISM: Homo sapiens

<400> SEQUENCE: 61
aguuuugcau aguugcacua ca                                            22

<210> SEQ ID NO 62
<211> LENGTH: 22
<212> TYPE: RNA

```
<213> ORGANISM: Homo sapiens

<400> SEQUENCE: 62
aucaugaugg gcuccucggu gu                                              22

<210> SEQ ID NO 63
<211> LENGTH: 22
<212> TYPE: RNA
<213> ORGANISM: Homo sapiens

<400> SEQUENCE: 63
cuccugagcc auucugagcc uc                                              22

<210> SEQ ID NO 64
<211> LENGTH: 22
<212> TYPE: RNA
<213> ORGANISM: Homo sapiens

<400> SEQUENCE: 64
aaaaugguuc ccuuuagagu gu                                              22

<210> SEQ ID NO 65
<211> LENGTH: 22
<212> TYPE: RNA
<213> ORGANISM: Homo sapiens

<400> SEQUENCE: 65
aagugcuucc uuuuagaggg uu                                              22

<210> SEQ ID NO 66
<211> LENGTH: 22
<212> TYPE: RNA
<213> ORGANISM: Homo sapiens

<400> SEQUENCE: 66
cucuagaggg aagcgcuuuc ug                                              22

<210> SEQ ID NO 67
<211> LENGTH: 21
<212> TYPE: RNA
<213> ORGANISM: Homo sapiens

<400> SEQUENCE: 67
cugaccuaug aauugacagc c                                               21

<210> SEQ ID NO 68
<211> LENGTH: 21
<212> TYPE: RNA
<213> ORGANISM: Homo sapiens

<400> SEQUENCE: 68
aagugaucua aaggccuaca u                                               21

<210> SEQ ID NO 69
<211> LENGTH: 21
<212> TYPE: RNA
<213> ORGANISM: Homo sapiens

<400> SEQUENCE: 69
ucgaggagcu cacagucuag u                                               21

<210> SEQ ID NO 70
<211> LENGTH: 21
```

<212> TYPE: RNA
<213> ORGANISM: Homo sapiens

<400> SEQUENCE: 70
uggacugccc ugaucuggag a                                    21

<210> SEQ ID NO 71
<211> LENGTH: 23
<212> TYPE: RNA
<213> ORGANISM: Homo sapiens

<400> SEQUENCE: 71
uagcagcggg aacaguucug cag                                  23

<210> SEQ ID NO 72
<211> LENGTH: 19
<212> TYPE: RNA
<213> ORGANISM: Homo sapiens

<400> SEQUENCE: 72
agguugacau acguuuccc                                       19

<210> SEQ ID NO 73
<211> LENGTH: 22
<212> TYPE: RNA
<213> ORGANISM: Homo sapiens

<400> SEQUENCE: 73
gguggcccgg ccgugccuga gg                                   22

<210> SEQ ID NO 74
<211> LENGTH: 22
<212> TYPE: RNA
<213> ORGANISM: Homo sapiens

<400> SEQUENCE: 74
cuauacgacc ugcugccuuu cu                                   22

<210> SEQ ID NO 75
<211> LENGTH: 23
<212> TYPE: RNA
<213> ORGANISM: Homo sapiens

<400> SEQUENCE: 75
cccaguguuc agacuaccug uuc                                  23

<210> SEQ ID NO 76
<211> LENGTH: 17
<212> TYPE: RNA
<213> ORGANISM: Homo sapiens

<400> SEQUENCE: 76
ucucgcuggg gccucca                                         17

<210> SEQ ID NO 77
<211> LENGTH: 19
<212> TYPE: RNA
<213> ORGANISM: Homo sapiens

<400> SEQUENCE: 77
aauggauuuu uggagcagg                                       19

<210> SEQ ID NO 78

-continued

```
<211> LENGTH: 22
<212> TYPE: RNA
<213> ORGANISM: Homo sapiens

<400> SEQUENCE: 78
aacaauaucc uggugcugag ug                                              22

<210> SEQ ID NO 79
<211> LENGTH: 21
<212> TYPE: RNA
<213> ORGANISM: Homo sapiens

<400> SEQUENCE: 79
auguaugugu gcaugugcau g                                               21

<210> SEQ ID NO 80
<211> LENGTH: 19
<212> TYPE: RNA
<213> ORGANISM: Homo sapiens

<400> SEQUENCE: 80
auggauaagg cuuggcuu                                                   19

<210> SEQ ID NO 81
<211> LENGTH: 23
<212> TYPE: RNA
<213> ORGANISM: Homo sapiens

<400> SEQUENCE: 81
gcagcagaga auaggacuac guc                                             23

<210> SEQ ID NO 82
<211> LENGTH: 22
<212> TYPE: RNA
<213> ORGANISM: Homo sapiens

<400> SEQUENCE: 82
uggagagaaa ggcaguuccu ga                                              22

<210> SEQ ID NO 83
<211> LENGTH: 23
<212> TYPE: RNA
<213> ORGANISM: Homo sapiens

<400> SEQUENCE: 83
gcgaggaccc cucggggucu gac                                             23

<210> SEQ ID NO 84
<211> LENGTH: 26
<212> TYPE: RNA
<213> ORGANISM: Homo sapiens

<400> SEQUENCE: 84
gaugaugaug gcagcaaauu cugaaa                                          26

<210> SEQ ID NO 85
<211> LENGTH: 22
<212> TYPE: RNA
<213> ORGANISM: Homo sapiens

<400> SEQUENCE: 85
uucuggaauu cugugugagg ga                                              22
```

-continued

```
<210> SEQ ID NO 86
<211> LENGTH: 22
<212> TYPE: RNA
<213> ORGANISM: Homo sapiens

<400> SEQUENCE: 86
uuuuucauua uugcuccuga cc                                                  22

<210> SEQ ID NO 87
<211> LENGTH: 21
<212> TYPE: RNA
<213> ORGANISM: Homo sapiens

<400> SEQUENCE: 87
cagcagcaca cuggguuug u                                                    21

<210> SEQ ID NO 88
<211> LENGTH: 18
<212> TYPE: RNA
<213> ORGANISM: Homo sapiens

<400> SEQUENCE: 88
ucagcuggcc cucauuuc                                                       18

<210> SEQ ID NO 89
<211> LENGTH: 22
<212> TYPE: RNA
<213> ORGANISM: Homo sapiens

<400> SEQUENCE: 89
uagcagcacg uaaauauugg cg                                                  22

<210> SEQ ID NO 90
<211> LENGTH: 22
<212> TYPE: RNA
<213> ORGANISM: Homo sapiens

<400> SEQUENCE: 90
uggaauguaa agaaguaugu au                                                  22

<210> SEQ ID NO 91
<211> LENGTH: 24
<212> TYPE: RNA
<213> ORGANISM: Homo sapiens

<400> SEQUENCE: 91
uggcccugac ugaagaccag cagu                                                24

<210> SEQ ID NO 92
<211> LENGTH: 22
<212> TYPE: RNA
<213> ORGANISM: Homo sapiens

<400> SEQUENCE: 92
gcuauuucac gacaccaggg uu                                                  22

<210> SEQ ID NO 93
<211> LENGTH: 23
<212> TYPE: RNA
<213> ORGANISM: Homo sapiens

<400> SEQUENCE: 93
acuccauuug uuuugaugau gga                                                 23
```

```
<210> SEQ ID NO 94
<211> LENGTH: 22
<212> TYPE: RNA
<213> ORGANISM: Homo sapiens

<400> SEQUENCE: 94
caaaaaccac aguucuuuu gc                                              22

<210> SEQ ID NO 95
<211> LENGTH: 22
<212> TYPE: RNA
<213> ORGANISM: Homo sapiens

<400> SEQUENCE: 95
caaaguuuaa gauccuugaa gu                                             22

<210> SEQ ID NO 96
<211> LENGTH: 22
<212> TYPE: RNA
<213> ORGANISM: Homo sapiens

<400> SEQUENCE: 96
aaaaguaauc gcgguuuuug uc                                             22

<210> SEQ ID NO 97
<211> LENGTH: 21
<212> TYPE: RNA
<213> ORGANISM: Homo sapiens

<400> SEQUENCE: 97
gccccugggc cuauccuaga a                                              21

<210> SEQ ID NO 98
<211> LENGTH: 22
<212> TYPE: RNA
<213> ORGANISM: Homo sapiens

<400> SEQUENCE: 98
gcccaaaggu gaauuuuuug gg                                             22

<210> SEQ ID NO 99
<211> LENGTH: 23
<212> TYPE: RNA
<213> ORGANISM: Homo sapiens

<400> SEQUENCE: 99
guccaguuuu cccaggaauc ccu                                            23

<210> SEQ ID NO 100
<211> LENGTH: 23
<212> TYPE: RNA
<213> ORGANISM: Homo sapiens

<400> SEQUENCE: 100
caaagugcuu acagugcagg uag                                            23

<210> SEQ ID NO 101
<211> LENGTH: 22
<212> TYPE: RNA
<213> ORGANISM: Homo sapiens

<400> SEQUENCE: 101
uguaaacauc cuacacucag cu                                             22
```

```
<210> SEQ ID NO 102
<211> LENGTH: 22
<212> TYPE: RNA
<213> ORGANISM: Homo sapiens

<400> SEQUENCE: 102
cuauacaauc uauugccuuc cc                                              22

<210> SEQ ID NO 103
<211> LENGTH: 22
<212> TYPE: RNA
<213> ORGANISM: Homo sapiens

<400> SEQUENCE: 103
uuuucaacuc uaaugggaga ga                                              22

<210> SEQ ID NO 104
<211> LENGTH: 21
<212> TYPE: RNA
<213> ORGANISM: Homo sapiens

<400> SEQUENCE: 104
cuuuuugcgg ucugggcuug c                                               21

<210> SEQ ID NO 105
<211> LENGTH: 21
<212> TYPE: RNA
<213> ORGANISM: Homo sapiens

<400> SEQUENCE: 105
ucguggccug gucuccauua u                                               21

<210> SEQ ID NO 106
<211> LENGTH: 22
<212> TYPE: RNA
<213> ORGANISM: Homo sapiens

<400> SEQUENCE: 106
ccgcacugug gguacuugcu gc                                              22

<210> SEQ ID NO 107
<211> LENGTH: 24
<212> TYPE: RNA
<213> ORGANISM: Homo sapiens

<400> SEQUENCE: 107
gaccuggaca uguuugugcc cagu                                            24

<210> SEQ ID NO 108
<211> LENGTH: 22
<212> TYPE: RNA
<213> ORGANISM: Homo sapiens

<400> SEQUENCE: 108
caaucagcaa guauacugcc cu                                              22

<210> SEQ ID NO 109
<211> LENGTH: 21
<212> TYPE: RNA
<213> ORGANISM: Homo sapiens

<400> SEQUENCE: 109
```
aauggcgcca cuagguugu g                          21

<210> SEQ ID NO 110
<211> LENGTH: 22
<212> TYPE: RNA
<213> ORGANISM: Homo sapiens

<400> SEQUENCE: 110
aggcauugac uucucacuag cu                        22

<210> SEQ ID NO 111
<211> LENGTH: 22
<212> TYPE: RNA
<213> ORGANISM: Homo sapiens

<400> SEQUENCE: 111
acuguaguau gggcacuucc ag                        22

<210> SEQ ID NO 112
<211> LENGTH: 21
<212> TYPE: RNA
<213> ORGANISM: Homo sapiens

<400> SEQUENCE: 112
caaaacguga ggcgcugcua u                         21

<210> SEQ ID NO 113
<211> LENGTH: 22
<212> TYPE: RNA
<213> ORGANISM: Homo sapiens

<400> SEQUENCE: 113
aucgugcauc ccuuuagagu gu                        22

<210> SEQ ID NO 114
<211> LENGTH: 22
<212> TYPE: RNA
<213> ORGANISM: Homo sapiens

<400> SEQUENCE: 114
ucuauacaga cccuggcuuu uc                        22

<210> SEQ ID NO 115
<211> LENGTH: 22
<212> TYPE: RNA
<213> ORGANISM: Homo sapiens

<400> SEQUENCE: 115
acaguagucu gcacauuggu ua                        22

<210> SEQ ID NO 116
<211> LENGTH: 20
<212> TYPE: RNA
<213> ORGANISM: Homo sapiens

<400> SEQUENCE: 116
guugugucag uuuaucaaac                           20

<210> SEQ ID NO 117
<211> LENGTH: 21
<212> TYPE: RNA
<213> ORGANISM: Homo sapiens

<400> SEQUENCE: 117

```
uaguagaccg uauagcguac g                                          21

<210> SEQ ID NO 118
<211> LENGTH: 21
<212> TYPE: RNA
<213> ORGANISM: Homo sapiens

<400> SEQUENCE: 118
aucacauugc cagggauuac c                                          21

<210> SEQ ID NO 119
<211> LENGTH: 21
<212> TYPE: RNA
<213> ORGANISM: Homo sapiens

<400> SEQUENCE: 119
uugggacaua cuuaugcuaa a                                          21

<210> SEQ ID NO 120
<211> LENGTH: 22
<212> TYPE: RNA
<213> ORGANISM: Homo sapiens

<400> SEQUENCE: 120
uggcagugua uuguuagcug gu                                         22

<210> SEQ ID NO 121
<211> LENGTH: 19
<212> TYPE: RNA
<213> ORGANISM: Homo sapiens

<400> SEQUENCE: 121
aaaaacugua auuacuuuu                                             19

<210> SEQ ID NO 122
<211> LENGTH: 22
<212> TYPE: RNA
<213> ORGANISM: Homo sapiens

<400> SEQUENCE: 122
ugugucacuc gaugaccacu gu                                         22

<210> SEQ ID NO 123
<211> LENGTH: 22
<212> TYPE: RNA
<213> ORGANISM: Homo sapiens

<400> SEQUENCE: 123
cacacacugc aauuacuuuu gc                                         22

<210> SEQ ID NO 124
<211> LENGTH: 22
<212> TYPE: RNA
<213> ORGANISM: Homo sapiens

<400> SEQUENCE: 124
acccgucccg uucgucccccg ga                                        22

<210> SEQ ID NO 125
<211> LENGTH: 21
<212> TYPE: RNA
<213> ORGANISM: Homo sapiens
```

```
<400> SEQUENCE: 125
uccugcgcgu cccagaugcc c                                      21

<210> SEQ ID NO 126
<211> LENGTH: 23
<212> TYPE: RNA
<213> ORGANISM: Homo sapiens

<400> SEQUENCE: 126
ugaguaccgc caugucuguu ggg                                    23

<210> SEQ ID NO 127
<211> LENGTH: 23
<212> TYPE: RNA
<213> ORGANISM: Homo sapiens

<400> SEQUENCE: 127
ccuaguaggu guccaguaag ugu                                    23

<210> SEQ ID NO 128
<211> LENGTH: 23
<212> TYPE: RNA
<213> ORGANISM: Homo sapiens

<400> SEQUENCE: 128
agguuacccg agcaacuuug cau                                    23

<210> SEQ ID NO 129
<211> LENGTH: 24
<212> TYPE: RNA
<213> ORGANISM: Homo sapiens

<400> SEQUENCE: 129
uuuggcaaug guagaacuca cacu                                   24

<210> SEQ ID NO 130
<211> LENGTH: 25
<212> TYPE: RNA
<213> ORGANISM: Homo sapiens

<400> SEQUENCE: 130
ggcggaggga aguagguccg uuggu                                  25

<210> SEQ ID NO 131
<211> LENGTH: 21
<212> TYPE: RNA
<213> ORGANISM: Homo sapiens

<400> SEQUENCE: 131
augaccuaug aauugacaga c                                      21

<210> SEQ ID NO 132
<211> LENGTH: 22
<212> TYPE: RNA
<213> ORGANISM: Homo sapiens

<400> SEQUENCE: 132
gugugcggaa augcuucugc ua                                     22

<210> SEQ ID NO 133
<211> LENGTH: 22
<212> TYPE: RNA
<213> ORGANISM: Homo sapiens
```

-continued

```
<400> SEQUENCE: 133
uguaaacauc cccgacugga ag                                              22

<210> SEQ ID NO 134
<211> LENGTH: 22
<212> TYPE: RNA
<213> ORGANISM: Homo sapiens

<400> SEQUENCE: 134
cuccugacuc cagguccugu gu                                              22

<210> SEQ ID NO 135
<211> LENGTH: 22
<212> TYPE: RNA
<213> ORGANISM: Homo sapiens

<400> SEQUENCE: 135
accuggcaua caauguagau uu                                              22

<210> SEQ ID NO 136
<211> LENGTH: 22
<212> TYPE: RNA
<213> ORGANISM: Homo sapiens

<400> SEQUENCE: 136
caaucacuaa cuccacugcc au                                              22

<210> SEQ ID NO 137
<211> LENGTH: 25
<212> TYPE: RNA
<213> ORGANISM: Homo sapiens

<400> SEQUENCE: 137
aggcaccagc caggcauugc ucagc                                           25

<210> SEQ ID NO 138
<211> LENGTH: 21
<212> TYPE: RNA
<213> ORGANISM: Homo sapiens

<400> SEQUENCE: 138
aacaggugac ugguuagaca a                                               21

<210> SEQ ID NO 139
<211> LENGTH: 21
<212> TYPE: RNA
<213> ORGANISM: Homo sapiens

<400> SEQUENCE: 139
acuggacuug gagucagaag g                                               21

<210> SEQ ID NO 140
<211> LENGTH: 22
<212> TYPE: RNA
<213> ORGANISM: Homo sapiens

<400> SEQUENCE: 140
ggugcagugc ugcaucucug gu                                              22

<210> SEQ ID NO 141
<211> LENGTH: 23
<212> TYPE: RNA
```

```
<213> ORGANISM: Homo sapiens

<400> SEQUENCE: 141
ccucagggcu guagaacagg gcu                                              23

<210> SEQ ID NO 142
<211> LENGTH: 21
<212> TYPE: RNA
<213> ORGANISM: Homo sapiens

<400> SEQUENCE: 142
gcuaguccug acucagccag u                                                21

<210> SEQ ID NO 143
<211> LENGTH: 21
<212> TYPE: RNA
<213> ORGANISM: Homo sapiens

<400> SEQUENCE: 143
agaccuggcc cagaccucag c                                                21

<210> SEQ ID NO 144
<211> LENGTH: 20
<212> TYPE: RNA
<213> ORGANISM: Homo sapiens

<400> SEQUENCE: 144
aggguguuuc ucucaucucu                                                  20

<210> SEQ ID NO 145
<211> LENGTH: 23
<212> TYPE: RNA
<213> ORGANISM: Homo sapiens

<400> SEQUENCE: 145
uguaaacauc cuacacucuc agc                                              23

<210> SEQ ID NO 146
<211> LENGTH: 22
<212> TYPE: RNA
<213> ORGANISM: Homo sapiens

<400> SEQUENCE: 146
aaggagcuca cagucuauug ag                                               22

<210> SEQ ID NO 147
<211> LENGTH: 21
<212> TYPE: RNA
<213> ORGANISM: Homo sapiens

<400> SEQUENCE: 147
aucacauugc cagggauuuc c                                                21

<210> SEQ ID NO 148
<211> LENGTH: 19
<212> TYPE: RNA
<213> ORGANISM: Homo sapiens

<400> SEQUENCE: 148
ucuaggcugg uacugcuga                                                   19

<210> SEQ ID NO 149
<211> LENGTH: 21
```

```
<212> TYPE: RNA
<213> ORGANISM: Homo sapiens

<400> SEQUENCE: 149
guggcugcac ucacuuccuu c                                               21

<210> SEQ ID NO 150
<211> LENGTH: 22
<212> TYPE: RNA
<213> ORGANISM: Homo sapiens

<400> SEQUENCE: 150
acuuuaacau ggaagugcuu uc                                              22

<210> SEQ ID NO 151
<211> LENGTH: 21
<212> TYPE: RNA
<213> ORGANISM: Homo sapiens

<400> SEQUENCE: 151
guucaaaucc agaucuauaa c                                               21

<210> SEQ ID NO 152
<211> LENGTH: 23
<212> TYPE: RNA
<213> ORGANISM: Homo sapiens

<400> SEQUENCE: 152
uggaguccag gaaucugcau uuu                                             23

<210> SEQ ID NO 153
<211> LENGTH: 24
<212> TYPE: RNA
<213> ORGANISM: Homo sapiens

<400> SEQUENCE: 153
ccagacagaa uucuaugcac uuuc                                            24

<210> SEQ ID NO 154
<211> LENGTH: 23
<212> TYPE: RNA
<213> ORGANISM: Homo sapiens

<400> SEQUENCE: 154
uaaauuucac cuuucugaga agg                                             23

<210> SEQ ID NO 155
<211> LENGTH: 24
<212> TYPE: RNA
<213> ORGANISM: Homo sapiens

<400> SEQUENCE: 155
uggggagcug aggcucuggg ggug                                            24

<210> SEQ ID NO 156
<211> LENGTH: 23
<212> TYPE: RNA
<213> ORGANISM: Homo sapiens

<400> SEQUENCE: 156
uagcaccauu ugaaaucagu guu                                             23

<210> SEQ ID NO 157
```

```
<211> LENGTH: 20
<212> TYPE: RNA
<213> ORGANISM: Homo sapiens

<400> SEQUENCE: 157
accaggaggc ugaggccccu                                               20

<210> SEQ ID NO 158
<211> LENGTH: 23
<212> TYPE: RNA
<213> ORGANISM: Homo sapiens

<400> SEQUENCE: 158
uaaggugcau cuagugcaga uag                                           23

<210> SEQ ID NO 159
<211> LENGTH: 19
<212> TYPE: RNA
<213> ORGANISM: Homo sapiens

<400> SEQUENCE: 159
gugaggacuc gggaggugg                                                19

<210> SEQ ID NO 160
<211> LENGTH: 22
<212> TYPE: RNA
<213> ORGANISM: Homo sapiens

<400> SEQUENCE: 160
caaauucgua ucuaggggaa ua                                            22

<210> SEQ ID NO 161
<211> LENGTH: 22
<212> TYPE: RNA
<213> ORGANISM: Homo sapiens

<400> SEQUENCE: 161
accaucgacc guugauugua cc                                            22

<210> SEQ ID NO 162
<211> LENGTH: 22
<212> TYPE: RNA
<213> ORGANISM: Homo sapiens

<400> SEQUENCE: 162
caugguucug ucaagcaccg cg                                            22

<210> SEQ ID NO 163
<211> LENGTH: 23
<212> TYPE: RNA
<213> ORGANISM: Homo sapiens

<400> SEQUENCE: 163
aagugccgcc aucuuugag ugu                                            23

<210> SEQ ID NO 164
<211> LENGTH: 22
<212> TYPE: RNA
<213> ORGANISM: Homo sapiens

<400> SEQUENCE: 164
aucacacaaa ggcaacuuuu gu                                            22
```

```
<210> SEQ ID NO 165
<211> LENGTH: 22
<212> TYPE: RNA
<213> ORGANISM: Homo sapiens

<400> SEQUENCE: 165
cagugguuuu acccuauggu ag                                          22

<210> SEQ ID NO 166
<211> LENGTH: 23
<212> TYPE: RNA
<213> ORGANISM: Homo sapiens

<400> SEQUENCE: 166
cagugcaaua guauugucaa agc                                         23

<210> SEQ ID NO 167
<211> LENGTH: 22
<212> TYPE: RNA
<213> ORGANISM: Homo sapiens

<400> SEQUENCE: 167
uacguagaua uauauguauu uu                                          22

<210> SEQ ID NO 168
<211> LENGTH: 22
<212> TYPE: RNA
<213> ORGANISM: Homo sapiens

<400> SEQUENCE: 168
uucacauugu gcuacugucu gc                                          22

<210> SEQ ID NO 169
<211> LENGTH: 22
<212> TYPE: RNA
<213> ORGANISM: Homo sapiens

<400> SEQUENCE: 169
uacccagagc augcagugug aa                                          22

<210> SEQ ID NO 170
<211> LENGTH: 22
<212> TYPE: RNA
<213> ORGANISM: Homo sapiens

<400> SEQUENCE: 170
aacuggcccu caaagucccg cu                                          22

<210> SEQ ID NO 171
<211> LENGTH: 22
<212> TYPE: RNA
<213> ORGANISM: Homo sapiens

<400> SEQUENCE: 171
ugccugucua cacuugcugu gc                                          22

<210> SEQ ID NO 172
<211> LENGTH: 22
<212> TYPE: RNA
<213> ORGANISM: Homo sapiens

<400> SEQUENCE: 172
aaaucucugc aggcaaaugu ga                                          22
```

```
<210> SEQ ID NO 173
<211> LENGTH: 17
<212> TYPE: RNA
<213> ORGANISM: Homo sapiens

<400> SEQUENCE: 173
uaauugcuuc cauguuu                                              17

<210> SEQ ID NO 174
<211> LENGTH: 22
<212> TYPE: RNA
<213> ORGANISM: Homo sapiens

<400> SEQUENCE: 174
cucuagaggg aagcgcuuuc ug                                        22

<210> SEQ ID NO 175
<211> LENGTH: 22
<212> TYPE: RNA
<213> ORGANISM: Homo sapiens

<400> SEQUENCE: 175
aaaaguaauu gcggucuuug gu                                        22

<210> SEQ ID NO 176
<211> LENGTH: 20
<212> TYPE: RNA
<213> ORGANISM: Homo sapiens

<400> SEQUENCE: 176
auguauaaau guauacacac                                           20

<210> SEQ ID NO 177
<211> LENGTH: 19
<212> TYPE: RNA
<213> ORGANISM: Homo sapiens

<400> SEQUENCE: 177
aagugugcag ggcacuggu                                            19

<210> SEQ ID NO 178
<211> LENGTH: 21
<212> TYPE: RNA
<213> ORGANISM: Homo sapiens

<400> SEQUENCE: 178
ucccacguug uggcccagca g                                         21

<210> SEQ ID NO 179
<211> LENGTH: 21
<212> TYPE: RNA
<213> ORGANISM: Homo sapiens

<400> SEQUENCE: 179
agcuacaucu ggcuacuggg u                                         21

<210> SEQ ID NO 180
<211> LENGTH: 22
<212> TYPE: RNA
<213> ORGANISM: Homo sapiens

<400> SEQUENCE: 180
ugcuggauca gugguucgag uc                                        22
```

<210> SEQ ID NO 181
<211> LENGTH: 22
<212> TYPE: RNA
<213> ORGANISM: Homo sapiens

<400> SEQUENCE: 181
ugcaacuuac cugagucauu ga                                           22

<210> SEQ ID NO 182
<211> LENGTH: 23
<212> TYPE: RNA
<213> ORGANISM: Homo sapiens

<400> SEQUENCE: 182
ucucacacag aaaucgcacc cgu                                          23

<210> SEQ ID NO 183
<211> LENGTH: 22
<212> TYPE: RNA
<213> ORGANISM: Homo sapiens

<400> SEQUENCE: 183
aagugcuguc auagcugagg uc                                           22

<210> SEQ ID NO 184
<211> LENGTH: 23
<212> TYPE: RNA
<213> ORGANISM: Homo sapiens

<400> SEQUENCE: 184
aucccuugca ggggcuguug ggu                                          23

<210> SEQ ID NO 185
<211> LENGTH: 22
<212> TYPE: RNA
<213> ORGANISM: Homo sapiens

<400> SEQUENCE: 185
auaagacgaa caaaagguuu gu                                           22

<210> SEQ ID NO 186
<211> LENGTH: 22
<212> TYPE: RNA
<213> ORGANISM: Homo sapiens

<400> SEQUENCE: 186
ccaguauuaa cugugcugcu ga                                           22

<210> SEQ ID NO 187
<211> LENGTH: 21
<212> TYPE: RNA
<213> ORGANISM: Homo sapiens

<400> SEQUENCE: 187
gcgacccaua cuugguuuca g                                            21

<210> SEQ ID NO 188
<211> LENGTH: 22
<212> TYPE: RNA
<213> ORGANISM: Homo sapiens

<400> SEQUENCE: 188
ugcccugugg acucaguucu gg                                    22

<210> SEQ ID NO 189
<211> LENGTH: 21
<212> TYPE: RNA
<213> ORGANISM: Homo sapiens

<400> SEQUENCE: 189
aaagugcuuc cuuuuagagg g                                     21

<210> SEQ ID NO 190
<211> LENGTH: 22
<212> TYPE: RNA
<213> ORGANISM: Homo sapiens

<400> SEQUENCE: 190
aggcagugua uuguuagcug gc                                    22

<210> SEQ ID NO 191
<211> LENGTH: 24
<212> TYPE: RNA
<213> ORGANISM: Homo sapiens

<400> SEQUENCE: 191
acaaagugcu ucccuuuaga gugu                                  24

<210> SEQ ID NO 192
<211> LENGTH: 22
<212> TYPE: RNA
<213> ORGANISM: Homo sapiens

<400> SEQUENCE: 192
ugccuacuga gcugaaacac ag                                    22

<210> SEQ ID NO 193
<211> LENGTH: 21
<212> TYPE: RNA
<213> ORGANISM: Homo sapiens

<400> SEQUENCE: 193
gaaagcgcuu cucuuuagag g                                     21

<210> SEQ ID NO 194
<211> LENGTH: 22
<212> TYPE: RNA
<213> ORGANISM: Homo sapiens

<400> SEQUENCE: 194
aaaccugugu uguucaagag uc                                    22

<210> SEQ ID NO 195
<211> LENGTH: 22
<212> TYPE: RNA
<213> ORGANISM: Homo sapiens

<400> SEQUENCE: 195
uauugcacau uacuaaguug ca                                    22

<210> SEQ ID NO 196
<211> LENGTH: 21
<212> TYPE: RNA
<213> ORGANISM: Homo sapiens

<400> SEQUENCE: 196

```
cuagacugaa gcuccuugag g                                          21

<210> SEQ ID NO 197
<211> LENGTH: 23
<212> TYPE: RNA
<213> ORGANISM: Homo sapiens

<400> SEQUENCE: 197
uagugcaaua uugcuuauag ggu                                        23

<210> SEQ ID NO 198
<211> LENGTH: 21
<212> TYPE: RNA
<213> ORGANISM: Homo sapiens

<400> SEQUENCE: 198
uacaguacug ugauaacuga a                                          21

<210> SEQ ID NO 199
<211> LENGTH: 23
<212> TYPE: RNA
<213> ORGANISM: Homo sapiens

<400> SEQUENCE: 199
aguuuugcag guuugcaucc agc                                        23

<210> SEQ ID NO 200
<211> LENGTH: 21
<212> TYPE: RNA
<213> ORGANISM: Homo sapiens

<400> SEQUENCE: 200
uacugcagac aguggcaauc a                                          21

<210> SEQ ID NO 201
<211> LENGTH: 20
<212> TYPE: RNA
<213> ORGANISM: Homo sapiens

<400> SEQUENCE: 201
uacaguauag augauguacu                                            20

<210> SEQ ID NO 202
<211> LENGTH: 23
<212> TYPE: RNA
<213> ORGANISM: Homo sapiens

<400> SEQUENCE: 202
uacuccagag ggcgucacuc aug                                        23

<210> SEQ ID NO 203
<211> LENGTH: 21
<212> TYPE: RNA
<213> ORGANISM: Homo sapiens

<400> SEQUENCE: 203
aguuaaugaa uccuggaaag u                                          21

<210> SEQ ID NO 204
<211> LENGTH: 23
<212> TYPE: RNA
<213> ORGANISM: Homo sapiens
```

```
<400> SEQUENCE: 204
ugugcuugcu cgucccgccc gca                                              23

<210> SEQ ID NO 205
<211> LENGTH: 22
<212> TYPE: RNA
<213> ORGANISM: Homo sapiens

<400> SEQUENCE: 205
auccgcgcuc ugacucucug cc                                               22

<210> SEQ ID NO 206
<211> LENGTH: 23
<212> TYPE: RNA
<213> ORGANISM: Homo sapiens

<400> SEQUENCE: 206
ugucugcccg caugccugcc ucu                                              23

<210> SEQ ID NO 207
<211> LENGTH: 21
<212> TYPE: RNA
<213> ORGANISM: Homo sapiens

<400> SEQUENCE: 207
uaaggcaccc uucugaguag a                                                21

<210> SEQ ID NO 208
<211> LENGTH: 22
<212> TYPE: RNA
<213> ORGANISM: Homo sapiens

<400> SEQUENCE: 208
uauguaacau gguccacuaa cu                                               22

<210> SEQ ID NO 209
<211> LENGTH: 23
<212> TYPE: RNA
<213> ORGANISM: Homo sapiens

<400> SEQUENCE: 209
ccugcagcga cuugauggcu ucc                                              23

<210> SEQ ID NO 210
<211> LENGTH: 23
<212> TYPE: RNA
<213> ORGANISM: Homo sapiens

<400> SEQUENCE: 210
uucauuuggu auaaaccgcg auu                                              23

<210> SEQ ID NO 211
<211> LENGTH: 22
<212> TYPE: RNA
<213> ORGANISM: Homo sapiens

<400> SEQUENCE: 211
uggguuccug gcaugcugau uu                                               22

<210> SEQ ID NO 212
<211> LENGTH: 22
<212> TYPE: RNA
<213> ORGANISM: Homo sapiens
```

```
<400> SEQUENCE: 212
augggugaau uuguagaagg au                                              22

<210> SEQ ID NO 213
<211> LENGTH: 22
<212> TYPE: RNA
<213> ORGANISM: Homo sapiens

<400> SEQUENCE: 213
uugcauaguc acaaaaguga uc                                              22

<210> SEQ ID NO 214
<211> LENGTH: 21
<212> TYPE: RNA
<213> ORGANISM: Homo sapiens

<400> SEQUENCE: 214
aaagugcuuc cuuuugagg g                                                21

<210> SEQ ID NO 215
<211> LENGTH: 19
<212> TYPE: RNA
<213> ORGANISM: Homo sapiens

<400> SEQUENCE: 215
gugucugcuu ccuguggga                                                  19

<210> SEQ ID NO 216
<211> LENGTH: 22
<212> TYPE: RNA
<213> ORGANISM: Homo sapiens

<400> SEQUENCE: 216
cugcaaugua agcacuucuu ac                                              22

<210> SEQ ID NO 217
<211> LENGTH: 22
<212> TYPE: RNA
<213> ORGANISM: Homo sapiens

<400> SEQUENCE: 217
ugcuaugcca acauauugcc au                                              22

<210> SEQ ID NO 218
<211> LENGTH: 22
<212> TYPE: RNA
<213> ORGANISM: Homo sapiens

<400> SEQUENCE: 218
cagugccucg gcagugcagc cc                                              22

<210> SEQ ID NO 219
<211> LENGTH: 22
<212> TYPE: RNA
<213> ORGANISM: Homo sapiens

<400> SEQUENCE: 219
uaugucugcu gaccaucacc uu                                              22

<210> SEQ ID NO 220
<211> LENGTH: 22
<212> TYPE: RNA
```

```
<213> ORGANISM: Homo sapiens

<400> SEQUENCE: 220
caagcucgug ucugggguc cg                                              22

<210> SEQ ID NO 221
<211> LENGTH: 22
<212> TYPE: RNA
<213> ORGANISM: Homo sapiens

<400> SEQUENCE: 221
uaguacugug cauaucaucu au                                             22

<210> SEQ ID NO 222
<211> LENGTH: 23
<212> TYPE: RNA
<213> ORGANISM: Homo sapiens

<400> SEQUENCE: 222
uauggcuuuu cauuccuaug uga                                            23

<210> SEQ ID NO 223
<211> LENGTH: 22
<212> TYPE: RNA
<213> ORGANISM: Homo sapiens

<400> SEQUENCE: 223
uagaguuaca cccugggagu ua                                             22

<210> SEQ ID NO 224
<211> LENGTH: 21
<212> TYPE: RNA
<213> ORGANISM: Homo sapiens

<400> SEQUENCE: 224
cuccguuugc cuguuucgcu g                                              21

<210> SEQ ID NO 225
<211> LENGTH: 22
<212> TYPE: RNA
<213> ORGANISM: Homo sapiens

<400> SEQUENCE: 225
cuuagcaggu uguauuauca uu                                             22

<210> SEQ ID NO 226
<211> LENGTH: 21
<212> TYPE: RNA
<213> ORGANISM: Homo sapiens

<400> SEQUENCE: 226
auugacacuu cugugaguag a                                              21

<210> SEQ ID NO 227
<211> LENGTH: 21
<212> TYPE: RNA
<213> ORGANISM: Homo sapiens

<400> SEQUENCE: 227
uaauuuuaug uauaagcuag u                                              21

<210> SEQ ID NO 228
<211> LENGTH: 21
```

<212> TYPE: RNA
<213> ORGANISM: Homo sapiens

<400> SEQUENCE: 228
aaacuacuga aaaucaaaga u            21

<210> SEQ ID NO 229
<211> LENGTH: 21
<212> TYPE: RNA
<213> ORGANISM: Homo sapiens

<400> SEQUENCE: 229
aauaauacau gguugaucuu u            21

<210> SEQ ID NO 230
<211> LENGTH: 21
<212> TYPE: RNA
<213> ORGANISM: Homo sapiens

<400> SEQUENCE: 230
uugaaaggcu auuucuuggu c            21

<210> SEQ ID NO 231
<211> LENGTH: 21
<212> TYPE: RNA
<213> ORGANISM: Homo sapiens

<400> SEQUENCE: 231
ucacagugaa ccggucucuu u            21

<210> SEQ ID NO 232
<211> LENGTH: 24
<212> TYPE: RNA
<213> ORGANISM: Homo sapiens

<400> SEQUENCE: 232
aauccuugga accaggugu gagu          24

<210> SEQ ID NO 233
<211> LENGTH: 23
<212> TYPE: RNA
<213> ORGANISM: Homo sapiens

<400> SEQUENCE: 233
aggaagcccu ggaggggcug gag          23

<210> SEQ ID NO 234
<211> LENGTH: 22
<212> TYPE: RNA
<213> ORGANISM: Homo sapiens

<400> SEQUENCE: 234
cugcccuggc ccgagggacc ga           22

<210> SEQ ID NO 235
<211> LENGTH: 20
<212> TYPE: RNA
<213> ORGANISM: Homo sapiens

<400> SEQUENCE: 235
caccaggcau uguggucucc              20

<210> SEQ ID NO 236

```
<211> LENGTH: 25
<212> TYPE: RNA
<213> ORGANISM: Homo sapiens

<400> SEQUENCE: 236
ugggaacggg uuccggcaga cgcug                                            25

<210> SEQ ID NO 237
<211> LENGTH: 22
<212> TYPE: RNA
<213> ORGANISM: Homo sapiens

<400> SEQUENCE: 237
uguaacagca acuccaugug ga                                               22

<210> SEQ ID NO 238
<211> LENGTH: 22
<212> TYPE: RNA
<213> ORGANISM: Homo sapiens

<400> SEQUENCE: 238
uagcagcaca ucaugguuua ca                                               22

<210> SEQ ID NO 239
<211> LENGTH: 21
<212> TYPE: RNA
<213> ORGANISM: Homo sapiens

<400> SEQUENCE: 239 agggguugcua ucugugauug a                                               21

<210> SEQ ID NO 240
<211> LENGTH: 22
<212> TYPE: RNA
<213> ORGANISM: Homo sapiens

<400> SEQUENCE: 240
ucacaaguca ggcucuuggg ac                                               22

<210> SEQ ID NO 241
<211> LENGTH: 17
<212> TYPE: RNA
<213> ORGANISM: Homo sapiens

<400> SEQUENCE: 241
uucaaguaau ucaggug                                                     17

<210> SEQ ID NO 242
<211> LENGTH: 22
<212> TYPE: RNA
<213> ORGANISM: Homo sapiens

<400> SEQUENCE: 242
ugugcgcagg gagaccucuc cc                                               22

<210> SEQ ID NO 243
<211> LENGTH: 22
<212> TYPE: RNA
<213> ORGANISM: Homo sapiens

<400> SEQUENCE: 243
uuguacaugg uaggcuuuca uu                                               22
```

```
<210> SEQ ID NO 244
<211> LENGTH: 23
<212> TYPE: RNA
<213> ORGANISM: Homo sapiens

<400> SEQUENCE: 244
ucaaaugcuc agacuccugu ggu                                              23

<210> SEQ ID NO 245
<211> LENGTH: 22
<212> TYPE: RNA
<213> ORGANISM: Homo sapiens

<400> SEQUENCE: 245
uaacacuguc ugguaaagau gg                                               22

<210> SEQ ID NO 246
<211> LENGTH: 22
<212> TYPE: RNA
<213> ORGANISM: Homo sapiens

<400> SEQUENCE: 246
aaccaucgac cguugagugg ac                                               22

<210> SEQ ID NO 247
<211> LENGTH: 22
<212> TYPE: RNA
<213> ORGANISM: Homo sapiens

<400> SEQUENCE: 247
aacuggccua caaaguccca gu                                               22

<210> SEQ ID NO 248
<211> LENGTH: 23
<212> TYPE: RNA
<213> ORGANISM: Homo sapiens

<400> SEQUENCE: 248
uaagugcuuc cauguuucag ugg                                              23

<210> SEQ ID NO 249
<211> LENGTH: 22
<212> TYPE: RNA
<213> ORGANISM: Homo sapiens

<400> SEQUENCE: 249
agaggcuggc cgugaugaau uc                                               22

<210> SEQ ID NO 250
<211> LENGTH: 22
<212> TYPE: RNA
<213> ORGANISM: Homo sapiens

<400> SEQUENCE: 250
aacaucacag caagucugug cu                                               22

<210> SEQ ID NO 251
<211> LENGTH: 22
<212> TYPE: RNA
<213> ORGANISM: Homo sapiens

<400> SEQUENCE: 251
ucagcaaaca uuuauugugu gc                                               22
```

```
<210> SEQ ID NO 252
<211> LENGTH: 22
<212> TYPE: RNA
<213> ORGANISM: Homo sapiens

<400> SEQUENCE: 252
aaaaguaauu gugguuuugg cc                                              22

<210> SEQ ID NO 253
<211> LENGTH: 21
<212> TYPE: RNA
<213> ORGANISM: Homo sapiens

<400> SEQUENCE: 253
ugacaacuau ggaugagcuc u                                               21

<210> SEQ ID NO 254
<211> LENGTH: 22
<212> TYPE: RNA
<213> ORGANISM: Homo sapiens

<400> SEQUENCE: 254
auucuaauuu cuccacgucu uu                                              22

<210> SEQ ID NO 255
<211> LENGTH: 21
<212> TYPE: RNA
<213> ORGANISM: Homo sapiens

<400> SEQUENCE: 255
uagauaaaau auugguaccu g                                               21

<210> SEQ ID NO 256
<211> LENGTH: 21
<212> TYPE: RNA
<213> ORGANISM: Homo sapiens

<400> SEQUENCE: 256
caaagaggaa ggucccauua c                                               21

<210> SEQ ID NO 257
<211> LENGTH: 21
<212> TYPE: RNA
<213> ORGANISM: Homo sapiens

<400> SEQUENCE: 257
uuuccauagg ugaugaguca c                                               21

<210> SEQ ID NO 258
<211> LENGTH: 21
<212> TYPE: RNA
<213> ORGANISM: Homo sapiens

<400> SEQUENCE: 258
cacaagguau ugguauuacc u                                               21

<210> SEQ ID NO 259
<211> LENGTH: 19
<212> TYPE: RNA
<213> ORGANISM: Homo sapiens

<400> SEQUENCE: 259
aagcagcugc cucugaggc                                                  19
```

<210> SEQ ID NO 260
<211> LENGTH: 22
<212> TYPE: RNA
<213> ORGANISM: Homo sapiens

<400> SEQUENCE: 260
auaauacaug guuaaccucu uu         22

<210> SEQ ID NO 261
<211> LENGTH: 22
<212> TYPE: RNA
<213> ORGANISM: Homo sapiens

<400> SEQUENCE: 261
uccauuacac uacccugccu cu         22

<210> SEQ ID NO 262
<211> LENGTH: 22
<212> TYPE: RNA
<213> ORGANISM: Homo sapiens

<400> SEQUENCE: 262
ccaguggggc ugcuguuauc ug         22

<210> SEQ ID NO 263
<211> LENGTH: 22
<212> TYPE: RNA
<213> ORGANISM: Homo sapiens

<400> SEQUENCE: 263
ugguuuaccg ucccacauac au         22

<210> SEQ ID NO 264
<211> LENGTH: 22
<212> TYPE: RNA
<213> ORGANISM: Homo sapiens

<400> SEQUENCE: 264
cuccuauaug augccuuucu uc         22

<210> SEQ ID NO 265
<211> LENGTH: 22
<212> TYPE: RNA
<213> ORGANISM: Homo sapiens

<400> SEQUENCE: 265
ugaaggucua cugugugcca gg         22

<210> SEQ ID NO 266
<211> LENGTH: 22
<212> TYPE: RNA
<213> ORGANISM: Homo sapiens

<400> SEQUENCE: 266
caaaccacac uguggguguua ga        22

<210> SEQ ID NO 267
<211> LENGTH: 22
<212> TYPE: RNA
<213> ORGANISM: Homo sapiens

<400> SEQUENCE: 267
aaagugcauc cuuuuagagu gu                                                  22

<210> SEQ ID NO 268
<211> LENGTH: 22
<212> TYPE: RNA
<213> ORGANISM: Homo sapiens

<400> SEQUENCE: 268
caagcucgcu ucuauggguc ug                                                  22

<210> SEQ ID NO 269
<211> LENGTH: 17
<212> TYPE: RNA
<213> ORGANISM: Homo sapiens

<400> SEQUENCE: 269
ucccaccgcu gccaccc                                                        17

<210> SEQ ID NO 270
<211> LENGTH: 22
<212> TYPE: RNA
<213> ORGANISM: Homo sapiens

<400> SEQUENCE: 270
cucuagaggg aagcgcuuuc ug                                                  22

<210> SEQ ID NO 271
<211> LENGTH: 22
<212> TYPE: RNA
<213> ORGANISM: Homo sapiens

<400> SEQUENCE: 271
gguccagagg ggagauaggu uc                                                  22

<210> SEQ ID NO 272
<211> LENGTH: 22
<212> TYPE: RNA
<213> ORGANISM: Homo sapiens

<400> SEQUENCE: 272
ugucuacuac uggagacacu gg                                                  22

<210> SEQ ID NO 273
<211> LENGTH: 22
<212> TYPE: RNA
<213> ORGANISM: Homo sapiens

<400> SEQUENCE: 273
cuuucaguca gauguuugcu gc                                                  22

<210> SEQ ID NO 274
<211> LENGTH: 22
<212> TYPE: RNA
<213> ORGANISM: Homo sapiens

<400> SEQUENCE: 274
cucaucugca aagaaguaag ug                                                  22

<210> SEQ ID NO 275
<211> LENGTH: 22
<212> TYPE: RNA
<213> ORGANISM: Homo sapiens

<400> SEQUENCE: 275

```
caagaaccuc aguugcuuuu gu                                                    22

<210> SEQ ID NO 276
<211> LENGTH: 22
<212> TYPE: RNA
<213> ORGANISM: Homo sapiens

<400> SEQUENCE: 276
uaugcauugu auuuuaggu cc                                                     22

<210> SEQ ID NO 277
<211> LENGTH: 22
<212> TYPE: RNA
<213> ORGANISM: Homo sapiens

<400> SEQUENCE: 277
uauugcacuc gucccggccu cc                                                    22

<210> SEQ ID NO 278
<211> LENGTH: 22
<212> TYPE: RNA
<213> ORGANISM: Homo sapiens

<400> SEQUENCE: 278
ucgugcaucc cuuuagagug uu                                                    22

<210> SEQ ID NO 279
<211> LENGTH: 22
<212> TYPE: RNA
<213> ORGANISM: Homo sapiens

<400> SEQUENCE: 279
caaaacuggc aauuacuuuu gc                                                    22

<210> SEQ ID NO 280
<211> LENGTH: 22
<212> TYPE: RNA
<213> ORGANISM: Homo sapiens

<400> SEQUENCE: 280
uauaccucag uuuuaucagg ug                                                    22

<210> SEQ ID NO 281
<211> LENGTH: 22
<212> TYPE: RNA
<213> ORGANISM: Homo sapiens

<400> SEQUENCE: 281
caggucgucu ugcagggcuu cu                                                    22

<210> SEQ ID NO 282
<211> LENGTH: 20
<212> TYPE: RNA
<213> ORGANISM: Homo sapiens

<400> SEQUENCE: 282
auuccuagaa auuguucaua                                                       20

<210> SEQ ID NO 283
<211> LENGTH: 19
<212> TYPE: RNA
<213> ORGANISM: Homo sapiens
```

-continued

```
<400> SEQUENCE: 283
aguguggcuu ucuuagagc                                                    19

<210> SEQ ID NO 284
<211> LENGTH: 21
<212> TYPE: RNA
<213> ORGANISM: Homo sapiens

<400> SEQUENCE: 284
agaggauacc cuuuguaugu u                                                 21

<210> SEQ ID NO 285
<211> LENGTH: 22
<212> TYPE: RNA
<213> ORGANISM: Homo sapiens

<400> SEQUENCE: 285
cugguuucac augguggcuu ag                                                22

<210> SEQ ID NO 286
<211> LENGTH: 22
<212> TYPE: RNA
<213> ORGANISM: Homo sapiens

<400> SEQUENCE: 286
gugacaucac auauacggca gc                                                22

<210> SEQ ID NO 287
<211> LENGTH: 19
<212> TYPE: RNA
<213> ORGANISM: Homo sapiens

<400> SEQUENCE: 287
gggcgccugu gaucccaac                                                    19

<210> SEQ ID NO 288
<211> LENGTH: 23
<212> TYPE: RNA
<213> ORGANISM: Homo sapiens

<400> SEQUENCE: 288
cggcccgggc ugcugcuguu ccu                                               23

<210> SEQ ID NO 289
<211> LENGTH: 22
<212> TYPE: RNA
<213> ORGANISM: Homo sapiens

<400> SEQUENCE: 289
cacuagauug ugagcuccug ga                                                22

<210> SEQ ID NO 290
<211> LENGTH: 22
<212> TYPE: RNA
<213> ORGANISM: Homo sapiens

<400> SEQUENCE: 290
cuauacaguc uacugucuuu cc                                                22

<210> SEQ ID NO 291
<211> LENGTH: 19
<212> TYPE: RNA
<213> ORGANISM: Homo sapiens
```

```
<400> SEQUENCE: 291
gaugaugcug cugaugcug                                               19

<210> SEQ ID NO 292
<211> LENGTH: 18
<212> TYPE: RNA
<213> ORGANISM: Homo sapiens

<400> SEQUENCE: 292
ugaggcagua gauugaau                                                18

<210> SEQ ID NO 293
<211> LENGTH: 22
<212> TYPE: RNA
<213> ORGANISM: Homo sapiens

<400> SEQUENCE: 293
cugccaauuc cauaggucac ag                                           22

<210> SEQ ID NO 294
<211> LENGTH: 17
<212> TYPE: RNA
<213> ORGANISM: Homo sapiens

<400> SEQUENCE: 294
uaagugcuuc caugcuu                                                 17

<210> SEQ ID NO 295
<211> LENGTH: 22
<212> TYPE: RNA
<213> ORGANISM: Homo sapiens

<400> SEQUENCE: 295
uauguaacac gguccacuaa cc                                           22

<210> SEQ ID NO 296
<211> LENGTH: 22
<212> TYPE: RNA
<213> ORGANISM: Homo sapiens

<400> SEQUENCE: 296
cagcagcaau ucauguuuug aa                                           22

<210> SEQ ID NO 297
<211> LENGTH: 22
<212> TYPE: RNA
<213> ORGANISM: Homo sapiens

<400> SEQUENCE: 297
uaacugguug aacaacugaa cc                                           22

<210> SEQ ID NO 298
<211> LENGTH: 22
<212> TYPE: RNA
<213> ORGANISM: Homo sapiens

<400> SEQUENCE: 298
guucucccaa cguaagccca gc                                           22

<210> SEQ ID NO 299
<211> LENGTH: 22
<212> TYPE: RNA
```

```
<213> ORGANISM: Homo sapiens

<400> SEQUENCE: 299
cuuaugcaag auucccuucu ac                                              22

<210> SEQ ID NO 300
<211> LENGTH: 22
<212> TYPE: RNA
<213> ORGANISM: Homo sapiens

<400> SEQUENCE: 300
aaagugcauc cuuuuagagg uu                                              22

<210> SEQ ID NO 301
<211> LENGTH: 21
<212> TYPE: RNA
<213> ORGANISM: Homo sapiens

<400> SEQUENCE: 301
uaggacacau ggucuacuuc u                                               21

<210> SEQ ID NO 302
<211> LENGTH: 22
<212> TYPE: RNA
<213> ORGANISM: Homo sapiens

<400> SEQUENCE: 302
cugaagcuca gagggcucug au                                              22

<210> SEQ ID NO 303
<211> LENGTH: 21
<212> TYPE: RNA
<213> ORGANISM: Homo sapiens

<400> SEQUENCE: 303
ugcaggacca agaugagccc u                                               21

<210> SEQ ID NO 304
<211> LENGTH: 22
<212> TYPE: RNA
<213> ORGANISM: Homo sapiens

<400> SEQUENCE: 304
accguggcuu ucgauuguua cu                                              22

<210> SEQ ID NO 305
<211> LENGTH: 20
<212> TYPE: RNA
<213> ORGANISM: Homo sapiens

<400> SEQUENCE: 305
gugcauugcu guugcauugc                                                 20

<210> SEQ ID NO 306
<211> LENGTH: 21
<212> TYPE: RNA
<213> ORGANISM: Homo sapiens

<400> SEQUENCE: 306
aaaacgguga gauuuuguuu u                                               21

<210> SEQ ID NO 307
<211> LENGTH: 20
```

```
<212> TYPE: RNA
<213> ORGANISM: Homo sapiens

<400> SEQUENCE: 307
auggagauag auauagaaau                                               20

<210> SEQ ID NO 308
<211> LENGTH: 23
<212> TYPE: RNA
<213> ORGANISM: Homo sapiens

<400> SEQUENCE: 308
aaggagcuua caaucuagcu ggg                                           23

<210> SEQ ID NO 309
<211> LENGTH: 22
<212> TYPE: RNA
<213> ORGANISM: Homo sapiens

<400> SEQUENCE: 309
cacuggcucc uuucugggua ga                                            22

<210> SEQ ID NO 310
<211> LENGTH: 22
<212> TYPE: RNA
<213> ORGANISM: Homo sapiens

<400> SEQUENCE: 310
acaaagugcu ucccuuuaga gu                                            22

<210> SEQ ID NO 311
<211> LENGTH: 22
<212> TYPE: RNA
<213> ORGANISM: Homo sapiens

<400> SEQUENCE: 311
augcaccugg gcaaggauuc ug                                            22

<210> SEQ ID NO 312
<211> LENGTH: 22
<212> TYPE: RNA
<213> ORGANISM: Homo sapiens

<400> SEQUENCE: 312
gaaaucaagc gugggugaga cc                                            22

<210> SEQ ID NO 313
<211> LENGTH: 22
<212> TYPE: RNA
<213> ORGANISM: Homo sapiens

<400> SEQUENCE: 313
caaagaauuc uccuuuggg cu                                             22

<210> SEQ ID NO 314
<211> LENGTH: 19
<212> TYPE: RNA
<213> ORGANISM: Homo sapiens

<400> SEQUENCE: 314
ugagcugcug uaccaaaau                                                19

<210> SEQ ID NO 315
```

```
<211> LENGTH: 22
<212> TYPE: RNA
<213> ORGANISM: Homo sapiens

<400> SEQUENCE: 315
uucaaguaau ccaggauagg cu                                              22

<210> SEQ ID NO 316
<211> LENGTH: 22
<212> TYPE: RNA
<213> ORGANISM: Homo sapiens

<400> SEQUENCE: 316
augguacccu ggcauacuga gu                                              22

<210> SEQ ID NO 317
<211> LENGTH: 22
<212> TYPE: RNA
<213> ORGANISM: Homo sapiens

<400> SEQUENCE: 317
uucccuuugu cauccuucgc cu                                              22

<210> SEQ ID NO 318
<211> LENGTH: 22
<212> TYPE: RNA
<213> ORGANISM: Homo sapiens

<400> SEQUENCE: 318
uuugaggcua cagugagaug ug                                              22

<210> SEQ ID NO 319
<211> LENGTH: 21
<212> TYPE: RNA
<213> ORGANISM: Homo sapiens

<400> SEQUENCE: 319
ccaccaccgu gucugacacu u                                               21

<210> SEQ ID NO 320
<211> LENGTH: 22
<212> TYPE: RNA
<213> ORGANISM: Homo sapiens

<400> SEQUENCE: 320
ugcaacgaac cugagccacu ga                                              22

<210> SEQ ID NO 321
<211> LENGTH: 21
<212> TYPE: RNA
<213> ORGANISM: Homo sapiens

<400> SEQUENCE: 321
agagaagaag aucagccugc a                                               21

<210> SEQ ID NO 322
<211> LENGTH: 20
<212> TYPE: RNA
<213> ORGANISM: Homo sapiens

<400> SEQUENCE: 322
ucugcagggu uugcuuugag                                                 20
```

-continued

```
<210> SEQ ID NO 323
<211> LENGTH: 23
<212> TYPE: RNA
<213> ORGANISM: Homo sapiens

<400> SEQUENCE: 323
uuauugcuua agaauacgcg uag                                              23

<210> SEQ ID NO 324
<211> LENGTH: 22
<212> TYPE: RNA
<213> ORGANISM: Homo sapiens

<400> SEQUENCE: 324
aaucauacac gguugaccua uu                                               22

<210> SEQ ID NO 325
<211> LENGTH: 21
<212> TYPE: RNA
<213> ORGANISM: Homo sapiens

<400> SEQUENCE: 325
aggguaagcu gaaccucuga u                                                21

<210> SEQ ID NO 326
<211> LENGTH: 22
<212> TYPE: RNA
<213> ORGANISM: Homo sapiens

<400> SEQUENCE: 326
gugaacgggc gccaucccga gg                                               22

<210> SEQ ID NO 327
<211> LENGTH: 22
<212> TYPE: RNA
<213> ORGANISM: Homo sapiens

<400> SEQUENCE: 327
aauugcacgg uauccaucug ua                                               22

<210> SEQ ID NO 328
<211> LENGTH: 22
<212> TYPE: RNA
<213> ORGANISM: Homo sapiens

<400> SEQUENCE: 328
aaaaccgucu aguuacaguu gu                                               22

<210> SEQ ID NO 329
<211> LENGTH: 22
<212> TYPE: RNA
<213> ORGANISM: Homo sapiens

<400> SEQUENCE: 329
agaguugagu cuggacgucc cg                                               22

<210> SEQ ID NO 330
<211> LENGTH: 21
<212> TYPE: RNA
<213> ORGANISM: Homo sapiens

<400> SEQUENCE: 330
ccacaccgua ucugacacuu u                                                21
```

<210> SEQ ID NO 331
<211> LENGTH: 22
<212> TYPE: RNA
<213> ORGANISM: Homo sapiens

<400> SEQUENCE: 331
cucaguagcc aguguagauc cu                                              22

<210> SEQ ID NO 332
<211> LENGTH: 21
<212> TYPE: RNA
<213> ORGANISM: Homo sapiens

<400> SEQUENCE: 332
cacauuacac ggucgaccuc u                                               21

<210> SEQ ID NO 333
<211> LENGTH: 22
<212> TYPE: RNA
<213> ORGANISM: Homo sapiens

<400> SEQUENCE: 333
aucauagagg aaaauccaug uu                                              22

<210> SEQ ID NO 334
<211> LENGTH: 20
<212> TYPE: RNA
<213> ORGANISM: Homo sapiens

<400> SEQUENCE: 334
ccauggaucu ccaggugggu                                                 20

<210> SEQ ID NO 335
<211> LENGTH: 23
<212> TYPE: RNA
<213> ORGANISM: Homo sapiens

<400> SEQUENCE: 335
gaacgcgcuu cccuauagag ggu                                             23

<210> SEQ ID NO 336
<211> LENGTH: 23
<212> TYPE: RNA
<213> ORGANISM: Homo sapiens

<400> SEQUENCE: 336
acuuaaacgu ggauguacuu gcu                                             23

<210> SEQ ID NO 337
<211> LENGTH: 22
<212> TYPE: RNA
<213> ORGANISM: Homo sapiens

<400> SEQUENCE: 337
agagcuuagc ugauugguga ac                                              22

<210> SEQ ID NO 338
<211> LENGTH: 20
<212> TYPE: RNA
<213> ORGANISM: Homo sapiens

<400> SEQUENCE: 338
agaccauggg uucucauugu                                                 20

```
<210> SEQ ID NO 339
<211> LENGTH: 21
<212> TYPE: RNA
<213> ORGANISM: Homo sapiens

<400> SEQUENCE: 339
uacucaaaaa gcugucaguc a                                              21

<210> SEQ ID NO 340
<211> LENGTH: 22
<212> TYPE: RNA
<213> ORGANISM: Homo sapiens

<400> SEQUENCE: 340
guagauucuc cuucuaugag ua                                             22

<210> SEQ ID NO 341
<211> LENGTH: 23
<212> TYPE: RNA
<213> ORGANISM: Homo sapiens

<400> SEQUENCE: 341
aaacucuacu uguccuucug agu                                            23

<210> SEQ ID NO 342
<211> LENGTH: 23
<212> TYPE: RNA
<213> ORGANISM: Homo sapiens

<400> SEQUENCE: 342
gagggucuug ggagggaugu gac                                            23

<210> SEQ ID NO 343
<211> LENGTH: 22
<212> TYPE: RNA
<213> ORGANISM: Homo sapiens

<400> SEQUENCE: 343
ccucccacac ccaaggcuug ca                                             22

<210> SEQ ID NO 344
<211> LENGTH: 23
<212> TYPE: RNA
<213> ORGANISM: Homo sapiens

<400> SEQUENCE: 344
aacauucauu gcugucggug ggu                                            23

<210> SEQ ID NO 345
<211> LENGTH: 22
<212> TYPE: RNA
<213> ORGANISM: Homo sapiens

<400> SEQUENCE: 345
aacgcacuuc ccuuuagagu gu                                             22

<210> SEQ ID NO 346
<211> LENGTH: 22
<212> TYPE: RNA
<213> ORGANISM: Homo sapiens

<400> SEQUENCE: 346
```
ucaguaaaug uuuauuagau ga                                                22

<210> SEQ ID NO 347
<211> LENGTH: 22
<212> TYPE: RNA
<213> ORGANISM: Homo sapiens

<400> SEQUENCE: 347
auaaagcuag auaaccgaaa gu                                                22

<210> SEQ ID NO 348
<211> LENGTH: 20
<212> TYPE: RNA
<213> ORGANISM: Homo sapiens

<400> SEQUENCE: 348
ggggagcugu ggaagcagua                                                   20

<210> SEQ ID NO 349
<211> LENGTH: 21
<212> TYPE: RNA
<213> ORGANISM: Homo sapiens

<400> SEQUENCE: 349
ugaguuggcc aucugaguga g                                                 21

<210> SEQ ID NO 350
<211> LENGTH: 23
<212> TYPE: RNA
<213> ORGANISM: Homo sapiens

<400> SEQUENCE: 350
acuugggcac ugaaacaaug ucc                                               23

<210> SEQ ID NO 351
<211> LENGTH: 22
<212> TYPE: RNA
<213> ORGANISM: Homo sapiens

<400> SEQUENCE: 351
uaauacugcc ugguaaugau ga                                                22

<210> SEQ ID NO 352
<211> LENGTH: 22
<212> TYPE: RNA
<213> ORGANISM: Homo sapiens

<400> SEQUENCE: 352
uaugugccuu uggacuacau cg                                                22

<210> SEQ ID NO 353
<211> LENGTH: 22
<212> TYPE: RNA
<213> ORGANISM: Homo sapiens

<400> SEQUENCE: 353
uggugguuua caaaguaauu ca                                                22

<210> SEQ ID NO 354
<211> LENGTH: 22
<212> TYPE: RNA
<213> ORGANISM: Homo sapiens

<400> SEQUENCE: 354
acucaaaaug ggggcgcuuu cc                                              22

<210> SEQ ID NO 355
<211> LENGTH: 22
<212> TYPE: RNA
<213> ORGANISM: Homo sapiens

<400> SEQUENCE: 355
ccucugaaau ucaguucuuc ag                                              22

<210> SEQ ID NO 356
<211> LENGTH: 22
<212> TYPE: RNA
<213> ORGANISM: Homo sapiens

<400> SEQUENCE: 356
aacgccauua ucacacuaaa ua                                              22

<210> SEQ ID NO 357
<211> LENGTH: 22
<212> TYPE: RNA
<213> ORGANISM: Homo sapiens

<400> SEQUENCE: 357
uugggaucau uuugcaucca ua                                              22

<210> SEQ ID NO 358
<211> LENGTH: 22
<212> TYPE: RNA
<213> ORGANISM: Homo sapiens

<400> SEQUENCE: 358
uggcucaguu cagcaggaac ag                                              22

<210> SEQ ID NO 359
<211> LENGTH: 22
<212> TYPE: RNA
<213> ORGANISM: Homo sapiens

<400> SEQUENCE: 359
ucaggcucag uccccucccg au                                              22

<210> SEQ ID NO 360
<211> LENGTH: 23
<212> TYPE: RNA
<213> ORGANISM: Homo sapiens

<400> SEQUENCE: 360
ucauagcccu guacaaugcu gcu                                             23

<210> SEQ ID NO 361
<211> LENGTH: 22
<212> TYPE: RNA
<213> ORGANISM: Homo sapiens

<400> SEQUENCE: 361
uauguaauau gguccacauc uu                                              22

<210> SEQ ID NO 362
<211> LENGTH: 18
<212> TYPE: RNA
<213> ORGANISM: Homo sapiens

```
<400> SEQUENCE: 362
uucacaggga ggugucau                                              18

<210> SEQ ID NO 363
<211> LENGTH: 22
<212> TYPE: RNA
<213> ORGANISM: Homo sapiens

<400> SEQUENCE: 363
uacugcagac guggcaauca ug                                         22

<210> SEQ ID NO 364
<211> LENGTH: 21
<212> TYPE: RNA
<213> ORGANISM: Homo sapiens

<400> SEQUENCE: 364
gcaggaacuu gugagucucc u                                          21

<210> SEQ ID NO 365
<211> LENGTH: 22
<212> TYPE: RNA
<213> ORGANISM: Homo sapiens

<400> SEQUENCE: 365
gaugagcuca uuguaauaug ag                                         22

<210> SEQ ID NO 366
<211> LENGTH: 22
<212> TYPE: RNA
<213> ORGANISM: Homo sapiens

<400> SEQUENCE: 366
agaucgaccg uguuauauuc gc                                         22

<210> SEQ ID NO 367
<211> LENGTH: 21
<212> TYPE: RNA
<213> ORGANISM: Homo sapiens

<400> SEQUENCE: 367
guguugaaac aaucucuacu g                                          21

<210> SEQ ID NO 368
<211> LENGTH: 23
<212> TYPE: RNA
<213> ORGANISM: Homo sapiens

<400> SEQUENCE: 368
ucugcucaua ccccaugguu ucu                                        23

<210> SEQ ID NO 369
<211> LENGTH: 18
<212> TYPE: RNA
<213> ORGANISM: Homo sapiens

<400> SEQUENCE: 369
ugcuuccuuu cagagggu                                              18

<210> SEQ ID NO 370
<211> LENGTH: 22
<212> TYPE: RNA
<213> ORGANISM: Homo sapiens
```

```
<400> SEQUENCE: 370
aaagugcuuc cuuuuagagg gu                                          22

<210> SEQ ID NO 371
<211> LENGTH: 22
<212> TYPE: RNA
<213> ORGANISM: Homo sapiens

<400> SEQUENCE: 371
caacuagacu gugagcuucu ag                                          22

<210> SEQ ID NO 372
<211> LENGTH: 20
<212> TYPE: RNA
<213> ORGANISM: Homo sapiens

<400> SEQUENCE: 372
agagucuugu gaugucuugc                                             20

<210> SEQ ID NO 373
<211> LENGTH: 20
<212> TYPE: RNA
<213> ORGANISM: Homo sapiens

<400> SEQUENCE: 373
cuacaaaggg aagcccuuuc                                             20

<210> SEQ ID NO 374
<211> LENGTH: 23
<212> TYPE: RNA
<213> ORGANISM: Homo sapiens

<400> SEQUENCE: 374
cacucagccu ugagggcacu uuc                                         23

<210> SEQ ID NO 375
<211> LENGTH: 22
<212> TYPE: RNA
<213> ORGANISM: Homo sapiens

<400> SEQUENCE: 375
cuuaucagau uguauuguaa uu                                          22

<210> SEQ ID NO 376
<211> LENGTH: 25
<212> TYPE: RNA
<213> ORGANISM: Homo sapiens

<400> SEQUENCE: 376
cuagugaggg acagaaccag gauuc                                       25

<210> SEQ ID NO 377
<211> LENGTH: 21
<212> TYPE: RNA
<213> ORGANISM: Homo sapiens

<400> SEQUENCE: 377
uguucaugua gauguuuaag c                                           21

<210> SEQ ID NO 378
<211> LENGTH: 21
<212> TYPE: RNA
```

```
<213> ORGANISM: Homo sapiens

<400> SEQUENCE: 378
auauaugaug acuuagcuuu u                                              21

<210> SEQ ID NO 379
<211> LENGTH: 21
<212> TYPE: RNA
<213> ORGANISM: Homo sapiens

<400> SEQUENCE: 379
cuccagaggg augcacuuuc u                                              21

<210> SEQ ID NO 380
<211> LENGTH: 22
<212> TYPE: RNA
<213> ORGANISM: Homo sapiens

<400> SEQUENCE: 380
caucuuaccg gacagugcug ga                                             22

<210> SEQ ID NO 381
<211> LENGTH: 22
<212> TYPE: RNA
<213> ORGANISM: Homo sapiens

<400> SEQUENCE: 381
uggguggucu ggagauuugu gc                                             22

<210> SEQ ID NO 382
<211> LENGTH: 23
<212> TYPE: RNA
<213> ORGANISM: Homo sapiens

<400> SEQUENCE: 382
aaagugcugc gacauuugag cgu                                            23

<210> SEQ ID NO 383
<211> LENGTH: 22
<212> TYPE: RNA
<213> ORGANISM: Homo sapiens

<400> SEQUENCE: 383
aaaaguaauu gcgaguuuua cc                                             22

<210> SEQ ID NO 384
<211> LENGTH: 22
<212> TYPE: RNA
<213> ORGANISM: Homo sapiens

<400> SEQUENCE: 384
aaaaguacuu gcggauuuug cu                                             22

<210> SEQ ID NO 385
<211> LENGTH: 18
<212> TYPE: RNA
<213> ORGANISM: Homo sapiens

<400> SEQUENCE: 385
uugagaagga ggcugcug                                                  18

<210> SEQ ID NO 386
<211> LENGTH: 23
```

<212> TYPE: RNA
<213> ORGANISM: Homo sapiens

<400> SEQUENCE: 386
caagucuuau uugagcaccu guu                                              23

<210> SEQ ID NO 387
<211> LENGTH: 21
<212> TYPE: RNA
<213> ORGANISM: Homo sapiens

<400> SEQUENCE: 387
gcgacccacu cuugguuucc a                                                21

<210> SEQ ID NO 388
<211> LENGTH: 22
<212> TYPE: RNA
<213> ORGANISM: Homo sapiens

<400> SEQUENCE: 388
uagguaguuu ccuguuguug gg                                               22

<210> SEQ ID NO 389
<211> LENGTH: 22
<212> TYPE: RNA
<213> ORGANISM: Homo sapiens

<400> SEQUENCE: 389
caauuuagug ugugugauau uu                                               22

<210> SEQ ID NO 390
<211> LENGTH: 21
<212> TYPE: RNA
<213> ORGANISM: Homo sapiens

<400> SEQUENCE: 390
gugcauugua guugcauugc a                                                21

<210> SEQ ID NO 391
<211> LENGTH: 22
<212> TYPE: RNA
<213> ORGANISM: Homo sapiens

<400> SEQUENCE: 391
aaaaguaauu gugguuuuug cc                                               22

<210> SEQ ID NO 392
<211> LENGTH: 22
<212> TYPE: RNA
<213> ORGANISM: Homo sapiens

<400> SEQUENCE: 392
agucauugga ggguuugagc ag                                               22

<210> SEQ ID NO 393
<211> LENGTH: 22
<212> TYPE: RNA
<213> ORGANISM: Homo sapiens

<400> SEQUENCE: 393
uggauuucuu ugugaaucac ca                                               22

<210> SEQ ID NO 394

```
<211> LENGTH: 23
<212> TYPE: RNA
<213> ORGANISM: Homo sapiens

<400> SEQUENCE: 394
ugauuguagc cuuuggagu aga                                                 23

<210> SEQ ID NO 395
<211> LENGTH: 22
<212> TYPE: RNA
<213> ORGANISM: Homo sapiens

<400> SEQUENCE: 395
ccuauucuug auuacuuguu uc                                                 22

<210> SEQ ID NO 396
<211> LENGTH: 22
<212> TYPE: RNA
<213> ORGANISM: Homo sapiens

<400> SEQUENCE: 396
ucgugucuug uguugcagcc gg                                                 22

<210> SEQ ID NO 397
<211> LENGTH: 22
<212> TYPE: RNA
<213> ORGANISM: Homo sapiens

<400> SEQUENCE: 397
acaguagucu gcacauuggu ua                                                 22

<210> SEQ ID NO 398
<211> LENGTH: 22
<212> TYPE: RNA
<213> ORGANISM: Homo sapiens

<400> SEQUENCE: 398
aaucaugugc agugccaaua ug                                                 22

<210> SEQ ID NO 399
<211> LENGTH: 23
<212> TYPE: RNA
<213> ORGANISM: Homo sapiens

<400> SEQUENCE: 399
uaaggugcau cuagugcagu uag                                                23

<210> SEQ ID NO 400
<211> LENGTH: 21
<212> TYPE: RNA
<213> ORGANISM: Homo sapiens

<400> SEQUENCE: 400
cuggauggcu ccuccauguc u                                                  21

<210> SEQ ID NO 401
<211> LENGTH: 22
<212> TYPE: RNA
<213> ORGANISM: Homo sapiens

<400> SEQUENCE: 401
ugauugguac gucuguggu ag                                                  22
```

```
<210> SEQ ID NO 402
<211> LENGTH: 27
<212> TYPE: RNA
<213> ORGANISM: Homo sapiens

<400> SEQUENCE: 402
cacuguaggu gauggugaga gugggca                                            27

<210> SEQ ID NO 403
<211> LENGTH: 19
<212> TYPE: RNA
<213> ORGANISM: Homo sapiens

<400> SEQUENCE: 403
agcugucuga aaaugucuu                                                     19

<210> SEQ ID NO 404
<211> LENGTH: 22
<212> TYPE: RNA
<213> ORGANISM: Homo sapiens

<400> SEQUENCE: 404
uucacaagga ggugucauuu au                                                 22

<210> SEQ ID NO 405
<211> LENGTH: 22
<212> TYPE: RNA
<213> ORGANISM: Homo sapiens

<400> SEQUENCE: 405
agacuuccca uuugaaggug gc                                                 22

<210> SEQ ID NO 406
<211> LENGTH: 23
<212> TYPE: RNA
<213> ORGANISM: Homo sapiens

<400> SEQUENCE: 406
ucuuugguua ucuagcugua uga                                                23

<210> SEQ ID NO 407
<211> LENGTH: 22
<212> TYPE: RNA
<213> ORGANISM: Homo sapiens

<400> SEQUENCE: 407
aagugccucc uuuuagagug uu                                                 22

<210> SEQ ID NO 408
<211> LENGTH: 22
<212> TYPE: RNA
<213> ORGANISM: Homo sapiens

<400> SEQUENCE: 408
uucccuuugu cauccuaugc cu                                                 22

<210> SEQ ID NO 409
<211> LENGTH: 22
<212> TYPE: RNA
<213> ORGANISM: Homo sapiens

<400> SEQUENCE: 409
uagcaccauu ugaaaucggu ua                                                 22
```

```
<210> SEQ ID NO 410
<211> LENGTH: 18
<212> TYPE: RNA
<213> ORGANISM: Homo sapiens

<400> SEQUENCE: 410
cgggcguggu ggugggg                                          18

<210> SEQ ID NO 411
<211> LENGTH: 22
<212> TYPE: RNA
<213> ORGANISM: Homo sapiens

<400> SEQUENCE: 411
uggaguguga caauguguu ug                                     22

<210> SEQ ID NO 412
<211> LENGTH: 22
<212> TYPE: RNA
<213> ORGANISM: Homo sapiens

<400> SEQUENCE: 412
caacaaaucc cagucuaccu aa                                    22

<210> SEQ ID NO 413
<211> LENGTH: 22
<212> TYPE: RNA
<213> ORGANISM: Homo sapiens

<400> SEQUENCE: 413
caggccauau ugugcugccu ca                                    22

<210> SEQ ID NO 414
<211> LENGTH: 23
<212> TYPE: RNA
<213> ORGANISM: Homo sapiens

<400> SEQUENCE: 414
aacauucauu guugucggug ggu                                   23

<210> SEQ ID NO 415
<211> LENGTH: 21
<212> TYPE: RNA
<213> ORGANISM: Homo sapiens

<400> SEQUENCE: 415
ugauugucca aacgcaauuc u                                     21

<210> SEQ ID NO 416
<211> LENGTH: 23
<212> TYPE: RNA
<213> ORGANISM: Homo sapiens

<400> SEQUENCE: 416
uaagugcuuc cauguuugag ugu                                   23

<210> SEQ ID NO 417
<211> LENGTH: 22
<212> TYPE: RNA
<213> ORGANISM: Homo sapiens

<400> SEQUENCE: 417
uggcaguguc uuagcugguu gu                                    22
```

-continued

```
<210> SEQ ID NO 418
<211> LENGTH: 21
<212> TYPE: RNA
<213> ORGANISM: Homo sapiens

<400> SEQUENCE: 418
aauauaacac agauggccug u                                              21

<210> SEQ ID NO 419
<211> LENGTH: 22
<212> TYPE: RNA
<213> ORGANISM: Homo sapiens

<400> SEQUENCE: 419
caauguuucc acagugcauc ac                                             22

<210> SEQ ID NO 420
<211> LENGTH: 22
<212> TYPE: RNA
<213> ORGANISM: Homo sapiens

<400> SEQUENCE: 420
aaugcaccug ggcaaggauu ca                                             22

<210> SEQ ID NO 421
<211> LENGTH: 21
<212> TYPE: RNA
<213> ORGANISM: Homo sapiens

<400> SEQUENCE: 421
ugguagacua uggaacguag g                                              21

<210> SEQ ID NO 422
<211> LENGTH: 23
<212> TYPE: RNA
<213> ORGANISM: Homo sapiens

<400> SEQUENCE: 422
uuucaagcca gggggcguuu uuc                                            23

<210> SEQ ID NO 423
<211> LENGTH: 22
<212> TYPE: RNA
<213> ORGANISM: Homo sapiens

<400> SEQUENCE: 423
cucuagaggg aagcacuuuc ug                                             22

<210> SEQ ID NO 424
<211> LENGTH: 22
<212> TYPE: RNA
<213> ORGANISM: Homo sapiens

<400> SEQUENCE: 424
auauuaccau uagcucaucu uu                                             22

<210> SEQ ID NO 425
<211> LENGTH: 21
<212> TYPE: RNA
<213> ORGANISM: Homo sapiens

<400> SEQUENCE: 425
```

-continued auccuugcua ucugggugcu a                                              21

<210> SEQ ID NO 426
<211> LENGTH: 21
<212> TYPE: RNA
<213> ORGANISM: Homo sapiens

<400> SEQUENCE: 426
aggcaagaug cuggcauagc u                                              21

<210> SEQ ID NO 427
<211> LENGTH: 22
<212> TYPE: RNA
<213> ORGANISM: Homo sapiens

<400> SEQUENCE: 427
aacccguaga uccgaacuug ug                                             22

<210> SEQ ID NO 428
<211> LENGTH: 22
<212> TYPE: RNA
<213> ORGANISM: Homo sapiens

<400> SEQUENCE: 428
gaggguuggg uggaggcucu cc                                             22

<210> SEQ ID NO 429
<211> LENGTH: 22
<212> TYPE: RNA
<213> ORGANISM: Homo sapiens

<400> SEQUENCE: 429 ggggguccccc ggugcucgga uc                                            22

<210> SEQ ID NO 430
<211> LENGTH: 21
<212> TYPE: RNA
<213> ORGANISM: Homo sapiens

<400> SEQUENCE: 430
caacaccagu cgaugggcug u                                              21

<210> SEQ ID NO 431
<211> LENGTH: 23
<212> TYPE: RNA
<213> ORGANISM: Homo sapiens

<400> SEQUENCE: 431
ggcagguucu cacccucucu agg                                            23

<210> SEQ ID NO 432
<211> LENGTH: 22
<212> TYPE: RNA
<213> ORGANISM: Homo sapiens

<400> SEQUENCE: 432
uuuaggauaa gcuugacuuu ug                                             22

<210> SEQ ID NO 433
<211> LENGTH: 21
<212> TYPE: RNA
<213> ORGANISM: Homo sapiens

<400> SEQUENCE: 433
uggaggagaa ggaaggugau g                                    21

<210> SEQ ID NO 434
<211> LENGTH: 21
<212> TYPE: RNA
<213> ORGANISM: Homo sapiens

<400> SEQUENCE: 434
caaagguauu ugugguuuuu g                                    21

<210> SEQ ID NO 435
<211> LENGTH: 22
<212> TYPE: RNA
<213> ORGANISM: Homo sapiens

<400> SEQUENCE: 435 agaaugugg cuggacaucu gu                                    22

<210> SEQ ID NO 436
<211> LENGTH: 22
<212> TYPE: RNA
<213> ORGANISM: Homo sapiens

<400> SEQUENCE: 436
aaugcacccg ggcaaggauu cu                                   22

<210> SEQ ID NO 437
<211> LENGTH: 23
<212> TYPE: RNA
<213> ORGANISM: Homo sapiens

<400> SEQUENCE: 437
uaagugcuuc cauguuuugg uga                                  23

<210> SEQ ID NO 438
<211> LENGTH: 22
<212> TYPE: RNA
<213> ORGANISM: Homo sapiens

<400> SEQUENCE: 438
uuccuaugca uauacuucuu ug                                   22

<210> SEQ ID NO 439
<211> LENGTH: 22
<212> TYPE: RNA
<213> ORGANISM: Homo sapiens

<400> SEQUENCE: 439
uggaauguaa ggaagugugu gg                                   22

<210> SEQ ID NO 440
<211> LENGTH: 22
<212> TYPE: RNA
<213> ORGANISM: Homo sapiens

<400> SEQUENCE: 440
aaagugcuuc ucuuuggugg gu                                   22

<210> SEQ ID NO 441
<211> LENGTH: 22
<212> TYPE: RNA
<213> ORGANISM: Homo sapiens

```
<400> SEQUENCE: 441
aaaaguaauu gcggauuuug cc                                              22

<210> SEQ ID NO 442
<211> LENGTH: 21
<212> TYPE: RNA
<213> ORGANISM: Homo sapiens

<400> SEQUENCE: 442
gugucuuuug cucugcaguc a                                               21

<210> SEQ ID NO 443
<211> LENGTH: 22
<212> TYPE: RNA
<213> ORGANISM: Homo sapiens

<400> SEQUENCE: 443
uguaaacauc cucgacugga ag                                              22

<210> SEQ ID NO 444
<211> LENGTH: 21
<212> TYPE: RNA
<213> ORGANISM: Homo sapiens

<400> SEQUENCE: 444
ccccaccucc ucucuccuca g                                               21

<210> SEQ ID NO 445
<211> LENGTH: 22
<212> TYPE: RNA
<213> ORGANISM: Homo sapiens

<400> SEQUENCE: 445
gaaggcgcuu cccuuuagag cg                                              22

<210> SEQ ID NO 446
<211> LENGTH: 22
<212> TYPE: RNA
<213> ORGANISM: Homo sapiens

<400> SEQUENCE: 446
guggguacgg cccagugggg gg                                              22

<210> SEQ ID NO 447
<211> LENGTH: 22
<212> TYPE: RNA
<213> ORGANISM: Homo sapiens

<400> SEQUENCE: 447
cguguauuug acaagcugag uu                                              22

<210> SEQ ID NO 448
<211> LENGTH: 22
<212> TYPE: RNA
<213> ORGANISM: Homo sapiens

<400> SEQUENCE: 448
uccgagccug ggucucccuc uu                                              22

<210> SEQ ID NO 449
<211> LENGTH: 22
<212> TYPE: RNA
<213> ORGANISM: Homo sapiens
```

```
<400> SEQUENCE: 449
cgaaaacagc aauuaccuuu gc                                              22

<210> SEQ ID NO 450
<211> LENGTH: 22
<212> TYPE: RNA
<213> ORGANISM: Homo sapiens

<400> SEQUENCE: 450
aaaagcuggg uugagagggc ga                                              22

<210> SEQ ID NO 451
<211> LENGTH: 23
<212> TYPE: RNA
<213> ORGANISM: Homo sapiens

<400> SEQUENCE: 451
uccaguacca cgugucaggg cca                                             23

<210> SEQ ID NO 452
<211> LENGTH: 23
<212> TYPE: RNA
<213> ORGANISM: Homo sapiens

<400> SEQUENCE: 452
uuacaguugu ucaaccaguu acu                                             23

<210> SEQ ID NO 453
<211> LENGTH: 22
<212> TYPE: RNA
<213> ORGANISM: Homo sapiens

<400> SEQUENCE: 453
gagcuuauuc auaaaagugc ag                                              22

<210> SEQ ID NO 454
<211> LENGTH: 22
<212> TYPE: RNA
<213> ORGANISM: Homo sapiens

<400> SEQUENCE: 454
cuugguucag ggaggguccc ca                                              22

<210> SEQ ID NO 455
<211> LENGTH: 21
<212> TYPE: RNA
<213> ORGANISM: Homo sapiens

<400> SEQUENCE: 455
acucuagcug ccaaaggcgc u                                               21

<210> SEQ ID NO 456
<211> LENGTH: 23
<212> TYPE: RNA
<213> ORGANISM: Homo sapiens

<400> SEQUENCE: 456
uauucauuua uccccagccu aca                                             23

<210> SEQ ID NO 457
<211> LENGTH: 21
<212> TYPE: RNA
```

```
<213> ORGANISM: Homo sapiens

<400> SEQUENCE: 457
cccagauaau ggcacucuca a                                             21

<210> SEQ ID NO 458
<211> LENGTH: 22
<212> TYPE: RNA
<213> ORGANISM: Homo sapiens

<400> SEQUENCE: 458
aaaacuguaa uuacuuuugu ac                                            22

<210> SEQ ID NO 459
<211> LENGTH: 23
<212> TYPE: RNA
<213> ORGANISM: Homo sapiens

<400> SEQUENCE: 459
caguaacaaa gauucauccu ugu                                           23

<210> SEQ ID NO 460
<211> LENGTH: 23
<212> TYPE: RNA
<213> ORGANISM: Homo sapiens

<400> SEQUENCE: 460
ucggggauca ucaugucacg aga                                           23

<210> SEQ ID NO 461
<211> LENGTH: 22
<212> TYPE: RNA
<213> ORGANISM: Homo sapiens

<400> SEQUENCE: 461
ugauauguuu gauauauuag gu                                            22

<210> SEQ ID NO 462
<211> LENGTH: 22
<212> TYPE: RNA
<213> ORGANISM: Homo sapiens

<400> SEQUENCE: 462
augguuccgu caagcaccau gg                                            22

<210> SEQ ID NO 463
<211> LENGTH: 22
<212> TYPE: RNA
<213> ORGANISM: Homo sapiens

<400> SEQUENCE: 463
acuguugcua auaugcaacu cu                                            22

<210> SEQ ID NO 464
<211> LENGTH: 22
<212> TYPE: RNA
<213> ORGANISM: Homo sapiens

<400> SEQUENCE: 464
uuuugcgaug uguuccuaau au                                            22

<210> SEQ ID NO 465
<211> LENGTH: 22
```

<212> TYPE: RNA
<213> ORGANISM: Homo sapiens

<400> SEQUENCE: 465
aauugcacuu uagcaauggu ga                                      22

<210> SEQ ID NO 466
<211> LENGTH: 20
<212> TYPE: RNA
<213> ORGANISM: Homo sapiens

<400> SEQUENCE: 466
uaaggcacgc ggugaaugcc                                         20

<210> SEQ ID NO 467
<211> LENGTH: 23
<212> TYPE: RNA
<213> ORGANISM: Homo sapiens

<400> SEQUENCE: 467
ugcaccaugg uugucugagc aug                                     23

<210> SEQ ID NO 468
<211> LENGTH: 23
<212> TYPE: RNA
<213> ORGANISM: Homo sapiens

<400> SEQUENCE: 468
uaauacugcc ggguaaugau gga                                     23

<210> SEQ ID NO 469
<211> LENGTH: 20
<212> TYPE: RNA
<213> ORGANISM: Homo sapiens

<400> SEQUENCE: 469
guccgcucgg cgguggccca                                         20

<210> SEQ ID NO 470
<211> LENGTH: 22
<212> TYPE: RNA
<213> ORGANISM: Homo sapiens

<400> SEQUENCE: 470
cucuagaggg aagcacuuuc ug                                      22

<210> SEQ ID NO 471
<211> LENGTH: 22
<212> TYPE: RNA
<213> ORGANISM: Homo sapiens

<400> SEQUENCE: 471
acaguagagg gaggaaucgc ag                                      22

<210> SEQ ID NO 472
<211> LENGTH: 22
<212> TYPE: RNA
<213> ORGANISM: Homo sapiens

<400> SEQUENCE: 472
caaaaguaau uguggauuuu gu                                      22

<210> SEQ ID NO 473

```
<211> LENGTH: 22
<212> TYPE: RNA
<213> ORGANISM: Homo sapiens

<400> SEQUENCE: 473
uagcuuauca gacugauguu ga                                              22

<210> SEQ ID NO 474
<211> LENGTH: 21
<212> TYPE: RNA
<213> ORGANISM: Homo sapiens

<400> SEQUENCE: 474
ugguucuaga cuugccaacu a                                               21

<210> SEQ ID NO 475
<211> LENGTH: 23
<212> TYPE: RNA
<213> ORGANISM: Homo sapiens

<400> SEQUENCE: 475
aggcagugua guuagcugau ugc                                             23

<210> SEQ ID NO 476
<211> LENGTH: 22
<212> TYPE: RNA
<213> ORGANISM: Homo sapiens

<400> SEQUENCE: 476
uaauacuguc ugguaaaacc gu                                              22

<210> SEQ ID NO 477
<211> LENGTH: 22
<212> TYPE: RNA
<213> ORGANISM: Homo sapiens

<400> SEQUENCE: 477
augcugacau auuuacuaga gg                                              22

<210> SEQ ID NO 478
<211> LENGTH: 22
<212> TYPE: RNA
<213> ORGANISM: Homo sapiens

<400> SEQUENCE: 478
acugauuucu uuggcguuc ag                                               22

<210> SEQ ID NO 479
<211> LENGTH: 22
<212> TYPE: RNA
<213> ORGANISM: Homo sapiens

<400> SEQUENCE: 479
gccugcuggg guggaaccug gu                                              22

<210> SEQ ID NO 480
<211> LENGTH: 21
<212> TYPE: RNA
<213> ORGANISM: Homo sapiens

<400> SEQUENCE: 480
cuauacaauc uacugucuuu c                                               21
```

```
<210> SEQ ID NO 481
<211> LENGTH: 22
<212> TYPE: RNA
<213> ORGANISM: Homo sapiens

<400> SEQUENCE: 481
caguuaucac agugcugaug cu                                                22

<210> SEQ ID NO 482
<211> LENGTH: 21
<212> TYPE: RNA
<213> ORGANISM: Homo sapiens

<400> SEQUENCE: 482
uaaaguaaau augcaccaaa a                                                 21

<210> SEQ ID NO 483
<211> LENGTH: 23
<212> TYPE: RNA
<213> ORGANISM: Homo sapiens

<400> SEQUENCE: 483
uacugcauca ggaacugauu gga                                               23

<210> SEQ ID NO 484
<211> LENGTH: 22
<212> TYPE: RNA
<213> ORGANISM: Homo sapiens

<400> SEQUENCE: 484
cucuagaggg aagcgcuuuc ug                                                22

<210> SEQ ID NO 485
<211> LENGTH: 22
<212> TYPE: RNA
<213> ORGANISM: Homo sapiens

<400> SEQUENCE: 485
cuuucagucg gauguuuaca gc                                                22

<210> SEQ ID NO 486
<211> LENGTH: 20
<212> TYPE: RNA
<213> ORGANISM: Homo sapiens

<400> SEQUENCE: 486
guguguggaa augcuucugc                                                   20

<210> SEQ ID NO 487
<211> LENGTH: 22
<212> TYPE: RNA
<213> ORGANISM: Homo sapiens

<400> SEQUENCE: 487
aaucguacag ggucauccac uu                                                22

<210> SEQ ID NO 488
<211> LENGTH: 22
<212> TYPE: RNA
<213> ORGANISM: Homo sapiens

<400> SEQUENCE: 488
gacugacacc ucuuugggug aa                                                22
```

```
<210> SEQ ID NO 489
<211> LENGTH: 22
<212> TYPE: RNA
<213> ORGANISM: Homo sapiens

<400> SEQUENCE: 489
uccuucauuc caccggaguc ug                                             22

<210> SEQ ID NO 490
<211> LENGTH: 21
<212> TYPE: RNA
<213> ORGANISM: Homo sapiens

<400> SEQUENCE: 490
agugaaugau ggguucugac c                                              21

<210> SEQ ID NO 491
<211> LENGTH: 23
<212> TYPE: RNA
<213> ORGANISM: Homo sapiens

<400> SEQUENCE: 491
uggaagacua gugauuuugu ugu                                            23

<210> SEQ ID NO 492
<211> LENGTH: 21
<212> TYPE: RNA
<213> ORGANISM: Homo sapiens

<400> SEQUENCE: 492 agggccccccc cucaauccug u                                             21

<210> SEQ ID NO 493
<211> LENGTH: 23
<212> TYPE: RNA
<213> ORGANISM: Homo sapiens

<400> SEQUENCE: 493
aggaugagca aagaaaguag auu                                            23

<210> SEQ ID NO 494
<211> LENGTH: 22
<212> TYPE: RNA
<213> ORGANISM: Homo sapiens

<400> SEQUENCE: 494
ugguugacca uagaacaugc gc                                             22

<210> SEQ ID NO 495
<211> LENGTH: 17
<212> TYPE: RNA
<213> ORGANISM: Homo sapiens

<400> SEQUENCE: 495 guggggaga ggcuguc                                                    17

<210> SEQ ID NO 496
<211> LENGTH: 22
<212> TYPE: RNA
<213> ORGANISM: Homo sapiens

<400> SEQUENCE: 496
ucucugggcc ugugucuuag gc                                             22
```

```
<210> SEQ ID NO 497
<211> LENGTH: 22
<212> TYPE: RNA
<213> ORGANISM: Homo sapiens

<400> SEQUENCE: 497
aacuggauca auuauaggag ug                                            22

<210> SEQ ID NO 498
<211> LENGTH: 22
<212> TYPE: RNA
<213> ORGANISM: Homo sapiens

<400> SEQUENCE: 498
caucaucguc ucaaaugagu cu                                            22

<210> SEQ ID NO 499
<211> LENGTH: 22
<212> TYPE: RNA
<213> ORGANISM: Homo sapiens

<400> SEQUENCE: 499
caucuuccag uacaguguug ga                                            22

<210> SEQ ID NO 500
<211> LENGTH: 22
<212> TYPE: RNA
<213> ORGANISM: Homo sapiens

<400> SEQUENCE: 500
aucgugcauc cuuuuagagu gu                                            22

<210> SEQ ID NO 501
<211> LENGTH: 21
<212> TYPE: RNA
<213> ORGANISM: Homo sapiens

<400> SEQUENCE: 501
ggcuagcaac agcgcuuacc u                                             21

<210> SEQ ID NO 502
<211> LENGTH: 22
<212> TYPE: RNA
<213> ORGANISM: Homo sapiens

<400> SEQUENCE: 502
accuugccuu gcugcccggg cc                                            22

<210> SEQ ID NO 503
<211> LENGTH: 22
<212> TYPE: RNA
<213> ORGANISM: Homo sapiens

<400> SEQUENCE: 503
uggugggcac agaaucugga cu                                            22

<210> SEQ ID NO 504
<211> LENGTH: 22
<212> TYPE: RNA
<213> ORGANISM: Homo sapiens

<400> SEQUENCE: 504
```
aaacauucgc ggugcacuuc uu                                              22

<210> SEQ ID NO 505
<211> LENGTH: 22
<212> TYPE: RNA
<213> ORGANISM: Homo sapiens

<400> SEQUENCE: 505
ucuucucugu uuuggccaug ug                                              22

<210> SEQ ID NO 506
<211> LENGTH: 22
<212> TYPE: RNA
<213> ORGANISM: Homo sapiens

<400> SEQUENCE: 506
ccuauucuug guuacuugca cg                                              22

<210> SEQ ID NO 507
<211> LENGTH: 23
<212> TYPE: RNA
<213> ORGANISM: Homo sapiens

<400> SEQUENCE: 507
aguauguucu uccaggacag aac                                             23

<210> SEQ ID NO 508
<211> LENGTH: 22
<212> TYPE: RNA
<213> ORGANISM: Homo sapiens

<400> SEQUENCE: 508
uggacggaga acugauaagg gu                                              22

<210> SEQ ID NO 509
<211> LENGTH: 21
<212> TYPE: RNA
<213> ORGANISM: Homo sapiens

<400> SEQUENCE: 509
aucauagagg aaaauccacg u                                               21

<210> SEQ ID NO 510
<211> LENGTH: 22
<212> TYPE: RNA
<213> ORGANISM: Homo sapiens

<400> SEQUENCE: 510
cguguucaca gcggaccuug au                                              22

<210> SEQ ID NO 511
<211> LENGTH: 24
<212> TYPE: RNA
<213> ORGANISM: Homo sapiens

<400> SEQUENCE: 511
agccuggaag cuggagccug cagu                                            24

<210> SEQ ID NO 512
<211> LENGTH: 21
<212> TYPE: RNA
<213> ORGANISM: Homo sapiens

<400> SEQUENCE: 512

-continued uggcagggag gcugggaggg g								21

<210> SEQ ID NO 513
<211> LENGTH: 22
<212> TYPE: RNA
<213> ORGANISM: Homo sapiens

<400> SEQUENCE: 513
uugagaauga ugaaucauua gg							22

<210> SEQ ID NO 514
<211> LENGTH: 22
<212> TYPE: RNA
<213> ORGANISM: Homo sapiens

<400> SEQUENCE: 514
cuauacaacc uacugccuuc cc							22

<210> SEQ ID NO 515
<211> LENGTH: 22
<212> TYPE: RNA
<213> ORGANISM: Homo sapiens

<400> SEQUENCE: 515
ggagaaauua uccuuggugu gu							22

<210> SEQ ID NO 516
<211> LENGTH: 22
<212> TYPE: RNA
<213> ORGANISM: Homo sapiens

<400> SEQUENCE: 516
aaagugcuuc ccuuuggacu gu							22

<210> SEQ ID NO 517
<211> LENGTH: 19
<212> TYPE: RNA
<213> ORGANISM: Homo sapiens

<400> SEQUENCE: 517
ugggcguauc uguaugcua								19

<210> SEQ ID NO 518
<211> LENGTH: 20
<212> TYPE: RNA
<213> ORGANISM: Homo sapiens

<400> SEQUENCE: 518
cuguaugccc ucaccgcuca								20

<210> SEQ ID NO 519
<211> LENGTH: 21
<212> TYPE: RNA
<213> ORGANISM: Homo sapiens

<400> SEQUENCE: 519
cugacuguug ccguccucca g								21

<210> SEQ ID NO 520
<211> LENGTH: 24
<212> TYPE: RNA
<213> ORGANISM: Homo sapiens

```
<400> SEQUENCE: 520
cugaagugau guguaacuga ucag                                              24

<210> SEQ ID NO 521
<211> LENGTH: 23
<212> TYPE: RNA
<213> ORGANISM: Homo sapiens

<400> SEQUENCE: 521
caaagugcug uucgugcagg uag                                               23

<210> SEQ ID NO 522
<211> LENGTH: 22
<212> TYPE: RNA
<213> ORGANISM: Homo sapiens

<400> SEQUENCE: 522
agggcuuagc ugcuugugag ca                                                22

<210> SEQ ID NO 523
<211> LENGTH: 20
<212> TYPE: RNA
<213> ORGANISM: Homo sapiens

<400> SEQUENCE: 523
aggaauguuc cuucuuugcc                                                   20

<210> SEQ ID NO 524
<211> LENGTH: 22
<212> TYPE: RNA
<213> ORGANISM: Homo sapiens

<400> SEQUENCE: 524
acacagggcu guugugaaga cu                                                22

<210> SEQ ID NO 525
<211> LENGTH: 21
<212> TYPE: RNA
<213> ORGANISM: Homo sapiens

<400> SEQUENCE: 525
gaaggcgcuu cccuuuggag u                                                 21

<210> SEQ ID NO 526
<211> LENGTH: 23
<212> TYPE: RNA
<213> ORGANISM: Homo sapiens

<400> SEQUENCE: 526
uaauccuugc uaccugggug aga                                               23

<210> SEQ ID NO 527
<211> LENGTH: 24
<212> TYPE: RNA
<213> ORGANISM: Homo sapiens

<400> SEQUENCE: 527
agccugauua aacacaugcu cuga                                              24

<210> SEQ ID NO 528
<211> LENGTH: 22
<212> TYPE: RNA
<213> ORGANISM: Homo sapiens
```

-continued

```
<400> SEQUENCE: 528
acugcauuau gagcacuuaa ag                                              22

<210> SEQ ID NO 529
<211> LENGTH: 22
<212> TYPE: RNA
<213> ORGANISM: Homo sapiens

<400> SEQUENCE: 529
ggaggggucc cgcacuggga gg                                              22

<210> SEQ ID NO 530
<211> LENGTH: 22
<212> TYPE: RNA
<213> ORGANISM: Homo sapiens

<400> SEQUENCE: 530
aucgggaaug ucguguccgc cc                                              22

<210> SEQ ID NO 531
<211> LENGTH: 22
<212> TYPE: RNA
<213> ORGANISM: Homo sapiens

<400> SEQUENCE: 531
gagugccuuc uuuuggagcg uu                                              22

<210> SEQ ID NO 532
<211> LENGTH: 22
<212> TYPE: RNA
<213> ORGANISM: Homo sapiens

<400> SEQUENCE: 532
agagguugcc cuuggugaau uc                                              22

<210> SEQ ID NO 533
<211> LENGTH: 22
<212> TYPE: RNA
<213> ORGANISM: Homo sapiens

<400> SEQUENCE: 533
agacccuggu cugcacucua uc                                              22

<210> SEQ ID NO 534
<211> LENGTH: 22
<212> TYPE: RNA
<213> ORGANISM: Homo sapiens

<400> SEQUENCE: 534
caaaaaucuc aauuacuuuu gc                                              22

<210> SEQ ID NO 535
<211> LENGTH: 20
<212> TYPE: RNA
<213> ORGANISM: Homo sapiens

<400> SEQUENCE: 535
uaaagagccc uguggagaca                                                 20

<210> SEQ ID NO 536
<211> LENGTH: 23
<212> TYPE: RNA
```

```
<213> ORGANISM: Homo sapiens

<400> SEQUENCE: 536
agcugguguu gugaaucagg ccg                                          23

<210> SEQ ID NO 537
<211> LENGTH: 21
<212> TYPE: RNA
<213> ORGANISM: Homo sapiens

<400> SEQUENCE: 537
ugucuugcag gccgucaugc a                                            21

<210> SEQ ID NO 538
<211> LENGTH: 22
<212> TYPE: RNA
<213> ORGANISM: Homo sapiens

<400> SEQUENCE: 538
ugaaacauac acgggaaacc uc                                           22

<210> SEQ ID NO 539
<211> LENGTH: 22
<212> TYPE: RNA
<213> ORGANISM: Homo sapiens

<400> SEQUENCE: 539
uugcauaugu aggauguccc au                                           22

<210> SEQ ID NO 540
<211> LENGTH: 23
<212> TYPE: RNA
<213> ORGANISM: Homo sapiens

<400> SEQUENCE: 540
cuaauaguau cuaccacaau aaa                                          23

<210> SEQ ID NO 541
<211> LENGTH: 22
<212> TYPE: RNA
<213> ORGANISM: Homo sapiens

<400> SEQUENCE: 541
aaucauacag ggacauccag uu                                           22

<210> SEQ ID NO 542
<211> LENGTH: 23
<212> TYPE: RNA
<213> ORGANISM: Homo sapiens

<400> SEQUENCE: 542
ucuggcuccg ugucuucacu ccc                                          23

<210> SEQ ID NO 543
<211> LENGTH: 22
<212> TYPE: RNA
<213> ORGANISM: Homo sapiens

<400> SEQUENCE: 543
uauacaaggg cagacucucu cu                                           22

<210> SEQ ID NO 544
<211> LENGTH: 27
```

```
<212> TYPE: RNA
<213> ORGANISM: Homo sapiens

<400> SEQUENCE: 544
auugaucauc gacacuucga acgcaau                                           27

<210> SEQ ID NO 545
<211> LENGTH: 22
<212> TYPE: RNA
<213> ORGANISM: Homo sapiens

<400> SEQUENCE: 545
ucggauccgu cugagcuugg cu                                                22

<210> SEQ ID NO 546
<211> LENGTH: 22
<212> TYPE: RNA
<213> ORGANISM: Homo sapiens

<400> SEQUENCE: 546
uccuguacug agcugccccg ag                                                22

<210> SEQ ID NO 547
<211> LENGTH: 22
<212> TYPE: RNA
<213> ORGANISM: Homo sapiens

<400> SEQUENCE: 547
ucagugcacu acagaacuuu gu                                                22

<210> SEQ ID NO 548
<211> LENGTH: 22
<212> TYPE: RNA
<213> ORGANISM: Homo sapiens

<400> SEQUENCE: 548
ugugagguug gcauuguugu cu                                                22

<210> SEQ ID NO 549
<211> LENGTH: 22
<212> TYPE: RNA
<213> ORGANISM: Homo sapiens

<400> SEQUENCE: 549
aaaaguauuu gcgggutuug uc                                                22

<210> SEQ ID NO 550
<211> LENGTH: 21
<212> TYPE: RNA
<213> ORGANISM: Homo sapiens

<400> SEQUENCE: 550
cauaaaguag aaagcacuac u                                                 21

<210> SEQ ID NO 551
<211> LENGTH: 21
<212> TYPE: RNA
<213> ORGANISM: Homo sapiens

<400> SEQUENCE: 551
uuaauaucgg acaaccauug u                                                 21

<210> SEQ ID NO 552
```

```
<211> LENGTH: 22
<212> TYPE: RNA
<213> ORGANISM: Homo sapiens

<400> SEQUENCE: 552 uaaugcccu aaaaauccuu au                                              22

<210> SEQ ID NO 553
<211> LENGTH: 22
<212> TYPE: RNA
<213> ORGANISM: Homo sapiens

<400> SEQUENCE: 553
cacccguaga accgaccuug cg                                             22

<210> SEQ ID NO 554
<211> LENGTH: 22
<212> TYPE: RNA
<213> ORGANISM: Homo sapiens

<400> SEQUENCE: 554
caucuuacug ggcagcauug ga                                             22

<210> SEQ ID NO 555
<211> LENGTH: 22
<212> TYPE: RNA
<213> ORGANISM: Homo sapiens

<400> SEQUENCE: 555
uaacacuguc ugguaacgau gu                                             22

<210> SEQ ID NO 556
<211> LENGTH: 21
<212> TYPE: RNA
<213> ORGANISM: Homo sapiens

<400> SEQUENCE: 556
aaagcgcuuc ccuucagagu g                                              21

<210> SEQ ID NO 557
<211> LENGTH: 25
<212> TYPE: RNA
<213> ORGANISM: Homo sapiens

<400> SEQUENCE: 557
gcugggcagg gcuucugagc uccuu                                          25

<210> SEQ ID NO 558
<211> LENGTH: 22
<212> TYPE: RNA
<213> ORGANISM: Homo sapiens

<400> SEQUENCE: 558
gugaauuacc gaagggccau aa                                             22

<210> SEQ ID NO 559
<211> LENGTH: 22
<212> TYPE: RNA
<213> ORGANISM: Homo sapiens

<400> SEQUENCE: 559
ucagugcauc acagaacuuu gu                                             22
```

```
<210> SEQ ID NO 560
<211> LENGTH: 23
<212> TYPE: RNA
<213> ORGANISM: Homo sapiens

<400> SEQUENCE: 560
agcagcauug uacagggcua uga                                              23

<210> SEQ ID NO 561
<211> LENGTH: 22
<212> TYPE: RNA
<213> ORGANISM: Homo sapiens

<400> SEQUENCE: 561
ccaaaacugc aguuacuuuu gc                                               22

<210> SEQ ID NO 562
<211> LENGTH: 21
<212> TYPE: RNA
<213> ORGANISM: Homo sapiens

<400> SEQUENCE: 562
cccggagcca ggaugcagcu c                                                21

<210> SEQ ID NO 563
<211> LENGTH: 22
<212> TYPE: RNA
<213> ORGANISM: Homo sapiens

<400> SEQUENCE: 563
uauagggauu ggagccgugg cg                                               22

<210> SEQ ID NO 564
<211> LENGTH: 22
<212> TYPE: RNA
<213> ORGANISM: Homo sapiens

<400> SEQUENCE: 564
agaucagaag gugauugugg cu                                               22

<210> SEQ ID NO 565
<211> LENGTH: 22
<212> TYPE: RNA
<213> ORGANISM: Homo sapiens

<400> SEQUENCE: 565
ucugcccccu ccgcugcugc ca                                               22

<210> SEQ ID NO 566
<211> LENGTH: 23
<212> TYPE: RNA
<213> ORGANISM: Homo sapiens

<400> SEQUENCE: 566
gaagugcuuc gauuuugggg ugu                                              23

<210> SEQ ID NO 567
<211> LENGTH: 20
<212> TYPE: RNA
<213> ORGANISM: Homo sapiens

<400> SEQUENCE: 567
acucaaacug uggggcacu                                                   20
```

```
<210> SEQ ID NO 568
<211> LENGTH: 24
<212> TYPE: RNA
<213> ORGANISM: Homo sapiens

<400> SEQUENCE: 568
agcagaagca gggagguucu ccca                                              24

<210> SEQ ID NO 569
<211> LENGTH: 22
<212> TYPE: RNA
<213> ORGANISM: Homo sapiens

<400> SEQUENCE: 569
uuugugaccu gguccacuaa cc                                                22

<210> SEQ ID NO 570
<211> LENGTH: 23
<212> TYPE: RNA
<213> ORGANISM: Homo sapiens

<400> SEQUENCE: 570
acuucaccug guccacuagc cgu                                               23

<210> SEQ ID NO 571
<211> LENGTH: 23
<212> TYPE: RNA
<213> ORGANISM: Homo sapiens

<400> SEQUENCE: 571
caaagcgcuu cucuuuagag ugu                                               23

<210> SEQ ID NO 572
<211> LENGTH: 24
<212> TYPE: RNA
<213> ORGANISM: Homo sapiens

<400> SEQUENCE: 572
ucagaacaaa ugccgguucc caga                                              24

<210> SEQ ID NO 573
<211> LENGTH: 22
<212> TYPE: RNA
<213> ORGANISM: Homo sapiens

<400> SEQUENCE: 573
acuuguaugc uagcucaggu ag                                                22

<210> SEQ ID NO 574
<211> LENGTH: 22
<212> TYPE: RNA
<213> ORGANISM: Homo sapiens

<400> SEQUENCE: 574
uugugucaau augcgaugau gu                                                22

<210> SEQ ID NO 575
<211> LENGTH: 21
<212> TYPE: RNA
<213> ORGANISM: Homo sapiens

<400> SEQUENCE: 575
cacugugucc uuucugcgua g                                                 21
```

```
<210> SEQ ID NO 576
<211> LENGTH: 22
<212> TYPE: RNA
<213> ORGANISM: Homo sapiens

<400> SEQUENCE: 576
aaauuauugu acaucggaug ag                                              22

<210> SEQ ID NO 577
<211> LENGTH: 22
<212> TYPE: RNA
<213> ORGANISM: Homo sapiens

<400> SEQUENCE: 577
aagaugugga aaaauuggaa uc                                              22

<210> SEQ ID NO 578
<211> LENGTH: 21
<212> TYPE: RNA
<213> ORGANISM: Homo sapiens

<400> SEQUENCE: 578
ucuuguguuc ucuagaucag u                                               21

<210> SEQ ID NO 579
<211> LENGTH: 22
<212> TYPE: RNA
<213> ORGANISM: Homo sapiens

<400> SEQUENCE: 579
gacuauagaa cuuuccccu ca                                               22

<210> SEQ ID NO 580
<211> LENGTH: 18
<212> TYPE: RNA
<213> ORGANISM: Homo sapiens

<400> SEQUENCE: 580
aucccaccuc ugccacca                                                   18

<210> SEQ ID NO 581
<211> LENGTH: 17
<212> TYPE: RNA
<213> ORGANISM: Homo sapiens

<400> SEQUENCE: 581
ucgccuccuc cucuccc                                                    17

<210> SEQ ID NO 582
<211> LENGTH: 21
<212> TYPE: RNA
<213> ORGANISM: Homo sapiens

<400> SEQUENCE: 582
gaacggcuuc auacaggagu u                                               21

<210> SEQ ID NO 583
<211> LENGTH: 22
<212> TYPE: RNA
<213> ORGANISM: Homo sapiens

<400> SEQUENCE: 583
```

```
uuuggucccc uucaaccagc ua                                              22

<210> SEQ ID NO 584
<211> LENGTH: 22
<212> TYPE: RNA
<213> ORGANISM: Homo sapiens

<400> SEQUENCE: 584
ggguggggau uuguugcauu ac                                              22

<210> SEQ ID NO 585
<211> LENGTH: 22
<212> TYPE: RNA
<213> ORGANISM: Homo sapiens

<400> SEQUENCE: 585
caagcuugua ucuauaggua ug                                              22

<210> SEQ ID NO 586
<211> LENGTH: 22
<212> TYPE: RNA
<213> ORGANISM: Homo sapiens

<400> SEQUENCE: 586
ugagaaccac gucugcucug ag                                              22

<210> SEQ ID NO 587
<211> LENGTH: 21
<212> TYPE: RNA
<213> ORGANISM: Homo sapiens

<400> SEQUENCE: 587
uugugcuuga ucuaaccaug u                                               21

<210> SEQ ID NO 588
<211> LENGTH: 21
<212> TYPE: RNA
<213> ORGANISM: Homo sapiens

<400> SEQUENCE: 588
caagucacua gugguuccgu u                                               21

<210> SEQ ID NO 589
<211> LENGTH: 22
<212> TYPE: RNA
<213> ORGANISM: Homo sapiens

<400> SEQUENCE: 589
ccaauauuac ugugcugcuu ua                                              22

<210> SEQ ID NO 590
<211> LENGTH: 23
<212> TYPE: RNA
<213> ORGANISM: Homo sapiens

<400> SEQUENCE: 590
cagugcaaug auauugucaa agc                                             23

<210> SEQ ID NO 591
<211> LENGTH: 21
<212> TYPE: RNA
<213> ORGANISM: Homo sapiens

<400> SEQUENCE: 591
```
ugauauguuu gauaugggu u                                          21

<210> SEQ ID NO 592
<211> LENGTH: 22
<212> TYPE: RNA
<213> ORGANISM: Homo sapiens

<400> SEQUENCE: 592
uuuguucguu cggcucgcgu ga                                        22

<210> SEQ ID NO 593
<211> LENGTH: 22
<212> TYPE: RNA
<213> ORGANISM: Homo sapiens

<400> SEQUENCE: 593
uagcaaaaac ugcaguuacu uu                                        22

<210> SEQ ID NO 594
<211> LENGTH: 22
<212> TYPE: RNA
<213> ORGANISM: Homo sapiens

<400> SEQUENCE: 594
aggggcuggc uuccucugg uc                                         22

<210> SEQ ID NO 595
<211> LENGTH: 22
<212> TYPE: RNA
<213> ORGANISM: Homo sapiens

<400> SEQUENCE: 595
caaagugccu cccuuuagag ug                                        22

<210> SEQ ID NO 596
<211> LENGTH: 23
<212> TYPE: RNA
<213> ORGANISM: Homo sapiens

<400> SEQUENCE: 596
uaaaucccau ggugccuucu ccu                                       23

<210> SEQ ID NO 597
<211> LENGTH: 20
<212> TYPE: RNA
<213> ORGANISM: Homo sapiens

<400> SEQUENCE: 597
guagaggaga uggcgcaggg                                           20

<210> SEQ ID NO 598
<211> LENGTH: 22
<212> TYPE: RNA
<213> ORGANISM: Homo sapiens

<400> SEQUENCE: 598
acaggugagg uucuugggag cc                                        22

<210> SEQ ID NO 599
<211> LENGTH: 22
<212> TYPE: RNA
<213> ORGANISM: Homo sapiens

<400> SEQUENCE: 599
cuguugccac uaaccucaac cu                                              22

<210> SEQ ID NO 600
<211> LENGTH: 22
<212> TYPE: RNA
<213> ORGANISM: Homo sapiens

<400> SEQUENCE: 600
cucuagaggg aagcacuuuc ug                                              22

<210> SEQ ID NO 601
<211> LENGTH: 22
<212> TYPE: RNA
<213> ORGANISM: Homo sapiens

<400> SEQUENCE: 601
aaaguucuga gacacuccga cu                                              22

<210> SEQ ID NO 602
<211> LENGTH: 21
<212> TYPE: RNA
<213> ORGANISM: Homo sapiens

<400> SEQUENCE: 602
uaacagucuc cagucacggc c                                               21

<210> SEQ ID NO 603
<211> LENGTH: 22
<212> TYPE: RNA
<213> ORGANISM: Homo sapiens

<400> SEQUENCE: 603
cgucaacacu ugcugguuuc cu                                              22

<210> SEQ ID NO 604
<211> LENGTH: 22
<212> TYPE: RNA
<213> ORGANISM: Homo sapiens

<400> SEQUENCE: 604
ugaguauuac auggccaauc uc                                              22

<210> SEQ ID NO 605
<211> LENGTH: 22
<212> TYPE: RNA
<213> ORGANISM: Homo sapiens

<400> SEQUENCE: 605
ucaaaacuga ggggcauuuu cu                                              22

<210> SEQ ID NO 606
<211> LENGTH: 22
<212> TYPE: RNA
<213> ORGANISM: Homo sapiens

<400> SEQUENCE: 606
aaaaacugag acuacuuuug ca                                              22

<210> SEQ ID NO 607
<211> LENGTH: 21
<212> TYPE: RNA
<213> ORGANISM: Homo sapiens

<400> SEQUENCE: 607
ucuaguaaga guggcagucg a                                                          21

<210> SEQ ID NO 608
<211> LENGTH: 22
<212> TYPE: RNA
<213> ORGANISM: Homo sapiens

<400> SEQUENCE: 608
cccugugccc ggcccacuuc ug                                                         22

<210> SEQ ID NO 609
<211> LENGTH: 22
<212> TYPE: RNA
<213> ORGANISM: Homo sapiens

<400> SEQUENCE: 609
uuaugguuug ccugggacug ag                                                         22

<210> SEQ ID NO 610
<211> LENGTH: 22
<212> TYPE: RNA
<213> ORGANISM: Homo sapiens

<400> SEQUENCE: 610
auguagggcu aaaagccaug gg                                                         22

<210> SEQ ID NO 611
<211> LENGTH: 21
<212> TYPE: RNA
<213> ORGANISM: Homo sapiens

<400> SEQUENCE: 611
uuaggccgca gaucugggug a                                                          21

<210> SEQ ID NO 612
<211> LENGTH: 22
<212> TYPE: RNA
<213> ORGANISM: Homo sapiens

<400> SEQUENCE: 612
uucaacgggu auuuauugag ca                                                         22

<210> SEQ ID NO 613
<211> LENGTH: 22
<212> TYPE: RNA
<213> ORGANISM: Homo sapiens

<400> SEQUENCE: 613
uuuggucccc uucaaccagc ug                                                         22

<210> SEQ ID NO 614
<211> LENGTH: 22
<212> TYPE: RNA
<213> ORGANISM: Homo sapiens

<400> SEQUENCE: 614
gucauacacg gcucuccucu cu                                                         22

<210> SEQ ID NO 615
<211> LENGTH: 25
<212> TYPE: RNA

```
<213> ORGANISM: Homo sapiens

<400> SEQUENCE: 615
aaaggauucu gcugucgguc ccacu                                          25

<210> SEQ ID NO 616
<211> LENGTH: 22
<212> TYPE: RNA
<213> ORGANISM: Homo sapiens

<400> SEQUENCE: 616
auauaauaca accugcuaag ug                                             22

<210> SEQ ID NO 617
<211> LENGTH: 22
<212> TYPE: RNA
<213> ORGANISM: Homo sapiens

<400> SEQUENCE: 617
aacacaccug guuaaccucu uu                                             22

<210> SEQ ID NO 618
<211> LENGTH: 22
<212> TYPE: RNA
<213> ORGANISM: Homo sapiens

<400> SEQUENCE: 618
aagacgggag gaaagaaggg ag                                             22

<210> SEQ ID NO 619
<211> LENGTH: 22
<212> TYPE: RNA
<213> ORGANISM: Homo sapiens

<400> SEQUENCE: 619
aggcagcggg guguagugga ua                                             22

<210> SEQ ID NO 620
<211> LENGTH: 22
<212> TYPE: RNA
<213> ORGANISM: Homo sapiens

<400> SEQUENCE: 620
cugcgcaagc uacugccuug cu                                             22

<210> SEQ ID NO 621
<211> LENGTH: 23
<212> TYPE: RNA
<213> ORGANISM: Homo sapiens

<400> SEQUENCE: 621
ccaguuaccg cuuccgcuac cgc                                            23

<210> SEQ ID NO 622
<211> LENGTH: 22
<212> TYPE: RNA
<213> ORGANISM: Homo sapiens

<400> SEQUENCE: 622
cagugcaaug augaaagggc au                                             22

<210> SEQ ID NO 623
<211> LENGTH: 18
```

<212> TYPE: RNA
<213> ORGANISM: Homo sapiens

<400> SEQUENCE: 623
gucccuguuc aggcgcca                                                18

<210> SEQ ID NO 624
<211> LENGTH: 22
<212> TYPE: RNA
<213> ORGANISM: Homo sapiens

<400> SEQUENCE: 624
ucaccagccc uguguucccu ag                                           22

<210> SEQ ID NO 625
<211> LENGTH: 22
<212> TYPE: RNA
<213> ORGANISM: Homo sapiens

<400> SEQUENCE: 625
cucuagaggg aagcgcuuuc ug                                           22

<210> SEQ ID NO 626
<211> LENGTH: 22
<212> TYPE: RNA
<213> ORGANISM: Homo sapiens

<400> SEQUENCE: 626
ugagccccug ugccgccccc ag                                           22

<210> SEQ ID NO 627
<211> LENGTH: 21
<212> TYPE: RNA
<213> ORGANISM: Homo sapiens

<400> SEQUENCE: 627
gucagcggag gaaaagaaac u                                            21

<210> SEQ ID NO 628
<211> LENGTH: 22
<212> TYPE: RNA
<213> ORGANISM: Homo sapiens

<400> SEQUENCE: 628
cggcaacaag aaacugccug ag                                           22

<210> SEQ ID NO 629
<211> LENGTH: 23
<212> TYPE: RNA
<213> ORGANISM: Homo sapiens

<400> SEQUENCE: 629
cuggagauau ggaagagcug ugu                                          23

<210> SEQ ID NO 630
<211> LENGTH: 22
<212> TYPE: RNA
<213> ORGANISM: Homo sapiens

<400> SEQUENCE: 630
cuuggcaccu agcaagcacu ca                                           22

<210> SEQ ID NO 631

```
<211> LENGTH: 21
<212> TYPE: RNA
<213> ORGANISM: Homo sapiens

<400> SEQUENCE: 631
ugagcuaaau gugugcuggg a                                              21

<210> SEQ ID NO 632
<211> LENGTH: 22
<212> TYPE: RNA
<213> ORGANISM: Homo sapiens

<400> SEQUENCE: 632
cacgcucaug cacacaccca ca                                             22

<210> SEQ ID NO 633
<211> LENGTH: 20
<212> TYPE: RNA
<213> ORGANISM: Homo sapiens

<400> SEQUENCE: 633
ucguuugccu uuucugcuu                                                 20

<210> SEQ ID NO 634
<211> LENGTH: 22
<212> TYPE: RNA
<213> ORGANISM: Homo sapiens

<400> SEQUENCE: 634
acagauucga uucuagggga au                                             22

<210> SEQ ID NO 635
<211> LENGTH: 22
<212> TYPE: RNA
<213> ORGANISM: Homo sapiens

<400> SEQUENCE: 635
uaaucucagc uggcaacugu ga                                             22

<210> SEQ ID NO 636
<211> LENGTH: 22
<212> TYPE: RNA
<213> ORGANISM: Homo sapiens

<400> SEQUENCE: 636
ggauaucauc auauacugua ag                                             22

<210> SEQ ID NO 637
<211> LENGTH: 22
<212> TYPE: RNA
<213> ORGANISM: Homo sapiens

<400> SEQUENCE: 637
gggguuccug gggaugggau uu                                             22

<210> SEQ ID NO 638
<211> LENGTH: 21
<212> TYPE: RNA
<213> ORGANISM: Homo sapiens

<400> SEQUENCE: 638
uuaagacuug cagugauguu u                                              21
```

```
<210> SEQ ID NO 639
<211> LENGTH: 22
<212> TYPE: RNA
<213> ORGANISM: Homo sapiens

<400> SEQUENCE: 639
uauggcacug guagaauuca cu                                              22

<210> SEQ ID NO 640
<211> LENGTH: 22
<212> TYPE: RNA
<213> ORGANISM: Homo sapiens

<400> SEQUENCE: 640
caaccuggag gacuccaugc ug                                              22

<210> SEQ ID NO 641
<211> LENGTH: 23
<212> TYPE: RNA
<213> ORGANISM: Homo sapiens

<400> SEQUENCE: 641
gcaaagcaca cggccugcag aga                                             23

<210> SEQ ID NO 642
<211> LENGTH: 21
<212> TYPE: RNA
<213> ORGANISM: Homo sapiens

<400> SEQUENCE: 642
cuguacaggc cacugccuug c                                               21

<210> SEQ ID NO 643
<211> LENGTH: 21
<212> TYPE: RNA
<213> ORGANISM: Homo sapiens

<400> SEQUENCE: 643
ucacuccucu ccucccgucu u                                               21

<210> SEQ ID NO 644
<211> LENGTH: 22
<212> TYPE: RNA
<213> ORGANISM: Homo sapiens

<400> SEQUENCE: 644
acagcaggca cagacaggca gu                                              22

<210> SEQ ID NO 645
<211> LENGTH: 23
<212> TYPE: RNA
<213> ORGANISM: Homo sapiens

<400> SEQUENCE: 645
uaggcagugu cauuagcuga uug                                             23

<210> SEQ ID NO 646
<211> LENGTH: 22
<212> TYPE: RNA
<213> ORGANISM: Homo sapiens

<400> SEQUENCE: 646
acuuuaacau ggaggcacuu gc                                              22
```

```
<210> SEQ ID NO 647
<211> LENGTH: 22
<212> TYPE: RNA
<213> ORGANISM: Homo sapiens

<400> SEQUENCE: 647
gaaguuguuc gugguggauu cg                                        22

<210> SEQ ID NO 648
<211> LENGTH: 22
<212> TYPE: RNA
<213> ORGANISM: Homo sapiens

<400> SEQUENCE: 648
acccuaucaa uauugucucu gc                                        22

<210> SEQ ID NO 649
<211> LENGTH: 21
<212> TYPE: RNA
<213> ORGANISM: Homo sapiens

<400> SEQUENCE: 649
gugccagcug caguggggga g                                         21

<210> SEQ ID NO 650
<211> LENGTH: 20
<212> TYPE: RNA
<213> ORGANISM: Homo sapiens

<400> SEQUENCE: 650
agagguauag ggcaugggaa                                           20

<210> SEQ ID NO 651
<211> LENGTH: 22
<212> TYPE: RNA
<213> ORGANISM: Homo sapiens

<400> SEQUENCE: 651
auucugcauu uuuagcaagu uc                                        22

<210> SEQ ID NO 652
<211> LENGTH: 19
<212> TYPE: RNA
<213> ORGANISM: Homo sapiens

<400> SEQUENCE: 652
ugucucugcu gggguuucu                                            19

<210> SEQ ID NO 653
<211> LENGTH: 20
<212> TYPE: RNA
<213> ORGANISM: Homo sapiens

<400> SEQUENCE: 653
cggcucuggg ucuguggga                                            20

<210> SEQ ID NO 654
<211> LENGTH: 21
<212> TYPE: RNA
<213> ORGANISM: Homo sapiens

<400> SEQUENCE: 654
aaggcagggc ccccgcuccc c                                         21
```

```
<210> SEQ ID NO 655
<211> LENGTH: 22
<212> TYPE: RNA
<213> ORGANISM: Homo sapiens

<400> SEQUENCE: 655
cuauacggcc uccuagcuuu cc                                              22

<210> SEQ ID NO 656
<211> LENGTH: 21
<212> TYPE: RNA
<213> ORGANISM: Homo sapiens

<400> SEQUENCE: 656
uccuucugcu ccguccccca g                                               21

<210> SEQ ID NO 657
<211> LENGTH: 22
<212> TYPE: RNA
<213> ORGANISM: Homo sapiens

<400> SEQUENCE: 657
ugcccuaaau gccccuucug gc                                              22

<210> SEQ ID NO 658
<211> LENGTH: 22
<212> TYPE: RNA
<213> ORGANISM: Homo sapiens

<400> SEQUENCE: 658
aguauucugu accagggaag gu                                              22

<210> SEQ ID NO 659
<211> LENGTH: 22
<212> TYPE: RNA
<213> ORGANISM: Homo sapiens

<400> SEQUENCE: 659
uucuccaaaa gggagcacuu uc                                              22

<210> SEQ ID NO 660
<211> LENGTH: 22
<212> TYPE: RNA
<213> ORGANISM: Homo sapiens

<400> SEQUENCE: 660
aacuguuugc agaggaaacu ga                                              22

<210> SEQ ID NO 661
<211> LENGTH: 22
<212> TYPE: RNA
<213> ORGANISM: Homo sapiens

<400> SEQUENCE: 661
ccuguucucc auuacuuggc uc                                              22

<210> SEQ ID NO 662
<211> LENGTH: 22
<212> TYPE: RNA
<213> ORGANISM: Homo sapiens

<400> SEQUENCE: 662
```
aucuggaggu aagaagcacu uu                                          22

<210> SEQ ID NO 663
<211> LENGTH: 22
<212> TYPE: RNA
<213> ORGANISM: Homo sapiens

<400> SEQUENCE: 663 uauguggau gguaaaccgc uu                                           22

<210> SEQ ID NO 664
<211> LENGTH: 22
<212> TYPE: RNA
<213> ORGANISM: Homo sapiens

<400> SEQUENCE: 664
uauacaaggg caagcucucu gu                                          22

<210> SEQ ID NO 665
<211> LENGTH: 22
<212> TYPE: RNA
<213> ORGANISM: Homo sapiens

<400> SEQUENCE: 665
uuauaaagca augagacuga uu                                          22

<210> SEQ ID NO 666
<211> LENGTH: 22
<212> TYPE: RNA
<213> ORGANISM: Homo sapiens

<400> SEQUENCE: 666
uaacagucua cagccauggu cg                                          22

<210> SEQ ID NO 667
<211> LENGTH: 23
<212> TYPE: RNA
<213> ORGANISM: Homo sapiens

<400> SEQUENCE: 667
uguaguguuu ccuacuuuau gga                                         23

<210> SEQ ID NO 668
<211> LENGTH: 22
<212> TYPE: RNA
<213> ORGANISM: Homo sapiens

<400> SEQUENCE: 668
acggguuagg cucuugggag cu                                          22

<210> SEQ ID NO 669
<211> LENGTH: 22
<212> TYPE: RNA
<213> ORGANISM: Homo sapiens

<400> SEQUENCE: 669
cugggagaag gcuguuuacu cu                                          22

<210> SEQ ID NO 670
<211> LENGTH: 22
<212> TYPE: RNA
<213> ORGANISM: Homo sapiens

<400> SEQUENCE: 670
gugagucucu aagaaaagag ga                                                        22

<210> SEQ ID NO 671
<211> LENGTH: 21
<212> TYPE: RNA
<213> ORGANISM: Homo sapiens

<400> SEQUENCE: 671
cggcggggac ggcgauuggu c                                                         21

<210> SEQ ID NO 672
<211> LENGTH: 21
<212> TYPE: RNA
<213> ORGANISM: Homo sapiens

<400> SEQUENCE: 672
ccuguugaag uguaaucccc a                                                         21

<210> SEQ ID NO 673
<211> LENGTH: 21
<212> TYPE: RNA
<213> ORGANISM: Homo sapiens

<400> SEQUENCE: 673
uuuugcaccu uuuggaguga a                                                         21

<210> SEQ ID NO 674
<211> LENGTH: 21
<212> TYPE: RNA
<213> ORGANISM: Homo sapiens

<400> SEQUENCE: 674
caucccuugc augguggagg g                                                         21

<210> SEQ ID NO 675
<211> LENGTH: 21
<212> TYPE: RNA
<213> ORGANISM: Homo sapiens

<400> SEQUENCE: 675
cggggcagcu caguacagga u                                                         21

<210> SEQ ID NO 676
<211> LENGTH: 21
<212> TYPE: RNA
<213> ORGANISM: Homo sapiens

<400> SEQUENCE: 676
aagccugccc ggcuccucgg g                                                         21

<210> SEQ ID NO 677
<211> LENGTH: 22
<212> TYPE: RNA
<213> ORGANISM: Homo sapiens

<400> SEQUENCE: 677
ugggucuuug cgggcgagau ga                                                        22

<210> SEQ ID NO 678
<211> LENGTH: 21
<212> TYPE: RNA
<213> ORGANISM: Homo sapiens

```
<400> SEQUENCE: 678
uccgguucuc agggcuccac c                                              21

<210> SEQ ID NO 679
<211> LENGTH: 22
<212> TYPE: RNA
<213> ORGANISM: Homo sapiens

<400> SEQUENCE: 679
ugccuacuga gcugauauca gu                                             22

<210> SEQ ID NO 680
<211> LENGTH: 22
<212> TYPE: RNA
<213> ORGANISM: Homo sapiens

<400> SEQUENCE: 680
aguuuugcag guuugcauuu ca                                             22

<210> SEQ ID NO 681
<211> LENGTH: 18
<212> TYPE: RNA
<213> ORGANISM: Homo sapiens

<400> SEQUENCE: 681
gcaugggugg uucagugg                                                  18

<210> SEQ ID NO 682
<211> LENGTH: 22
<212> TYPE: RNA
<213> ORGANISM: Homo sapiens

<400> SEQUENCE: 682
auaagacgag caaaaagcuu gu                                             22

<210> SEQ ID NO 683
<211> LENGTH: 23
<212> TYPE: RNA
<213> ORGANISM: Homo sapiens

<400> SEQUENCE: 683
uauggcuuuu uauuccuaug uga                                            23

<210> SEQ ID NO 684
<211> LENGTH: 22
<212> TYPE: RNA
<213> ORGANISM: Homo sapiens

<400> SEQUENCE: 684
cuagguaugg ucccagggau cc                                             22

<210> SEQ ID NO 685
<211> LENGTH: 22
<212> TYPE: RNA
<213> ORGANISM: Homo sapiens

<400> SEQUENCE: 685
aacauucaac cugucgguga gu                                             22

<210> SEQ ID NO 686
<211> LENGTH: 21
<212> TYPE: RNA
<213> ORGANISM: Homo sapiens
```

-continued

```
<400> SEQUENCE: 686
augauccagg aaccugccuc u                                              21

<210> SEQ ID NO 687
<211> LENGTH: 22
<212> TYPE: RNA
<213> ORGANISM: Homo sapiens

<400> SEQUENCE: 687
cgcaggggcc gggugcucac cg                                             22

<210> SEQ ID NO 688
<211> LENGTH: 21
<212> TYPE: RNA
<213> ORGANISM: Homo sapiens

<400> SEQUENCE: 688
uggguuuacg uugggagaac u                                              21

<210> SEQ ID NO 689
<211> LENGTH: 23
<212> TYPE: RNA
<213> ORGANISM: Homo sapiens

<400> SEQUENCE: 689
uacccuguag auccgaauuu gug                                            23

<210> SEQ ID NO 690
<211> LENGTH: 22
<212> TYPE: RNA
<213> ORGANISM: Homo sapiens

<400> SEQUENCE: 690 agugggaac ccuuccauga gg                                              22

<210> SEQ ID NO 691
<211> LENGTH: 23
<212> TYPE: RNA
<213> ORGANISM: Homo sapiens

<400> SEQUENCE: 691
aggaccugcg ggacaagauu cuu                                            23

<210> SEQ ID NO 692
<211> LENGTH: 23
<212> TYPE: RNA
<213> ORGANISM: Homo sapiens

<400> SEQUENCE: 692
uucucgagga aagaagcacu uuc                                            23

<210> SEQ ID NO 693
<211> LENGTH: 22
<212> TYPE: RNA
<213> ORGANISM: Homo sapiens

<400> SEQUENCE: 693
uacucaggag aguggcaauc ac                                             22

<210> SEQ ID NO 694
<211> LENGTH: 20
<212> TYPE: RNA
```

```
<213> ORGANISM: Homo sapiens

<400> SEQUENCE: 694
ccccagggcg acgcggcggg                                               20

<210> SEQ ID NO 695
<211> LENGTH: 23
<212> TYPE: RNA
<213> ORGANISM: Homo sapiens

<400> SEQUENCE: 695
ucucuggagg gaagcacuuu cug                                           23

<210> SEQ ID NO 696
<211> LENGTH: 25
<212> TYPE: RNA
<213> ORGANISM: Homo sapiens

<400> SEQUENCE: 696
gggcgacaaa gcaagacucu uucuu                                         25

<210> SEQ ID NO 697
<211> LENGTH: 21
<212> TYPE: RNA
<213> ORGANISM: Homo sapiens

<400> SEQUENCE: 697
aggcggagac uugggcaauu g                                             21

<210> SEQ ID NO 698
<211> LENGTH: 22
<212> TYPE: RNA
<213> ORGANISM: Homo sapiens

<400> SEQUENCE: 698
ugcggggcua gggcuaacag ca                                            22

<210> SEQ ID NO 699
<211> LENGTH: 23
<212> TYPE: RNA
<213> ORGANISM: Homo sapiens

<400> SEQUENCE: 699
agugccugag ggaguaagag ccc                                           23

<210> SEQ ID NO 700
<211> LENGTH: 21
<212> TYPE: RNA
<213> ORGANISM: Homo sapiens

<400> SEQUENCE: 700
uacuuggaaa ggcaucaguu g                                             21

<210> SEQ ID NO 701
<211> LENGTH: 22
<212> TYPE: RNA
<213> ORGANISM: Homo sapiens

<400> SEQUENCE: 701
uuuagagacg gggucuugcu cu                                            22

<210> SEQ ID NO 702
<211> LENGTH: 21
```

```
<212> TYPE: RNA
<213> ORGANISM: Homo sapiens

<400> SEQUENCE: 702
aggaggcagc gcucucagga c                                           21

<210> SEQ ID NO 703
<211> LENGTH: 20
<212> TYPE: RNA
<213> ORGANISM: Homo sapiens

<400> SEQUENCE: 703
cgugccaccc uuuuccccag                                             20

<210> SEQ ID NO 704
<211> LENGTH: 21
<212> TYPE: RNA
<213> ORGANISM: Homo sapiens

<400> SEQUENCE: 704
gaagugugcc gugguguguc u                                           21

<210> SEQ ID NO 705
<211> LENGTH: 22
<212> TYPE: RNA
<213> ORGANISM: Homo sapiens

<400> SEQUENCE: 705
cggaugagca aagaaagugg uu                                          22

<210> SEQ ID NO 706
<211> LENGTH: 22
<212> TYPE: RNA
<213> ORGANISM: Homo sapiens

<400> SEQUENCE: 706
agaaggaaau ugaauucauu ua                                          22

<210> SEQ ID NO 707
<211> LENGTH: 21
<212> TYPE: RNA
<213> ORGANISM: Homo sapiens

<400> SEQUENCE: 707
gcaguccaug ggcauauaca c                                           21

<210> SEQ ID NO 708
<211> LENGTH: 22
<212> TYPE: RNA
<213> ORGANISM: Homo sapiens

<400> SEQUENCE: 708
gcugacuccu aguccagggc uc                                          22

<210> SEQ ID NO 709
<211> LENGTH: 23
<212> TYPE: RNA
<213> ORGANISM: Homo sapiens

<400> SEQUENCE: 709
uuuggcacua gcacauuuuu gcu                                         23

<210> SEQ ID NO 710
```

```
<211> LENGTH: 18
<212> TYPE: RNA
<213> ORGANISM: Homo sapiens

<400> SEQUENCE: 710
cagggaggug aaugugau                                                    18

<210> SEQ ID NO 711
<211> LENGTH: 22
<212> TYPE: RNA
<213> ORGANISM: Homo sapiens

<400> SEQUENCE: 711
uucucaagga ggugucguuu au                                               22

<210> SEQ ID NO 712
<211> LENGTH: 22
<212> TYPE: RNA
<213> ORGANISM: Homo sapiens

<400> SEQUENCE: 712
aaaaguaauu gcgguuuuug cc                                               22

<210> SEQ ID NO 713
<211> LENGTH: 22
<212> TYPE: RNA
<213> ORGANISM: Homo sapiens

<400> SEQUENCE: 713
aggcggggcg ccgcgggacc gc                                               22

<210> SEQ ID NO 714
<211> LENGTH: 20
<212> TYPE: RNA
<213> ORGANISM: Homo sapiens

<400> SEQUENCE: 714
aaaagcuggg uugagagggu                                                  20

<210> SEQ ID NO 715
<211> LENGTH: 22
<212> TYPE: RNA
<213> ORGANISM: Homo sapiens

<400> SEQUENCE: 715
aaaagcuggg uugagagggc aa                                               22

<210> SEQ ID NO 716
<211> LENGTH: 22
<212> TYPE: RNA
<213> ORGANISM: Homo sapiens

<400> SEQUENCE: 716
uggugggccg cagaacaugu gc                                               22

<210> SEQ ID NO 717
<211> LENGTH: 20
<212> TYPE: RNA
<213> ORGANISM: Homo sapiens

<400> SEQUENCE: 717 ccucuggggcc cuuccuccag                                                 20
```

```
<210> SEQ ID NO 718
<211> LENGTH: 18
<212> TYPE: RNA
<213> ORGANISM: Homo sapiens

<400> SEQUENCE: 718
uccagugccc uccucucc                                                    18

<210> SEQ ID NO 719
<211> LENGTH: 22
<212> TYPE: RNA
<213> ORGANISM: Homo sapiens

<400> SEQUENCE: 719
cuggcccucu cugcccuucc gu                                               22

<210> SEQ ID NO 720
<211> LENGTH: 22
<212> TYPE: RNA
<213> ORGANISM: Homo sapiens

<400> SEQUENCE: 720
ugagaacuga auuccauagg cu                                               22

<210> SEQ ID NO 721
<211> LENGTH: 21
<212> TYPE: RNA
<213> ORGANISM: Homo sapiens

<400> SEQUENCE: 721
cgcgggugcu uacugacccu u                                                21

<210> SEQ ID NO 722
<211> LENGTH: 21
<212> TYPE: RNA
<213> ORGANISM: Homo sapiens

<400> SEQUENCE: 722
ugagugccgg ugccugcccu g                                                21

<210> SEQ ID NO 723
<211> LENGTH: 22
<212> TYPE: RNA
<213> ORGANISM: Homo sapiens

<400> SEQUENCE: 723
cucggcgcgg ggcgcgggcu cc                                               22

<210> SEQ ID NO 724
<211> LENGTH: 22
<212> TYPE: RNA
<213> ORGANISM: Homo sapiens

<400> SEQUENCE: 724
uccagcauca gugauuuugu ug                                               22

<210> SEQ ID NO 725
<211> LENGTH: 23
<212> TYPE: RNA
<213> ORGANISM: Homo sapiens

<400> SEQUENCE: 725
cgggucggag uuagcucaag cgg                                              23
```

```
<210> SEQ ID NO 726
<211> LENGTH: 22
<212> TYPE: RNA
<213> ORGANISM: Homo sapiens

<400> SEQUENCE: 726
uggucuagga uuguuggagg ag                                                  22

<210> SEQ ID NO 727
<211> LENGTH: 22
<212> TYPE: RNA
<213> ORGANISM: Homo sapiens

<400> SEQUENCE: 727
uucauucggc uguccagaug ua                                                  22

<210> SEQ ID NO 728
<211> LENGTH: 21
<212> TYPE: RNA
<213> ORGANISM: Homo sapiens

<400> SEQUENCE: 728
ccaguccugu gccugccgcc u                                                   21

<210> SEQ ID NO 729
<211> LENGTH: 26
<212> TYPE: RNA
<213> ORGANISM: Homo sapiens

<400> SEQUENCE: 729
gugagggcau gcaggccugg augggg                                              26

<210> SEQ ID NO 730
<211> LENGTH: 23
<212> TYPE: RNA
<213> ORGANISM: Homo sapiens

<400> SEQUENCE: 730
aucaacagac auuaauuggg cgc                                                 23

<210> SEQ ID NO 731
<211> LENGTH: 22
<212> TYPE: RNA
<213> ORGANISM: Homo sapiens

<400> SEQUENCE: 731
gcccgcgugu ggagccaggu gu                                                  22

<210> SEQ ID NO 732
<211> LENGTH: 22
<212> TYPE: RNA
<213> ORGANISM: Homo sapiens

<400> SEQUENCE: 732
cugguacagg ccuggggac ag                                                   22

<210> SEQ ID NO 733
<211> LENGTH: 23
<212> TYPE: RNA
<213> ORGANISM: Homo sapiens

<400> SEQUENCE: 733
cucucaccac ugcccuccca cag                                                 23
```

```
<210> SEQ ID NO 734
<211> LENGTH: 22
<212> TYPE: RNA
<213> ORGANISM: Homo sapiens

<400> SEQUENCE: 734
acugcaguga aggcacuugu ag                                              22

<210> SEQ ID NO 735
<211> LENGTH: 19
<212> TYPE: RNA
<213> ORGANISM: Homo sapiens

<400> SEQUENCE: 735
aaaagcuggg uugagagga                                                  19

<210> SEQ ID NO 736
<211> LENGTH: 23
<212> TYPE: RNA
<213> ORGANISM: Homo sapiens

<400> SEQUENCE: 736
uacccuguag aaccgaauuu gug                                             23

<210> SEQ ID NO 737
<211> LENGTH: 22
<212> TYPE: RNA
<213> ORGANISM: Homo sapiens

<400> SEQUENCE: 737
acuccagccc cacagccuca gc                                              22

<210> SEQ ID NO 738
<211> LENGTH: 23
<212> TYPE: RNA
<213> ORGANISM: Homo sapiens

<400> SEQUENCE: 738
acuuacagac aagagccuug cuc                                             23

<210> SEQ ID NO 739
<211> LENGTH: 24
<212> TYPE: RNA
<213> ORGANISM: Homo sapiens

<400> SEQUENCE: 739
aaagacauag gauagaguca ccuc                                            24

<210> SEQ ID NO 740
<211> LENGTH: 22
<212> TYPE: RNA
<213> ORGANISM: Homo sapiens

<400> SEQUENCE: 740
uccgucucag uuacuuuaua gc                                              22

<210> SEQ ID NO 741
<211> LENGTH: 22
<212> TYPE: RNA
<213> ORGANISM: Homo sapiens

<400> SEQUENCE: 741
```
acucaaaacc cuucagugac uu                                             22

<210> SEQ ID NO 742
<211> LENGTH: 21
<212> TYPE: RNA
<213> ORGANISM: Homo sapiens

<400> SEQUENCE: 742
cuccagaggg aaguacuuuc u                                              21

<210> SEQ ID NO 743
<211> LENGTH: 21
<212> TYPE: RNA
<213> ORGANISM: Homo sapiens

<400> SEQUENCE: 743
aagcauucuu ucauugguug g                                              21

<210> SEQ ID NO 744
<211> LENGTH: 21
<212> TYPE: RNA
<213> ORGANISM: Homo sapiens

<400> SEQUENCE: 744
uugcucacug uucuucccua g                                              21

<210> SEQ ID NO 745
<211> LENGTH: 22
<212> TYPE: RNA
<213> ORGANISM: Homo sapiens

<400> SEQUENCE: 745
cugggaggug gauguuuacu uc                                             22

<210> SEQ ID NO 746
<211> LENGTH: 22
<212> TYPE: RNA
<213> ORGANISM: Homo sapiens

<400> SEQUENCE: 746
cuccuacaua uuagcauuaa ca                                             22

<210> SEQ ID NO 747
<211> LENGTH: 22
<212> TYPE: RNA
<213> ORGANISM: Homo sapiens

<400> SEQUENCE: 747
gcuacuucac aacaccaggg cc                                             22

<210> SEQ ID NO 748
<211> LENGTH: 22
<212> TYPE: RNA
<213> ORGANISM: Homo sapiens

<400> SEQUENCE: 748
aauccuuugu cccuggguga ga                                             22

<210> SEQ ID NO 749
<211> LENGTH: 23
<212> TYPE: RNA
<213> ORGANISM: Homo sapiens

<400> SEQUENCE: 749

```
caacggaauc ccaaaagcag cug                                            23

<210> SEQ ID NO 750
<211> LENGTH: 23
<212> TYPE: RNA
<213> ORGANISM: Homo sapiens

<400> SEQUENCE: 750
agcagcauug uacagggcua uca                                            23

<210> SEQ ID NO 751
<211> LENGTH: 23
<212> TYPE: RNA
<213> ORGANISM: Homo sapiens

<400> SEQUENCE: 751
aucgcugcgg uugcgagcgc ugu                                            23

<210> SEQ ID NO 752
<211> LENGTH: 21
<212> TYPE: RNA
<213> ORGANISM: Homo sapiens

<400> SEQUENCE: 752
caaagcgcuu cccuuuggag c                                              21

<210> SEQ ID NO 753
<211> LENGTH: 21
<212> TYPE: RNA
<213> ORGANISM: Homo sapiens

<400> SEQUENCE: 753
uaaagugcug acagugcaga u                                              21

<210> SEQ ID NO 754
<211> LENGTH: 22
<212> TYPE: RNA
<213> ORGANISM: Homo sapiens

<400> SEQUENCE: 754
aagcccuuac cccaaaaagc au                                             22

<210> SEQ ID NO 755
<211> LENGTH: 18
<212> TYPE: RNA
<213> ORGANISM: Homo sapiens

<400> SEQUENCE: 755
acguuggcuc ugguggug                                                  18

<210> SEQ ID NO 756
<211> LENGTH: 22
<212> TYPE: RNA
<213> ORGANISM: Homo sapiens

<400> SEQUENCE: 756
ggcuacaaca caggacccgg gc                                             22

<210> SEQ ID NO 757
<211> LENGTH: 22
<212> TYPE: RNA
<213> ORGANISM: Homo sapiens
```

```
<400> SEQUENCE: 757
ucccugagac ccuaacuugu ga                                            22

<210> SEQ ID NO 758
<211> LENGTH: 22
<212> TYPE: RNA
<213> ORGANISM: Homo sapiens

<400> SEQUENCE: 758
gucccucucc aaaugugucu ug                                            22

<210> SEQ ID NO 759
<211> LENGTH: 22
<212> TYPE: RNA
<213> ORGANISM: Homo sapiens

<400> SEQUENCE: 759
cuuucagucg gauguuugca gc                                            22

<210> SEQ ID NO 760
<211> LENGTH: 22
<212> TYPE: RNA
<213> ORGANISM: Homo sapiens

<400> SEQUENCE: 760
ucuacagugc acgugucucc ag                                            22

<210> SEQ ID NO 761
<211> LENGTH: 22
<212> TYPE: RNA
<213> ORGANISM: Homo sapiens

<400> SEQUENCE: 761
acucggcgug gcgucggucg ug                                            22

<210> SEQ ID NO 762
<211> LENGTH: 23
<212> TYPE: RNA
<213> ORGANISM: Homo sapiens

<400> SEQUENCE: 762
cugggaucuc cggggucuug guu                                           23

<210> SEQ ID NO 763
<211> LENGTH: 22
<212> TYPE: RNA
<213> ORGANISM: Homo sapiens

<400> SEQUENCE: 763
caugccuuga guguaggacc gu                                            22

<210> SEQ ID NO 764
<211> LENGTH: 22
<212> TYPE: RNA
<213> ORGANISM: Homo sapiens

<400> SEQUENCE: 764
caacaaauca cagucugcca ua                                            22

<210> SEQ ID NO 765
<211> LENGTH: 22
<212> TYPE: RNA
<213> ORGANISM: Homo sapiens
```

```
<400> SEQUENCE: 765
uagguaguuu cauguuguug gg                                          22

<210> SEQ ID NO 766
<211> LENGTH: 22
<212> TYPE: RNA
<213> ORGANISM: Homo sapiens

<400> SEQUENCE: 766
uuagggcccu ggcuccaucu cc                                          22

<210> SEQ ID NO 767
<211> LENGTH: 22
<212> TYPE: RNA
<213> ORGANISM: Homo sapiens

<400> SEQUENCE: 767
gcugcgcuug gauuucgucc cc                                          22

<210> SEQ ID NO 768
<211> LENGTH: 23
<212> TYPE: RNA
<213> ORGANISM: Homo sapiens

<400> SEQUENCE: 768
agcuacauug ucugcugggu uuc                                         23

<210> SEQ ID NO 769
<211> LENGTH: 23
<212> TYPE: RNA
<213> ORGANISM: Homo sapiens

<400> SEQUENCE: 769
agguugggau cgguugcaau gcu                                         23

<210> SEQ ID NO 770
<211> LENGTH: 22
<212> TYPE: RNA
<213> ORGANISM: Homo sapiens

<400> SEQUENCE: 770
ucugggcaac aaagugagac cu                                          22

<210> SEQ ID NO 771
<211> LENGTH: 22
<212> TYPE: RNA
<213> ORGANISM: Homo sapiens

<400> SEQUENCE: 771
cucuagaggg aagcacuuuc uc                                          22

<210> SEQ ID NO 772
<211> LENGTH: 20
<212> TYPE: RNA
<213> ORGANISM: Homo sapiens

<400> SEQUENCE: 772
ugagcccugu ccucccgcag                                             20

<210> SEQ ID NO 773
<211> LENGTH: 19
<212> TYPE: RNA
```

<213> ORGANISM: Homo sapiens

<400> SEQUENCE: 773
uggauuuuug gaucaggga                                        19

<210> SEQ ID NO 774
<211> LENGTH: 22
<212> TYPE: RNA
<213> ORGANISM: Homo sapiens

<400> SEQUENCE: 774
uacgucaucg uugucaucgu ca                                    22

<210> SEQ ID NO 775
<211> LENGTH: 22
<212> TYPE: RNA
<213> ORGANISM: Homo sapiens

<400> SEQUENCE: 775
ugagaccucu ggguucugag cu                                    22

<210> SEQ ID NO 776
<211> LENGTH: 23
<212> TYPE: RNA
<213> ORGANISM: Homo sapiens

<400> SEQUENCE: 776
gaacgccugu ucuugccagg ugg                                   23

<210> SEQ ID NO 777
<211> LENGTH: 21
<212> TYPE: RNA
<213> ORGANISM: Homo sapiens

<400> SEQUENCE: 777
cuucuugugc ucuaggauug u                                     21

<210> SEQ ID NO 778
<211> LENGTH: 24
<212> TYPE: RNA
<213> ORGANISM: Homo sapiens

<400> SEQUENCE: 778
uugcagcugc cugggaguga cuuc                                  24

<210> SEQ ID NO 779
<211> LENGTH: 24
<212> TYPE: RNA
<213> ORGANISM: Homo sapiens

<400> SEQUENCE: 779
uucuccaaaa gaaagcacuu ucug                                  24

<210> SEQ ID NO 780
<211> LENGTH: 19
<212> TYPE: RNA
<213> ORGANISM: Homo sapiens

<400> SEQUENCE: 780
aggcacggug ucagcaggc                                        19

<210> SEQ ID NO 781
<211> LENGTH: 22

```
<212> TYPE: RNA
<213> ORGANISM: Homo sapiens

<400> SEQUENCE: 781
aaccagcacc ccaacuuugg ac                                              22

<210> SEQ ID NO 782
<211> LENGTH: 22
<212> TYPE: RNA
<213> ORGANISM: Homo sapiens

<400> SEQUENCE: 782
caaagcgcuc cccuuuagag gu                                              22

<210> SEQ ID NO 783
<211> LENGTH: 23
<212> TYPE: RNA
<213> ORGANISM: Homo sapiens

<400> SEQUENCE: 783
cacccggcug ugugcacaug ugc                                             23

<210> SEQ ID NO 784
<211> LENGTH: 21
<212> TYPE: RNA
<213> ORGANISM: Homo sapiens

<400> SEQUENCE: 784
aacauagagg aaauuccacg u                                               21

<210> SEQ ID NO 785
<211> LENGTH: 22
<212> TYPE: RNA
<213> ORGANISM: Homo sapiens

<400> SEQUENCE: 785
ccaauauugg cugugcugcu cc                                              22

<210> SEQ ID NO 786
<211> LENGTH: 20
<212> TYPE: RNA
<213> ORGANISM: Homo sapiens

<400> SEQUENCE: 786
cugcaaaggg aagcccuuuc                                                 20

<210> SEQ ID NO 787
<211> LENGTH: 23
<212> TYPE: RNA
<213> ORGANISM: Homo sapiens

<400> SEQUENCE: 787
guuugcacgg gugggccuug ucu                                             23

<210> SEQ ID NO 788
<211> LENGTH: 21
<212> TYPE: RNA
<213> ORGANISM: Homo sapiens

<400> SEQUENCE: 788
gugggcgggg gcaggugugu g                                               21

<210> SEQ ID NO 789
```

```
<211> LENGTH: 22
<212> TYPE: RNA
<213> ORGANISM: Homo sapiens

<400> SEQUENCE: 789
aguucuucag uggcaagcuu ua                                              22

<210> SEQ ID NO 790
<211> LENGTH: 22
<212> TYPE: RNA
<213> ORGANISM: Homo sapiens

<400> SEQUENCE: 790
ucggccugac cacccacccc ac                                              22

<210> SEQ ID NO 791
<211> LENGTH: 21
<212> TYPE: RNA
<213> ORGANISM: Homo sapiens

<400> SEQUENCE: 791
agggagggac gggggcugug c                                               21

<210> SEQ ID NO 792
<211> LENGTH: 22
<212> TYPE: RNA
<213> ORGANISM: Homo sapiens

<400> SEQUENCE: 792
cugggagagg guuguuuacu cc                                              22

<210> SEQ ID NO 793
<211> LENGTH: 22
<212> TYPE: RNA
<213> ORGANISM: Homo sapiens

<400> SEQUENCE: 793
cgucuuaccc agcaguguuu gg                                              22

<210> SEQ ID NO 794
<211> LENGTH: 21
<212> TYPE: RNA
<213> ORGANISM: Homo sapiens

<400> SEQUENCE: 794
ccgucgccgc cacccgagcc g                                               21

<210> SEQ ID NO 795
<211> LENGTH: 22
<212> TYPE: RNA
<213> ORGANISM: Homo sapiens

<400> SEQUENCE: 795
aggugguccg uggcgcguuc gc                                              22

<210> SEQ ID NO 796
<211> LENGTH: 20
<212> TYPE: RNA
<213> ORGANISM: Homo sapiens

<400> SEQUENCE: 796
gugucugggc ggacagcugc                                                 20
```

```
<210> SEQ ID NO 797
<211> LENGTH: 22
<212> TYPE: RNA
<213> ORGANISM: Homo sapiens

<400> SEQUENCE: 797
gugaaauguu uaggaccacu ag                                              22

<210> SEQ ID NO 798
<211> LENGTH: 22
<212> TYPE: RNA
<213> ORGANISM: Homo sapiens

<400> SEQUENCE: 798
uuuaacaugg ggguaccugc ug                                              22

<210> SEQ ID NO 799
<211> LENGTH: 22
<212> TYPE: RNA
<213> ORGANISM: Homo sapiens

<400> SEQUENCE: 799
aacccguaga uccgaucuug ug                                              22

<210> SEQ ID NO 800
<211> LENGTH: 22
<212> TYPE: RNA
<213> ORGANISM: Homo sapiens

<400> SEQUENCE: 800
ugagaacuga auuccauggg uu                                              22

<210> SEQ ID NO 801
<211> LENGTH: 21
<212> TYPE: RNA
<213> ORGANISM: Homo sapiens

<400> SEQUENCE: 801
aauauuauac agucaaccuc u                                               21

<210> SEQ ID NO 802
<211> LENGTH: 22
<212> TYPE: RNA
<213> ORGANISM: Homo sapiens

<400> SEQUENCE: 802
gaaagugcuu ccuuuuagag gc                                              22

<210> SEQ ID NO 803
<211> LENGTH: 22
<212> TYPE: RNA
<213> ORGANISM: Homo sapiens

<400> SEQUENCE: 803
aaguucuguu auacacucag gc                                              22

<210> SEQ ID NO 804
<211> LENGTH: 23
<212> TYPE: RNA
<213> ORGANISM: Homo sapiens

<400> SEQUENCE: 804
aacauucaac gcugucggug agu                                             23
```

```
<210> SEQ ID NO 805
<211> LENGTH: 21
<212> TYPE: RNA
<213> ORGANISM: Homo sapiens

<400> SEQUENCE: 805
acagucugcu gagguuggag c                                           21

<210> SEQ ID NO 806
<211> LENGTH: 24
<212> TYPE: RNA
<213> ORGANISM: Homo sapiens

<400> SEQUENCE: 806
ucccugagac ccuuuaaccu guga                                        24

<210> SEQ ID NO 807
<211> LENGTH: 21
<212> TYPE: RNA
<213> ORGANISM: Homo sapiens

<400> SEQUENCE: 807
ucagugcaug acagaacuug g                                           21

<210> SEQ ID NO 808
<211> LENGTH: 22
<212> TYPE: RNA
<213> ORGANISM: Homo sapiens

<400> SEQUENCE: 808
uucaccaccu ucuccaccca gc                                          22

<210> SEQ ID NO 809
<211> LENGTH: 21
<212> TYPE: RNA
<213> ORGANISM: Homo sapiens

<400> SEQUENCE: 809
uucacagugg cuaaguucug c                                           21

<210> SEQ ID NO 810
<211> LENGTH: 22
<212> TYPE: RNA
<213> ORGANISM: Homo sapiens

<400> SEQUENCE: 810
ccucuucccc uugucucucc ag                                          22

<210> SEQ ID NO 811
<211> LENGTH: 22
<212> TYPE: RNA
<213> ORGANISM: Homo sapiens

<400> SEQUENCE: 811
aaacaaacau ggugcacuuc uu                                          22

<210> SEQ ID NO 812
<211> LENGTH: 21
<212> TYPE: RNA
<213> ORGANISM: Homo sapiens

<400> SEQUENCE: 812
ugagaugaag cacuguagcu c                                           21
```

<210> SEQ ID NO 813
<211> LENGTH: 22
<212> TYPE: RNA
<213> ORGANISM: Homo sapiens

<400> SEQUENCE: 813
aacacaccua uucaaggauu ca                                              22

<210> SEQ ID NO 814
<211> LENGTH: 23
<212> TYPE: RNA
<213> ORGANISM: Homo sapiens

<400> SEQUENCE: 814
uggugcggag agggcccaca gug                                             23

<210> SEQ ID NO 815
<211> LENGTH: 17
<212> TYPE: RNA
<213> ORGANISM: Homo sapiens

<400> SEQUENCE: 815
ucccuguucg ggcgcca                                                    17

<210> SEQ ID NO 816
<211> LENGTH: 22
<212> TYPE: RNA
<213> ORGANISM: Homo sapiens

<400> SEQUENCE: 816
ggagacgcgg cccuguugga gu                                              22

<210> SEQ ID NO 817
<211> LENGTH: 21
<212> TYPE: RNA
<213> ORGANISM: Homo sapiens

<400> SEQUENCE: 817
acucuuuccc uguugcacua c                                               21

<210> SEQ ID NO 818
<211> LENGTH: 20
<212> TYPE: RNA
<213> ORGANISM: Homo sapiens

<400> SEQUENCE: 818
ucacaccugc cucgcccccc                                                 20

<210> SEQ ID NO 819
<211> LENGTH: 22
<212> TYPE: RNA
<213> ORGANISM: Homo sapiens

<400> SEQUENCE: 819
uuuccggcuc gcgugggugu gu                                              22

<210> SEQ ID NO 820
<211> LENGTH: 19
<212> TYPE: RNA
<213> ORGANISM: Homo sapiens

<400> SEQUENCE: 820
gagccaguug gacaggagc                                              19

<210> SEQ ID NO 821
<211> LENGTH: 22
<212> TYPE: RNA
<213> ORGANISM: Homo sapiens

<400> SEQUENCE: 821
ugugacuggu ugaccagagg gg                                          22

<210> SEQ ID NO 822
<211> LENGTH: 21
<212> TYPE: RNA
<213> ORGANISM: Homo sapiens

<400> SEQUENCE: 822
ccuggaaaca cugagguugu g                                           21

<210> SEQ ID NO 823
<211> LENGTH: 22
<212> TYPE: RNA
<213> ORGANISM: Homo sapiens

<400> SEQUENCE: 823
agggacggga cgcggugcag ug                                          22

<210> SEQ ID NO 824
<211> LENGTH: 22
<212> TYPE: RNA
<213> ORGANISM: Homo sapiens

<400> SEQUENCE: 824
uacccauugc auaucggagu ug                                          22

<210> SEQ ID NO 825
<211> LENGTH: 23
<212> TYPE: RNA
<213> ORGANISM: Homo sapiens

<400> SEQUENCE: 825
cucuugaggg aagcacuuuc ugu                                         23

<210> SEQ ID NO 826
<211> LENGTH: 22
<212> TYPE: RNA
<213> ORGANISM: Homo sapiens

<400> SEQUENCE: 826
acuggacuua gggucagaag gc                                          22

<210> SEQ ID NO 827
<211> LENGTH: 21
<212> TYPE: RNA
<213> ORGANISM: Homo sapiens

<400> SEQUENCE: 827
acggugcugg auguggccuu u                                           21

<210> SEQ ID NO 828
<211> LENGTH: 22
<212> TYPE: RNA
<213> ORGANISM: Homo sapiens

<400> SEQUENCE: 828
ugcccuuaaa ggugaaccca gu                                                    22

<210> SEQ ID NO 829
<211> LENGTH: 25
<212> TYPE: RNA
<213> ORGANISM: Homo sapiens

<400> SEQUENCE: 829 aggggugug uugggacagc uccgu                                                  25

<210> SEQ ID NO 830
<211> LENGTH: 17
<212> TYPE: RNA
<213> ORGANISM: Homo sapiens

<400> SEQUENCE: 830
ucauauugcu ucuuucu                                                          17

<210> SEQ ID NO 831
<211> LENGTH: 22
<212> TYPE: RNA
<213> ORGANISM: Homo sapiens

<400> SEQUENCE: 831
acgcccuucc cccccuucuu ca                                                    22

<210> SEQ ID NO 832
<211> LENGTH: 24
<212> TYPE: RNA
<213> ORGANISM: Homo sapiens

<400> SEQUENCE: 832
ugccuggguc ucuggccugc gcgu                                                  24

<210> SEQ ID NO 833
<211> LENGTH: 20
<212> TYPE: RNA
<213> ORGANISM: Homo sapiens

<400> SEQUENCE: 833
ucacuguuca gacaggcgga                                                       20

<210> SEQ ID NO 834
<211> LENGTH: 22
<212> TYPE: RNA
<213> ORGANISM: Homo sapiens

<400> SEQUENCE: 834
cagugcaaug uuaaaagggc au                                                    22

<210> SEQ ID NO 835
<211> LENGTH: 22
<212> TYPE: RNA
<213> ORGANISM: Homo sapiens

<400> SEQUENCE: 835
uuuugcaaua uguuccugaa ua                                                    22

<210> SEQ ID NO 836
<211> LENGTH: 23
<212> TYPE: RNA
<213> ORGANISM: Homo sapiens

```
<400> SEQUENCE: 836
ucuuggagua ggucauuggg ugg                                              23

<210> SEQ ID NO 837
<211> LENGTH: 22
<212> TYPE: RNA
<213> ORGANISM: Homo sapiens

<400> SEQUENCE: 837
gaauguugcu cggugaaccc cu                                               22

<210> SEQ ID NO 838
<211> LENGTH: 20
<212> TYPE: RNA
<213> ORGANISM: Homo sapiens

<400> SEQUENCE: 838
cugcaaaggg aagcccuuuc                                                  20

<210> SEQ ID NO 839
<211> LENGTH: 21
<212> TYPE: RNA
<213> ORGANISM: Homo sapiens

<400> SEQUENCE: 839
uccucuucuc ccuccuccca g                                                21

<210> SEQ ID NO 840
<211> LENGTH: 20
<212> TYPE: RNA
<213> ORGANISM: Homo sapiens

<400> SEQUENCE: 840
cuuccucguc ugucugcccc                                                  20

<210> SEQ ID NO 841
<211> LENGTH: 22
<212> TYPE: RNA
<213> ORGANISM: Homo sapiens

<400> SEQUENCE: 841
ccucuagaug gaagcacugu cu                                               22

<210> SEQ ID NO 842
<211> LENGTH: 22
<212> TYPE: RNA
<213> ORGANISM: Homo sapiens

<400> SEQUENCE: 842
cgggguuuug agggcgagau ga                                               22

<210> SEQ ID NO 843
<211> LENGTH: 22
<212> TYPE: RNA
<213> ORGANISM: Homo sapiens

<400> SEQUENCE: 843
cuacaaaggg aagcacuuuc uc                                               22

<210> SEQ ID NO 844
<211> LENGTH: 21
<212> TYPE: RNA
<213> ORGANISM: Homo sapiens
```

-continued

<400> SEQUENCE: 844
aguuaggauu aggucgugga a                                    21

<210> SEQ ID NO 845
<211> LENGTH: 22
<212> TYPE: RNA
<213> ORGANISM: Homo sapiens

<400> SEQUENCE: 845
uagguuaucc guguugccuu cg                                   22

<210> SEQ ID NO 846
<211> LENGTH: 24
<212> TYPE: RNA
<213> ORGANISM: Homo sapiens

<400> SEQUENCE: 846 acuggggcu uucgggcucu gcgu                                  24

<210> SEQ ID NO 847
<211> LENGTH: 21
<212> TYPE: RNA
<213> ORGANISM: Homo sapiens

<400> SEQUENCE: 847
uuggccacaa ugggullagaa c                                   21

<210> SEQ ID NO 848
<211> LENGTH: 23
<212> TYPE: RNA
<213> ORGANISM: Homo sapiens

<400> SEQUENCE: 848
uuaaugcuaa ucgugauagg ggu                                  23

<210> SEQ ID NO 849
<211> LENGTH: 24
<212> TYPE: RNA
<213> ORGANISM: Homo sapiens

<400> SEQUENCE: 849
acuggcuagg gaaaaugauu ggau                                 24

<210> SEQ ID NO 850
<211> LENGTH: 21
<212> TYPE: RNA
<213> ORGANISM: Homo sapiens

<400> SEQUENCE: 850
gcccuccgcc cgugcacccc g                                    21

<210> SEQ ID NO 851
<211> LENGTH: 22
<212> TYPE: RNA
<213> ORGANISM: Homo sapiens

<400> SEQUENCE: 851
acggauguuu gagcaugugc ua                                   22

<210> SEQ ID NO 852
<211> LENGTH: 23
<212> TYPE: RNA

```
<213> ORGANISM: Homo sapiens

<400> SEQUENCE: 852 cgcaucccu agggcauugg ugu                                    23

<210> SEQ ID NO 853
<211> LENGTH: 22
<212> TYPE: RNA
<213> ORGANISM: Homo sapiens

<400> SEQUENCE: 853
aagcccuuac cccaaaaagu au                                    22

<210> SEQ ID NO 854
<211> LENGTH: 21
<212> TYPE: RNA
<213> ORGANISM: Homo sapiens

<400> SEQUENCE: 854 aggggggaaag uucuauaguc c                                    21

<210> SEQ ID NO 855
<211> LENGTH: 22
<212> TYPE: RNA
<213> ORGANISM: Homo sapiens

<400> SEQUENCE: 855
cucuagaggg aagcgcuuuc ug                                    22

<210> SEQ ID NO 856
<211> LENGTH: 22
<212> TYPE: RNA
<213> ORGANISM: Homo sapiens

<400> SEQUENCE: 856
accacugacc guugacugua cc                                    22

<210> SEQ ID NO 857
<211> LENGTH: 23
<212> TYPE: RNA
<213> ORGANISM: Homo sapiens

<400> SEQUENCE: 857
cccaguguuu agacuaucug uuc                                   23

<210> SEQ ID NO 858
<211> LENGTH: 21
<212> TYPE: RNA
<213> ORGANISM: Homo sapiens

<400> SEQUENCE: 858
uucacagugg cuaaguuccg c                                     21

<210> SEQ ID NO 859
<211> LENGTH: 22
<212> TYPE: RNA
<213> ORGANISM: Homo sapiens

<400> SEQUENCE: 859
gaaagcgcuu cccuuugcug ga                                    22

<210> SEQ ID NO 860
<211> LENGTH: 22
```

```
<212> TYPE: RNA
<213> ORGANISM: Homo sapiens

<400> SEQUENCE: 860
caggaugugg ucaaguguug uu                                              22

<210> SEQ ID NO 861
<211> LENGTH: 22
<212> TYPE: RNA
<213> ORGANISM: Homo sapiens

<400> SEQUENCE: 861
uauugcacuu gucccggccu gu                                              22

<210> SEQ ID NO 862
<211> LENGTH: 24
<212> TYPE: RNA
<213> ORGANISM: Homo sapiens

<400> SEQUENCE: 862
gcugguuuca uauggugguu uaga                                            24

<210> SEQ ID NO 863
<211> LENGTH: 22
<212> TYPE: RNA
<213> ORGANISM: Homo sapiens

<400> SEQUENCE: 863
ucucccaacc cuuguaccag ug                                              22

<210> SEQ ID NO 864
<211> LENGTH: 23
<212> TYPE: RNA
<213> ORGANISM: Homo sapiens

<400> SEQUENCE: 864
ucaagagcaa uaacgaaaaa ugu                                             23

<210> SEQ ID NO 865
<211> LENGTH: 25
<212> TYPE: RNA
<213> ORGANISM: Homo sapiens

<400> SEQUENCE: 865
agggaucgcg ggcggguggc ggccu                                           25

<210> SEQ ID NO 866
<211> LENGTH: 20
<212> TYPE: RNA
<213> ORGANISM: Homo sapiens

<400> SEQUENCE: 866
aaaguagcug uaccauuugc                                                 20

<210> SEQ ID NO 867
<211> LENGTH: 22
<212> TYPE: DNA
<213> ORGANISM: Homo sapiens

<400> SEQUENCE: 867
actccatcat ccaacatatc aa                                              22

<210> SEQ ID NO 868
```

```
<211> LENGTH: 22
<212> TYPE: DNA
<213> ORGANISM: Homo sapiens

<400> SEQUENCE: 868
aactatacaa cctactacct ca                                          22
```